US012442035B2

(12) United States Patent
Hung et al.

(10) Patent No.: US 12,442,035 B2
(45) Date of Patent: Oct. 14, 2025

(54) COMPOSITIONS AND METHODS FOR DETECTING ANTIBIOTIC RESPONSIVE MRNA EXPRESSION SIGNATURES AND USES THEREOF

(71) Applicants: THE BROAD INSTITUTE, INC., Cambridge, MA (US); THE GENERAL HOSPITAL CORPORATION, Boston, MA (US)

(72) Inventors: Deborah Hung, Cambridge, MA (US); Roby Bhattacharyya, Boston, MA (US); Jonathan Livny, Cambridge, MA (US); Peijun Ma, Cambridge, MA (US)

(73) Assignees: THE BROAD INSTITUTE, INC., Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 1263 days.

(21) Appl. No.: 17/271,496

(22) PCT Filed: Aug. 26, 2019

(86) PCT No.: PCT/US2019/048114

§ 371 (c)(1),
(2) Date: Feb. 25, 2021

(87) PCT Pub. No.: WO2020/046801

PCT Pub. Date: Mar. 5, 2020

(65) Prior Publication Data

US 2021/0230675 A1 Jul. 29, 2021

Related U.S. Application Data

(60) Provisional application No. 62/834,786, filed on Apr. 16, 2019, provisional application No. 62/723,417, filed on Aug. 27, 2018.

(51) Int. Cl.

| | |
|---|---|
| ***C12Q 1/6816*** | (2018.01) |
| ***C12N 1/06*** | (2006.01) |
| ***C12N 1/20*** | (2006.01) |
| ***C12Q 1/6876*** | (2018.01) |
| ***C12Q 1/689*** | (2018.01) |

(52) U.S. Cl.

CPC ............. *C12Q 1/6816* (2013.01); *C12N 1/06* (2013.01); *C12N 1/20* (2013.01); *C12Q 1/6876* (2013.01); *C12Q 1/689* (2013.01)

(58) Field of Classification Search

CPC .... C12Q 1/6816; C12Q 1/6876; C12Q 1/689; C12N 1/06; C12N 1/20

See application file for complete search history.

(56) References Cited

U.S. PATENT DOCUMENTS

| | | | |
|---|---|---|---|
| 9,885,088 | B2 | 2/2018 | Hung et al. |
| 2010/0136534 | A1 | 6/2010 | Wang et al. |

FOREIGN PATENT DOCUMENTS

| | | | |
|---|---|---|---|
| EP | 3231874 | A1 | 10/2017 |
| WO | 2011094514 | A1 | 8/2011 |
| WO | 2018144918 | A1 | 8/2018 |

OTHER PUBLICATIONS

Codjoe et al. ("Carbapenem resistance: a review." Medical Sciences 6.1 (2017)).*

Klebsiella pneumoniae capsular polysaccharide biosynthesis gene cluster, type: KL106-1: Genbank Accession LT174576.1; Publication [online]. Jun. 13, 2013 [retrieved Dec. 17, 2019]. Retrieved from the internet: <https://www.ncbi.nlm.nih.gov/nucleotide/LT174576.1?report=genbank&log$=nuclalign&blast_rank=14&RID=ZJ5BK3RD016>; pp. 1-10.

Klebsiella pneumoniae strain KpMDU1 cpsC capsular synthesis gene cluster, complete sequence: Genbank Accession KR007677.1; Publication [online]. Jun. 8, 2015 [retrieved Dec. 17, 2017]. Retrieved from the internet: <https://www.ncbi.nlm.nih.gov/nucleotide/KR007677.1?report=genbank&log$=nuclalign&blast_rank=19&RID=ZJ5BK3RD016>, pp. 1-10.

International Search Report dated Jan. 9, 2020 for related Application No. PCT/US2019/048114.

International Search Report dated Mar. 11, 2021 for related Application No. PCT/US2019/048114.

Extended European Search Report in corresponding application No. 19853410.9 dated May 13, 2022.

* cited by examiner

*Primary Examiner* — Kimberly Chong

(74) *Attorney, Agent, or Firm* — Day Pitney LLP; Richard B. Emmons; Christopher R. Cowles

(57) ABSTRACT

The present disclosure relates to compositions, methods, and kits for rapid phenotypic detection of antibiotic resistance/susceptibility.

11 Claims, 30 Drawing Sheets

Specification includes a Sequence Listing.

COMPOSITIONS AND METHODS FOR DETECTING ANTIBIOTIC RESPONSIVE MRNA EXPRESSION SIGNATURES AND USES THEREOF

CROSS-REFERENCE TO RELATED APPLICATIONS

This application is a national stage application, filed under 35 U.S.C. § 371, of International Patent Application No. PCT/US19/48114, filed Aug. 26, 2019, entitled "Compositions and Methods for Detecting Antibiotic Responsive mRNA Expression Signatures and Uses Thereof" and published Mar. 5, 2020 as WO 2020/046801, which claims the benefit of priority under 35 U.S.C. § 119(e) to U.S. Provisional Application No: 62/723,417, filed on Aug. 27, 2018, entitled, "Compositions and Methods for Detecting Antibiotic Responsive mRNA Expression Signatures and Uses Thereof"; and to U.S. Provisional Application No: 62/834,786, filed on Apr. 16, 2019, entitled, "Compositions and Methods for Detecting Antibiotic Responsive mRNA Expression Signatures and Uses Thereof." The entire contents of each of these applications are hereby incorporated by reference herein.

STATEMENT REGARDING FEDERALLY SPONSORED RESEARCH

The invention was made with government support under Grant Nos. AI117043, AI119157, and HHSN272200900018C awarded by the National Institutes of Health. The government has certain rights in the invention.

FIELD OF THE DISCLOSURE

The present disclosure relates to compositions, methods, and kits for rapid phenotypic detection of antibiotic resistance/susceptibility.

SEQUENCE LISTING

The instant application contains a Sequence Listing which has been filed electronically in ASCII format and is hereby incorporated by reference in its entirety. Said ASCII copy, created on Aug. 19, 2019, is named 52199_534001WO_BI10397_SL.txt and is 800 kB in size.

BACKGROUND OF THE DISCLOSURE

Antimicrobial agents such as antibiotics have been used successfully for many decades treat patients who have infectious diseases related to microbial pathogens. Unfortunately, these antimicrobial agents have been broadly used for such a long period of time that many microbial pathogens have become resistant to the antibiotics that are designed to kill them, which greatly reduces the efficacy of the antimicrobial agents that are currently available. This creates a significant healthcare issue. For example, each year in the United States at least 2 million people become infected with antibiotic resistant bacteria, which results in the death of at least 23,000 people each year. Accordingly, there is an urgent need for compositions and methods that enable rapid and accurate detection of antibiotic resistance in microbial pathogens.

BRIEF SUMMARY OF THE DISCLOSURE

The current disclosure relates, at least in part, to compositions, methods, and kits for rapid phenotypic detection of antibiotic resistance. The techniques herein provide compositions and methods that provide rapid phenotypic detection of antibiotic resistance/susceptibility in microbial pathogens, and are faster than the prior art growth-based phenotypic assays that currently comprise the gold standard for such detection (e.g., antibiotic susceptibility testing (AST)). The techniques herein also provide compositions and methods that enable simultaneous detection of multiple resistance genes in the same assay. In this manner, the techniques herein enable more accurate determination of antibiotic resistance, as well as provide: 1) mechanistic explanations for key antibiotic resistant strains, 2) epidemiologic tracking of known resistance mechanisms, and 3) immediate identification of unknown or potentially novel resistance mechanisms (such as, e.g., discordant cases when a resistant organism does not display a known resistance phenotype). Currently, detection of antibiotic resistance genes typically requires separate PCR or sequencing assays, which require different assay infrastructure and often necessitate sending samples out to reference laboratories.

In one aspect, the disclosure provides a method that includes the following steps: obtaining a sample including one or more bacterial cells, wherein the sample is obtained from a patient or an environmental source; processing the sample to enrich the one or more bacterial cells; contacting the sample with one or more antibiotic compounds; lysing the sample to release messenger ribonucleic acid (mRNA) from the one or more bacterial cells; hybridizing the released mRNA to at least one set of two nucleic acid probes, wherein each nucleic acid probe includes a unique barcode or tag; detecting the hybridized nucleic acid probes; identifying one or more genetic resistance determinants; and determining the identity of the one or more bacterial cells and the antibiotic susceptibility of each of the identified one or more bacterial cells.

In embodiments, the at least one set of two nucleic acid probes includes one or more probes from Table 3 and one or more probes from Table 4.

In embodiments, the at least one set of two nucleic acid probes includes one or more probes from Table 5 and one or more probes from Table 6.

In some embodiments, the at least one set of two nucleic acid probes includes a first probe that possesses a sequence of SEQ ID NOs: 1877-2762 and a second probe that possesses a sequence of SEQ ID NOs: 2763-3648. Optionally, the first probe possesses a sequence of SED ID NO: (1877+n) and the second probe possesses a sequence of SEQ ID NO: (2763+n), where n=an integer ranging from 0 to 885 in value. Optionally, one or both probes further includes a tag sequence.

In embodiments, the at least one set of two nucleic acid probes binds to one or more Cre2 target sequences listed in Table 1.

In embodiments, the at least one set of two nucleic acid probes binds to one or more KpMero4 target sequences listed in Table 2.

In embodiments, the hybridizing may occur at a temperature between about 64° C. and about 69° C. The hybridizing may occur at a temperature between about 65° C. and about 67° C. The hybridizing may also occur at a temperature of about 65° C. or about 66° C. or about 67° C. The hybridizing may occur at a temperature of about 65.0° C., 65.1° C., 65.2° C., 65.3° C., 65.4° C., 65.5° C., 65.6° C., 65.7° C., 65.8° C., 65.9° C., 66.0° C., 66.1° C., 66.2° C., 66.3° C., 66.4° C., 66.5° C., 66.6° C., 66.7° C., 66.8° C., 66.9° C., 67.0° C., 67.1° C., 67.2° C., 67.3° C., 67.4° C., 67.5° C., 67.6° C., 67.7° C., 67.8° C., or 67.9° C.

In one aspect, the disclosure provides a composition comprising a set of nucleic acid probes corresponding to the probes listed in Table 3 and Table 4.

In one aspect, the disclosure provides a composition comprising a set of nucleic acid probes corresponding to the probes listed in Table 5 and Table 6.

In an aspect, the disclosure provides a composition that includes at least one set of two nucleic acid probes including a first probe that possesses a sequence of SEQ ID NOs: 1877-2762 and a second probe that possesses a sequence of SEQ ID NOs: 2763-3648. Optionally, the first probe possesses a sequence of SED ID NO: (1877+n) and the second probe possesses a sequence of SEQ ID NO: (2763+n), where n=an integer ranging from 0 to 885 in value. Optionally, one or both probes further includes a tag sequence.

In one aspect, the disclosure provides a method of treating a patient that includes the steps of: obtaining a sample including one or more bacterial cells, wherein the sample is obtained from a patient or an environmental source; processing the sample to enrich the one or more bacterial cells; contacting the sample with one or more antibiotic compounds;

lysing the sample to release messenger ribonucleic acid (mRNA) from the one or more bacterial cells; hybridizing the released mRNA to at least one set of two nucleic acid probes at 65-67° C., wherein each nucleic acid probe includes a unique barcode or tag; detecting the hybridized nucleic acid probes; identifying one or more genetic resistance determinants; determining the identity of the one or more bacterial cells and the antibiotic susceptibility of each of the identified one or more bacterial cells; and administering to the patient an appropriate antibiotic based on the determination of the identity and the antibiotic susceptibility of the one or more bacterial cells.

In embodiments, the processing includes subjecting the sample to centrifugation or differential centrifugation.

In embodiments, the one or more antibiotic compounds are at a clinical breakpoint concentration.

In embodiments, lysing occurs by a method selected from the group consisting of mechanical lysis, liquid homogenization lysis, sonication, freeze-thaw lysis, and manual grinding.

In embodiments, the at least one set of two nucleic acid probes includes one control set and one responsive set, 3-5 control sets and 3-5 responsive sets, or 8-10 control sets and 8-10 responsive sets.

In embodiments, the hybridizing may occur at a temperature between about 64° C. and about 69° C. The hybridizing may occur at a temperature between about 65° C. and about 67° C. The hybridizing may also occur at a temperature of about 65° C. or about 66° C. or about 67° C. The hybridizing may occur at a temperature of about 65.0° C., 65.1° C., 65.2° C., 65.3° C., 65.4° C., 65.5° C., 65.6° C., 65.7° C., 65.8° C., 65.9° C., 66.0° C., 66.1° C., 66.2° C., 66.3° C., 66.4° C., 66.5° C., 66.6° C., 66.7° C., 66.8° C., 66.9° C., 67.0° C., 67.1° C., 67.2° C., 67.3° C., 67.4° C., 67.5° C., 67.6° C., 67.7° C., 67.8° C., or 67.9° C.

In one aspect, the disclosure provides a kit, including a set of nucleic acid probes corresponding to the probes listed in Table 3 and Table 4.

In one aspect, the disclosure provides a kit, comprising a set of nucleic acid probes corresponding to the probes listed in Table 5 and Table 6.

Another aspect of the instant disclosure provides a kit, including at least one set of two nucleic acid probes including a first probe that possesses a sequence of SEQ ID NOs: 1877-2762 and a second probe that possesses a sequence of SEQ ID NOs: 2763-3648, and instructions for its use.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless otherwise clear from context, all numerical values provided herein are modified by the term "about."

The term "administration" refers to introducing a substance into a subject. In general, any route of administration applicable to antimicrobial agents (e.g., an antibiotic) may be utilized including, for example, parenteral (e.g., intravenous), oral, topical, subcutaneous, peritoneal, intra-arterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

As herein, the term "algorithm" refers to any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, statistical weights, and neural networks trained on populations or datasets.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed disclosure.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

"Detect" refers to identifying the presence, absence or amount of the analyte (e.g., rRNA, mRNA, and the like) to be detected.

By "detectable label" is meant a composition that when linked to a molecule of interest (e.g., a nucleic acid probe) renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. As used herein, the term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The disclosure provides a number of specific nucleic acid targets (e.g., mRNA transcripts) or sets of nucleic acid targets that are useful for the identifying microbial pathogens (e.g., bacteria) that are susceptible or resistant to treatment with specific antibiotics. In addition, the methods of the disclosure provide a facile means to identify therapies that are safe and efficacious for use in subjects that have acquired bacterial infections involving antibiotic resistant strains of bacteria. In addition, the methods of the disclosure provide a route for analyzing virtually any number of bacterial strains via antibiotic susceptibility testing (AST) to identify mRNA signature patterns indicative of antibiotic susceptibility or resistance, which may then be used to rapidly identify such traits in the clinic, and direct appropriate therapeutic intervention.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

"Infectious diseases," also known as communicable diseases or transmissible diseases, comprise clinically evident illness (i.e., characteristic medical signs and/or symptoms of disease) resulting from the infection, presence, and growth of pathogenic biological agents (e.g., bacteria) in a subject (Ryan and Ray (eds.) (2004). Sherris Medical Microbiology (4th ed.). McGraw Hill). A diagnosis of an infectious disease can confirmed by a physician through, e.g., diagnostic tests (e.g., blood tests), chart review, and a review of clinical history. In certain cases, infectious diseases may be asymptomatic for some or all of their course. Infectious pathogens can include viruses, bacteria, fungi, protozoa, multicellular parasites, and prions. One of skill in the art would recognize that transmission of a pathogen can occur through different routes, including without exception physical contact, contaminated food, body fluids, objects, airborne inhalation, and through vector organisms. Infectious diseases that are especially infective are sometimes referred to as contagious and can be transmitted by contact with an ill person or their secretions.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

By "isolated polynucleotide" is meant a nucleic acid (e.g., a DNA) that is free of the genes which, in the naturally-occurring genome of the organism from which the nucleic acid molecule of the disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By "marker" is meant any protein or polynucleotide having an alteration in expression level or activity that is associated with a disease or disorder (e.g., increased or decreased expression in a bacterial strain indicative of antibiotic susceptibility).

As used herein, the term "next-generation sequencing (NGS)" refers to a variety of high-throughput sequencing technologies that parallelize the sequencing process, producing thousands or millions of sequence reads at once. NGS parallelization of sequencing reactions can generate hundreds of megabases to gigabases of nucleotide sequence reads in a single instrument run. Unlike conventional sequencing techniques, such as Sanger sequencing, which typically report the average genotype of an aggregate collection of molecules, NGS technologies typically digitally tabulate the sequence of numerous individual DNA fragments (sequence reads discussed in detail below), such that low frequency variants (e.g., variants present at less than about 10%, 5% or 1% frequency in a heterogeneous population of nucleic acid molecules) can be detected. The term "massively parallel" can also be used to refer to the simultaneous generation of sequence information from many different template molecules by NGS. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLID technology (Applied Biosystems); Ion semiconductor sequencing (ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141;

Su, et al., "Next-generation sequencing and its applications in molecular diagnostics" Expert Rev Mol Diagn, 2011, 11 (3): 333-43; and Zhang et al., "The impact of next-generation sequencing on genomics," J Genet Genomics, 201, 38 (3): 95-109.

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

Unless specifically stated or obvious from context, as used herein, the term "or" is understood to be inclusive. Unless specifically stated or obvious from context, as used herein, the terms "a", "an", and "the" are understood to be singular or plural.

The term "probe" as used herein refers to an oligonucleotide that binds specifically to a target mRNA. A probe can be single stranded at the time of hybridization to a target.

By "reference" is meant a standard or control condition.

A "reference sequence" is a defined sequence used as a basis for sequence comparison. A reference sequence may be a subset of or the entirety of a specified sequence; for example, a segment of a full-length mRNA or cDNA or gene sequence, or the complete mRNA or cDNA or gene sequence. For nucleic acids, the length of the reference nucleic acid sequence will generally be at least about 25 nucleotides, about 50 nucleotides, about 60 nucleotides, about 75 nucleotides, about 100 nucleotides, or about 300 nucleotides, or any integer thereabout or therebetween.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect (e.g., reduction or elimination of a bacterial infection). The effect can be prophylactic in terms of completely or partially preventing a disease or infection or symptom thereof and/or can be therapeutic in terms of a partial or complete cure for a disease or infection and/or adverse effect attributable to the disease or infection. "Treatment," as used herein, covers any treatment of a disease or condition or infection in a mammal, particularly in a human, and includes: (a) preventing the disease or infection from occurring in a subject which can be predisposed to the disease or infection but has not yet been diagnosed as having it; (b) inhibiting the disease or infection, e.g., arresting its development; and (c) relieving the disease or infection, e.g., reducing or eliminating a bacterial infection.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethlyamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.).

Ranges can be expressed herein as from "about" one particular value and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "therapeutically effective amount" of an agent described herein is an amount sufficient to provide a therapeutic benefit in the treatment of a condition or to delay or minimize one or more symptoms associated with the condition (e.g., an amount sufficient to reduce or eliminate a bacterial infection). A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

By "KpMero4_C_KPN_00050 nucleic acid molecule" is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding "N" residues, that is part of the KpMero4 probeset.

```
>KpMero4_C_KPN_00050
                                        (SEQ ID NO: 1)
ATGAAGAACTGGAAAACGCTGCTTCTCGGTATCGCCATGATCGCGAATA
CCAGTTTCGCTGCCCCCCAGGTGGTCGATAAAGTAGCGGCCGTCGTCAA
TAATGGCGTCGTGCTGGAAAGCGACGTCGATGGTTTGATGCAATCGGTT
AAGCTCAATGCNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNCAGA
AAGATCGTGCTTACCGCATGCTGATGAACCGCAAATTCTCTGAAGAAGC
GGCAACCTGGATGCAGGAACAGCGCGCCAGTGCGTATGTTAAAATTCTG
AGCAACTAAN
```

By "KpMero4_C_KPN_00098 nucleic acid molecule" is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding "N" residues, that is part of the KpMero4 probeset.

```
>KpMero4_C_KPN_00098
                                        (SEQ ID NO: 2)
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
```

-continued

```
NNNNNNNNNNNNNNNNNNNNNNNNNGTGAAATGCGTACAGCGCGCCATCG
ACCAGGCCGAACTGATGGCGGATTGCCAGATTTCATCAGTTTATTTGGC
ACTTTCGGGTAAACATATAAGCTGTCAGAATGAAATCGGGATGGTACCG
ATTTCGGAAGAAGAAGTGACGCAGGANNNNNNNNNNNNNNNNNNNNNNNN
NNNNNNNNNNNNNNNNNNNNNNNNNNNNNNNNNNNGTCCTGCACGTGATT
CCGCAGGAATATGCTATCGACTACCAGGAAGGGATTAAAAACCCGGTAG
GGCTGTCCGGCGTGCGTATGCAGGCGAAGGTGCATCTGATCACCTGCCA
TAACGATATGGCNNNNNNNNNNNNNNNNNNNGTGGAACGTTGTGGTCTGA
AAGTTGACCAACTTATTTTCGCCGGGTTAGCGGCCAGTTATTCGGTATT
AACAGAAGACGAACGTGAGCTGGGCGTCTGCGTTGTGGANNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNN
```

By "KpMero4_C_KPN_00100 nucleic acid molecule" is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding "N" residues, that is part of the KpMero4 probeset.

```
>KpMero4_C_KPN_00100
                                        (SEQ ID NO: 3)
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNGCGATTGATGCCAGCACCCAGCGCTATACGCTGAACTTCTCGGCCGA
TGCGTTCATGCGTCAGATTAGCCGTGCGCGTACCTTCGGTTTTATGCGC
```

-continued

```
GATATCGAATATCTGCAGTCCCGCGGCCTGTGCCTGGGCGGCAGCTTCG

ATTGTGCCATCGTTGTTGACGATTATCGCGTACTGAACGAAGACGGTCT

GCGCTTTGAAGACGAATTTGTTCGCCACAAAATGCTGGATGCGATCGGT

GACCTGTTTATGTGTGGTCACAACATTATCGGCGCATTCACGGCGTACA

AATCGGGTCACGCGTTGAACAACAAACTGCTGCAGGCGGTNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNN
```

By “KpMero4_C_KPN_01276 nucleic acid molecule” is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding “N” residues, that is part of the KpMero4 probeset.

```
>KpMero4_C_KPN_01276
                                                (SEQ ID NO: 4)
ATGCTGGAGTTGTTGTTTCTGCTTTTACCCGTTGCCGCCGCTTACGGCT

GGTACATGGGGCGCAGAAGTGCACAACAGTCCAAACAGGACGATGCGAG

CCGCCTGTCGCGAGATTACGTGGCGGGGGTTAACTTCCTGCTCAGCAAC

CAGCAGGATAAAGCCGTCGACCTGTTCCTTGATATGCTGAAAGAGGATA

CCGGTACCGTTGAGGCNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNN
```

By “KpMero4_C_KPN_02846 nucleic acid molecule” is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding “N” residues, that is part of the KpMero4 probeset.

```
>KpMero4_C_KPN_02846
                                                (SEQ ID NO: 5)
ATGAATACTGAAGCCACTCAAGATCATCAAGAAGCAAACACCACGGGCG

CGCGTCTGCGTCACGCCCGCGAACAACTCGGACTTAGCCAGCAAGCGGT

GGCCGAACGCTTATGCCTGAAGGTGTCCACGGTTCGTGATATTGAAGAC

GATAAGGCCCCCGCCGACCTCGCCTCCACCTTCCTGCGCGGNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNCCGGCGGCGTCGGCGC

AGGATCTGGTGATGAACTTTTCCGCCGACTGCTGGCTGGAAGTGAGCGA

TGCCACCGGTAAAAAACTGTTCAGCGGCCTGCAGCGTAAAGGCGGTAAN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNN
```

By “KpMero4_C_KPN_03317 nucleic acid molecule” is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding “N” residues, that is part of the KpMero4 probeset.

```
>KpMero4_C_KPN_03317
                                                (SEQ ID NO: 6)
NNNNNNNNNNNNNNNNNNNNNNNNNNNNNNNN--ATGGCCGGGGAACACG

TCATTTTGCTGGATGAGCAGGATCAGCCTGCCGGTATGCTGGAGAAGTA

TGCCGCCCATACGTTTGATACCCCTTTACATCTCGCGTTTTCCTGCTGG

CTGTTTAANNNNNNNNNNNNNNNNNNNNNNNNNNNNCGTTCGTTGGGCAA

AAAAGCCTGGCCCGGGGTATGGACCAACTCGGTCTGCGGACACCCCCAG

CAGGGCGAGACCTTCGAGCAGGCCGTCACGCGCCGCTGTCGCTTCGAAC

TCGGTGTGGAGATCTCNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNCGCGTGGTAAGCGAAGTGCAGCCTAACGACGATGAAGTCA

TGGACTATCAGTGGGTTGACCTGGCAACCATGTTAAGCGCGCTGGCCGC

CACGCCGTGGGCGTTCAGCCCGTGGATGGTGCTGGAAGCGGAAAATCGG

GACGCCCGCCAGGCGCTGACCGAN
```

By “KpMero4_C_KPN_03634 nucleic acid molecule” is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding “N” residues, that is part of the KpMero4 probeset.

```
>KpMero4_C_KPN_03634
                                                (SEQ ID NO: 7)
NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN
```

-continued

```
NNNNNNNNNNNAACGATACGGCAGACGACTCCCCGGCGAGCTATAACGCC
GCGGTGCGCCCGCGCGGCGCCCGCCGTGGTGAACGTCTATAACCGCGCCC
TTAACAGCACCAGCCATAATCAGCTGACGCTTGGCTCAGGGGTGATTAT
GGATCAGCGCGGCTATATCCTGACCAACAAGCATGTTATCAACGATGCC
GATCAGATTATCGTCGCCCTGCAGGACGGCCGCGTCTTCGAAGCGCTGC
TGGTAGGATCCGATTCCCTCACNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNCAGGGGATTATCAGCGCCACAGGGCGCATTGGCCTCAATCCGA
CCGGCCGCCAGAACTTCCTGCAGACTGACGCCTCGATCAACCACGGTAA
CTCCGGCGGGGCNCTGGTGAACTCCCTCGGCGAGCTGATGGGGATTAAC
ACCCTCTCCTTTGACAAGAGCAATGACGGCGAAACGCCGGAAGGCATTG
GCTTTGCGATCCCGTTCCAGTTAGCGACCAAAATTATGGATAAACTGAT
CCGCGATGGCCGGGTGATCCGCGGCTATATCGGCATTAGCGGCCGGGAG
ATCGCCCCGCTGCACGCGCAGGGCGGAGGGATCGATCAGATTCAGGGGA
TCGTNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNG
CGCTGGAGACGATGGATCAGGTGGCCGAGATCCGCCCGGGATCGGAAAT
TCCGGTGGTCATCATGCGTGATGATAAGAAAATCACGCTCCATATCGCC
GTCCAGGAATACCCGGCCACCAACTAAN
```

By “KpMero4_C_KPN_04666 nucleic acid molecule” is meant a control polynucleotide that is 95%, 96%, 97%, 98%, or 100% identical to the following *Klebsiella pneumoniae* (strain MGH 78578, also known as ATCC 700721; reference genome NC_009648) sequence, excluding “N” residues, that is part of the KpMero4 probeset.

```
>KpMero4_C_KPN_04666
                                        (SEQ ID NO: 8)
NNNNNNNNNNNNNNNNNNNNNNNNNNNNNNNNNNNNNNNNNNNNNGTTGG
CGATCCTATTCATCCTGTTACTGATTTTCTTTTGTCAGAAATTAGTCAG
GATCCTCGGCGCCGCGGTGGATGGCGATATCCCAACCAATCTGGTGCTC
TCGCTGTTGGGGCTCGGCATCCCGGAGATGGCGCAGCTTATCCTGCCGT
TAAGTCTGTTCCTTGGCCTGCTNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNAACCCCGGTATGGCGGCGCTGGCCCAGGGCC
AGTTCCAGCAGGCCAGCGATGGTAACGCGGTGATGTTTATCGAAAGCGT
CAACGGCAACCGCTTCCATGACGTCTTCCTTGCCCAGCTGCGTCCGAAA
GGCAATGCGCGCCCCTCGGTGGTGGTGGCGGATTCCGGCGAGCTGTCGC
AGCAGAAAGACGGCTCGCAGGTGGTGACCCTCAACAAGGGCACCCGCTT
TGAAGGCACCGCGATGCTGCGCGANNNNNNNNNNNNNNNNNNNNNNNNNN
NNNNNNNNNNNNNNNNNNNNNNNNNNNNNNNNNNNNNNNNNNNNNNNNNN
```

-continued

```
NNNNNNNNNNNNNNNNNNNNNNNNNNNNNNNNNNNNNNACCGACCGCGCG
CGCGCCGAACTGCACTGGCGCTTCACGCTGGTGGCGACCGTCTTCATTA
TGGCGCTGATGGTGGTGCCGCTCAGCGTGGTGAACCCGCGTCAGGGCCG
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNGGC
TATCTGGATGTGGGCGATTAACCTGCTCTATTTTGCGCTGGCGGTGCTG
TTAAACCTGTGGGACACGGTGCCGATGCGCCGCTTCCGCGCCCGTTTTA
ATAAAGGAGCGGCCTGAN
```

By “KpMero4_ROlup_KPN_01226 nucleic acid molecule” is meant an upregulated responsive polynucleotide that is 95%, 96%, 97%, 98%, or 100% identical to the following *Klebsiella pneumoniae* (strain MGH 78578, also known as ATCC 700721) sequence, excluding “N” residues, that is part of the KpMero4 probeset.

```
>KpMero4_R01up_KPN_01226
                                        (SEQ ID NO: 9)
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNGAA
GAACGCCGCGCGATGCACGATCTGATCGCCAGCGACACCTTCGATAAGG
CGAAGGCGGAAGCGCAGATCGATAAGATGGAAGCGCAGCATAAAGCGAT
GGCGCTGTCCCGCCTGGAAACGCAGAACAAGATCTACAACATTCTGACN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNN
```

By “KpMero4_R02up_KPN_01107 nucleic acid molecule” is meant an upregulated responsive polynucleotide that is 95%, 96%, 97%, 98%, or 100% identical to the following *Klebsiella pneumoniae* (strain MGH 78578, also known as ATCC 700721) sequence, excluding “N” residues, that is part of the KpMero4 probeset.

```
>KpMero4_R02up_KPN_01107
                                        (SEQ ID NO: 10)
NNNNNNNNNNNNNNNNNNNNNNNNNNNNNNNNNNNNNNNNNNNNNNNNNN
NNNNNNNNNNNNNNNNNNNNNNNNNNNGTGGCTGCCGCGCTGGGCGTTGC
AGCTGTCGCTGGTCTCAACGTGTTGGATCGCGGCCCGCAGTATGCGCAA
GTGGTCTCCAGTACACCGATTAAAGAAACCGTGAAAACGCCGCGTCAGG
AATGCCGCAATGTCACGGTGACTCATCGTCGTCCGGTNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
```

-continued

NNNNNNNNNNNNNNNNNNNNNNNNNNNNNNNNNNNNNNNNNNNNNNNNNN

NNNNNNNNNNNNNNNNNNNNNNNNNNNNNN

By "KpMero4_R03up_KPN_02345 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

```
>KpMero4_R03up_KPN_02345
                                          (SEQ ID NO: 11)
ATGATGCGAATCGCGCTTTTCCTGCTGACGAACCTGGCAGTGATGGTCGT

GTTCGGGCTGGTGTTAAGCCTCACGGGGATCCAATCCAGCAGCATGACCG

GTCTTCTGATTATGGCCCTGCTGTTCGGCTTCGGTGGTTCTATCGTTTCG

CTGATGATGTCGAAGTGGATGGCGCTGAAGTCNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNN
```

By "KpMero4_R04up_KPN_02742 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

```
>KpMero4_R04up_KPN_02742
                                          (SEQ ID NO: 12)
NNNNNNNNNNNNNNNNNNNNNNNNNNNNNNNNNNNNNNNNNNNNNNNNNN

NNNNNNNNNNNNNNNNNNNATCACCCTGCTGCCATCGGTAAAATTACAAA

TAGGCGATCGTGACAATTACGGTAACTACTGGGACGGTGGCAGCTGGCGC

GACCGTGATTACTGGCGTCGTCACTATGAATGGCGTGATAACCGTTGGCA

TCGTCATGACAACGGCTGGCACN
```

By "KpMero4_R05dn_KPN_02241 nucleic acid molecule" is meant a downregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

```
>KpMero4_R05dn KPN_02241
                                          (SEQ ID NO: 13)
ATGAAACGCAAAAACGCTTCGTTACTCGGTAACGTACTCATGGGGTTAGG

GTTGGTGGTGATGGTTGTGGGGGTAGGTTACTCCATTCTGAACCAGCTTC

CGCAGCTTAACCTGCCACAATTCTTTGCGCATGGCGCAATCCTAAGCATC

TTCGTTGGCGCAGTGCTCTGGCTGGCCGGTGCCCGTATTGGCGGCCACGA

GCAGGTCAGCGACCGCTACTGGTGGGTGCGCCACTACGATAAACGCTGCC

GTCGTAACCAGCATCGTCACAGCTAAN
```

By "KpMero4_R06up_KPN_03358 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

```
>KpMero4_R06up_KPN_03358
                                          (SEQ ID NO: 14)
NNNNNNNNNNNNNNNNNNNNNNNNNNNNNNNNNNNNNNNNNNNNNNNNNN

NNNNNNNNNNNNNNNNNNNNNNNNNAACATGGACTCCAACGGTCTGCTCA

GCTCAGGCGCCGAAGCCTTCCAGGCATACTCTCTCAGCGACGCGCAGGTG

AAAACCTTAAGCGACCAGGCCTGTAAAGAGATGGACGCCAAAGCGAAAAT

CGCCCCGGCCAACAGTGAATACAGCCAGCGGCTGAACAAAATCGCGNCTG

CGCTGGGCGATAACATCAATGGTCAGCCCGTGAACTACAAGGTCTATGAG

ACCAAGGATGTCAACGCCTTCGCCATGGCCAACGGCTGCATCCGCGTCTA

CAGCGGGCTGATGGATCTGATGAACGATAATGAAGTCGAGGCGGNGATCG

GCCACGAAATGGGCCACGTCGCGCTGGGCCACGTGAAGAAAGGCATGCAG

GTCGCCCTGGGTACCAACGCCGTGCGTGCGGCGGCGGCCTCCGCGGGCGG

NNNNNNNNNAGCCTGTCGCAGTCTCAGTTGGGCGATCTGGGCGAAAAACT

GGTGAACTCGCAGTTCTCCCAGCGTCAGGAATCGGAAGCGGATGACTACT

CTTACGACCTGCTGCGTAAGCGCGGTATCAATCCGTCGGGACTGGCCACC

AGCTTCGAGAAACTGGCCAAGCTGGAAGCCGGCCGTCAGAGCTCCATGTT

TGACGATCACCCGGCATCNNNNNNNNNNNNNNNNNNNNNNNNNNNNNNNN

NNNNNNNNNNNNNNNNNNNNNNNN
```

By "KpMero4_R07up_KPN_03934 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

```
>KpMero4_R07up_KPN_03934
                                          (SEQ ID NO: 15)
NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

N----ATGCCTTATATTACCAAGCAGAATCAGGCGATTACTGCGGATCGT
```

-continued

AACTGGCTTATTTCCAAGCAGTACGATGCTCGCTGGTCGCCGACTGAGAA

GGCGCGCCTGAAGGATATCGCTNCCCGTTATAAGGTGAAGTGGTCAGGCA

ATACGCGTCATGTGCCCTGGAACGCGCTGCTTGAGCGTGTCGACATTATT

CCGAACAGCATGGTGGCGACCATGGCGGCGGCGGAAAGTGGCTGGGGTAC

CTCCAGGCTGGCGCGCGAGAATAACAACCTGTTCGGCATGAAGTGCGGCG

CCGGTCGCTGCCGCGGCGCGATGAAAGGTTACTCGCAGTTTGAGTCNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNN

By "KpMero4_R08dn_KPN_00868 nucleic acid molecule" is meant a downregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

>KpMero4_R08dn_KPN_00868

(SEQ ID NO: 16)

NNNNNNNNNNNNNNNNNNNNNNNNNNNNNNNNNNNNNNNNNNNNNNNNNN

NNNNNNNNNNNNNNNNNNNNNNNNNNNNNNNNNNGCCAATATCGATATTG

ACGCCTATCTGCAACTGCGAAAGGCCAAAGGCTACATGTCAGTCAGCGAA

AATGACCATCTGCGTGATAACTTGTTTGAGCTTTGCCGTGAAATGCGTGC

GCAGGCGCCGCGCCTGCAGAATGCCATTTCACCGNNNNNNNNNNNNNNNN

NNNNNNNNNNGGCGAATCGGTCGCCGCCGCTGCACTATGCCTGATGAGCG

GGCATCATGATTGTCCGCTATACATCGCTGTTAACGTAGAGAAGCTAGAA

CGCTGTCTGACAGGATTGACCTCAAATATTCATAAATTGAATAAATTGGC

GCCAATCACTCATGCCTGAN

By "KpMero4_R09up_KPN_02342 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

>KpMero4_R09up_KPN_02342

(SEQ ID NO: 17)

NNNNNNNNNNNNNNNNNNNNNNNNNNNNNNGTGGCTATCTTATGGATTGG

CGTATTATTGAGCGGTTATGGGGTGTTATTCCACAGTGAGGAAAACGTCG

GCGGTCTGGGTCTTAAGTGCCAATACCTCACCGCCCGCGGAGTCAGCACC

GCACTTTATGTTCATTCCGACAGCGGAGTGATCGGCGTCAGCAGTTGCCC

TCTGCTGCGTAAAAGCACAACCGTGGTTGATAACGGCTAAN

By "KpMero4_R10up_KPN_00833 nucleic acid molecule" is meant an upregulated responsive polynucleotide that is 95%, 96%, 97%, 98%, or 100% identical to the following *Klebsiella pneumoniae* (strain MGH 78578, also known as ATCC 700721) sequence, excluding "N" residues, that is part of the KpMero4 probeset.

>KpMero4_R10up_KPN_00833

(SEQ ID NO: 18)

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNATCGGCGTGGTGTCTGCGCAAGGCGCAACCACTTTAGATGGTC

TGGAAGCAAAACTGGCTGCTAAAGCCGAAGCCGCTGGCGCGACCGGCTAC

AGCATTACTTCCGCTAACACCAACAACAAACTGAGCGGTACTGCGGTTAT

CTATAAATAAN

By "CRE2_KPC nucleic acid molecule" is meant a polynucleotide that is 95%, 96%, 97%, 98%, or 100% identical to the following sequence, and is part of the Cre2 probeset.

>CRE2_KPC (SEQ ID NO: 19)

TATCGCCGTCTAGTTCTGCTGTCTTGTCTCTCATGGCCGCTGGCTGGCTT

TTCTGCCACCGCGCTGACCAACCTCGTCGCGGAACCATTCGCTAAACTCG

AACAGGACTTTGGCGGCTCCATCGGTGTGTACGCGATGGATACCGGCTCA

GGCGCAACTGTAAGTTACCGCGCTGAGGAGCGCTTCCCACTGTGCAGCTC

ATTCAAGGGCTTTCTTGCTGCCGCTGTGCTGGCTCGCAGCCAGCAGCAGG

CCGGCTTGCTGGACACACCCATCCGTTACGGCAAAAATGCGCTGGTTCCG

TGGTCACCCATCTCGGAAAAATATCTGACAACAGGCATGACGGTGGCGGA

GCTGTCCGCGGCCGCCGTGCAATACAGTGATAACGCCGCCGCCAATTTGT

TGCTGAAGGAGTTGGGCGGCCCGGCCGGGCTGACGGCCTTCATGCGCTCT

ATCGGCGATACCACGTTCCGTCTGGACCGCTGGGAGCTGGAGCTGAACTC

CGCCATCCCAGGCGATGCGCGCGATACCTCATCGCCGCGCGCCGTGACGG

AAAGCTTACAAAAACTGACACTGGGCTCTGCACTGGCTGCGCCGCAGCGG

CAGCAGTTTGTTGATTGGCTAAAGGGAAACACGACCGGCAACCACCGCAT

CCGCGCGGCGGTGCCGGCAGACTGGGCAGTCGGAGACAAAACCGGAACCT

GCGGAGTGTATGGCACGGCAAATGACTATGCCGTCGTCTGGCCCACTGGG

CGCGCACCTATTGTGTTGGCCGTCTACACCCGGGCGCCTAACAAGGATGA

CAAGCACAGCGAGGCCGTCATCGCCGCTGCGGCTAGACTCGCGCTCGAGG

GA

By "CRE2_NDM nucleic acid molecule" is meant a polynucleotide that is 95%, 96%, 97%, 98%, or 100% identical to the following sequence, and is part of the Cre2 probeset.

>CRE2_NDM (SEQ ID NO: 20)

ATGGAATTGCCCAATATTATGCACCCGGTCGCGAAGCTGAGCACCGCATT

AGCCGCTGCATTGATGCTGAGCGGGTGCATGCCCGGTGAAATCCGCCCGA

CGATTGGCCAGCAAATGGAAACTGGCGACCAACGGTTTGGCGATCTGGTT

TTCCGCCAGCTCGCACCGAATGTCTGGCAGCACACTTCCTATCTCGACAT

GCCGGGTTTCGGGGCAGTCGCTTCCAACGGTTTGATCGTCAGGGATGGCG

GCCGCGTGCTGGTGGTCGATACCGCCTGGACCGATGACCAGACCGCCCAG

ATCCTCAACTGGATCAAGCAGGAGATCAACCTGCCGGTCGCGCTGGCGGT

-continued

GGTGACTCACGCGCATCAGGACAAGATGGGCGGTATGGACGCGCTGCATG

CGGCGGGGATTGCGACTTATGCCAATGCGTTGTCGAACCAGCTTGCCCCG

CAAGAGGGGATGGTTGCGGCGCAACACAGCCTGACTTTCGCCGCCAATGG

CTGGGTCGAACCAGCAACCGCGCCCAACTTTGGCCCGCTCAAGGTATTTT

ACCCCGGCCCCGGCCACACCAGTGACAATATCACCGTTGGGATCGACGGC

ACCGACATCGCTTTTGGTGGCTGCCTGATCAAGGACAGCAAGGCCAAGTC

GCTCGGCAATCTCGGTGATGCCGACACTGAGCACTACGCCGCGTCAGCGC

GCGCGTTTGGTGCGGCGTTCCCCAAGGCCAGCATGATCGTGATGAGCCAT

TCCGCCCCCGATAGCCGCGCCGCAATCACTCATACGGCCCGCATGGCCGA

CAAGCTGCGCT

By "CRE2_OXA48 nucleic acid molecule" is meant a polynucleotide that is 95%, 96%, 97%, 98%, or 100% identical to the following sequence, and is part of the Cre2 probeset.

>CRE2_OXA48

(SEQ ID NO: 21)

ATGCGTGTATTAGCCTTATCGGCTGTGTTTTTGGTGGCATCGATTATCGG

AATGCCTGCGGTAGCAAAGGAATGGCAAGAAAACAAAAGTTGGAATGCTC

ACTTTACTGAACATAAATCACAGGGCGTAGTTGTGCTCTGGAATGAGAAT

AAGCAGCAAGGATTTACCAATAATCTTAAACGGGCGAACCAAGCATTTTT

ACCCGCATCTACCTTTAAAATTCCCAATAGCTTGATCGCCCTCGATTTGG

GCGTGGTTAAGGATGAACACCAAGTCTTTAAGTGGGATGGACAGACGCGC

GATATCGCCACTTGGAATCGCGATCATAATCTAATCACCGCGATGAAATA

TTCAGTTGTGCCTGTTTATCAAGAATTTGCCCGCCAAATTGGCGAGGCAC

GTATGAGCAAGATGCTACATGCTTTCGATTATGGTAATGAGGACATTTCG

GGCAATGTAGACAGTTTCTGGCTCGACGGTGGTATTCGAATTTCGGCCAC

GGAGCAAATCAGCTTTTTAAGAAAGCTGTATCACAATAAGTTACACGTAT

CGGAGCGCAGCCAGCGTATTGTCAAACAAGCCATGCTGACCGAAGCCAAT

GGTGACTATATTATTCGGGCTAAAACTGGATACTCGACTAGAATCGAACC

TAAGATTGGCTGGTGGGTCGGTTGGGTTGAACTTGATGATAATGTGTGGT

TTTTTGCGATGAATATGGATATGCCCACATCGGATGGTTTAGGGCTGCGC

CAAGCCATCACAAAAGAAGTGCTCAAACAGGAAAAAATTATTCCCT

By "CRE2_CTXM15 nucleic acid molecule" is meant a polynucleotide that is 95%, 96%, 97%, 98%, or 100% identical to the following sequence, and is part of the Cre2 probeset.

>CRE2_CTXM15

(SEQ ID NO: 22)

ATGGTTAAAAAATCACTGCGCCAGTTCACGCTGATGGCGACGGCAACCGT

CACGCTGTTGTTAGGAAGTGTGCCGCTGTATGCGCAAACGGCGGACGTAC

AGCAAAAACTTGCCGAATTAGAGCGGCAGTCGGGAGGCAGACTGGGTGTG

GCATTGATTAACACAGCAGATAATTCGCAAATACTTTATCGTGCTGATGA

GCGCTTTGCGATGTGCAGCACCAGTAAAGTGATGGCCGCGGCCGCGGTGC

TGAAGAAAAGTGAAAGCGAACCGAATCTGTTAAATCAGCGAGTTGAGATC

-continued

AAAAAATCTGACCTTGTTAACTATAATCCGATTGCGGAAAAGCACGTCAA

TGGGACGATGTCACTGGCTGAGCTTAGCGCGGCCGCGCTACAGTACAGCG

ATAACGTGGCGATGAATAAGCTGATTGCTCACGTTGGCGGCCCGGCTAGC

GTCACCGCGTTCGCCCGACAGCTGGGAGACGAAACGTTCCGTCTCGACCG

TACCGAGCCGACGTTAAACACCGCCATTCCGGGCGATCCGCGTGATACCA

CTTCACCTCGGGCAATGGCGCAAACTCTGCGGAATCTGACGCTGGGTAAA

GCATTGGGCGACAGCCAACGGGCGCAGCTGGTGACATGGATGAAAGGCAA

TACCACCGGTGCAGCGAGCATTCAGGCTGGACTGCCTGCTTCCTGGGTTG

TGGGGGATAAAACCGGCAGCGGTGGCTATGGCACCACCAACGATATCGCG

GTGATCTGGCCAAAAGATCGTGCGCCGCTGATTCTGGTCACTTACTTCAC

CCAGCCTCAACCTAAGGCAGAAAGCCGTCGCGATGTATTAGCGTCGGCGG

CTAAAATCGTCACCGACGGTTTGT

By "CRE2_OXA10 nucleic acid molecule" is meant a polynucleotide that is 95%, 96%, 97%, 98%, or 100% identical to the following sequence, and is part of the Cre2 probeset.

>CRE2_OXA10

(SEQ ID NO: 23)

ATGAAAACATTTGCCGCATATGTAATTATCGCGTGTCTTTCGAGTACGGC

ATTAGCTGGTTCAATTACAGAAAATACGTCTTGGAACAAAGAGTTCTCTG

CCGAAGCCGTCAATGGTGTCTTCGTGCTTTGTAAAAGTAGCAGTAAATCC

TGCGCTACCAATGACTTAGCTCGTGCATCAAAGGAATATCTTCCAGCATC

AACATTTAAGATCCCCAACGCAATTATCGGCCTAGAAACTGGTGTCATAA

AGAATGAGCATCAGGTTTTCAAATGGGACGGAAAGCCAAGAGCCATGAAG

CAATGGGAAAGAGACTTGACCTTAAGAGGGGCAATACAAGTTTCAGCTGT

TCCCGTATTTCAACAAATCGCCAGAGAAGTTGGCGAAGTAAGAATGCAGA

AATACCTTAAAAAATTTTCCTATGGCAACCAGAATATCAGTGGTGGCATT

GACAAATTCTGGTTGGAAGGCCAGCTTAGAATTTCCGCAGTTAATCAAGT

GGAGTTTCTAGAGTCTCTATATTTAAATAAATTGTCAGCATCTAAAGAAA

ACCAGCTAATAGTAAAAGAGGCTTTGGTAACGGAGGCGGCACCTGAATAT

CTAGTGCATTCAAAAACTGGTTTTTCTGGTGTGGGAACTGAGTCAAATCC

TGGTGTCGCATGGTGGGTTGGGTGGGTTGAGAAGGAGACAGAGGTTTACT

TTTTCGCCTTTAACATGGATATAGACAACGAAAGTAAGTTGCCGCTAAGA

AAATCCATTCCCACCAAAATCATGGAAAGTGAGGGCATCATTGGTGGCT

By "CRE2_VIM_1 nucleic acid molecule" is meant a polynucleotide that is 95%, 96%, 97%, 98%, or 100% identical to the following sequence, and is part of the Cre2 probeset.

>CRE2_VIM_1

(SEQ ID NO: 24)

ATGTTTCAA---ATTCGCAGCTTTCTGGTTGGTATCAGTGCATTCGTCAT

GGCCGTACTTGGATCAGCAGCATATTCCGCACAGCCTGGCGGTGAATATC

CGACAGTAGATGACATACCGGTAGGGGAAGTTCGGCTGTACAAGATTGGC

-continued

GATGGCGTTTGGTCGCATATCGCAACTCAGAAACTCGGTGACACGGTGTA

CTCGTCTAATGGACTTATCGTCCGCGATGCTGATGAGTTGCTTCTTATTG

ATACAGCGTGGGGGGCGAAGAACACGGTAGCCCTTCTCGCGGAGATTGAA

AAGCAAATTGGACTTCCAGTAACGCGCTCAATTTCTACGCACTTCCATGA

CGATCGAGTCGGTGGAGTTGATGTCCTCCGGGCGGCTGGAGTGGCAACGT

ACACCTCACCCTTGACACGCCAGCTGGCCGAAGCGGCGGGAAACGAGGTG

CCTGCGCACTCTCTAAAAGCGCTCTCCTCTAGTGGAGATGTGGTGCGCTT

CGGTCCCGTAGAGGTTTTCTATCCTGGTGCTGCGCATTCGGGCGACAATC

TTGTGGTATACGTGCCGGCCGTGCGCGTACTGTTTGGTGGCTGTGCAGTT

CATGAGGCGTCACGCGAATCCGCGGGTAATGTTGCCGATGCCAATTTGGC

AGAATGGCCTGCTACCATTAAACGAATTCAACAGCGGTATCCGGAAGCAG

AGGTCGTCATCCCCGGCCACGGTCTACCGGGCGGTCTGGAATTGCTCCAA

CACACAACTAACGTTGTCAAAACGCACAAAGTACGCCCGGTGGCCGAGT

By “CRE2_VIM_2 nucleic acid molecule” is meant a polynucleotide that is 95%, 96%, 97%, 98%, or 100% identical to the following sequence, and is part of the Cre2 probeset.

>CRE2_VIM_2

(SEQ ID NO: 25)

CGAGTGGTGAGTATCCGACAGTCAACGAAATTCCGGTCGGAGAGGTCCGG

CTTTACCAGATTGCCGATGGTGTTTGGTCGCATATCGCAACGCAGTCGTT

TGATGGCGCGGTCTACCCGTCCAATGGTCTCATTGTCCGTGATGGTGATG

AGTTGCTTTTGATTGATACAGCGTGGGGTGCGAAAAACACAGCGGCACTT

CTCGCGGAGATTGAGAAGCAAATTGGACTTCCCGTAACGCGTGCAGTCTC

CACGCACTTTCATGACGACCGCGTCGGCGGCGTTGATGTCCTTCGGGCGG

CTGGGGTGGCAACGTACGCATCACCGTCGACACGCCGGCTAGCCGAGG

By “CRE2_VIM_3 nucleic acid molecule” is meant a polynucleotide that is 95%, 96%, 97%, 98%, or 100% identical to the following sequence, and is part of the Cre2 probeset.

>CRE2_VIM_3

(SEQ ID NO: 26)

TACCCGTCCAATGGTCTCATTGTCCGTGATGGTGATGAGTTGCTTTTGAT

TGATACAGCGTGGGGTGCGAAAAACACAGCGGCACTTCTCGCGGAGATTG

AGAAGCAAATTGGACTTCCCGTAACGCGTGCAGTCTCCACGCACTTTCAT

GACGACCGCGTCGGCG

By “CRE2_IMP_1 nucleic acid molecule” is meant a polynucleotide that is 95%, 96%, 97%, 98%, or 100% identical to the following sequence, and is part of the Cre2 probeset.

>CRE2_IMP_1

(SEQ ID NO: 27)

GGAGCGGCTTTGCCTGATTTAAAAATCGAGAAGCTTGAAGAAGGTGTTTA

TGTTCATACATCGTTCGAAGAAGTTAACGGTTGGGGTGTTGTTTCTAAAC

-continued

ACGGTTTGGTGGTTCTTGTAAACACTGACGCCTATCTGATTGACACTCCA

TTT

By “CRE2_IMP_2 nucleic acid molecule” is meant a polynucleotide that is 95%, 96%, 97%, 98%, or 100% identical to the following sequence, and is part of the Cre2 probeset.

>CRE2_IMP_2

(SEQ ID NO: 28)

ACTGAAAAGTTAGTCAATTGGTTTGTGGAGCGCGGCTATAAAATCAAAGG

CACTATTTCCTCACATTTCCATAGCGACAGCACAGGNGGAATAGAGTGGC

TTAATTCTCAATCTATTCCCACGTATGCATCTGAATTAACAAATGAACTT

By “CRE2_IMP_3 nucleic acid molecule” is meant a polynucleotide that is 95%, 96%, 97%, 98%, or 100% identical to the following sequence, and is part of the Cre2 probeset.

>CRE2_IMP_3

(SEQ ID NO: 29)

TCATTTAGCGGAGTTAGTTATTGGCTAGTTAAAAATAAAATTGAAGTTTT

TTATCCCGGCCCGGGGCACACTCAAGATAACGTAGTGGTTTGGTTACCTG

AAAAGAAAATTTTATTCGGTGGTTGTTTTGTTAAACCGGACGGTCTTGGT

AATTTGG

By “CRE2_IMP_4 nucleic acid molecule” is meant a polynucleotide that is 95%, 96%, 97%, 98%, or 100% identical to the following sequence, and is part of the Cre2 probeset.

>CRE2_IMP_4

(SEQ ID NO: 30)

CTGACGCCTATCTGATTGACACTCCATTTACTGCTACAGATACTGAAAAG

TTAGTCAATTGGTTTGTGGAGCGCGGCTATAAAATCAAAGGCACTATTTC

CTCACATTTCCATAGCGACAGCACAGGGGGAATAGAGTGGCTTAATTCTC

By “CRE2_IMP_5 nucleic acid molecule” is meant a polynucleotide that is 95%, 96%, 97%, 98%, or 100% identical to the following sequence, and is part of the Cre2 probeset.

>CRE2_IMP_5

(SEQ ID NO: 31)

ATGAAAAAAATATTTGTGTTATTTGTATTTTTGTTTTGCAGTATTACTGC

CGCCGGAGAGTCTTTGCCTGATATAAAAATTGAGAAACTTGACGAAGATG

TTTATGTTCATACTTCTTTTGAAAAAAAAAACGGCTGGGGTGTTATTACT

AAACACGGCTTGGTGGTTCTTGTAAATACTGATGCCTATATAATTGACAC

TCCATTTACAGCTAAAGATACTGAAAAATTAGTCCGCTGGTTTGTGGGGC

GTGGTTATAAAATCAAAGGCAGTATTTCCTCACATTTTCATAGCGATAGC

GCAGGTGGAATTGAGTGGCTTAATTCTCAATCTATCCCCACATATGCATC

TAAATTAACAAATGAGCTTCTTAAAAAGAACGGTAATGCGCAAGCCGAAA

ACTCATTTAGTGGCGTTAGCTATTGGCTAGTTAAACATAAAATTGAAGTT

TTCTATCCAGGACCAGGGCACACTCAGGATAATGTAGTGGTTTGGTTGCC

-continued

TGAAAAGAAAATTTTATTTGGCGGTTGTTTTATTAAGCCGGACGGTCTTG

GTTATTTGGGAGACGCAAATCTAGAAGCATGGCCTAAGTCCGCAGAAACA

TTAATGTCTAAGTATGGTAATGCAAAACTGGTTGTTTCGAGTCATAGTGA

AATTGGGGGCGCATCACTATTGAAGCGCACTTGGGAGCAGGCTGTTAAGG

GGCTAAAAGAAAGTAAAAAACCATCACAGCCAAACAAA

By "CRE2_IMP_6 nucleic acid molecule" is meant a polynucleotide that is 95%, 96%, 97%, 98%, or 100% identical to the following sequence, and is part of the Cre2 probeset.

>CRE2_IMP_6
(SEQ ID NO: 32)
CTGAGGCTTATCTAATTGACACTCCATTTACGGCTAAAGATACTGAAAAG

TTAGTCACTTGGTTTGTGGAACGTGGCTATAAAATAAAAGGCAGTATTTC

CTCTCATTTTCATAGCGACAGCACGGGCGGAATAGAGTGGCTTAATTCTC

AATCTATCCCCACGTATGCATCTGAATTAACAAATG

By "CRE2_IMP_7 nucleic acid molecule" is meant a polynucleotide that is 95%, 96%, 97%, 98%, or 100% identical to the following sequence, and is part of the Cre2 probeset.

>CRE2_IMP_7
(SEQ ID NO: 33)
TATGCATCTGAATTAACAAATGAACTTCTTAAAAAAGACGGTAAGGTACA

AGCTAAAAATTCATTTAGCGGAGTTAGCTATTGGCTAGTTAAGAAAAAGA

TTGAAGTTTTTTATCCTGGTCCAGGGCACACTCCAGATAACGTAGTGGTT

TGGC

By "CRE2_IMP_8 nucleic acid molecule" is meant a polynucleotide that is 95%, 96%, 97%, 98%, or 100% identical to the following sequence, and is part of the Cre2 probeset.

>CRE2_IMP_8
(SEQ ID NO: 34)
GGGCACACTCAAGATAACGTAGTGGTTTGGTTACCTGAAAAGAAAATTTT

ATTCGGTGGTTGTTTTGTTAAACCGGACGGTCTTGGTAATTTGGGTGACG

CAAATTTAGAAGCTTGGCCAAAGTCCGCCAAAATATTAATGTCTAAATAT

G

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows the bipartite probe bound to an exemplary target nucleic acid. FIG. 1B shows an exemplary embodiment in which Probe A and Probe B may be detected by tags that are directly coupled to one or both Probes. FIG. 1C shows an exemplary embodiment in which Probe A and Probe B may be detected by tags that are in directly coupled to one or both Probes.

FIG. 2A demonstrates that RNA-Seq data upon antibiotic exposure revealed differential gene expression between susceptible and resistant strains. Susceptible (left panels) or resistant (right panels) clinical isolates of *K. pneumoniae* (top), *E. coli* (middle), or *A. baumannii* (bottom) were treated with meropenem (left, 60 min), ciprofloxacin (center, 30 min), or gentamicin (right, 60 min) at CLSI breakpoint concentrations. Data are presented as MA plots, with mean transcript abundance plotted on the x-axis and fold-induction compared with untreated strains on the y-axis; each axis is $\log_2$ transformed. Transcripts whose expression was observed as statistically significantly changed upon antibiotic exposure are shown in red. FIGS. 2B-2D show that a timecourse of RNA-Seq data upon antibiotic exposure revealed differential gene expression between susceptible and resistant clinical isolates. Susceptible (left panels) or resistant (right panels) clinical isolates of *K. pneumoniae* (FIG. 2B), *E. coli* (FIG. 2C), or *A. baumannii* (FIG. 2D) were treated with meropenem (left), ciprofloxacin (center), or gentamicin (right) at CLSI breakpoint concentrations for the indicated times. Data are presented as MA plots, with mean transcript abundance plotted on the x-axis and fold-induction compared with untreated strains on the y-axis; each axis is $\log_2$ transformed. Transcripts whose expression is statistically significantly changed upon antibiotic exposure are shown in red.

FIG. 4A shows phase 1 NanoString® data from FIGS. 2A-2D above (i.e., normalized, log-transformed fold-induction for each responsive transcript), analyzed as described to generate squared projected distance (SPD) metrics (y-axes) for each strain (see Supplemental Methods below), and binned by CLSI classifications (x-axes), for the same 18-24 isolates shown in FIGS. 3 above and 6 and 7A below. By definition, an SPD of 0 indicates a transcriptional response to antibiotic equivalent to that of an average susceptible strain, while an SPD of 1 indicates a response equivalent to that of an average resistant strain. See Supplemental Methods sections below for details. Data are summarized as box-and-whisker plots, where boxes extend from 25th to 75th percentile for each category, with middle line at median, and whiskers extending from minimum to maximum; all data points are displayed as well. Note that for *A. baumannii* and meropenem, the clustering of the majority of susceptible strains by this simple metric (aside from one outlier which was misclassified as resistant by GoPhAST-R) underscores the true differences in transcription between susceptible and resistant isolates, despite the more subtle-appearing differences in heatmaps for this combination (FIGS. 3 and 6), which is largely caused by one strain exhibiting an exaggerated transcriptional response (seen here as the strain with a markedly negative SPD) that affects scaling of the heatmap. FIG. 4B shows the same SPD data (y-axes) plotted against broth microdilution MICs (x-axes), which revealed that the magnitude of the transcriptional response to antibiotic exposure correlated with MIC. In both FIGS. 4A and 4B, strains with large inoculum effect upon meropenem treatment have been displayed in red and enlarged. Vertical dashed line indicates the CLSI breakpoint between susceptible and not susceptible (i.e., intermediate or resistant).

FIG. 7A shows the probability of resistance obtained from a random forest model trained on NanoString® data and tested on validation cohort (y-axis), as compared with standard CLSI classification based on broth microdilution MIC (x-axis), for the nine indicated pathogen-antibiotic combinations tested in phase 1. FIG. 7B shows the probability of resistance obtained from a random forest model trained on NanoString® data and tested on validation cohort (y-axis), as compared with standard CLSI classification based on broth microdilution MIC (x-axis), for the new *K. pneumoniae* isolates tested in phase 2 for meropenem and ciprofloxacin susceptibility. Horizontal dashed lines indicate 50% chance of resistance based on random forest model. Vertical dashed lines indicate CLSI breakpoint between susceptible and not susceptible (i.e. intermediate/resistant); isolates also colored by CLSI classification as indicated. Numbers in each quadrant indicate concordant (green) and discordant (black) classifications between GoPhAST-R and broth microdilution. Carbapenemase (square outline) and select ESBL (diamond outline) gene content as detected by GoPhAST-R are also displayed on meropenem plots (none were found in the *A. baumannii* validation cohort). *=strains with large inoculum effects in meropenem MIC.

FIG. 11A shows heatmaps of normalized, log-transformed fold-induction NanoString® data from the top 10 antibiotic-responsive transcripts directly from 12 simulated positive blood culture bottles for each indicated pathogen-antibiotic combination, which revealed antibiotic-responsive transcription in susceptible but not resistant isolates. For meropenem, results of carbapenemase/ESBL gene detection are also displayed as a normalized, background-subtracted, log-transformed heatmap above. CLSI classifications of isolates, which were blinded until analysis was complete, are displayed below each heatmap. FIG. 11B shows the probability of resistance from random forest model trained by leave-one-out cross-validation on NanoString® data from FIG. 11A (y-axis) compared with standard CLSI classification based on broth microdilution MIC (x-axis) for each isolate. Horizontal dashed lines indicate 50% chance of resistance based on random forest model. Vertical dashed lines indicate CLSI breakpoint between susceptible and resistant; isolates have also been colored by CLSI classification as indicated. Carbapenemase (square outline) and select ESBL (diamond outline) gene content as detected by GoPhAST-R are also displayed on meropenem plots. See Supplemental Methods for details of spike-in protocol.

FIG. 12A shows a schematic of GoPhAST-R workflow on the Hyb & Seq detection platform. It is contemplated that pathogen identification can either be performed prior to this process, or in parallel by multiplexing mRNA targets from multiple organisms. FIG. 12B, at left, shows the Hyb & Seq hybridization scheme, in which probe pairs targeting each RNA transcript are hybridized in crude lysate. Each probe A contains a unique barcode sequence (green) for detection and a shared 3' capture sequence; each probe B contains a biotin group (gray circle) for surface immobilization and a shared 5' capture sequence. At middle, the Hyb & Seq detection strategy is shown: immobilized, purified ternary probe-target complexes undergo sequential cycles of multi-step imaging for spatially resolved single-molecule detection. Each cycle consists of reporter probe binding and detection, UV cleavage, a second round of reporter probe binding and detection, and a low-salt wash to regenerate the unbound probe-target complex. 5 Hyb & Seq cycles were used to generate the data shown. See Supplemental Methods sections below for details. At right, pilot study results for accelerated meropenem susceptibility testing of 6 clinical *K. pneumoniae* isolates are shown. At right top, heatmaps of normalized, log-transformed fold-induction of top 10 meropenem-responsive transcripts measured using the instant Hyb & Seq workflow are shown, with strains arranged in order of MIC for each antibiotic. CLSI classifications are shown immediately below. At right bottom, heatmaps of normalized, background-subtracted, log-transformed NanoString® data from carbapenemase ("CPase") and select ESBL transcripts measured in the same Hyb & Seq assay are shown.

FIG. 13A shows phylogenetic trees of all sequenced isolates deposited in NCBI for *Klebsiella pneumoniae* isolates, with all sequenced isolates used in the instant disclosure indicated by colored arrowheads around the periphery. FIG. 13B shows phylogenetic trees of all sequenced isolates deposited in NCBI for *Escherichia coli* isolates, with all sequenced isolates used in the instant disclosure indicated by colored arrowheads around the periphery. FIG. 13C shows phylogenetic trees of all sequenced isolates deposited in NCBI for *Acinetobacter baumanii* isolates isolates, with all sequenced isolates used in the instant disclosure indicated by colored arrowheads around the periphery. FIG. 13D shows phylogenetic trees of all sequenced isolates deposited in NCBI for *Pseudomonas aeruginosa* isolates, with all sequenced isolates used in the instant disclosure indicated by colored arrowheads around the periphery (ciprofloxacin sensitive strains are indicated by blue arrowheads and ciprofloxacin resistant strains are indicated by red arrowheads). See Supplemental Methods sections below for details.

FIG. 14A shows RNA-Seq data from susceptible or resistant clinical isolates of *S. aureus* treated with the indicated fluoroquinolone levofloxacin at 1 mg/L for 60 minutes. Data are presented as MA plots, with mean transcript abundance plotted on the x-axis and fold-induction compared with untreated strains on the y-axis; each axis is $\log_2$ transformed. Transcripts whose expression is statistically significantly changed upon antibiotic exposure are shown in red. FIG. 14B shows heatmaps of normalized, log-transformed fold-induction of antibiotic-responsive transcripts from 24 clinical isolates of *S. aureus* treated with the indicated fluoroquinolone levofloxacin at 1 mg/L for 60 minutes. NanoString® data from all candidate transcripts are shown at left, and top 10 transcripts selected from Phase 1 testing are shown at right. (FIG. 14C=*S. aureus*+levofloxacin; FIG. 14F=*P. aeruginosa*+ciprofloxacin) FIG. 14C depicts the probability of *S. aureus* resistance to the indicated fluoroquinolone levofloxacin from random forest model trained on Phase 1 NanoString® data from derivation cohort and tested on validation cohort (y-axis) compared with standard CLSI classification based on broth microdilution MIC (x-axis). Horizontal dashed lines indicate 50% chance of resistance based on random forest model. Vertical dashed lines indicate CLSI breakpoint between susceptible and not susceptible (i.e. intermediate/resistant); isolates also colored by CLSI classification as indicated. Numbers in each quadrant indicate concordant (green) and discordant (black) classifications between GoPhAST-R and broth microdilution. FIG. 14D shows RNA-Seq data from susceptible or resistant clinical isolates of *P. aeruginosa* treated with the indicated fluoroquinolone ciprofloxacin at 1 mg/L for 60 minutes. Data are presented as MA plots, with mean transcript abundance plotted on the x-axis and fold-induction compared with untreated strains on the y-axis; each axis is $\log_2$ transformed. Transcripts whose expression is statistically significantly changed upon antibiotic exposure are shown in red. FIG. 14E shows heatmaps of normalized, log-transformed fold-induction of antibiotic-responsive transcripts from 24 clinical isolates of *P. aeruginosa* treated with the indicated fluoroquinolone ciprofloxacin at 1 mg/L for 60 minutes. NanoString® data from all candidate transcripts are shown at left, and top 10 transcripts selected from Phase 1 testing are shown at right.

FIG. 14F depicts the probability of *P. aeruginosa* resistance to the indicated fluoroquinolone ciprofloxacin from random forest model trained on Phase 1 NanoString® data from derivation cohort and tested on validation cohort (y-axis) compared with standard CLSI classification based on broth microdilution MIC (x-axis). Horizontal dashed lines indicate 50% chance of resistance based on random forest model. Vertical dashed lines indicate CLSI breakpoint between susceptible and not susceptible (i.e. intermediate/resistant); isolates also colored by CLSI classification as indicated. Numbers in each quadrant indicate concordant (green) and discordant (black) classifications between GoPhAST-R and broth microdilution.

DETAILED DESCRIPTION OF THE DISCLOSURE

Figure 1A:
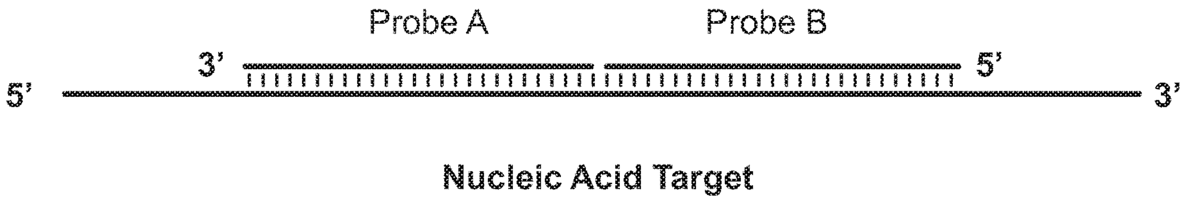
FIGS. 1A-1C are diagrams depicting a binding and detection of a bipartite probe structure including Probe A and Probe B according to an exemplary embodiment of the disclosure.

The present disclosure is based, at least in part, on the discovery of specific mRNA signature patterns that provide rapid phenotypic detection of single and multiple types of antibiotic resistance/susceptibility in specific microbial organisms (e.g., bacteria). In particular, the techniques herein relate, at least in part, to compositions, methods, and kits for rapid antibiotic susceptibility testing (AST) in microbial organisms (e.g., bacteria). The techniques herein provide compositions and methods that provide rapid phenotypic detection of antibiotic resistance/susceptibility in microbial pathogens, and are faster than the prior art growth-based phenotypic assays that currently comprise the gold standard. The techniques herein also provide compositions and methods that enable simultaneous detection of multiple resistance genes in the same assay. In this manner, the techniques herein enable more accurate determination of antibiotic resistance, as well as providing: 1) mechanistic explanations for key antibiotic resistant strains, 2) epidemiologic tracking of known resistance mechanisms, and 3) immediate identification of unknown or potentially novel resistance mechanisms (such as, e.g., discordant cases when a resistant organism does not display a known resistance phenotype). Currently, detection of antibiotic resistance genes typically requires separate PCR or sequencing assays, which require different assay infrastructure and often necessitate sending samples out to reference laboratories.

The techniques herein may be used for clinical diagnostics, e.g., to rapidly determine antibiotic susceptibility profiles on patient samples and easily allow antibiotic susceptibility testing (AST) to be performed on bacteria from any source, including environmental isolates. The techniques herein are based on the following steps: sample acquisition, processing to enrich for bacteria and remove host material (in order to increase signal-to-noise), antibiotic exposure, bacterial lysis, RNA measurement (hybridization followed by detection), and data interpretation. Advantageously, the techniques herein may be implemented within a single reaction that does not require sample purification.

As mentioned above, current growth-based antibiotic susceptibility testing (AST) is too slow to inform key clinical decisions. While genotypic assays hold promise, they remain incompletely predictive of susceptibility. The techniques herein provide rapid assays for combined genotypic and phenotypic AST through RNA detection (i.e., GoPhAST-R) that classifies strains with >94-99% accuracy by coupling machine learning analysis of quantitative early transcriptional responses to antibiotic exposure with simultaneous detection of key genetic resistance determinants. This two-pronged approach provides phenotypic AST as fast as <4 hours, increases accuracy of resistance detection, works directly from positive blood cultures, facilitates molecular epidemiology, and enables early detection of emerging resistance mechanisms.

Antibiotic resistance is one of the most pressing medical problems of modern times (Fauci & Morens; Nathan & Cars). The rise of multidrug resistant organisms (MDROs) has been recognized as one of the most serious threats to human health (Holdren et al.; WHO). Delays in identifying MDROs can lead to increased mortality (Kumar et al.; Kadri et al.) and increased use of broad-spectrum antibiotics to further select for resistant organisms. Rapid antibiotic susceptibility testing (AST) with pathogen identification would transform the care of infected patients while ensuring that the available antibiotic arsenal is deployed as efficiently as possible.

The current gold standard AST assays of measuring growth in the presence of an antibiotic, such as broth microdilution (Wiegand et al.), directly answer the key question of whether the antibiotic inhibits pathogen growth; however, their dependence on serial growth requires 2-3 days from sample collection to results. As an alternative approach, a new generation of assays has emerged to rapidly detect genotypic resistance determinants, yet these are simply proxies for antibiotic resistance in select cases with monogenic determinants (e.g., MRSA Xpert, VRE Xpert, GeneXpert; see Boehme et al., Ioannidis et al., Marlowe et al., Marner et al., and Wolk et al.), or limited to a subset of resistance determinants for a specific drug class (McMullen et al., Smith et al., Traczewski et al., Sullivan et al., Walker et al. *J Clin Microbiol*, Walker et al. *Clin Chem*, and Salimnia et al.). Such approaches fall short of universal AST because of the incomplete knowledge of the innumerable resistance-causing genes and mutations across a wide range of pathogens and antibiotics, and the interactions of these genetic factors with the wide diversity of genomic backgrounds within any given bacterial species (Arzanlou et al.; Cerqueira et al.). Genotypic resistance detection does, however, have the benefit of facilitating molecular epidemiology by allowing specific resistance mechanisms to be identified and tracked (Cerqueira et al.; Woodworth et al.). Whole genome sequencing (WGS) coupled with machine learning has promised the possibility of a more universal genomic approach to AST (Allcock et al.; Bradley et al.; Didelot et al.; Li, Y. et al.; and Nguyen et al.). But while the genomics revolution has undeniably transformed the microbiology field's understanding of antibiotic resistance (Burnham et al.; Gupta, S. K. et al.; Jia et al.; McArthur et al.; and Zankari et al.), as a clinical diagnostic, WGS remains technically demanding, costly, and slow. Moreover, the complexity and variability of bacterial genomes present serious challenges to the ability to predict antibiotic susceptibility with sufficient accuracy to direct patient care (Bhattacharyya et al.; Milheirico et al.; and Ellington et al.). Additionally, the inability to predict the emergence of new resistance mechanisms means that genotypic resistance detection, whether targeted or comprehensive, is fundamentally reactive as new resistance determinants are reported (see e.g., Caniaux et al. 2017; Ford 2018; Garcia-Alvarez et al. 2011; Liakopoulos et al. 2016; Liu et al. 2016; Ma et al. 2018; Paterson et al. 2014; Sun et al. 2018). While certain bacterial species or antibiotic classes are more amenable to genetic resistance prediction (see e.g., Bradley et al. 2015; Consortium et al. 2018), this approach is not readily generalizable (Bhattacharyya et al.; Ellington et al.; Rossen et al.; and Tagini & Greub). These gaps in genetic susceptibility prediction have motivated a number of novel approaches that focus on phenotypic AST but with a more rapid result, including rapid automated microscopy (see e.g., Charnot-Katsikas et al. 2018; Choi et al. 2017; Humphries and Di Martino 2019; Marschal et al. 2017), ultrafine mass measurements (see e.g., Cermak et al. 2016; Longo et al. 2013), and others (see e.g., Barczak et al; Quach et al. 2016; and van Belkum et al. 2017).

Of the current MDROs, carbapenem resistant organisms are the most alarming, as their resistance to this class of broad-spectrum antibiotics often leaves few to no treatment options available (Gupta, N. et al.; Iovleva & Doi et al.; and Nordmann et al. 2012). Yet phenotypic carbapenem resistance detection can be challenging (Lutgring and Limbago 2016; Miller and Humphries 2016), as some carbapenemase-producing strains, even those carrying canonical resistance determinants such as $bla_{KPC}$, may be mistakenly identified as susceptible by current phenotypic assays (Anderson et al. 2007; Arnold et al. 2011; Centers for Disease and Prevention 2009; Chea et al. 2015; Gupta, V. et al. 2018; Nordmann et al. 2009; and Chea et al.) while failing clinical carbapenem therapy (Weisenberg et al. 2009). Rapid genotypic approaches are now available that use multiplexed PCR assays to detect several common carbapenemases in carbapenem-resistant Enterobactericeae (CRE) (see e.g., Evans et al. 2016; Smith et al. 2016; Sullivan et al. 2014). While one advantage of these assays is that they identify the specific mechanism of resistance when present, they fail to identify a significant fraction (13-68%) of CRE isolates with unknown or non-carbapenemase resistance mechanisms (see e.g., Cerqueira et al. 2017; Woodworth et al. 2018; Ye et al. 2018). For non-Enterobacteriaceae, this problem is even more challenging, as unexplained genetic resistance mechanisms account for the vast majority of resistance. For example; just 1.9% of over 1000 carbapenem-resistant *Pseudomonas* in the 2017 CDC survey were found to encode known carbapenemases (see e.g., Woodworth et al. 2018). These challenges have left clinical microbiology laboratories still seeking consensus on how to best apply the multiple possible workflows that currently exist for detecting carbapenem resistance (McMullen et al.; Humphries, R. M.), including phenotypic (CLSI), genetic (McMullen et al., Smith et al., Traczewski et al., Sullivan et al., Walker et al. *J Clin Microbiol*, Walker et al. *Clin Chem*), and biochemical (Humphries, R. M.) assays.

The present disclosure provides a diagnostic approach that has been termed Genotypic and Phenotypic AST through RNA detection (GoPhAST-R), which addresses the above-mentioned prior art problems by detecting both genotype and phenotype in a single assay. Advantageously, this allows for integration of all information while simultaneously providing information about both resistance prediction and molecular epidemiology. mRNA is uniquely informative in this regard, as it encodes genotypic information in its sequence and phenotypic information in its abundance in response to antibiotic exposure. For example, susceptible cells that are stressed upon antibiotic exposure look transcriptionally distinct from resistant cells that are not (Barczak et al. 2012). Leveraging this principle for rapid phenotypic AST built upon multiplexed hybridization-based detection of early transcriptional responses that occur within minutes of antibiotic exposure, the present disclosure defines a phenotypic measure that distinguishes susceptible (by measuring a response in susceptible strains) from resistant organisms, agnostic to the mechanism of resistance. As described in detail below, these techniques are demonstrated for three major antibiotic classes-fluoroquinolones, aminoglycosides, and importantly, carbapenems—in *Klebsiella pneumoniae, Escherichia coli, Acinetobacter baumannii, Pseudomonas aeruginosa*, and *Staphylococcus aureus*, four gram-negative and one gram-positive pathogens that are classified as “critical” or “high priority” threats by the World Health Organization (Tacconelli et al.) and have a propensity for multi-drug resistance through diverse mechanisms that are difficult to determine based solely on genotypic determinants.

The working examples herein describe a generalizable process to extend this approach to any pathogen-antibiotic pair of interest, in certain aspects and without wishing to be bound by theory, the process requires only that an antibiotic elicit a differential transcriptional response in susceptible versus resistant isolates, a biological phenomenon that to date appears to be universal. An analytical framework is described to classify organisms as susceptible or resistant on the basis of 10-transcript signatures detected in a simple multiplexed fluorescent hybridization-based assay on an RNA detection platform (NanoString® nCounter™; Geiss et al.), demonstrating >94-99% categorical agreement with broth microdilution. For carbapenems, a simultaneous genotypic detection of key resistance determinants is incorporated into the same assay to improve accuracy of resistance detection, facilitate molecular epidemiology, and guide antibiotic selection for CRE treatment from among the newer available agents (Lomovskaya et al. 2017; Marshall et al. 2017; van Duin and Bonomo 2016), which has clearly demonstrated the superiority of GoPhAST-R techniques described herein over prior art approaches that measure either genotype or phenotype alone. This important feature shows that several of the discrepant results between GoPhAST-R and broth microdilution occur in carbapenemase-producing strains likely misclassified as susceptible by the gold standard, and correctly classified as resistant by GoPhAST-R. In this regard, the GoPhAST-R techniques described herein can be deployed directly on a positive blood culture bottle with a simple workflow, reporting phenotypic AST within hours of a positive culture, thus 24-36 hours faster than gold standard prior art methods in a head-to-head comparison, yielding AST results with 99% categorical agreement. Finally, GoPhAST-R can determine antibiotic susceptibilities in under 4 hours, using a pilot next-generation RNA detection platform (NanoString® Hyb & Seq™). Together, the techniques herein establish GoPhAST-R as a novel, accurate, rapid approach that can simultaneously report phenotypic and genotypic data and thus leverages the advantages of both approaches.

Treatment Selection

The methods described herein can be used for selecting, and then optionally administering, an optimal treatment (e.g., an antibiotic course) for a subject. Thus the methods described herein include methods for the treatment of bacterial infections. Generally, the methods include administering a therapeutically effective amount of a treatment as described herein, to a subject who is in need of, or who has been determined to be in need of, such treatment.

As used in this context, to “treat” means to ameliorate at least one symptom of the bacterial infection.

An “effective amount” is an amount sufficient to effect beneficial or desired results. For example, a therapeutic amount is one that achieves the desired therapeutic effect (e.g reduction or elimination of a bacterial infection). This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the bacterial infection, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Combination Treatments

The compositions and methods of the present disclosure may be used two direct the administration of combination antibiotic therapies to treat particular bacterial infections. In order to increase the effectiveness of a treatment with the compositions of the present disclosure, e.g., an antibiotic selected and/or administered as a single agent, or to augment the protection of another therapy (second therapy), it may be desirable to combine these compositions and methods with one another, or with other agents and methods effective in the treatment, amelioration, or prevention of diseases and pathologic conditions, for example, an antibiotic infection.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing a bacterial infection) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977): 1-19, incorporated herein by reference. The salts can be prepared in situ during the final isolation and purification of the compounds (e.g., FDA-approved compounds) of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with an antibiotic) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 μg/kg, followed by a weekly maintenance dose of about 100 μg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 μg/kg to about 2 mg/kg (such as about 3 μg/kg, about 10 μg/kg, about 30 μg/kg, about 100 μg/kg, about 300 μg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®) sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., an antibiotic) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

FDA-approved drugs provided herein are typically formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., an antibiotic) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

The FDA-approved drug or other therapy is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 μg/kg/day, at least 100 μg/kg/day, at least 250 μg/kg/day, at least 500 μg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 μg/kg/day, and less than 500 μg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., an antibiotic) described herein. In certain embodiments, a dose described herein includes independently between 1 mg and 3 mg, inclusive, of an agent (e.g., an antibiotic) described herein. In certain embodiments, a dose described herein includes independently between 3 mg and 10 mg, inclusive, of an agent (e.g., an antibiotic) described herein. In certain embodiments, a dose described herein includes independently between 10 mg and 30 mg, inclusive, of an agent (e.g., an antibiotic) described herein. In certain embodiments, a dose described herein includes independently between 30 mg and 100 mg, inclusive, of an agent (e.g., an antibiotic) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., an antibiotic) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., an antibiotic) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an antioxidant, an anti-inflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., a sample preparation reagent) of this disclosure and/or may contain agents (e.g., oligonucleotide primers, probes, and one or more detectable probes or probe sets etc.) for identifying a cancer or subject as possessing one or more variant sequences. In some embodiments, the kits further include instructions for use in accordance with the methods of this disclosure. In some embodiments, these instructions comprise a description of sample preparation and target binding/signal detection protocol. In some embodiments, the instructions comprise a description of how to detect antibiotic susceptibility and direct therapeutic intervention accordingly.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a class bacterial infections, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. In certain embodiments, at least one active agent in the composition is one or more by apartheid probe sets designed for detecting specific mRNAs or mRNA signature profiles. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Rapid Phenotypic Detection of Antibiotic Resistance

The techniques herein allow for rapid phenotypic detection of antibiotic resistance, faster than growth-based phenotypic assays that currently comprise the gold standard. Advantageously, the techniques herein provide compositions and methods that allow simultaneous detection of multiple resistance genes in the same assay. Additionally, the techniques herein provide more accurate determination of resistance, as well as mechanistic explanations for key antibiotic resistant strains, epidemiologic tracking of known resistance mechanisms, and immediate identification of unknown or potentially novel resistance mechanisms (e.g., discordant cases when a resistant organism does not display a known resistance phenotype). Currently, detection of antibiotic resistance genes typically requires separate PCR or sequencing assays, which require different assay infrastructure and often necessitate sending samples out to reference laboratories.

The phenotypic antibiotic susceptibility testing (AST) portion of the techniques herein relies on quantitative measurement of the most antibiotic-responsive transcripts in a microbial pathogen upon antibiotic exposure. According to the techniques herein, RNA-Seq may be used to identify antibiotic responsive genes that change the most in susceptible, but not resistant, bacterial strains in response to exposure to an antibiotic. In this way, the nucleic acid targets for use in AST may be identified.

Figure 1B:
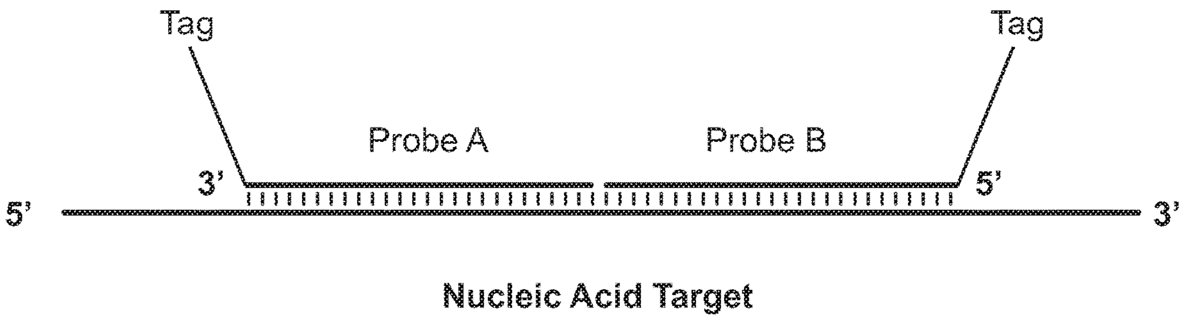
Figure 1C:
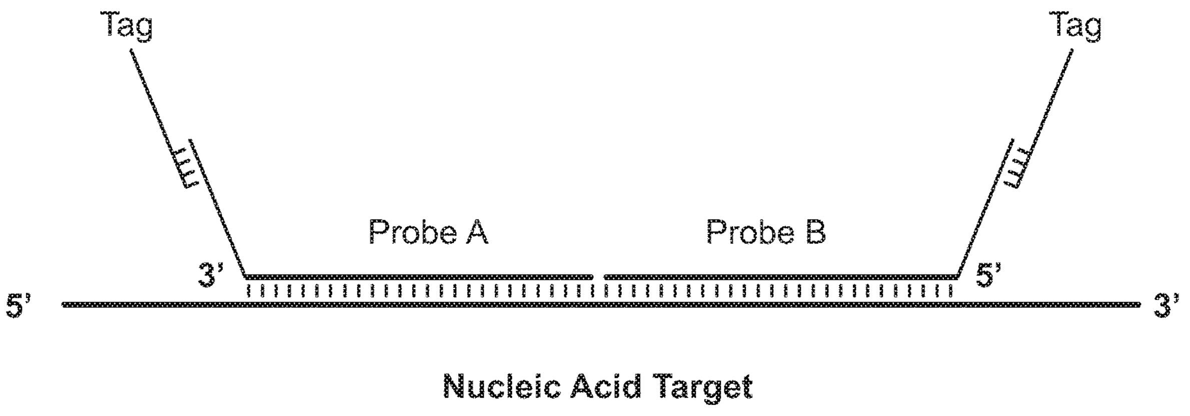

Once antibiotic responsive nucleic acid targets are identified, they can be assayed with target specific probes or sets of probes. According to the techniques herein, target specific probes may include bipartite probes (e.g., Probe A and Probe B) as shown in FIG. 1A. In embodiments, each such probe may range in length from about 15-100, 25-75, 30-70, 40-60, or 45-55 nucleotides in length. In embodiments, each such probe may be about 50 nucleotides in length. As shown in FIG. 1A, Probe A and Probe B are oriented in a tail to head configuration (e.g., 3' end of Probe B is positioned proximate to 5' end of Probe A). In embodiments, 3' end of Probe B abuts the 5' and of Probe A; however, it is contemplated within the scope of the disclosure that a gap of about 1-50 nucleotides may occur between 3' end of Probe B and 5' end of Probe A. As shown in FIGS. 1B-1C, bipartite probes according to the techniques herein may be detected via directly coupled tags or indirectly coupled tags, respectively.

Current assay conditions: hybridization of the bipartite probe sets at 65-67° C. for 1 hour, then detection on a NanoString® Sprint instrument. Briefly, 3 μl of crude lysate is incubated with unlabeled probe pairs (e.g. probe sets) for each target along with labeled NanoString® Elements TagSet reagents. Standard hybridization conditions according to the manufacturer's protocol are followed, except hybridizations are incubated for one hour at 67° C. instead of the recommended 16-24 hours. Hybridizations are then loaded and processed on a Sprint instrument (NanoString®) for purification and quantitative detection. These methods have been validated on: bacteria in pure culture; clinical urine samples; clinical blood culture samples.

Example 2: Genetic Basis for Carbapenem Resistance

To test and validate the techniques described herein, the genetic basis for carbapenem resistance, carbapenemases, was assessed by identifying and measuring the most important, transmissible cause of resistance to this last-line antibiotic. The techniques herein allowed antibiotic-responsive transcripts to be detected quantitatively, and in a multiplexed fashion in a single assay from crude lysate, which enhanced the speed of detection while minimizing sample processing/manipulation. The techniques herein were conducted on the NanoString® assay platform; however, one of skill in the art will readily comprehend that these techniques are not dependent on a single detection platform and may be conducted on any of a variety of detection platforms for quantitative RNA measurement (e.g., NanoString®, SHERLOCK, qRT-PCR, microarrays, etc.) capable of providing the above features.

The analysis herein identified seventeen relevant target sequences to be targeted by the Cre2 probe targets (e.g., probeset), which are shown in Table 1.

TABLE 1

Cre2 Target Sequences
CRE2 Probe Targets:

| Target: | target sequence in gene |
|---|---|
| ST258_wzi_1 (SEQ ID NO: 35) | ACCAGTCAATAAATAAAGCGTTCCCTCATGCCGATACTCTGAAAGGTGTTCAGCTGGGATGGAGTGGGAATGTTTATCAGTCGGTTCGAATTAACACTTC |
| ST258_wzy_1 (SEQ ID NO: 36) | AAAAAACTAATCTATATATTGCTAATACCAATTGCAGGCTTAGCAGTTTTTGCAATTTTTCAGGAGAGGCTGTCGCATGATGGTTATACATCATATGAAC |
| ST58_wzi_2 (SEQ ID NO: 37) | AAACCTTCCTATTCCTCTGAGCAGGTAGTTCTGGCTCGTATCAATCAGCGACTGTCAGCGTTAAAAGCCGATTTCCGGGTCACCGGCTATACCTCGACCG |
| ST258_wzy_2 (SEQ ID NO: 38) | GCCAACATTTATCAGCTATAAAGCGCAACTTTACTTTGACCTGAATACGGAAGGAGACCTTAAAAGAGTTACAGCAGTTGCAATGGGATTTGGAAGTCTT |
| CRE2_KPC_0.95 (SEQ ID NO: 39) | ACCCATCTCGGAAAAATATCTGACAACAGGCATGACGGTGGCGGAGCTGTCCGCGGCCGCCGTGCAATACAGTGATAACGCCGCCGCCAATTTGTTGCTG |
| CRE2_NDM_0.95 (SEQ ID NO: 40) | CAAATGGAAACTGGCGACCAACGGTTTGGCGATCTGGTTTTCCGCCAGCTCGCACCGAATGTCTGGCAGCACACTTCCTATCTCGACATGCCGGGTTTCG |
| CRE2_OXA48_0.95 (SEQ ID NO: 41) | TGCTACATGCTTTCGATTATGGTAATGAGGACATTTCGGGCAATGTAGACAGTTTCTGGCTCGACGGTGGTATTCGAATTTCGGCCACGGAGCAAATCAG |
| CRE2_CTXM15_0.95 (SEQ ID NO: 42) | AGTGAAAGCGAACCGAATCTGTTAAATCAGCGAGTTGAGATCAAAAAATCTGACCTTGTTAACTATAATCCGATTGCGGAAAAGCACGTCAATGGGACGA |
| CRE2_IMP_1_0.95 (SEQ ID NO: 43) | GAAGAAGGTGTTTATGTTCATACATCGTTCGAAGAAGTTAACGGTTGGGGTGTTGTTTCTAAACACGGTTTGGTGGTTCTTGTAAACACTGACGCCTATC |
| CRE2_IMP_3_8_0.95 (SEQ ID NO: 44) | GTTTTTTATCCCGGCCCGGGGCACACTCAAGATAACGTAGTGGTTTGGTTACCTGAAAAGAAAATTTTATTCGGTGGTTGTTTTGTTAAACCGGACGGTC |
| CRE2_IMP_2_4_0.95 (SEQ ID NO: 45) | GAAAAGTTAGTCAATTGGTTTGTGGAGCGCGGCTATAAAATCAAAGGCACTATTTCCTCACATTTCCATAGCGACAGCACAGGGGGAATAGAGTGGCTTA |
| CRE2_IMP_5_0.95 (SEQ ID NO: 46) | AAGTATGGTAATGCAAAACTGGTTGTTTCGAGTCATAGTGAAATTGGGGGCGCATCACTATTGAAGCGCACTTGGGAGCAGGCTGTTAAGGGGCTAAAAG |
| CRE2_IMP_6_0.95 (SEQ ID NO: 47) | GAAAAGTTAGTCACTTGGTTTGTGGAACGTGGCTATAAAATAAAAGGCAGTATTTCCTCTCATTTTCATAGCGACAGCACGGGCGGAATAGAGTGGCTTA |
| CRE2_IMP_7_0.95 (SEQ ID NO: 48) | TATGCATCTGAATTAACAAATGAACTTCTTAAAAAAGACGGTAAGGTACAAGCTAAAAATTCATTTAGCGGAGTTAGCTATTGGCTAGTTAAGAAAAAGA |
| CRE2_VIM_1_0.95 (SEQ ID NO: 49) | CTCTAGTGGAGATGTGGTGCGCTTCGGTCCCGTAGAGGTTTTCTATCCTGGTGCTGCGCATTCGGGCGACAATCTTGTGGTATACGTGCCGGCCGTGCGC |
| CRE2_VIM_2_3_0.95 (SEQ ID NO: 50) | TGATGGTGATGAGTTGCTTTTGATTGATACAGCGTGGGGTGCGAAAAACACAGCGGCACTTCTCGCGGAGATTGAGAAGCAAATTGGACTTCCCGTAACG |
| OXA10_0.95 (SEQ ID NO: 51) | CATAAAGAATGAGCATCAGGTTTTCAAATGGGACGGAAAGCCAAGAGCCATGAAGCAATGGGAAAGAGACTTGACCTTAAGAGGGGCAATACAAGTTTCA |

The analysis herein also identified eighteen relevant target sequences to be targeted by KpMero4 probe targets (e.g., probeset), which are shown in Table 2.

TABLE 2

KpMero4 Target Sequences
KpMero4 Probes Targets:

| Target: | target sequence in gene |
|---|---|
| KpMero4_C_KPN_00050_0.97 (SEQ ID NO: 52) | AGATCGTGCTTACCGCATGCTGATGAACCGCAAATTCTCTGAAGAAGCGGCAACCTGGATGCAGGAACAGCGCGCCAGTGCGTATGTTAAAATTCTGAGC |
| KpMero4_C_KPN_00098_0.97 (SEQ ID NO: 53) | GGAACGTTGTGGTCTGAAAGTTGACCAACTTATTTTCGCCGGGTTAGCGGCCAGTTATTCGGTATTAACAGAAGACGAACGTGAGCTGGGCGTCTGCGTT |
| KpMero4_C_KPN_00100_0.97 (SEQ ID NO: 54) | TCGATTGTGCCATCGTTGTTGACGATTATCGCGTACTGAACGAAGACGGTCTGCGCTTTGAAGACGAATTTGTTCGCCACAAAATGCTGGATGCGATCGG |
| KpMero4_C_KPN_01276_0.92 (SEQ ID NO: 55) | ATGCTGGAGTTGTTGTTTCTGCTTTTACCCGTTGCCGCCGCTTACGGCTGGTACATGGGGCGCAGAAGTGCACAACAGTCCAAACAGGACGATGCGAGCC |
| KpMero4_C_KPN_02846_0.95 (SEQ ID NO: 56) | GCGCAGGATCTGGTGATGAACTTTTCCGCCGACTGCTGGCTGGAAGTGAGCGATGCCACCGGTAAAAAACTGTTCAGCGGCCTGCAGCGTAAAGGCGGTA |
| KpMero4_C_KPN_03317_0.92 (SEQ ID NO: 57) | ATGGCCGGGGAACACGTCATTTTGCTGGATGAGCAGGATCAGCCTGCCGGTATGCTGGAGAAGTATGCCGCCCATACGTTTGATACCCCTTTACATCTCG |
| KpMero4_C_KPN_03634_0.92 (SEQ ID NO: 58) | AGCAATGACGGCGAAACGCCGGAAGGCATTGGCTTTGCGATCCCGTTCCAGTTAGCGACCAAAATTATGGATAAACTGATCCGCGATGGCCGGGTGATCC |
| KpMero4_C_KPN_04666_0.97 (SEQ ID NO: 59) | CAGGCCAGCGATGGTAACGCGGTGATGTTTATCGAAAGCGTCAACGGCAACCGCTTCCATGACGTCTTCCTTGCCCAGCTGCGTCCGAAAGGCAATGCGC |
| KpMero4_R01up_KPN_01226_0.97 (SEQ ID NO: 60) | GCGCGATGCACGATCTGATCGCCAGCGACACCTTCGATAAGGCGAAGGCGGAAGCGCAGATCGATAAGATGGAAGCGCAGCATAAAGCGATGGCGCTGTC |
| KpMero4_R02up_KPN_01107_0.97 (SEQ ID NO: 61) | GCTGTCGCTGGTCTCAACGTGTTGGATCGCGGCCCGCAGTATGCGCAAGTGGTCTCCAGTACACCGATTAAAGAAACCGTGAAAACGCCGCGTCAGGAAT |
| KpMero4_R03up_KPN_02345_0.95 (SEQ ID NO: 62) | ATGCGAATCGCGCTTTTCCTGCTGACGAACCTGGCAGTGATGGTCGTGTTCGGGCTGGTGTTAAGCCTCACGGGGATCCAATCCAGCAGCATGACCGGTC |
| KpMero4_R04up_KPN_02742_0.97 (SEQ ID NO: 63) | CAAATAGGCGATCGTGACAATTACGGTAACTACTGGGACGGTGGCAGCTGGCGCGACCGTGATTACTGGCGTCGTCACTATGAATGGCGTGATAACCGTT |
| KpMeRo4_R05dn_KPN_02241_0.92 (SEQ ID NO: 64) | GGGTAGGTTACTCCATTCTGAACCAGCTTCCGCAGCTTAACCTGCCACAATTCTTTGCGCATGGCGCAATCCTAAGCATCTTCGTTGGCGCAGTGCTCTG |
| KpMero4_R06up_KPN_03358_0.92 (SEQ ID NO: 65) | GGGCGAAAAACTGGTGAACTCGCAGTTCTCCCAGCGTCAGGAATCGGAAGCGGATGACTACTCTTACGACCTGCTGCGTAAGCGCGGTATCAATCCGTCG |
| KpMero4_R07up_KPN_03934_0.92 (SEQ ID NO: 66) | TGCCTTATATTACCAAGCAGAATCAGGCGATTACTGCGGATCGTAACTGGCTTATTTCCAAGCAGTACGATGCTCGCTGGTCGCCGACTGAGAAGGCGCG |
| KpMeRo4_R08dn_KPN_00868_0.92 (SEQ ID NO: 67) | TGCAACTGCGAAAGGCCAAAGGCTACATGTCAGTCAGCGAAAATGACCATCTGCGTGATAACTTGTTTGAGCTTTGCCGTGAAATGCGTGCGCAGGCGCC |
| KpMero4_R09up_KPN_02342_0.97 (SEQ ID NO: 68) | TATGGGGTGTTATTCCACAGTGAGGAAAACGTCGGCGGTCTGGGTCTTAAGTGCCAATACCTCACCGCCCGCGGAGTCAGCACCGCACTTTATGTTCATT |
| KpMero4_R010up_KPN_00833_0.97 (SEQ ID NO: 69) | AACCACTTTAGATGGTCTGGAAGCAAAACTGGCTGCTAAAGCCGAAGCCGCTGGCGCGACCGGCTACAGCATTACTTCCGCTAACACCAACAACAAACTG |

To facilitate identification of Cre2 probe targets, bipartite probes comprising a probe A and a probe B were constructed as shown in Table 3 and Table 4, respectively.

TABLE 3

Cre2 Probe A Sequences
CRE2 probes:

| Target: | probe A sequence |
|---|---|
| ST258_wzi_1 (SEQ ID NO: 70) | AACACCTTTCAGAGTATCGGCATGAGGGAACGCTTTATTTATTGACTGGTCCTCAAGACCTAAGCGACAGCGTGACCTTGTTTCA |

TABLE 3-continued

Cre2 Probe A Sequences
CRE2 probes:

| Target: | probe A sequence |
|---|---|
| ST258_wzy_1 (SEQ ID NO: 71) | AAAACTGCTAAGCCTGCAATTGGTATTAGCAATATATAGATTAGTTTTTTCATCCT CTTCTTTTCTTGGTGTTGAGAAGATGCTC |
| ST58_wzi_2 (SEQ ID NO: 72) | CGCTGATTGATACGAGCCAGAACTACCTGCTCAGAGGAATAGGAAGGTTTCACAAT TCTGCGGGTTAGCAGGAAGGTTAGGGAAC |
| ST258_wzy_2 (SEQ ID NO: 73) | CCGTATTCAGGTCAAAGTAAAGTTGCGCTTTATAGCTGATAAATGTTGGCCTGTTG AGATTATTGAGCTTCATCATGACCAGAAG |
| CRE2_KPC_0.95 (SEQ ID NO: 74) | ACAGCTCCGCCACCGTCATGCCTGTTGTCAGATATCAAAGACGCCTATCTTCCAGT TTGATCGGGAAACT |
| CRE2_NDM_0.95 (SEQ ID NO: 75) | AGCTGGCGGAAAACCAGATCGCCAAACCGTTGGTCGCCAGTTTCCATTTGCGAACC TAACTCCTCGCTACATTCCTATTGTTTTC |
| CRE2_OXA48_0.95 (SEQ ID NO: 76) | GTCTACATTGCCCGAAATGTCCTCATTACCATAATCGAAAGCATGTAGCACCAATT TGGTTTTACTCCCCTCGATTATGCGGAGT |
| CRE2_CTXM15_0.95 (SEQ ID NO: 77) | GATTTTTTGATCTCAACTCGCTGATTTAACAGATTCGGTTCGCTTTCACTCTTTCG GGTTATATCTATCATTTACTTGACACCCT |
| CRE2_IMP_1_0.95 (SEQ ID NO: 78) | CCCCAACCGTTAACTTCTTCGAACGATGTATGAACATAAACACCTTCTTCCAACAG CCACTTTTTTTCCAAATTTTGCAAGAGCC |
| CRE2_IMP_3_8_0.95 (SEQ ID NO: 79) | AACCAAACCACTACGTTATCTTGAGTGTGCCCCGGGCCGGGATAAAAAACCACCGT GTGGACGGCAACTCAGAGATAACGCATAT |
| CRE2_IMP_2_4_0.95 (SEQ ID NO: 80) | GTGCCTTTGATTTTATAGCCGCGCTCCACAAACCAATTGACTAACTTTTCCCTGGA GTTTATGTATTGCCAACGAGTTTGTCTTT |
| CRE2_IMP_5_0.95 (SEQ ID NO: 81) | CCCCCAATTTCACTATGACTCGAAACAACCAGTTTTGCATTACCATACTTCAGATA AGGTTGTTATTGTGGAGGATGTTACTACA |
| CRE2_IMP_6_0.95 (SEQ ID NO: 82) | CTGCCTTTTATTTTATAGCCACGTTCCACAAACCAAGTGACTAACTTTTCCTTCCT TCCTGTGTTCCAGCTACAAACTTAGAAAC |
| CRE2_IMP_7_0.95 (SEQ ID NO: 83) | TGTACCTTACCGTCTTTTTTAAGAAGTTCATTTGTTAATTCAGATGCATACATAAA ATTGGTTTTGCCTTTCAGCAATTCAACTT |
| CRE2_VIM_1_0.95 (SEQ ID NO: 84) | GAAAACCTCTACGGGACCGAAGCGCACCACATCTCCACTAGAGCTGGTCAAGACTT GCATGAGGACCCGCAAATTCCT |
| CRE2_VIM_2_3_0.95 (SEQ ID NO: 85) | CGCACCCCACGCTGTATCAATCAAAAGCAACTCATCACCATCACTTTCGTTGGGAC GCTTGAAGCGCAAGTAGAAAAC |
| OXA10_0.95 (SEQ ID NO: 86) | TGGCTCTTGGCTTTCCGTCCCATTTGAAAACCTGATGCTCATTCTTTATGCCAGCA GACCTGCAATATCAAAGTTATAAGCGCGT |

TABLE 4

Cre2 Probe B Sequences
CRE2 probes:

| Target: | probe B sequence |
|---|---|
| ST258_wzi_1 (SEQ ID NO: 87) | CGAAAGCCATGACCTCCGATCACTCGAAGTGTTAATTCGAACCGACTGATAAAC ATTCCCACTCCATCCCAGCTG |
| ST258_wzy_1 (SEQ ID NO: 88) | CGAAAGCCATGACCTCCGATCACTCGTTCATATGATGTATAACCATCATGCGAC AGCCTCTCCTGAAAAATTGCA |
| ST58_wzi_2 (SEQ ID NO: 89) | CGAAAGCCATGACCTCCGATCACTCCGGTCGAGGTATAGCCGGTGACCCGGAAA TCGGCTTTTAACGCTGACAGT |
| ST258_wzy_2 (SEQ ID NO: 90) | CGAAAGCCATGACCTCCGATCACTCAAGACTTCCAAATCCCATTGCAACTGCTG TAACTCTTTTAAGGTCTCCTT |
| CRE2_KPC_0.95 (SEQ ID NO: 91) | CGAAAGCCATGACCTCCGATCACTCCAGCAACAAATTGGCGGCGGCGTTATCAC TGTATTGCACGGCGGCCGCGG |
| CRE2_NDM_0.95 (SEQ ID NO: 92) | CGAAAGCCATGACCTCCGATCACTCCGAAACCCGGCATGTCGAGATAGGAAGTG TGCTGCCAGACATTCGGTGCG |

TABLE 4-continued

| Cre2 Probe B Sequences CRE2 probes: | |
|---|---|
| Target: | probe B sequence |
| CRE2_OXA48_0.95 (SEQ ID NO: 93) | CGAAAGCCATGACCTCCGATCACTCCTGATTTGCTCCGTGGCCGAAATTCGAAT ACCACCGTCGAGCCAGAAACT |
| CRE2_CTXM15_0.95 (SEQ ID NO: 94) | CGAAAGCCATGACCTCCGATCACTCTCGTCCCATTGACGTGCTTTTCCGCAATC GGATTATAGTTAACAAGGTCA |
| CRE2_IMP_1_0.95 (SEQ ID NO: 95) | CGAAAGCCATGACCTCCGATCACTCGATAGGCGTCAGTGTTTACAAGAACCACC AAACCGTGTTTAGAAACAACA |
| CRE2_IMP_3_8_0.95 (SEQ ID NO: 96) | CGAAAGCCATGACCTCCGATCACTCGACCGTCCGGTTTAACAAAACAACCACCG AATAAAATTTTCTTTTCAGGT |
| CRE2_IMP_2_4_0.95 (SEQ ID NO: 97) | CGAAAGCCATGACCTCCGATCACTCTAAGCCACTCTATTCCCCCTGTGCTGTCG CTATGGAAATGTGAGGAAATA |
| CRE2_IMP_5_0.95 (SEQ ID NO: 98) | CGAAAGCCATGACCTCCGATCACTCCCCTTAACAGCCTGCTCCCAAGTGCGCTT CAATAGTGATGCG |
| CRE2_IMP_6_0.95 (SEQ ID NO: 99) | CGAAAGCCATGACCTCCGATCACTCTAAGCCACTCTATTCCGCCCGTGCTGTCG CTATGAAAATGAGAGGAAATA |
| CRE2_IMP_7_0.95 (SEQ ID NO: 100) | CGAAAGCCATGACCTCCGATCACTCTCTTTTTCTTAACTAGCCAATAGCTAACT CCGCTAAATGAATTTTTAGCT |
| CRE2_VIM_1_0.95 (SEQ ID NO: 101) | CGAAAGCCATGACCTCCGATCACTCCGTATACCACAAGATTGTCGCCCGAATGC GCAGCACCAGGATA |
| CRE2_VIM_2_3_0.95 (SEQ ID NO: 102) | CGAAAGCCATGACCTCCGATCACTCCAATTTGCTTCTCAATCTCCGCGAGAAGT GCCGCTGTGTTTTT |
| OXA10_0.95 (SEQ ID NO: 103) | CGAAAGCCATGACCTCCGATCACTCTGAAACTTGTATTGCCCCTCTTAAGGTCA AGTCTCTTTCCCATTGCTTCA |

Similarly, to facilitate identification of KpMero4 probe targets, bipartite probes comprising a probe A and a probe B were constructed as shown in Table 5 and Table 6, respectively.

TABLE 5

| KpMero4 Probe A Sequences KpMero4 probes: | |
|---|---|
| Target: | probe A sequence |
| KpMero4_C_KPN_00050_0.97 (SEQ ID NO: 104) | CCGCTTCTTCAGAGAATTTGCGGTTCATCAGCATGCGGTAAGCACGATCCT GCCAATGCACTCGATCTTGTCATTTTTTTGCG |
| KpMero4_C_KPN_00098_0.97 (SEQ ID NO: 105) | CCGCTAACCCGGCGAAAATAAGTTGGTCAACTTTCAGACCACAACGTTCCC AAACTGGAGAGAGAAGTGAAGACGATTTAACCCA |
| KpMero4_C_KPN_00100_0.97 (SEQ ID NO: 106) | ACCGTCTTCGTTCAGTACGCGATAATCGTCAACAACGATGGCACAATCGAC GATTGCTGCATTCCGCTCAACGCTTGAGGAAGTA |
| KpMero4_C_KPN_01276_0.92 (SEQ ID NO: 107) | CAGCCGTAAGCGGCGGCAACGGGTAAAAGCAGAAACAACAACTCCAGCATC TGAGGCTGTTAAAGCTGTAGCAACTCTTCCACGA |
| KpMero4_C_KPN_02846_0.95 (SEQ ID NO: 108) | CTCACTTCCAGCCAGCAGTCGGCGGAAAAGTTCATCACCAGACTAGGACGC AAATCACTTGAAGAAGTGAAAGCGAG |
| KpMero4_C_KPN_03317_0.92 (SEQ ID NO: 109) | CCGGCAGGCTGATCCTGCTCATCCAGCAAAATGACGTGTTCCCCACGCGAT GACGTTCGTCAAGAGTCGCATAATCT |
| KpMero4_C_KPN_03634_0.92 (SEQ ID NO: 110) | TGGAACGGGATCGCAAAGCCAATGCCTTCCGGCGTTTCGCCGCATTTGGAA TGATGTGTACTGGGAATAAGACGACG |
| KpMero4_C_KPN_04666_0.97 (SEQ ID NO: 111) | TTGCCGTTGACGCTTTCGATAAACATCACCGCGTTACCATCGCTGGCCTGC ACAAGAATCCCTGCTAGCTGAAGGAGGGTCAAAC |
| KpMero4_R01up_KPN_01226_0.97 (SEQ ID NO: 112) | CGCCTTCGCCTTATCGAAGGTGTCGCTGGCGATCAGATCGTGCTTGACGTA GATTGCTATCAGGTTACGATGACTGC |

TABLE 5-continued

| KpMero4 Probe A Sequences<br>KpMero4 probes: | |
|---|---|
| Target: | probe A sequence |
| KpMero4_R02up_KPN_01107_0.97 (SEQ ID NO: 113) | ACTTGCGCATACTGCGGGCCGCGATCCAACACGTTGAGACCACTTACAGAT CGTGTGCTCATGACTTCCACAGACGT |
| KpMero4_R03up_KPN_02345_0.95 (SEQ ID NO: 114) | AACACGACCATCACTGCCAGGTTCGTCAGCAGGAAAAGCGCGATTCGCATC TTGGAGGAGTTGATAGTGGTAAAACAACATTAGC |
| KpMero4_R04up_KPN_02742_0.97 (SEQ ID NO: 115) | CAGCTGCCACCGTCCCAGTAGTTACCGTAATTGTCACGATCGCCTACGTAT ATATCCAAGTGGTTATGTCCGACGGC |
| KpMero4_R05dn_KPN_02241_0.92 (SEQ ID NO: 116) | TTGTGGCAGGTTAAGCTGCGGAAGCTGGTTCAGAATGGAGTAACCTACCAG CAAGAAGGAGTATGGAACTTATAGCAAGAGAG |
| KpMero4_R06up_KPN_03358_0.92 (SEQ ID NO: 117) | CTTCCGATTCCTGACGCTGGGAGAACTGCGAGTTCACCAGTTCACCCCTCC AAACGCATTCTTATTGGCAAATGGAA |
| KpMero4_R07up_KPN_03934_0.92 (SEQ ID NO: 118) | CCAGTTACGATCCGCAGTAATCGCCTGATTCTGCTTGGTAATATAAGGCAC CCGAAGCAATACTGTCGTCACTCTGTATGTCCGT |
| KpMero4_R08dn_KPN_00868_0.92 (SEQ ID NO: 119) | ATGGTCATTTTCGCTGACTGACATGTAGCCTTTGGCCTTTCGCCGGGAATC GGCATTTCGCATTCTTAGGATCTAAA |
| KpMero4_R09up_KPN_02342_0.97 (SEQ ID NO: 120) | TTAAGACCCAGACCGCCGACGTTTTCCTCACTGTGGAATAACACCCCATAC CGATCTTCATAACGGACAAACTGAACGGGCCATT |
| KpMero4_R10up_KPN_00833_0.97 (SEQ ID NO: 121) | CGGCTTCGGCTTTAGCAGCCAGTTTTGCTTCCAGACCATCTAAAGCGCTAT GCAGACGAGCTGGCAGAGGAGAGAAATCA |

TABLE 6

| KpMero4 Probe B Sequences<br>KpMero4 probes: | |
|---|---|
| Target: | probe B sequence |
| KpMero4_C_KPN_00050_0.97 (SEQ ID NO: 122) | CGAAAGCCATGACCTCCGATCACTCCAGAATTTTAACATACGCA CTGGCGCGCTGTTCCTGCATCCAGGTTG |
| KpMero4_C_KPN_00098_0.97 (SEQ ID NO: 123) | CGAAAGCCATGACCTCCGATCACTCAACGCAGACGCCCAGCTCA CGTTCGTCTTCTGTTAATACCGAATAACTGG |
| KpMero4_C_KPN_00100_0.97 (SEQ ID NO: 124) | CGAAAGCCATGACCTCCGATCACTCCCGATCGCATCCAGCATTT TGTGGCGAACAAATTCGTCTTCAAAGCGCAG |
| KpMero4_C_KPN_01276_0.92 (SEQ ID NO: 125) | CGAAAGCCATGACCTCCGATCACTCGTTTGGACTGTTGTGCACT TCTGCGCCCCATGTAC |
| KpMero4_C_KPN_02846_0.95 (SEQ ID NO: 126) | CGAAAGCCATGACCTCCGATCACTCTTACGCTGCAGGCCGCTGA ACAGTTTTTTACCGGTGGCATCG |
| KpMero4_C_KPN_03317_0.92 (SEQ ID NO: 127) | CGAAAGCCATGACCTCCGATCACTCCGAGATGTAAAGGGGTATC AAACGTATGGGCGGCATACTTCTCCAGCATA |
| KpMero4_C_KPN_03634_0.92 (SEQ ID NO: 128) | CGAAAGCCATGACCTCCGATCACTCGGATCACCCGGCCATCGCG GATCAGTTTATCCATAATTTTGGTCGCTAAC |
| KpMero4_C_KPN_04666_0.97 (SEQ ID NO: 129) | CGAAAGCCATGACCTCCGATCACTCATTGCCTTTCGGACGCAGC TGGGCAAGGAAGACGTCATGGAAGCGG |
| KpMero4_R01up_KPN_01226_0.97 (SEQ ID NO: 130) | CGAAAGCCATGACCTCCGATCACTCCATCGCTTTATGCTGCGCT TCCATCTTATCGATCTGCGCTTC |
| KpMero4_R02up_KPN_01107_0.97 (SEQ ID NO: 131) | CGAAAGCCATGACCTCCGATCACTCCTGACGCGGCGTTTTCACG GTTTCTTTAATCGGTGTACTGGAGACC |
| KpMero4_R03up_KPN_02345_0.95 (SEQ ID NO: 132) | CGAAAGCCATGACCTCCGATCACTCCTGGATTGGATCCCCGTGA GGCTTAACACCAGCCCG |
| KpMero4_R04up_KPN_02742_0.97 (SEQ ID NO: 133) | CGAAAGCCATGACCTCCGATCACTCAACGGTTATCACGCCATTC ATAGTGACGACGCCAGTAATCACGGTCGCGC |

TABLE 6-continued

| KpMero4 Probe B Sequences<br>KpMero4 probes: | |
|---|---|
| Target: | probe B sequence |
| KpMero4_R05dn_KPN_02241_0.92 (SEQ ID NO: 134) | CGAAAGCCATGACCTCCGATCACTCCAGAGCACTGCGCCAACGA AGATGCTTAGGATTGCGCCATGCGCAAAGAA |
| KpMero4_R06up_KPN_03358_0.92 (SEQ ID NO: 135) | CGAAAGCCATGACCTCCGATCACTCCGACGGATTGATACCGCGC TTACGCAGCAGGTCGTAAGAGTAGTCATCCG |
| KpMero4_R07up_KPN_03934_0.92 (SEQ ID NO: 136) | CGAAAGCCATGACCTCCGATCACTCCCTTCTCAGTCGGCGACCA GCGAGCATCGTACTGCTTGGAAATAAG |
| KpMero4_R08dn_KPN_00868_0.92 (SEQ ID NO: 137) | CGAAAGCCATGACCTCCGATCACTCGGCGCCTGCGCACGCATTT CACGGCAAAGCTCAAACAAGTTATCACGCAG |
| KpMero4_R09up_KPN_02342_0.97 (SEQ ID NO: 138) | CGAAAGCCATGACCTCCGATCACTCAATGAACATAAAGTGCGGT GCTGACTCCGCGGGCGGTGAGGTATTGGCAC |
| KpMero4_R10up_KPN_00833_0.97 (SEQ ID NO: 139) | CGAAAGCCATGACCTCCGATCACTCTTGGTGTTAGCGGAAGTAA TGCTGTAGCCGGTCGCGCCAG |

Antibiotic susceptibility testing is typically done by growth-based assays, including broth microdilution (may be automated e.g. on VITEK-2), disk diffusion, or E-test. Other approaches to rapid phenotypic AST include automated microscopy (Accelerate Diagnostics), ultrafine mass measurements (LifeScale). Genotypic approaches include resistance gene detection by PCR or other nucleic acid amplification methods, including Cepheid, BioFire, etc. but are limited to cases for which the genetic basis for resistance is well characterized.

Example 3: AST in ESKAPE Pathogens

The techniques herein are currently being used to conduct AST for: *Escherichia coli, Klebsiella pneumoniae*, and *Acinetobacter baumanii* for three different drug classes (meropenem; ciprofloxacin; gentamicin) along with carbapenemase detection. Additionally, the techniques herein are you being used to conduct AST on all of the ESKAPE pathogens including: *Enterococcus faecalis, Enterococcus faecium, Staphylococcus aureus, K. pneumoniae, A. baumanii, Pseudomonas aeruginosa, E. coli*, and *Enterobacter cloacae* with respect to all major clinically relevant drug classes (e.g., carbapenems, penicillins, cephalosporins, aminoglycosides, fluoroquinolones, rifamycins, and the like). The techniques herein are also being extended to conduct AST on *Mycobacterium tuberculosis* for all first-line and second-line drugs as well as the newer agents, bedaquiline and delamanid.

Figure 2A:
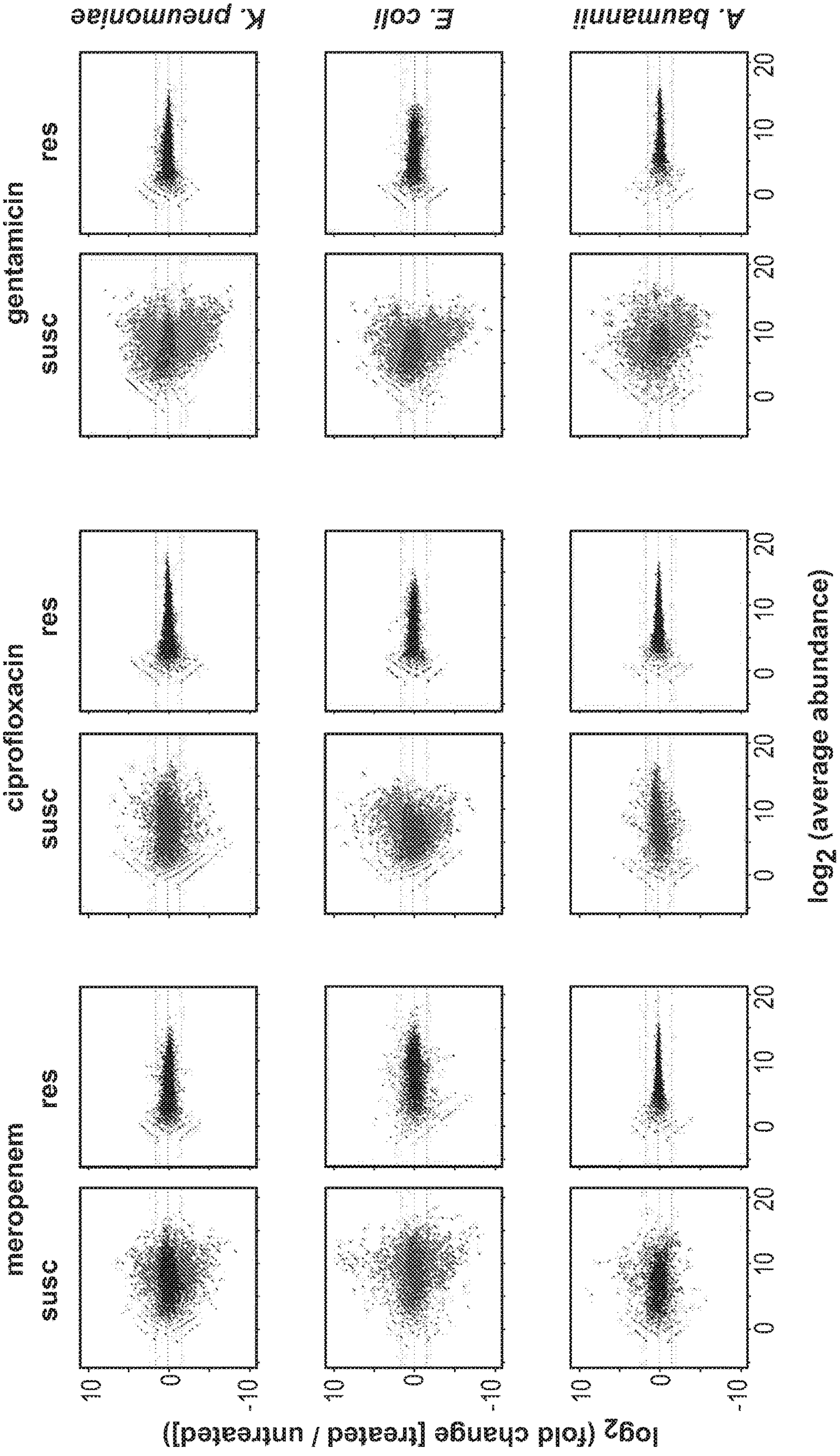
FIGS. 2A-2D depict MA plots showing RNA-Seq data.
Figure 2B:
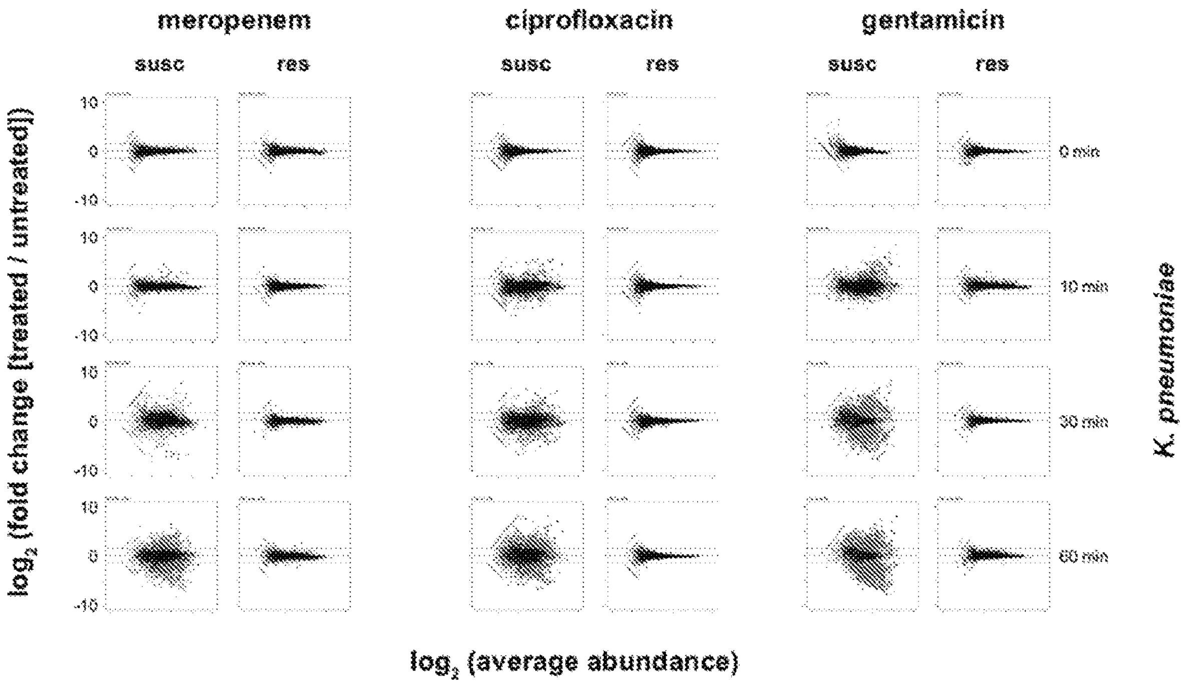
Figure 2C:
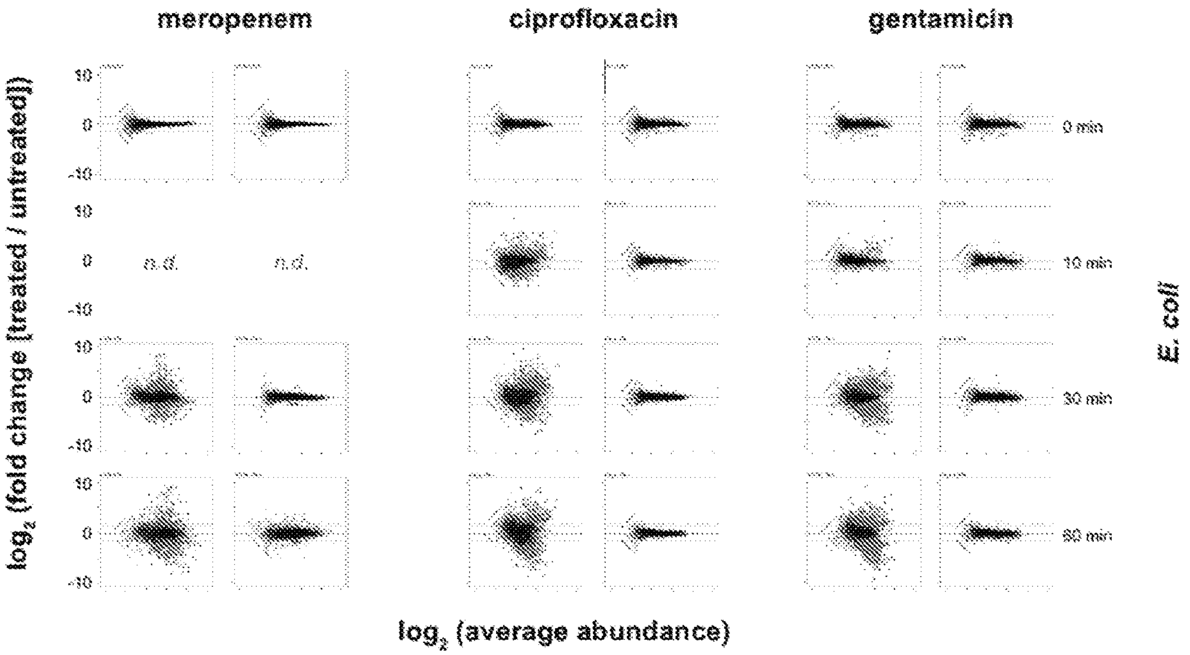
Figure 2D:
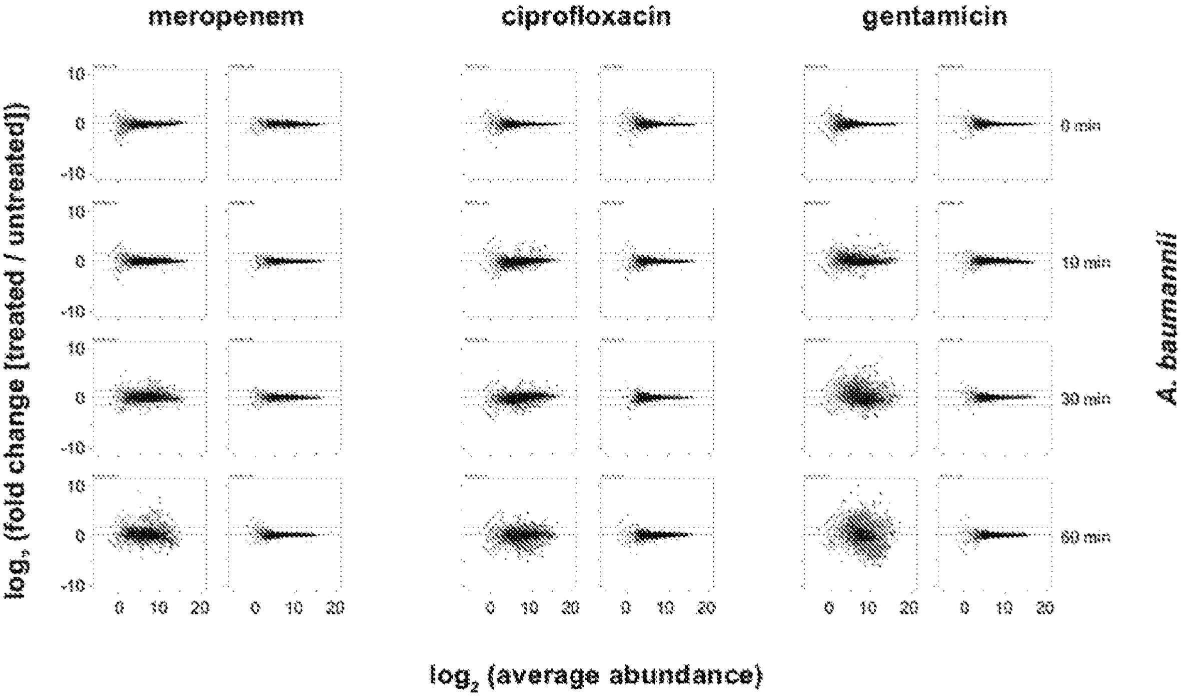

For example, FIGS. 2A-2D, which are described in further detail below, are MA plots showing RNA-Seq data upon antibiotic exposure. FIG. 2A shows MA plots of susceptible (left panels) or resistant (right panels) *Klebsiella pneumoniae, Escherichia coli* or *Acinetobacter baumanii* treated with meropenem for 60 min (left column), ciprofloxacin for 30 min (middle column), or gentamicin for 30-60 min (right column). Transcripts whose expression is statistically significantly changed upon antibiotic exposure are shown in red.

Figure 4A:
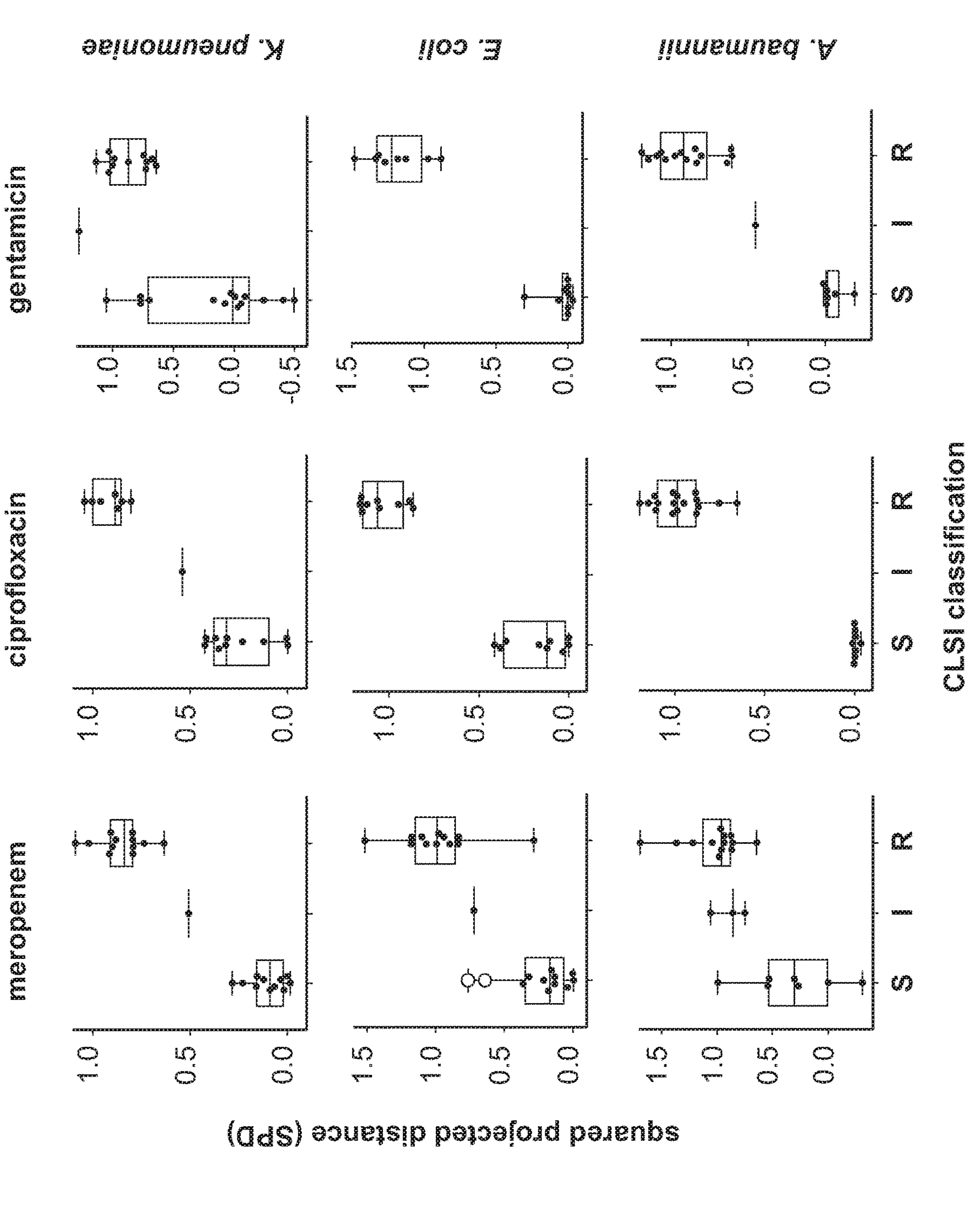
FIGS. 4A and 4B show that a one-dimensional projection of NanoString® data distinguished susceptible from resistant isolates and reflected MIC.
Figure 4B:
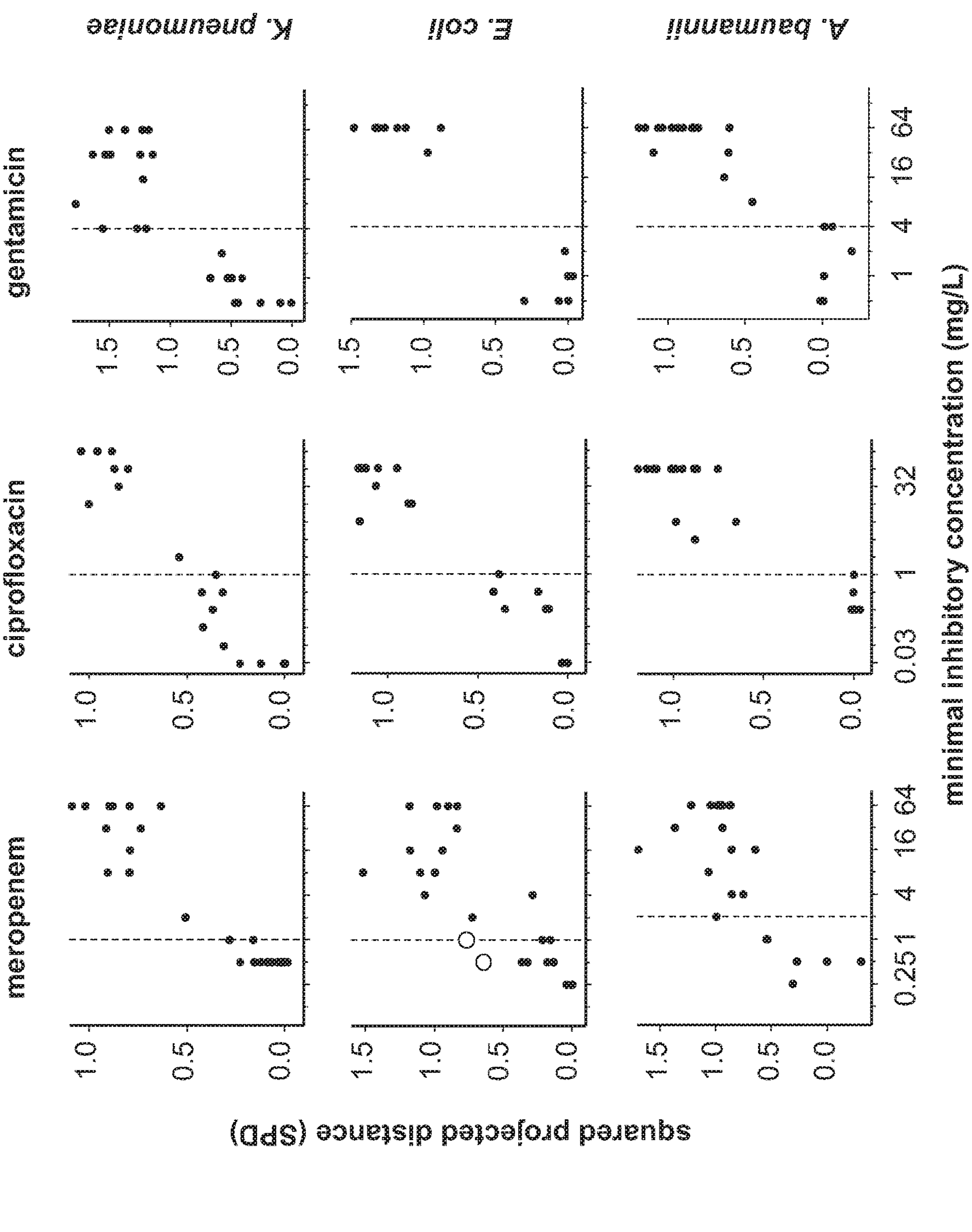

Additionally, FIGS. 4A and 4B, which are described in further detail below, depict graphs showing that the squared projected distance (SPD) from transcriptional signatures reflected antibiotic susceptibility. Clinical isolates of *Klebsiella pneumoniae, Escherichia coli* or *Acinetobacter baumanii* were treated with meropenem for 60 min (left column), ciprofloxacin for 30 min (middle column), or gentamicin for 30-60 min (right column).

Example 4: Determining Optimal Transcriptional Signatures to Discriminate Between Susceptible and Resistant Bacteria To identify the optimal transcripts that most robustly distinguish susceptible and resistant bacteria after brief antibiotic exposure, the transcriptomic responses of two susceptible and two resistant clinical isolates of *K. pneumoniae, E. coli*, and *A. baumannii* (see Table 7 below) treated with either meropenem (a carbapenem that inhibits cell wall biosynthesis), ciprofloxacin (a fluoroquinolone that targets DNA gyrase and topoisomerase), or gentamicin (an aminoglycoside that inhibits protein synthesis) were compared at clinical breakpoint concentrations (CLSI 2018) over time (e.g., 0, 10, 30, 60 minutes) using RNA-Seq. To enable these comparisons, a method optimized and modified from RNAtag-Seq (Shishkin et al. 2015), now termed RNAtag-Seqv2.0, was developed to dramatically decrease the cost and increase the throughput of library construction. For each pathogen, each antibiotic elicited a transcriptional response within 30-60 minutes in susceptible, but not in resistant, organisms (FIGS. 2A-2D).

Figure 3:
FIG. 3 shows that NanoString® data from dozens of antibiotic-responsive genes distinguished susceptible from resistant isolates. Heatmaps of normalized, log-transformed fold-induction of antibiotic-responsive transcripts from 18-24 clinical isolates of *K. pneumoniae* (top), *E. coli* (middle), or *A. baumannii* (bottom) treated at CLSI breakpoint concentrations with meropenem (left), ciprofloxacin (center), or gentamicin (right), with strains arranged in order of MIC for each antibiotic. CLSI classifications are shown below. All antibiotic-responsive transcripts chosen as described from RNA-Seq data are shown here; the subset of these chosen by reliefF as the 10 most discriminating transcripts are shown in FIG. 6 below. *=strains with large inoculum effects in meropenem MIC; +=one-dilution errors; x=strains discordant by more than one dilution.

To identify transcripts that best distinguish susceptible from resistant strains for each pathogen-antibiotic combination, a large number of candidate antibiotic-responsive transcripts from these RNA-Seq datasets was initially selected for evaluation in more clinical isolates using NanoString®. Complicating transcript selection is the fact that antibiotics arrest growth of susceptible strains, resulting in the rapid divergence of culture density and growth phase of treated and untreated cultures, factors that alone affect the transcription of hundreds of genes that can mistakenly be interpreted as the direct result of antibiotic exposure but may not generalize across growth conditions. To enrich for genes specifically perturbed by antibiotic exposure, DESeq2 (Love, Huber, and Anders 2014) was used to identify transcripts whose abundance changed most robustly upon antibiotic exposure (Table 9), followed by Fisher's combined probability test to identify transcripts whose expression changed more upon antibiotic treatment than under any phase of growth during the timecourse. Gene ontology enrichment analysis on the resulting gene lists (Table 8) revealed that meropenem affected lipopolysaccharide biosynthesis in both Enterobacteriaceae species, and induced a heat shock response in both *E. coli* and *Acinetobacter*. Ciprofloxacin induced the SOS response in all three species. Gentamicin induced the unfolded protein response and quinone binding in all three species. The top 60-100 responsive genes (see Methods) were selected as candidates for inclusion in the initial transcriptional signature (FIG. 3; Table 9). For normalization of these responsive genes across samples, DESeq2 was also used to select 10-20 transcripts for each pathogen-antibiotic pair that were most invariant to antibiotic treatment and growth phase ("control transcripts"; see Methods below).

Example 5: A Rapid, Multiplexed Phenotypic Assay to Classify Sensitive and Resistant Bacteria For each of the selected genes for each pathogen-antibiotic pair, probes for multiplexed detection were designed using NanoString®, a simple, quantitative fluorescent hybridization platform that does not require nucleic acid purification (Barczak et al. 2012; Geiss et al. 2008). Because diversity among clinical strains in gene content or sequence may hinder probe hybridization, a homology masking algorithm was devised to identify conserved regions of each target gene (see Methods below), then designed pairs of 50mer probes to the specified conserved regions of the remaining responsive and control transcripts for each pathogen-antibiotic pair (Table 9). Using an assay protocol that was modified from the standard NanoString® nCounter assay to accelerate detection (see Methods below), these probes were used to quantify their cognate transcripts in 18-24 diverse clinical isolates of each species collected from various geographic locations (Table 7), spanning the breadth of the known phylogenetic landscape of each species (Letunic & Bork) (FIGS. 13A-13D). Because of the homology screening step in probe design, each probe recognizes the target transcript from its cognate species, thereby enabling simultaneous species identification through mRNA recognition (see, e.g., Barczak et al.). Normalized expression signatures of all responsive genes are shown as heatmaps (FIG. 3) and summarized as one-dimensional projections (FIGS. 4A-4B). For each pathogen-antibiotic pair tested, the transcriptional profile of susceptible strains was distinct from that of resistant strains (FIG. 4A), with the magnitude of the transcriptional response reflecting the MIC of the exposed isolate (FIG. 4B).

Figure 14A:
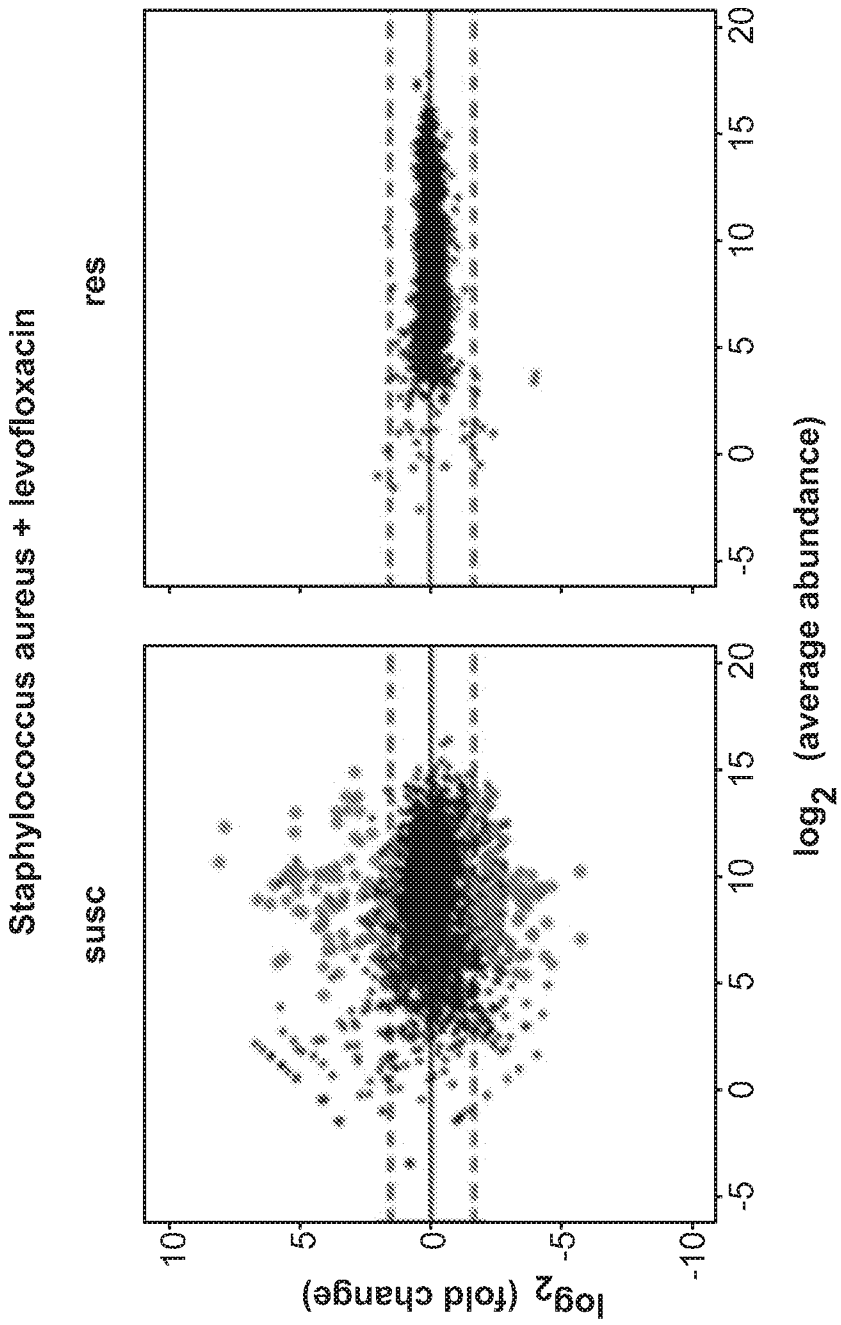
FIGS. 14A-14F show that RNA-Seq and NanoString® data revealed differential gene expression that distinguished susceptible from resistant clinical isolates for *S. aureus*+levofloxacin and *P. aeruginosa*+ciprofloxacin.
Figure 14B:
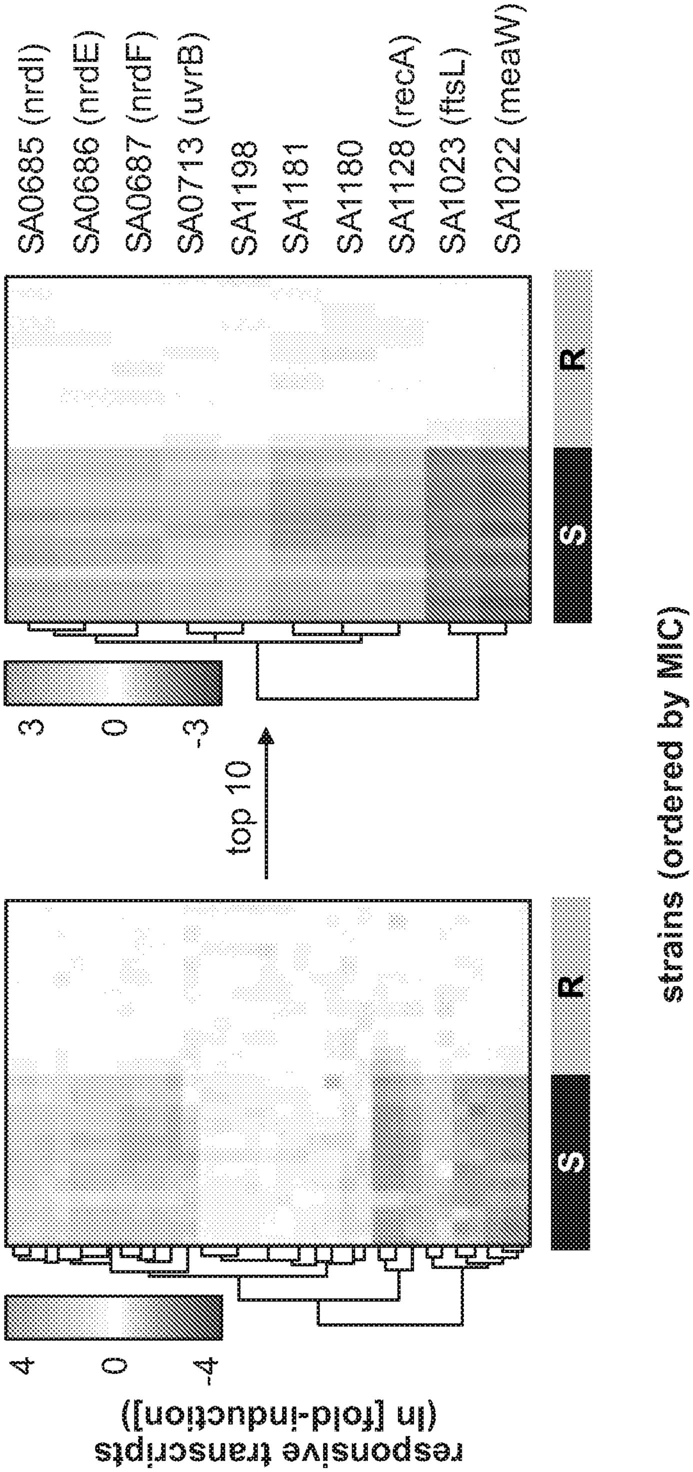
Figure 14C:
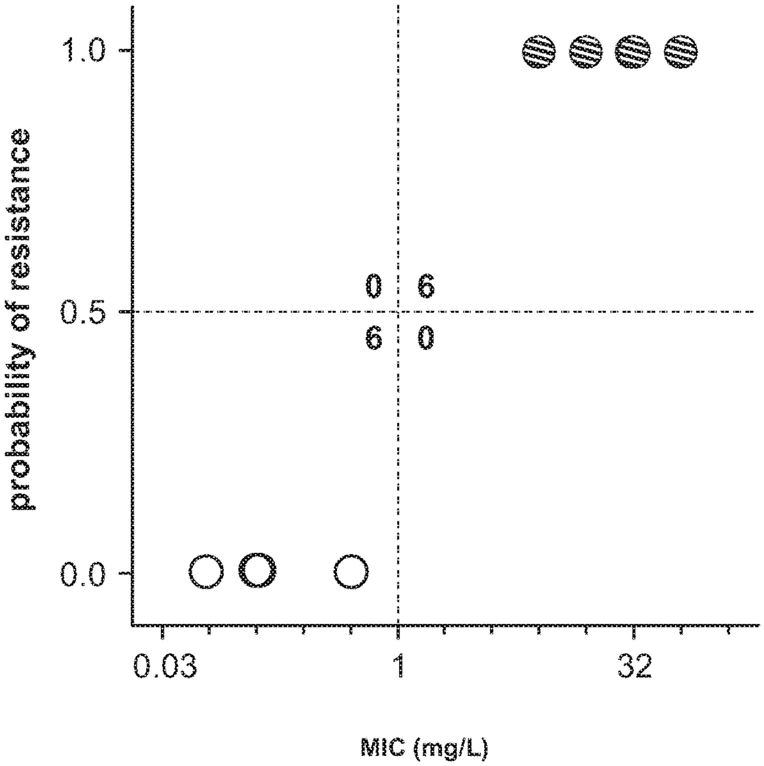
Figure 14D:
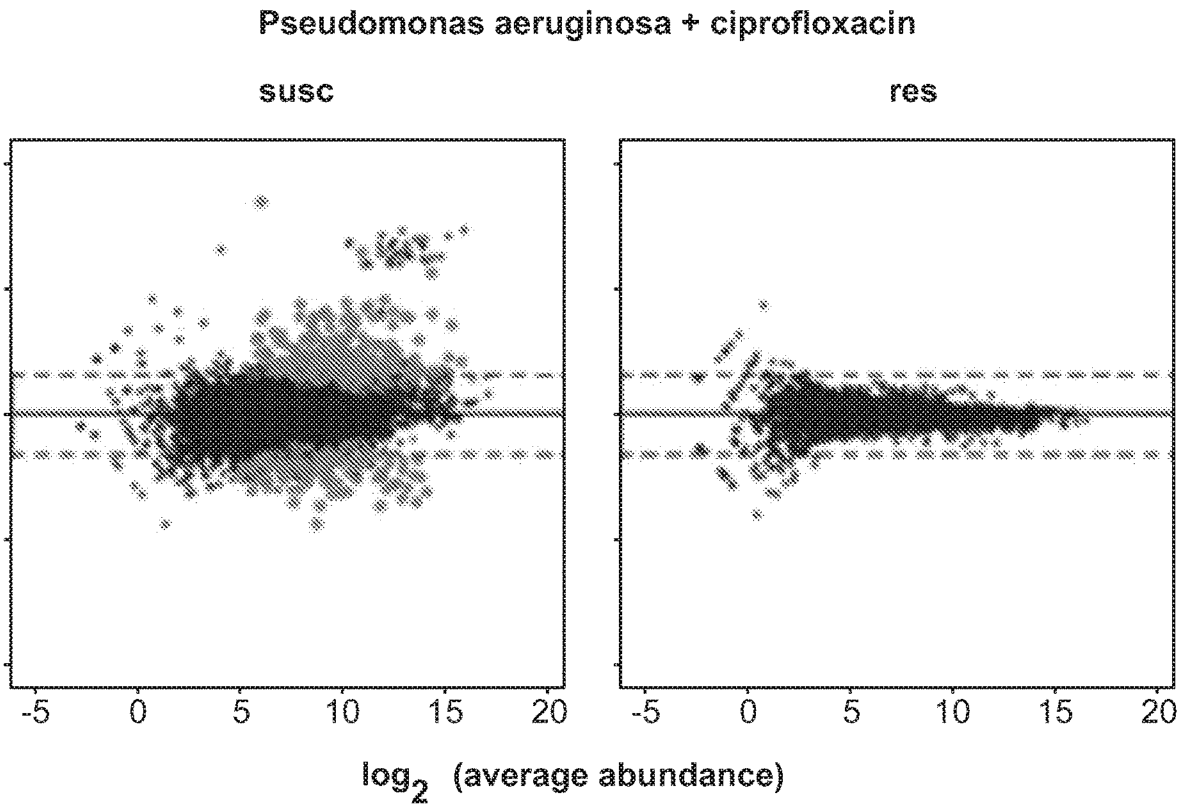
Figure 14E:
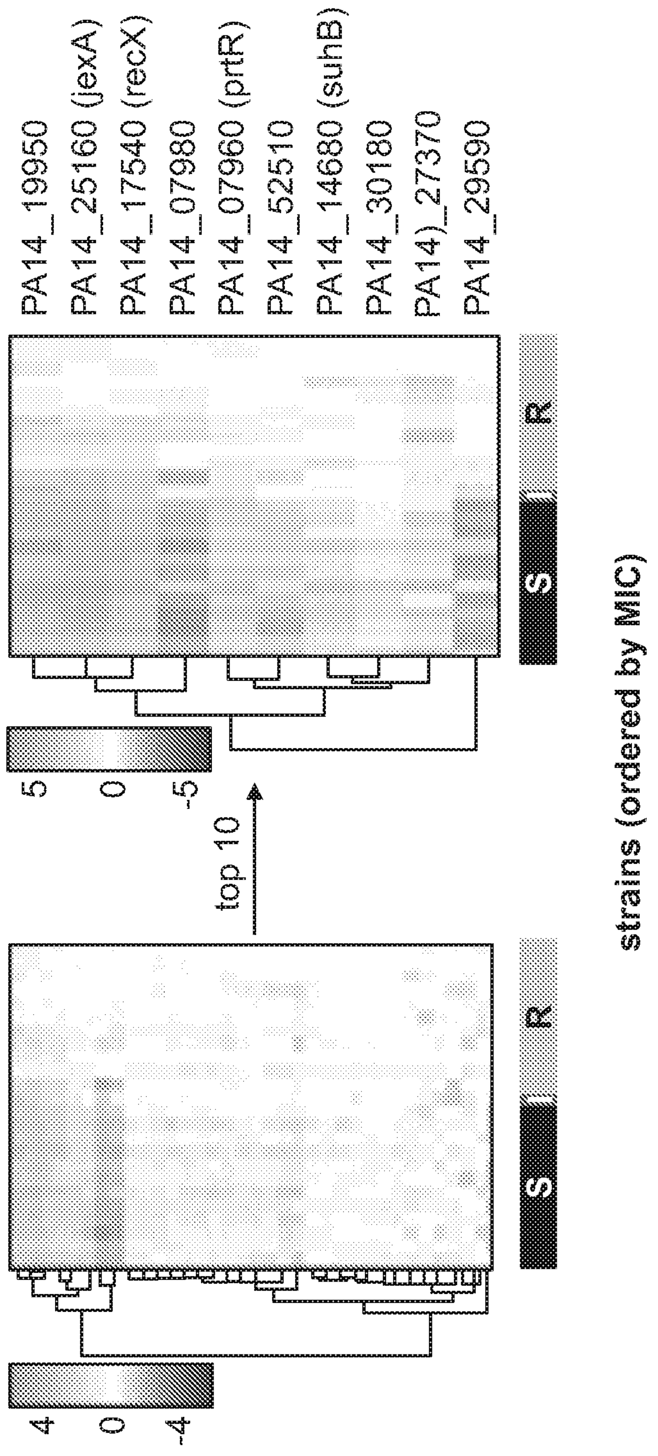
Figure 14F:
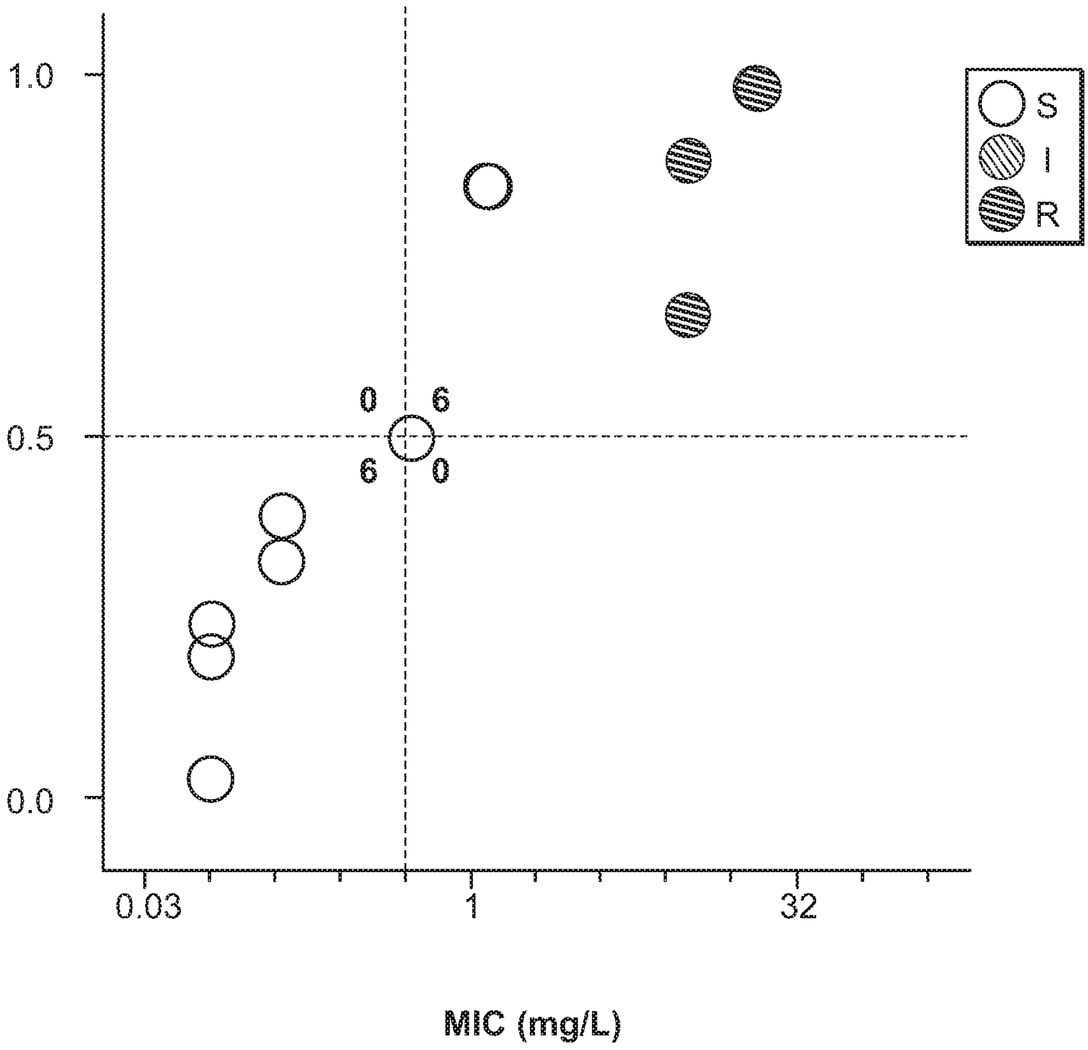

To further test the generalizability of this approach, the above-described steps from RNA-Seq through NanoString® detection of candidate responsive and control genes were repeated for two additional species including a Gram-positive pathogen, *S. aureus*, a common cause of serious infections, and *P. aeruginosa*, another high-priority and frequently multidrug-resistant Gram-negative pathogen, each treated with a fluoroquinolone, levofloxacin (given its greater potency against Gram positives (Hooper et al.)) and ciprofloxacin, respectively (FIGS. 14A-14F). Each showed a robust transcriptional response in susceptible clinical isolates, but no response in resistant isolates, by both RNA-Seq (FIGS. 14A and 14D) and NanoString® (FIGS. 14B and 14E). The overall responses of both pathogens to fluoroquinolones involved up-regulation of the SOS response, as expected (Table 8), including canonical DNA damage-responsive transcripts like lexA, recA, recX, uvrA, and uvrB, which were generally consistent with the genes identified for the other three Gram negative pathogens. However, the specific genes selected from the RNA-Seq data to best distinguish susceptible from resistant isolates included features particular to each species, even for such a stereotypical response pathway. In fact, recA was the only feature selected as a candidate responsive gene in all five species; lexA and uvrA emerged in four of the five, but no other single transcript was selected in more than three, underscoring the importance of deriving each antibiotic response signature individually.

Importantly, the expression signatures alone merely show that reliable differences occur in the transcriptional response in susceptible versus resistant organisms, while AST requires binary classification of a strain as susceptible or resistant. To address this general classification problem, machine-learning algorithms were deployed (FIG. 5, phase 1), first to identify the most informative transcripts, and second to use these select transcripts to classify unknown isolates. To avoid overtraining, the tested strains were partitioned into a training (derivation) cohort for both feature selection and classifier training, and a testing (validation) cohort as a naïve strain set for assessing classifier performance. ReliefF (Robnik-Šikonja and Kononenko 2003) was used to identify the 10 transcripts whose normalized expression best distinguished susceptible from resistant organisms among the training cohort (FIGS. 6, 14B, 14E; Table 9). Although fewer than 10 transcripts were required to robustly distinguish between the strains thus far tested, more genes were kept in the optimized signature to lessen the potential impact of unanticipated diversity in gene content, sequence, or regulation among clinical isolates.

Figure 6:
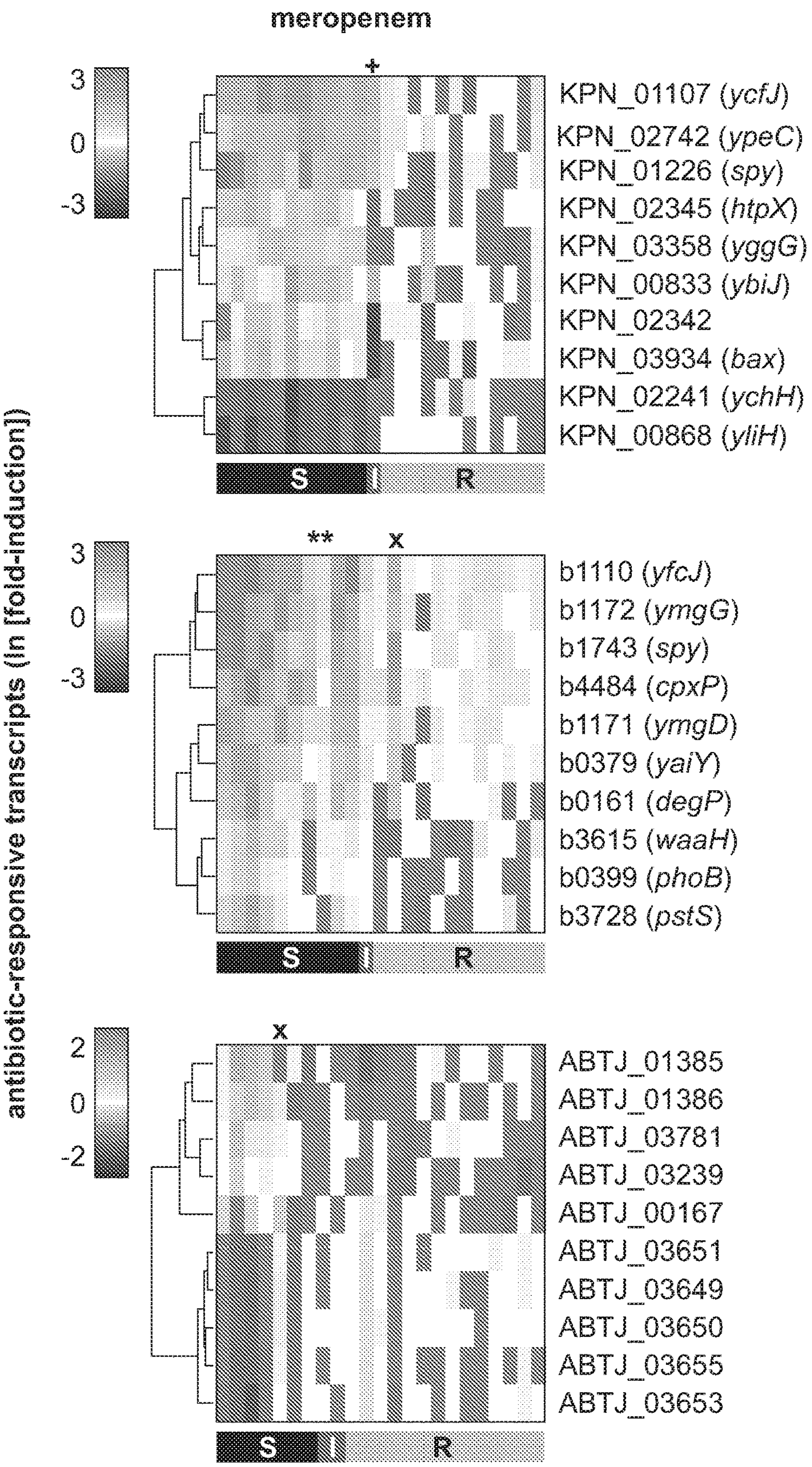
FIG. 6 shows that NanoString® data for top 10 antibiotic-responsive transcripts distinguished susceptible from resistant strains. Heatmaps of normalized, log-transformed fold-induction of top 10 antibiotic-responsive transcripts from 18-24 clinical isolates of *K. pneumoniae* (top), *E. coli* (middle), or *A. baumannii* (bottom) treated at CLSI breakpoint concentrations with meropenem (left), ciprofloxacin (center), or gentamicin (right) are shown, with strains arranged in order of MIC for each antibiotic. Gene identifiers are listed at right, along with gene names if available. CLSI classifications of each strain based on broth microdilution are shown below. *=strains with large inoculum effects in meropenem MIC; +=one-dilution errors; x=strains discordant by more than one dilution.
Figure 6:
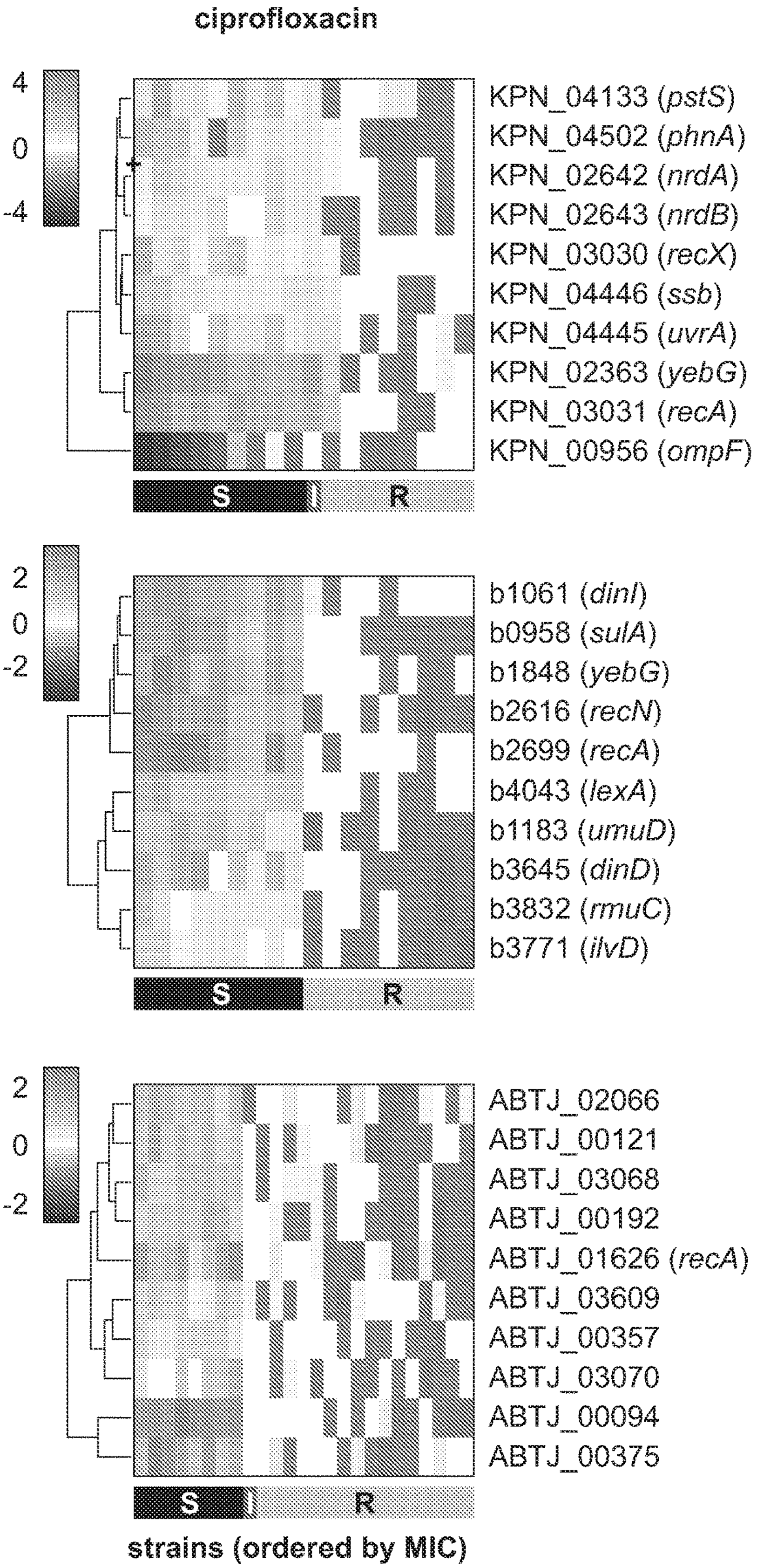
Figure 6:
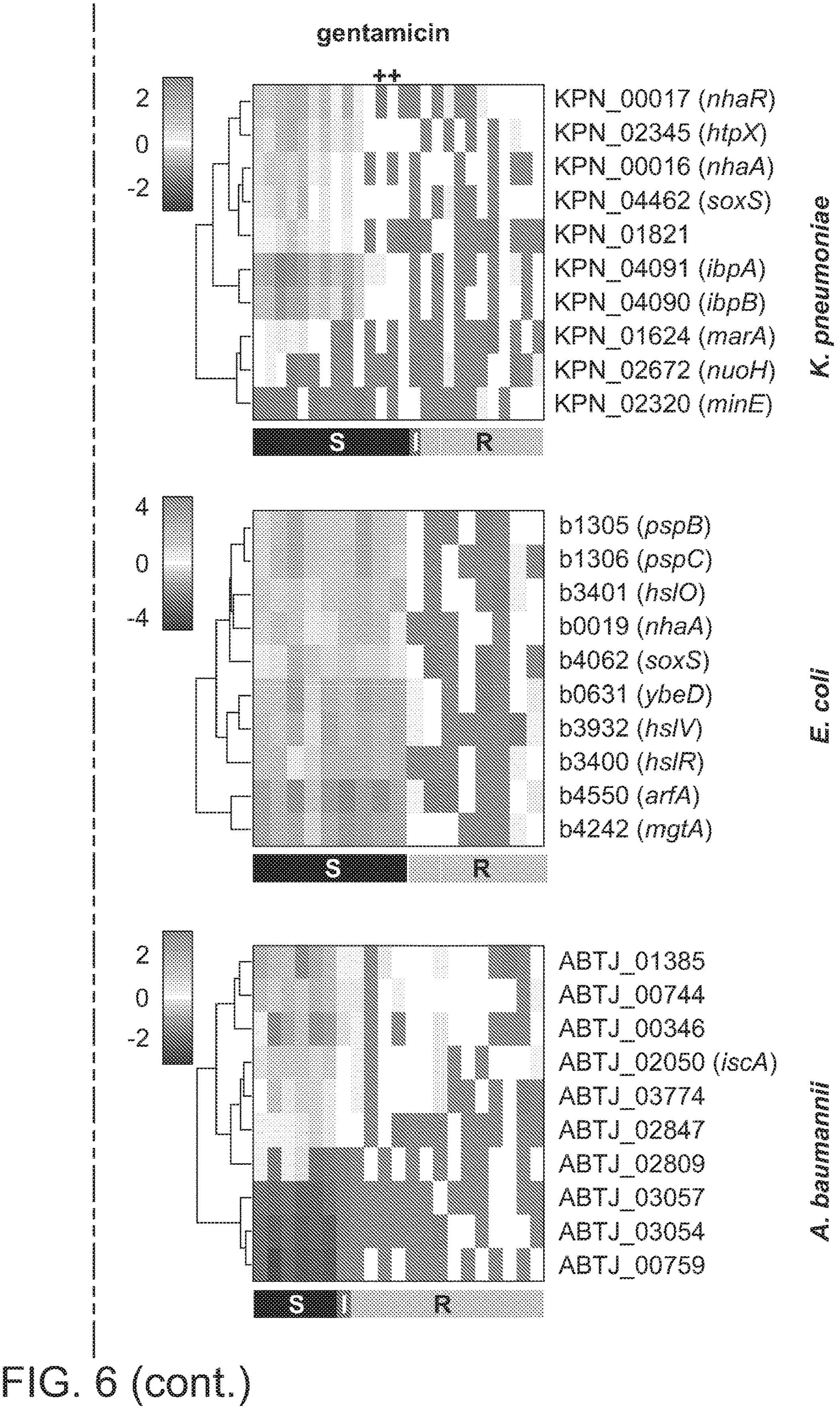
Figure 7A:
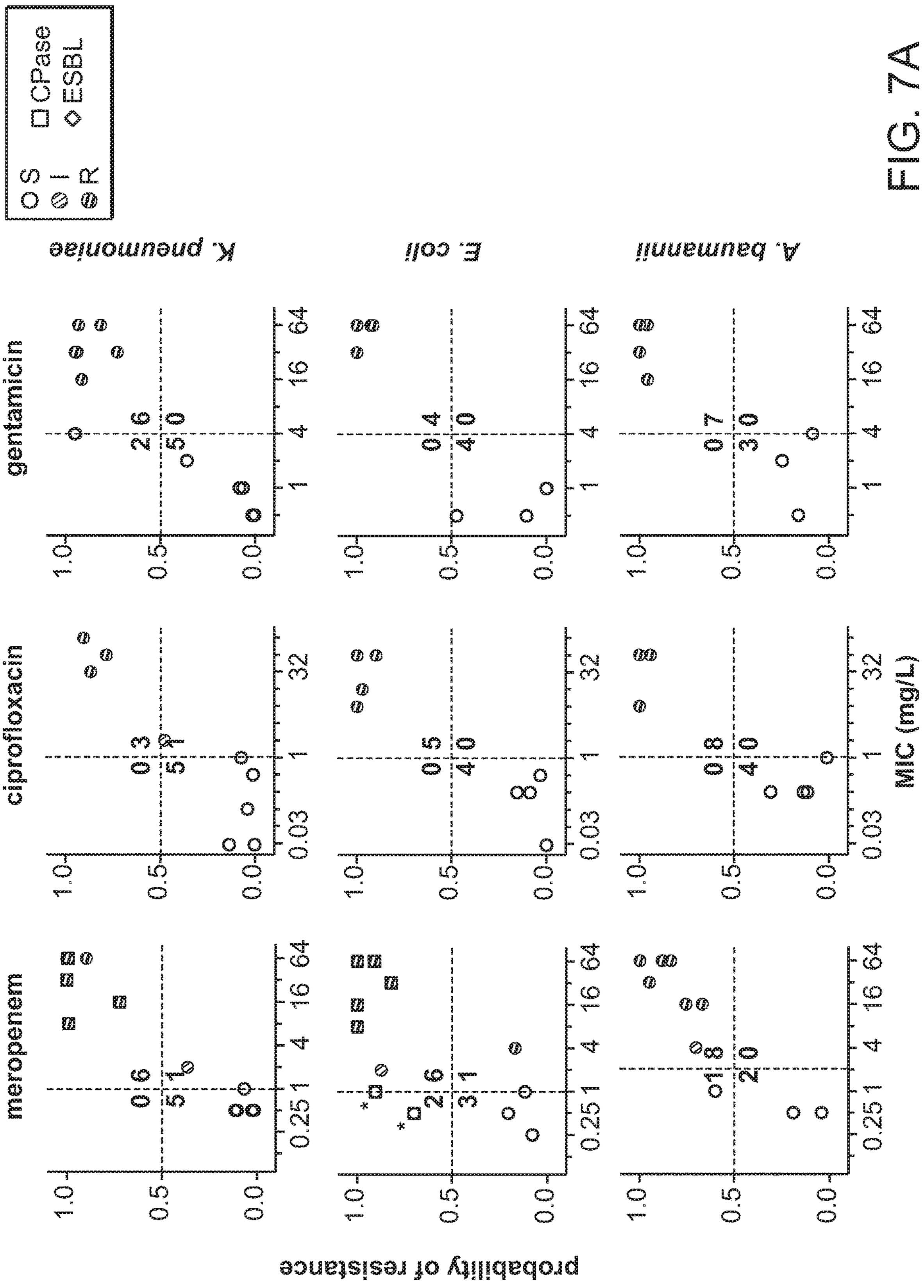
FIGS. 7A and 7B show that GoPhAST-R accurately classified clinical isolates.

Next, an ensemble classifier was trained using the random forest algorithm (Liaw & Wiener) to perform binary classification of isolates in the derivation cohort based solely on these selected features. Finally, this trained classifier was tested on the validation cohort. Across all 11 bacteria-antibiotic combinations, 109 isolates were used as derivation strains for training, and 108 isolates were tested as validation. The ensemble classifier correctly classified 100 of these 108 (93% categorical agreement, 95% confidence interval [CI] 87-96% by Jeffrey's interval (Brown et al.)), including 51 of 52 resistant isolates (1.9% very major error rate, 95% CI 0.21-8.6%) and 35 of 38 susceptible isolates (7.9% major error rate, 95% CI 2.3-20%), compared with standard broth microdilution (FIGS. 7A, 14C, 14F; Table 10). Of note, both categorical agreement and rates of very major and major errors are typically reported on a natural distribution of isolates. In contrast, as disclosed herein, a "challenge set" of isolates was deliberately assembled, one that was intentionally overrepresented for isolates near the clinical breakpoints, which will tend to artificially inflate all errors, since discrepant classifications are more common for strains with MICs near the breakpoint-both due to possible errors in the assay and to one-dilution errors inherent in the gold standard broth microdilution assay (CLSI). Consistent with this, all major and very major errors in Phase 1 testing involved strains less than or equal to two dilutions away from the breakpoint ("+" in FIG. 3). Two apparent major errors exhibited large inoculum effects ("*" in FIG. 6 and FIG. 3, discussed below) in carbapenemase-producing strains reported as resistant by GoPhAST-R but susceptible by standard broth microdiluton. These two likely represent isolates that are misclassified as susceptible by the gold standard method (Anderson et al. 2007; Centers for Disease and Prevention 2009; Nordmann, Cuzon, and Naas 2009; Weisenberg et al. 2009) but correctly recognized as resistant by GoPhAST-R.

Figure 5:
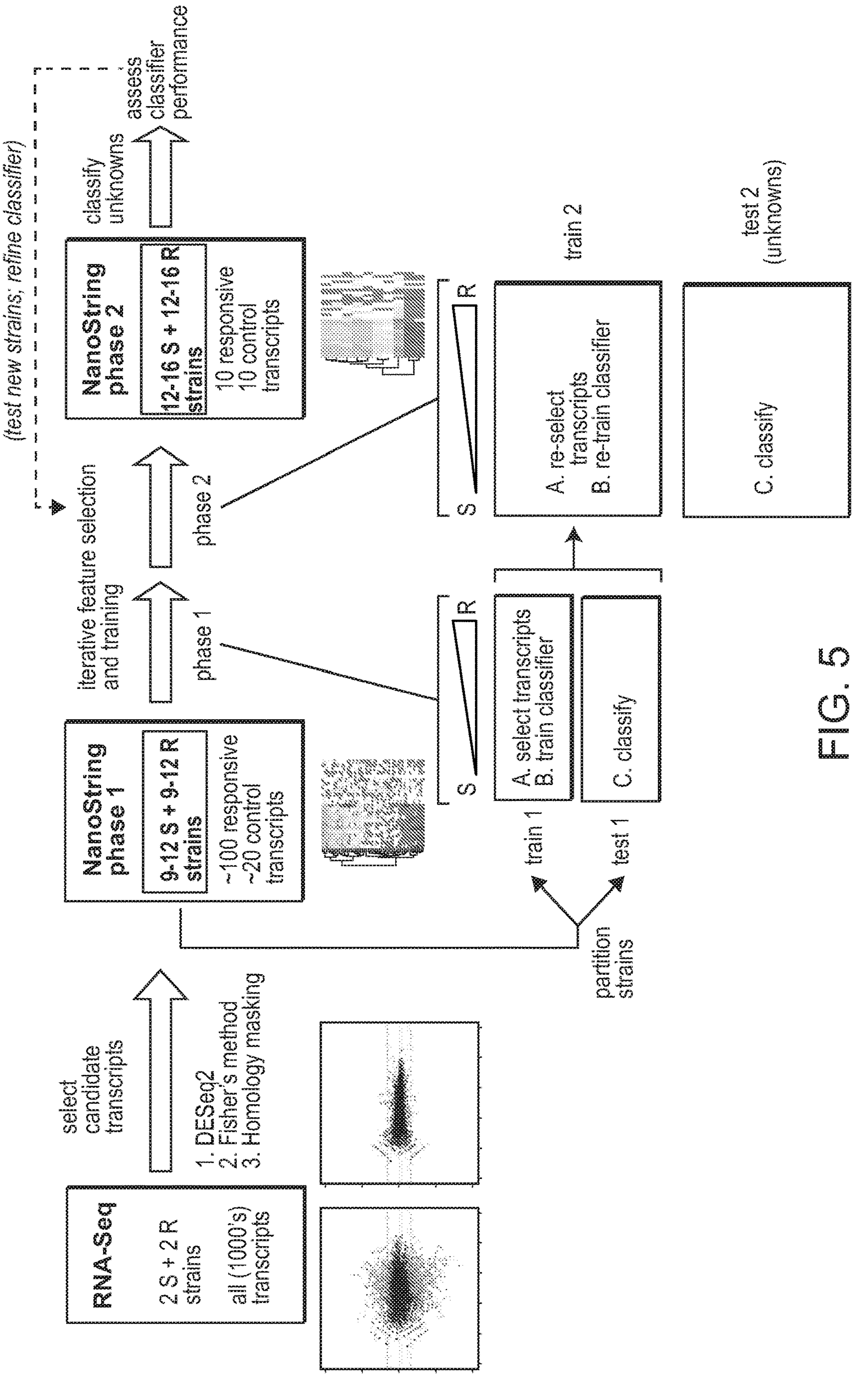
FIG. 5 depicts a schematic of the data analysis scheme of the instant disclosure, including the "two-phase" machine learning approach to feature selection and strain classification employed herein. The schematic representation shows major data analysis steps employed for identifying antibiotic-responsive transcriptional signatures from RNA-Seq data, validating and optimizing these signatures using NanoString® in two phases, and using these signatures to classify strains of unknown MIC, also in two phases. First, candidate antibiotic-responsive and control transcripts were chosen from RNA-Seq data using custom scripts built around the DESeq2 package, and conserved regions of these transcripts were identified for targeting in a hybridization assay. In phase 1 (implemented for all pathogen-antibiotic pairs), these candidate transcripts were quantitated on the NanoString® assay platform, and the resulting data were partitioned by strain into training and testing cohorts. Ten transcripts that best distinguished susceptible from resistant strains within the training cohort were then selected (step 1A) using the reliefF feature selection algorithm (implemented via the CORElearn package), then used to train an ensemble classifier (step 1B) on the same training cohort using a random forest algorithm (implemented via the caret package). This trained classifier was then used to predict susceptibilities of strains in the testing cohort (step 1C), and accuracy was assessed by comparing with broth microdilution results (Table 10). In phase 2 (implemented for *K. pneumoniae*+meropenem and ciprofloxacin), the same process was repeated, but the phase 1 training and testing cohorts were combined into a single, larger training cohort for feature selection (step 2A) and classifier training (step 2B), and a new set of strains was obtained as a testing cohort. The 10 genes selected from the phase 2 training cohort were measured from this phase 2 testing cohort, and the trained classifier was used for AST on these new strains (step 2C), with accuracy again assessed by comparison with broth microdilution (Table 10). See Supplemental Methods for detailed descriptions of each of these analysis steps.
Figure 7B:
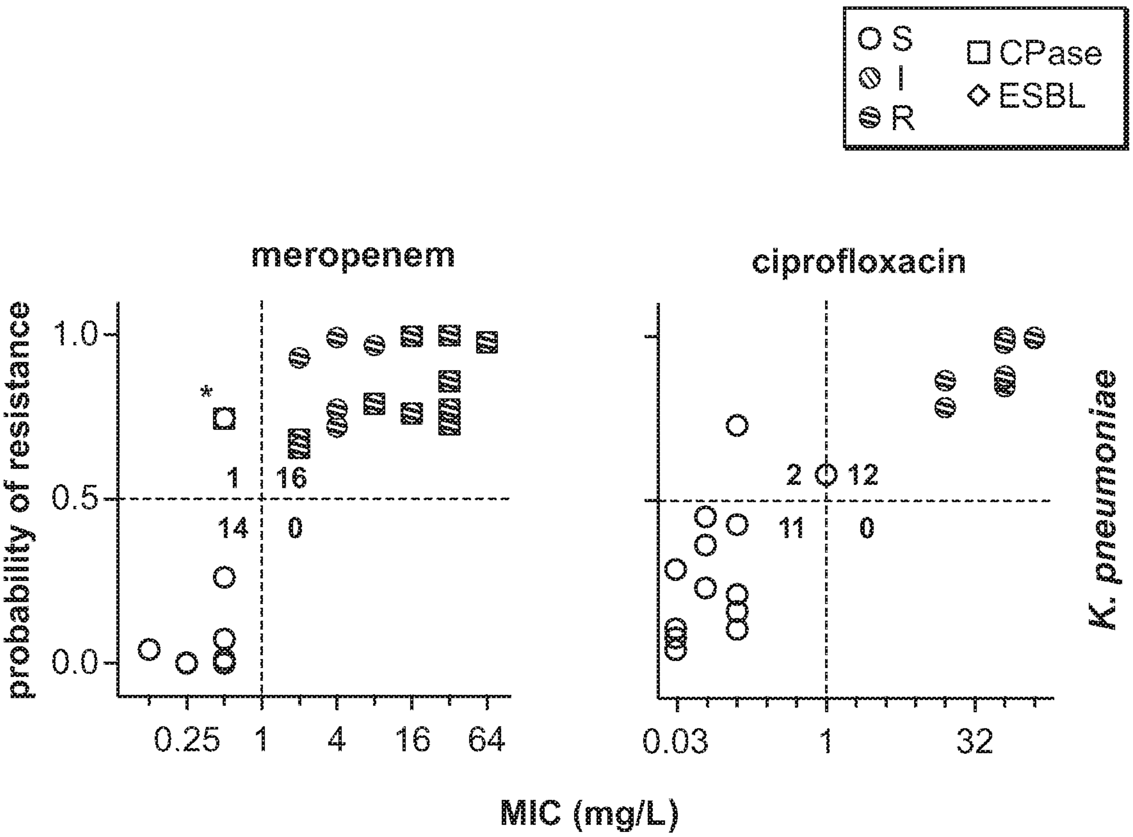
Figure 8:
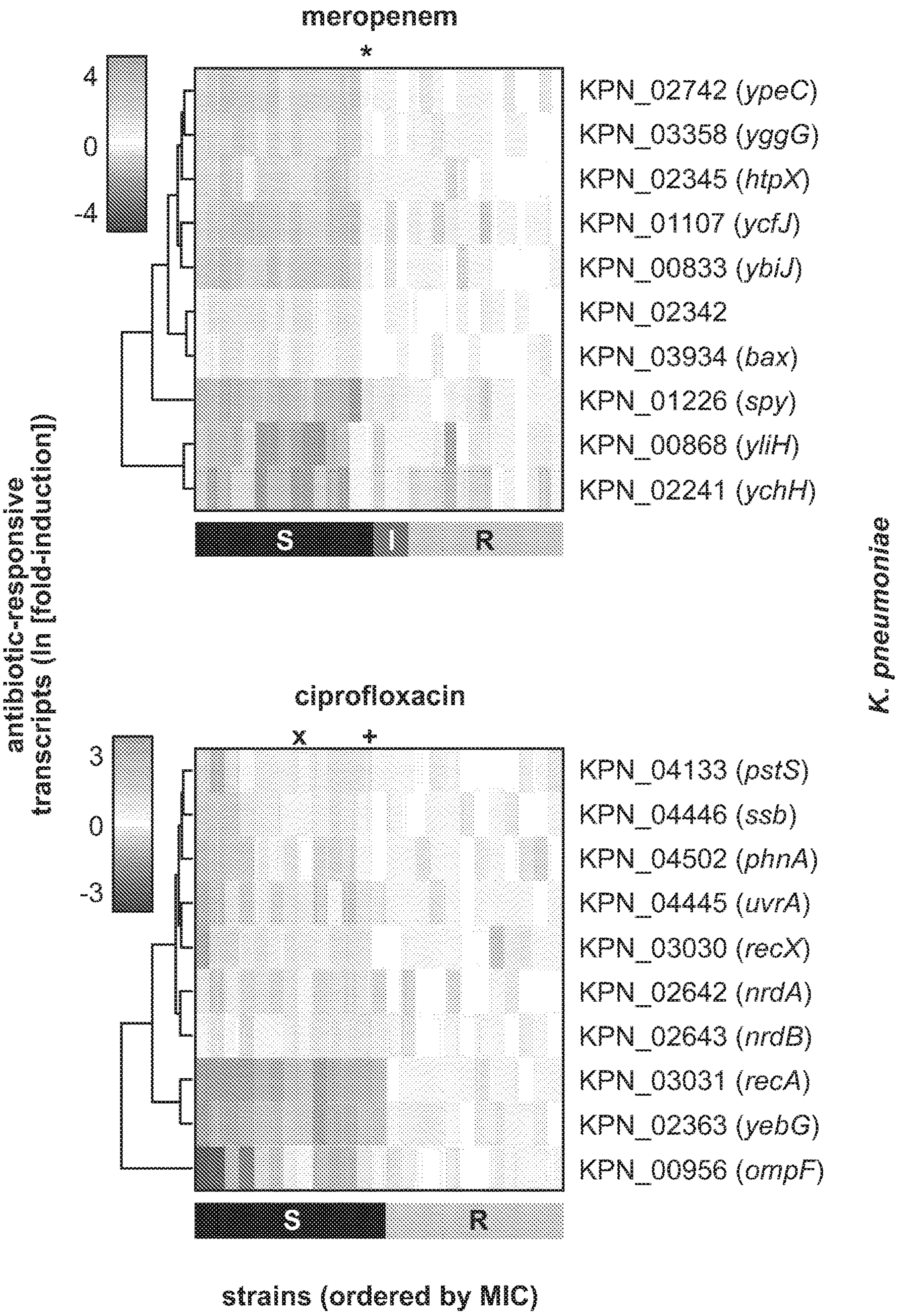
FIG. 8 shows NanoString® data for top 10 antibiotic-responsive transcripts for strains tested in phase 2. Heatmaps of normalized, log-transformed fold-induction of top 10 antibiotic-responsive transcripts observed from 25-31 clinical isolates of *K. pneumoniae* treated at CLSI breakpoint concentrations with meropenem (left) or ciprofloxacin (right) are shown, with strains arranged in order of MIC for each antibiotic. CLSI classifications are shown below. *=strain with large inoculum effects in meropenem MIC; +=one-dilution error; x=strain discordant by more than one dilution. Note that the 10 responsive transcripts shown were the only 10 tested for this second phase of GoPhAST-R implementation.

To assess this approach to classification as it would be deployed on unknown isolates, and to ensure against over-training on the initial set of isolates, a second, iterative round of training was performed on all strains from the initial phase of classification and tested a new set of *Klebsiella pneumoniae* isolates treated with meropenem and ciprofloxacin (FIG. 5, phase 2). The initial derivation and validation cohorts were combined into a single, larger training cohort, on which feature selection was repeated and retrained for the ensemble classifier. The top 10 features chosen in phase 2 were very similar to those chosen in phase 1 (Table 9), with 78% mean overlap in gene content, mean Jaccard similarity coefficient 0.67, and mean Spearman correlation coefficient 0.59 across all pathogen-antibiotic combinations. This refined classifier was then applied to predict susceptibility in a new test set of 25-30 isolates for each antibiotic (FIG. 8), this time measuring only the top 10 selected responsive transcripts, rather than the 60-100 transcripts measured in phase 1. Here, GoPhAST-R correctly classified 52 of 55 strains (95% categorical agreement, 95% CI 86-98%) (FIG. 7B), including all 25 resistant isolates (0% very major error rate, 95% CI 0-9.5%) and 25 of 27 susceptible isolates (7.4% major error rate, 95% CI 1.6-22%), compared with broth microdilution. One of the three discrepant isolates is only one dilution from the breakpoint (FIG. 8), and another exhibits a large inoculum effect (FIG. 8) in a carbapenemase-producing strain that was reported as resistant by GoPhAST-R, likely the same phenomenon described above.

Three isolates classified as meropenem-resistant by GoPhAST-R but susceptible by broth microdilution exhibited a large inoculum effect. These three isolates, a *K. pneumoniae* (BAA2524) and two *E. coli* (BAA2523 and AR0104), all had MICs of 0.5-1 mg/L on standard broth microdilution with an inoculum of $10^5$ cfu/mL, but MICs of ≥32 mg/L with an inoculum of $10^7$ cfu/mL. Each of these strains carried a carbapenemase gene: BAA2523 and BAA2524 contained $bla_{OXA\text{-}48}$, and AR0104 contained $bla_{kPC\text{-}4}$, as has been reported for other such strains with large inoculum effects (Adams-Sapper et al. 2015; Adler et al. 2015). While the clinical consequences of such large inoculum effects are uncertain, they may portend clinical failure (Paterson et al. 2001), particularly in the setting of carbapenemase production (Weisenberg et al. 2009); detection of this phenomenon is a known gap in standard broth microdilution assays (Humphries, R. M.) because they are performed at the lower inoculum (Smith and Kirby 2018; Wiegand, Hilpert, and Hancock 2008). GoPhAST-R recognized these strains as resistant, perhaps because the assay was performed at higher cell density (>$10^7$ cfu/mL), whereas conventional methods missed these CREs.

Importantly, the ability of the classifier disclosed herein to accurately call a strain susceptible or resistant was independent of resistance mechanism, as exemplified for meropenem resistance. In total, 22 of 47 meropenem-resistant isolates, including 7 of 22 *K. pneumoniae,* 4 of 12 *E. coli*, and 11 of 13 *A. baumannii*, lacked carbapenemases (Table 7; Cerqueira et al. 2017; (www)cdc.gov/ARIsolateBank/), yet 46 of these 47 isolates were correctly recognized as resistant by GoPhAST-R. These results underscore the ability of GoPhAST-R to assess phenotypic resistance, agnostic to its genotypic basis.

Example 6: Combining Genotypic and Phenotypic Information in a Single Assay Improves Accuracy in Carbapenem Resistance Detection and Enables Molecular Epidemiology Since GoPhAST-R involves multiplexed, hybridization-based RNA detection, the techniques herein can readily accommodate simultaneous profiling of additional transcripts, including genetic resistance determinants such as carbapenemases. GoPhAST-R can thus provide valuable epidemiological data as well as resolve discrepancies between phenotype-based detection and standard broth dilution methods by providing genotypic information. For example, in the three cases with discrepant classifications and prominent inoculum effects, each isolate carried a carbapenemase gene. By incorporating probes to simultaneously detect resistance determinants such as carbapenemase genes, the genotypic component of GoPhAST-R can provide complementary evidence to reinforce its phenotypic call of resistance. This can be critical for the complex case of CRE detection (Anderson et al. 2007; Arnold et al. 2011; Centers for Disease and Prevention 2009; Gupta et al. 2018; Nordmann, Cuzon, and Naas 2009; Weisenberg et al. 2009): even the American Type Culture Collection, the source of archived strains BAA2523 and BAA2524, recognized this discrepancy in AST, noting that these carbapenemase-producing isolates were reported as susceptible upon deposition but tested resistant by other methods (ref: ATCC pdf comments (see e.g., World Wide Web at (www)atcc.org/~/ps/BAA-2523.ashx).

Indeed, the most common known mechanism for carbapenem resistance among the Enterobacteriaceae involves the acquisition of one of several known carbapenemase genes (see e.g., Woodworth et al. 2018), most commonly the KPC, NDM, OXA-48, IMP, and VIM families (Martinez-Martinez and Gonzalez-Lopez 2014; Nordmann, Dortet, and Poirel 2012). Thus, probes were incorporated for these carbapenemases into the GoPhAST-R assay for meropenem AST, as well as two extended-spectrum beta-lactamase (ESBL) gene families that have been associated with carbapenem resistance when expressed in the context of porin loss-of-function, CTX-M-15 (Canton et al.; Cubero et al.) and OXA-10 (Ma et al. 2018) (Table 9). Of note, conventional PCR-based detection of the IMP and VIM gene families has been challenging because of their genetic diversity (Kaase et al.) and the relative intolerance of PCR to point mutations in primer binding sites, especially towards 3' end of the primer (Paterson et al.; Klungthong et al.). In contrast, hybridization is more tolerant to point mutations and is amenable to a multiplexed format that allows the inclusion of multiple probes to recognize different regions of the same target, and thus identify targets with greater diversity. For instance, the currently disclosed GoPhAST-R includes 4 separate probe pairs to increase robustness of IMP detection (Table 9; see section below on Homology Masking).

Figure 9A:
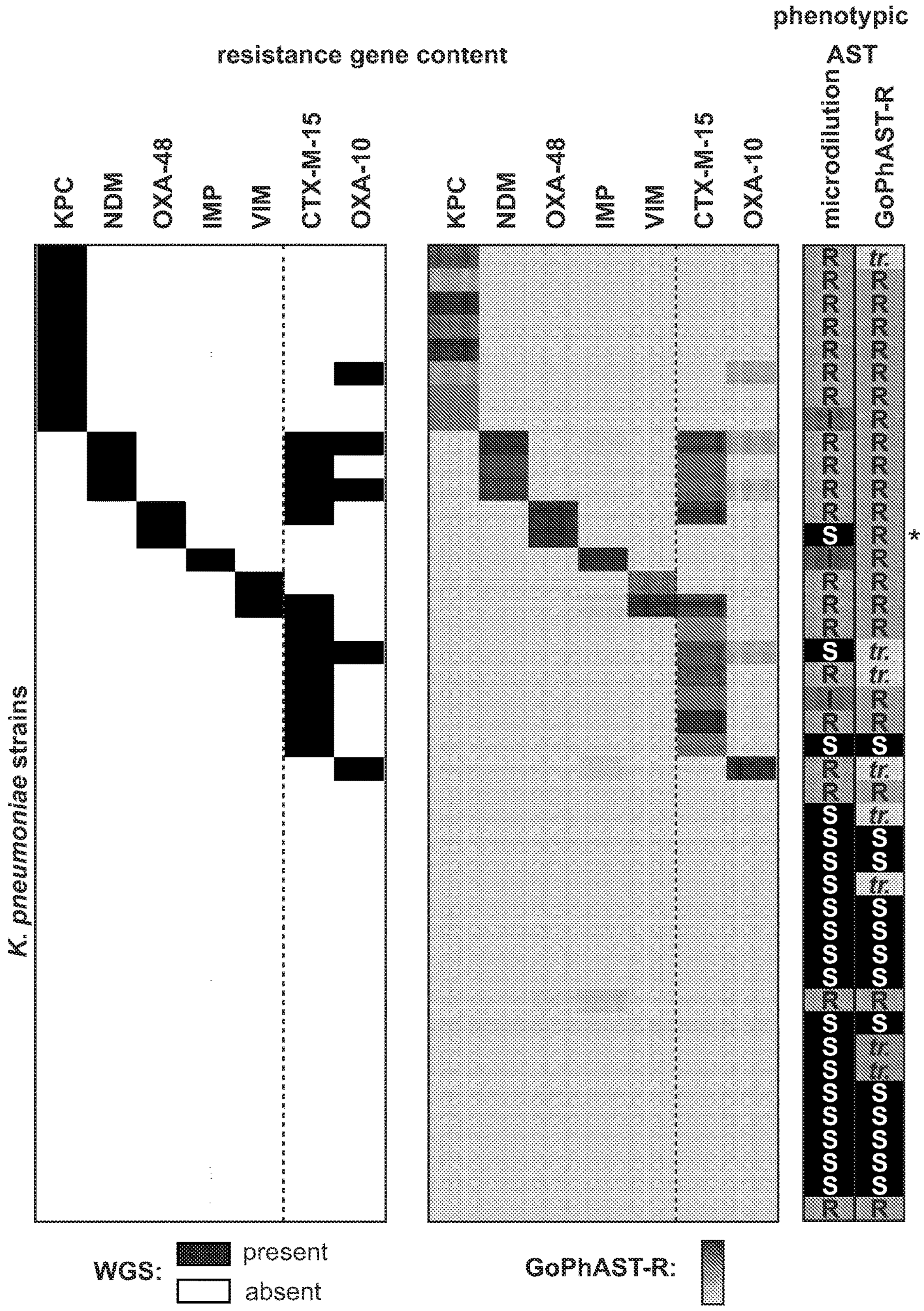
FIGS. 9A-9C show that GoPhAST-R detected carbapenemase and ESBL gene content from tested strains. Known carbapenemase and select ESBL transcript content based on WGS data (left panels) were compared with heatmaps of GoPhAST-R results (right panels) for all *K. pneumoniae* (FIG. 9A), *E. coli* (FIG. 9B), and *A. baumannii* (FIG. 9C) isolates tested for meropenem susceptibility for which WGS data were available. Heatmap intensity reflects normalized, background-subtracted, log-transformed NanoString® data from probes for the indicated gene families. Vertical dashed line separates carbapenemases (left) from ESBL genes (right). Phenotypic AST classification by broth microdilution and GoPhAST-R is shown at right ("S"=susceptible, "I"=intermediate, "R"=resistant; "tr."=strain used in training cohort, thus not classified by GoPhAST-R). *=strains with large inoculum effects in meropenem MIC; x=strain discordant by more than one dilution.
Figure 9B:
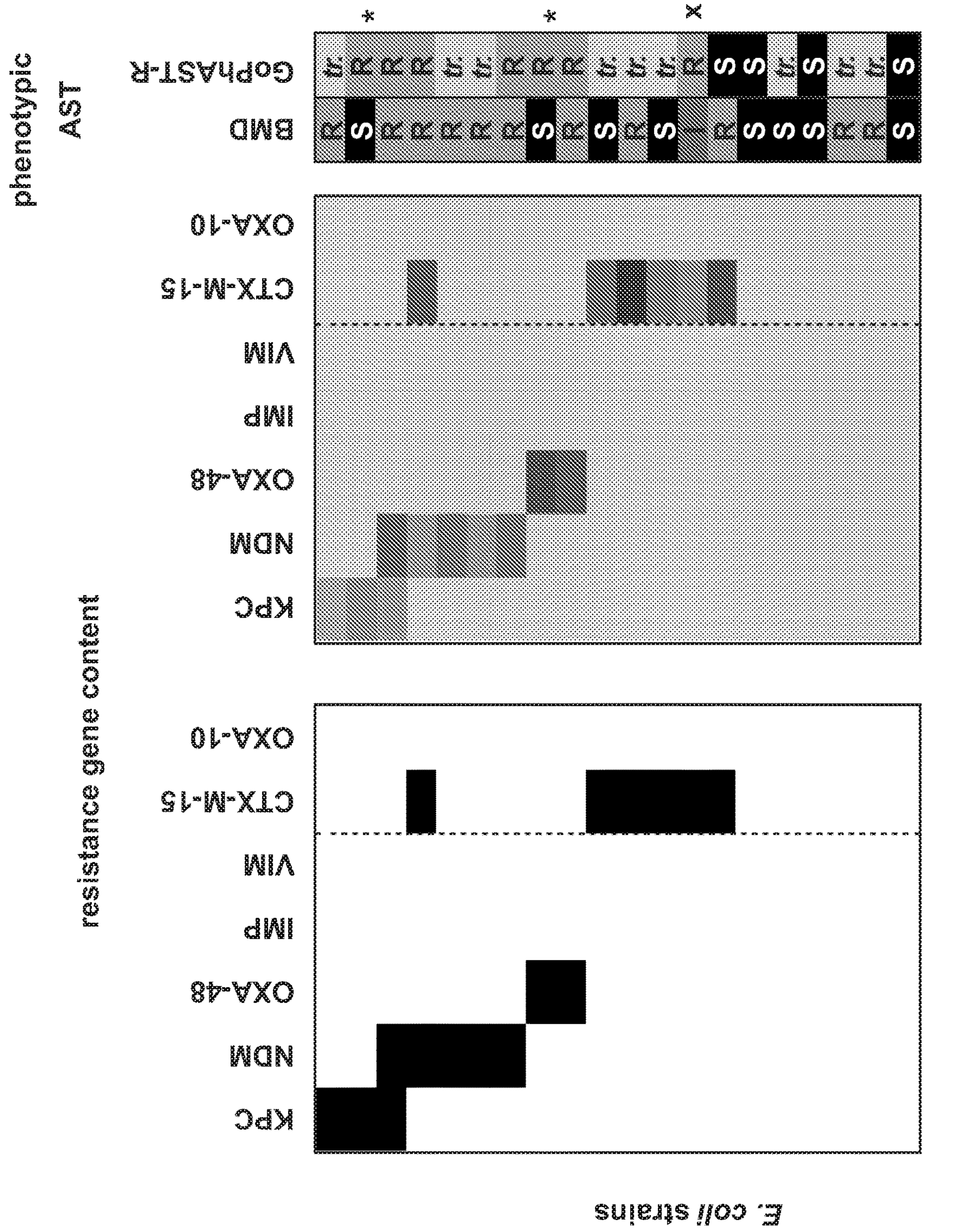
Figure 9C:
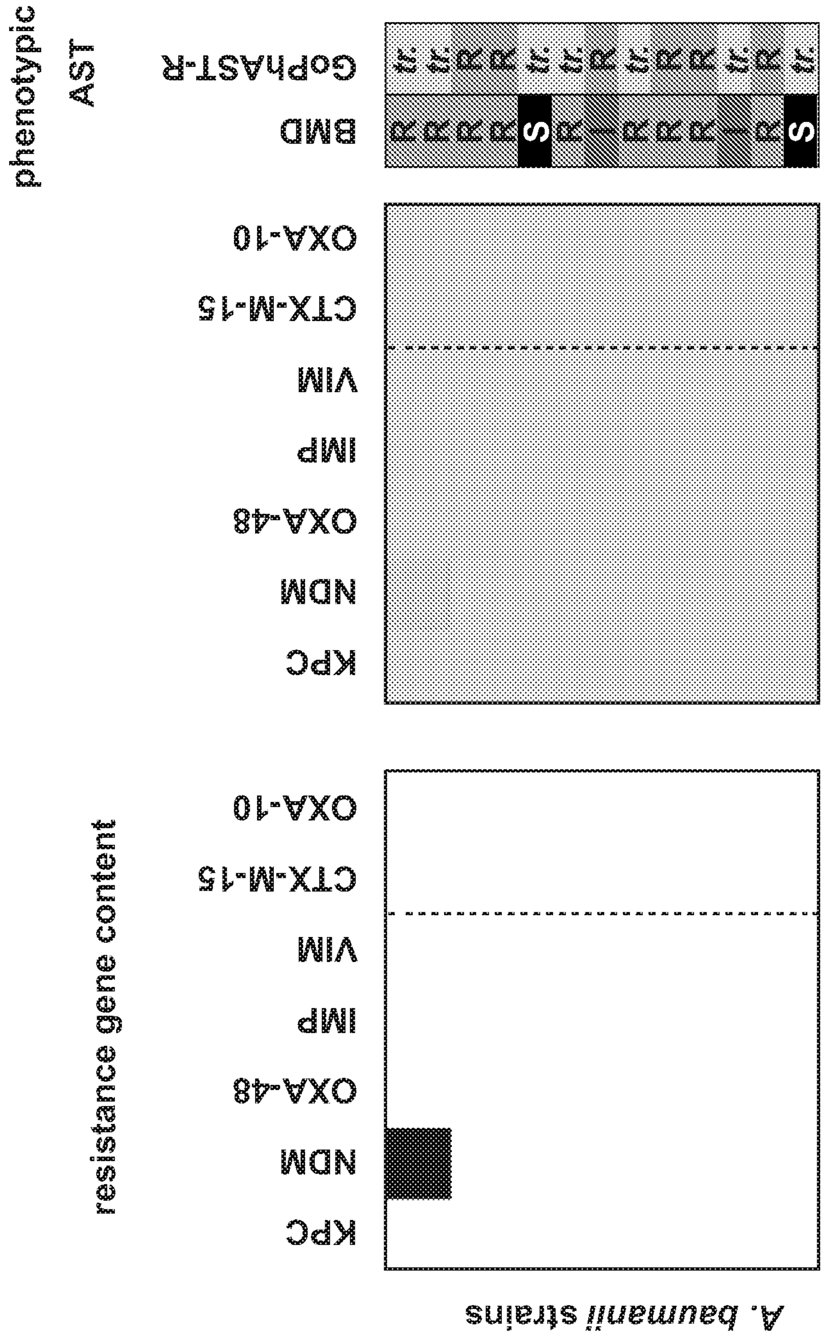

GoPhAST-R detected all 39 carbapenemase genes across 38 strains known to be present by WGS, including at least one member of each of the five targeted classes, and all 29 ESBL genes across 26 strains; no signal was detected in the 25 meropenem-resistant strains nor the 38 susceptible isolates known to lack these gene families, across all three species (FIGS. 9A-9C; Table 7). This included detection of OXA-48 or KPC in the three cases of discrepant phenotypic AST classification and prominent inoculum effects. Thus, in a single assay, GoPhAST-R can provide both phenotypic AST and genotypic information about resistance mechanism.

Figure 10:
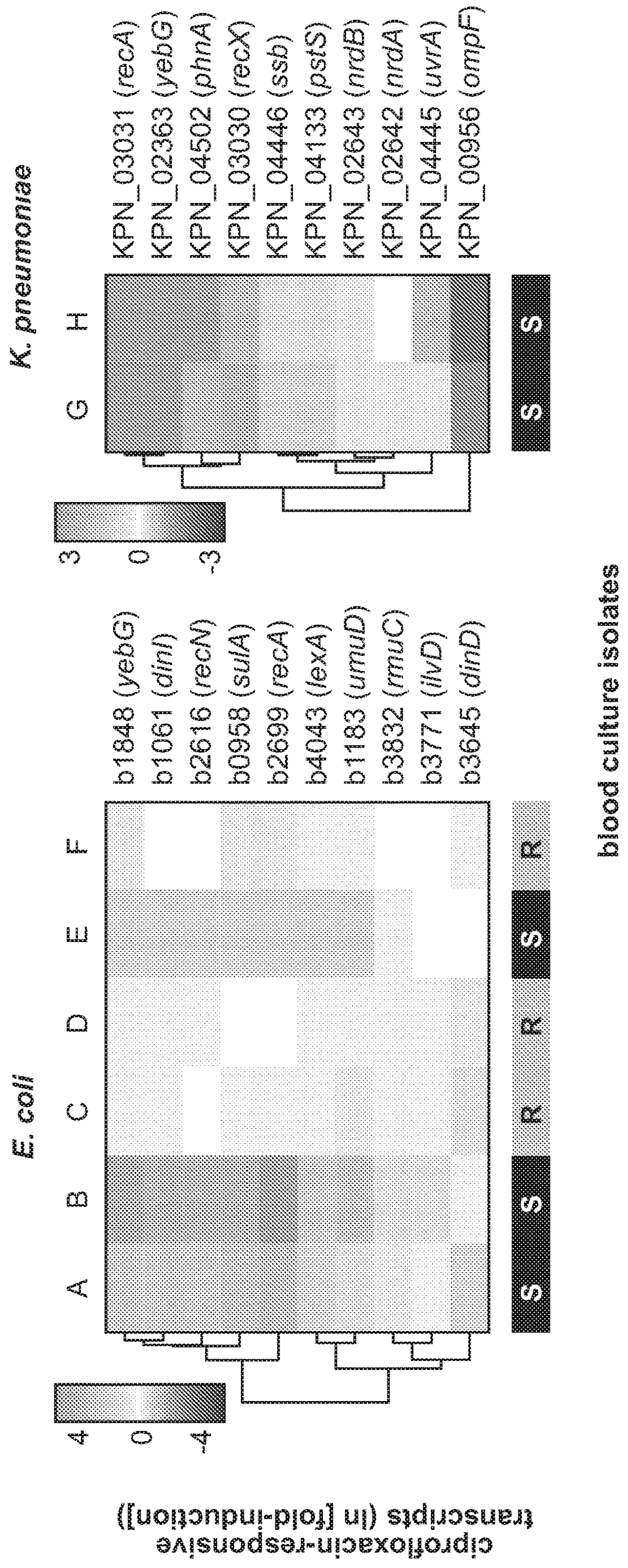
FIG. 10 shows that GoPhAST-R detected antibiotic-responsive transcripts directly from positive blood culture bottles. Heatmaps are shown of normalized, log-transformed fold-induction of the top 10 ciprofloxacin-responsive transcripts from 8 positive blood culture bottles that grew either *E. coli* (6 strains, A-F) or *K. pneumoniae* (2 bottles, G-H). CLSI classifications of isolates, which were blinded until analysis was complete, are displayed below each heatmap.
Figure 11A:
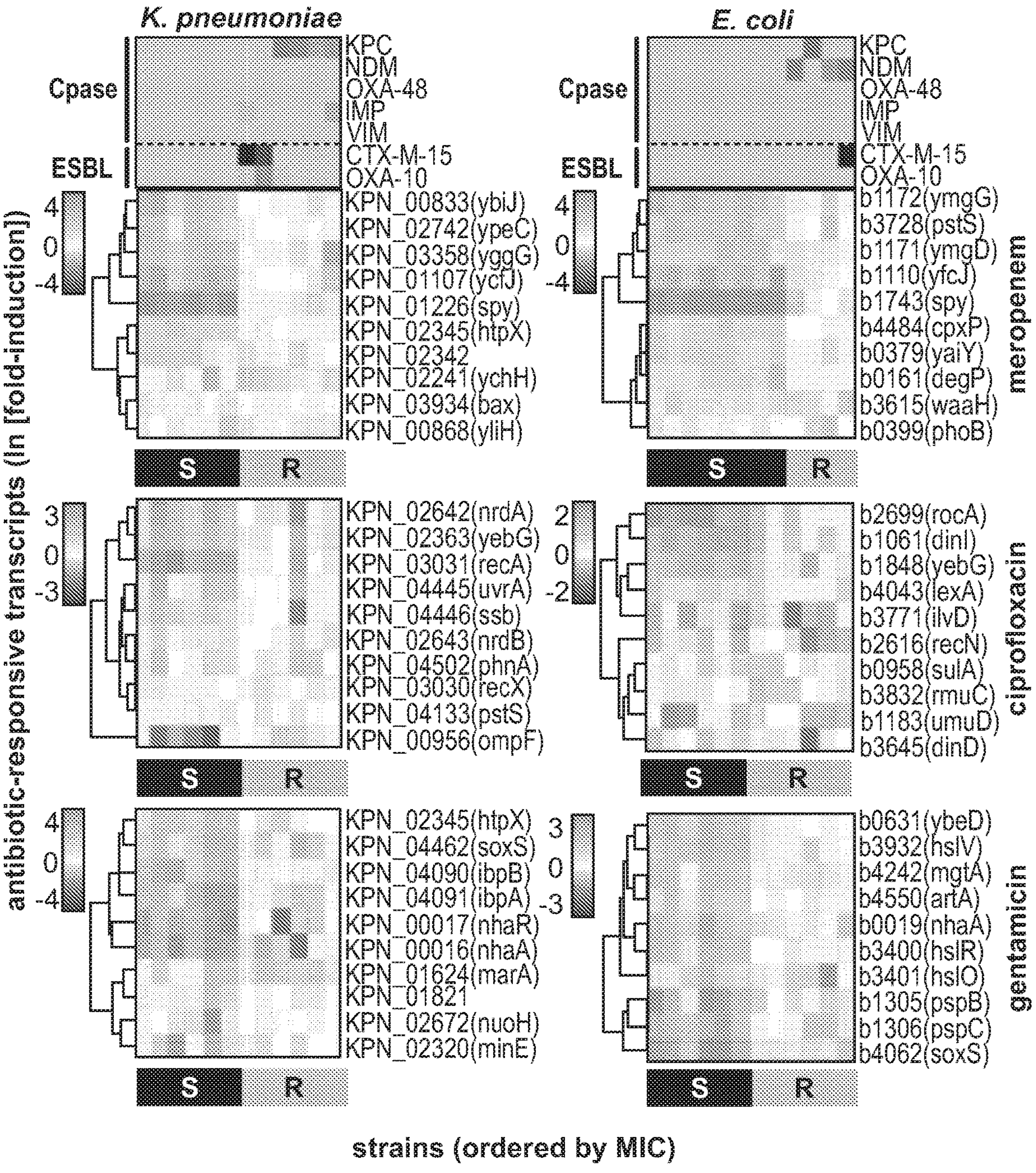
FIGS. 11A and 11B show that GoPhAST-R accurately classified AST and detected key resistance elements directly from simulated positive blood culture bottles in <4 hours.
Figure 11B:
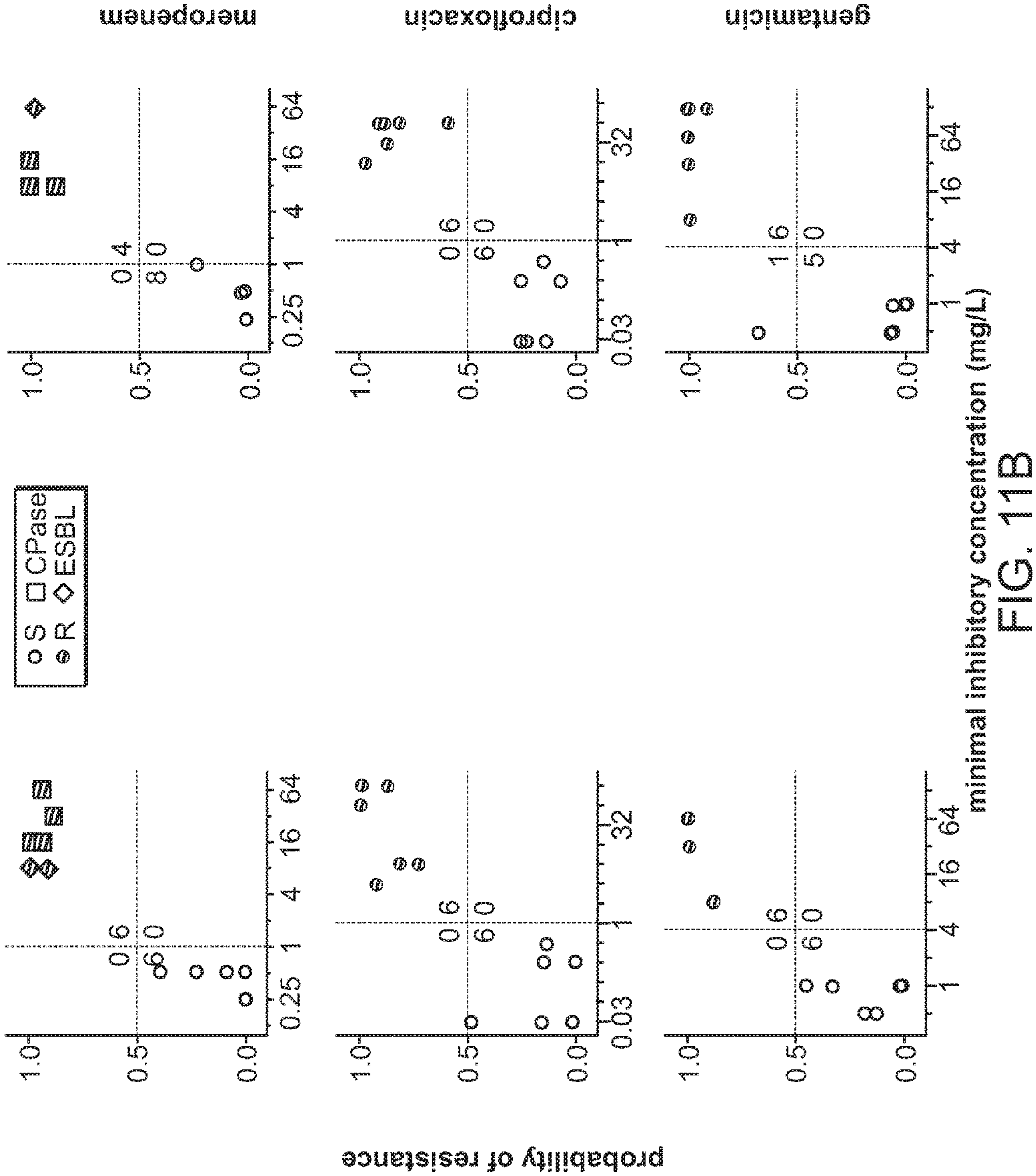

Example 7: GoPhAST-R can Measure Antibiotic Susceptibility Directly from Positive Blood Culture Bottles Previous work had demonstrated that a simulated positive blood culture bottle contains sufficient bacteria to permit mRNA detection (Hou et al. 2015). To demonstrate one clinical application, GoPhAST-R was used to rapidly determine ciprofloxacin susceptibility in blood culture bottles that grew gram-negative rods from the MGH clinical microbiology laboratory. Ciprofloxacin was chosen because no rapid genotypic method exists for detection of fluoroquinolone resistance due to the diversity of genetic alterations that can cause fluoroquinolone resistance, and because of the relative prevalence of fluoroquinolone resistance, making it feasible to acquire both sensitive and resistant cases. Six clinical *E. coli* and two *K. pneumoniae* positive blood cultures were tested (FIG. 10) and the techniques herein made it possible to clearly distinguish three susceptible from three resistant *E. coli*; both *K. pneumoniae* species were susceptible. Given the relative scarcity of gentamicin and meropenem resistant isolates available for the instant studies, to test assay performance in this growth format, simulated positive blood cultures were generated by spiking in susceptible or resistant isolates of *K. pneumoniae* and *E. coli*. GoPhAST-R detected optimized transcriptional signatures for each pathogen/antibiotic pair directly from these positive blood culture bottles (FIG. 11A), and AST prediction using a random forest model and leave-one-out cross-validation (Efron & Gong) (FIG. 11B) correctly classified 71 of 72 blood cultures (99% categorical agreement with broth microdilution, 95% CI 94-100%), including 0% very major error rate (31 of 31 resistant isolates classified correctly; 95% CI 0-7.7%) and 2.6% major error rate (37 of 38 susceptible isolates classified correctly; 95% CI 0.29-11%).

Figure 12A:
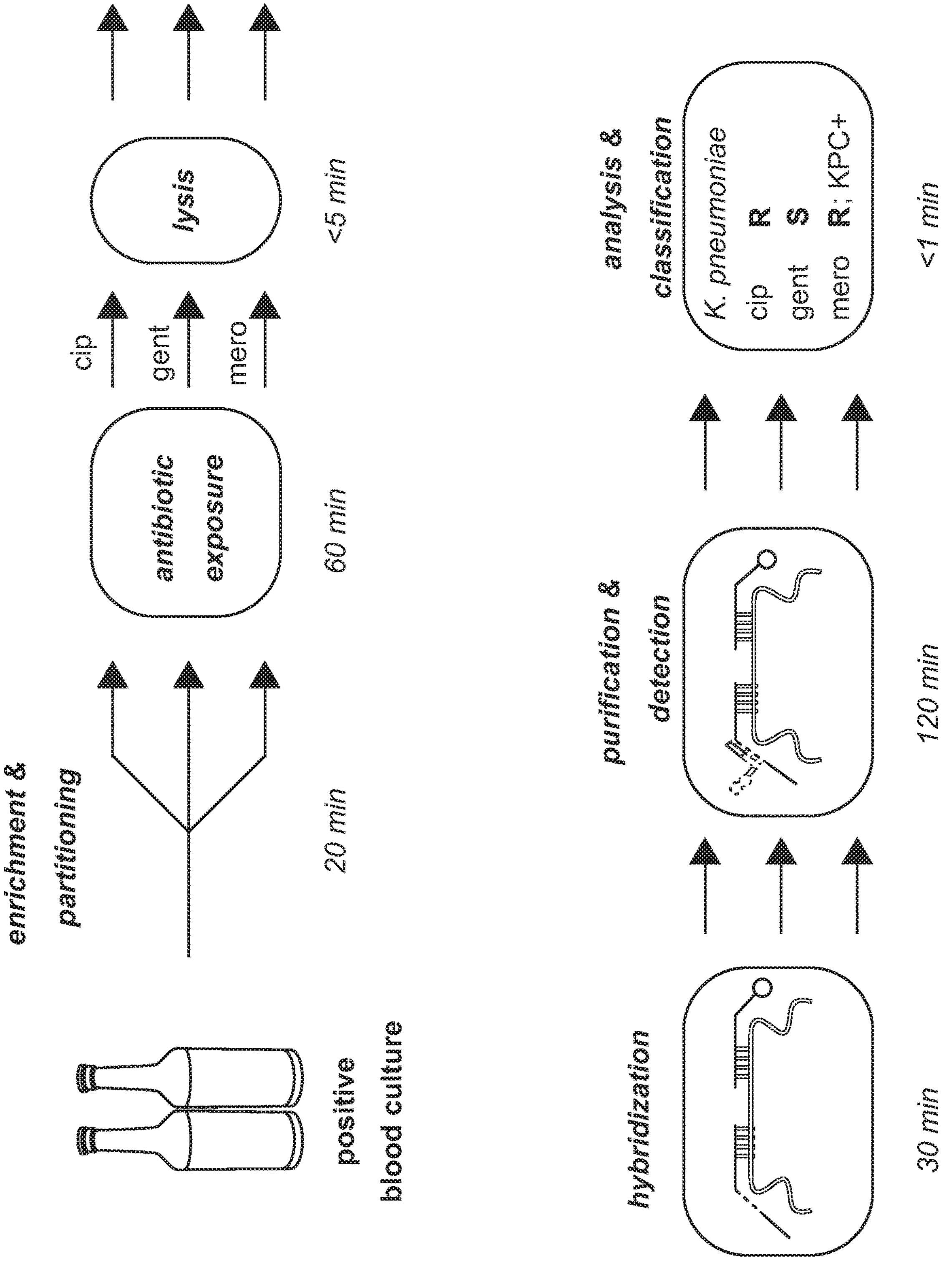
FIGS. 12A and 12B show for an exemplary GoPhAST-R workflow that the NanoString® Hyb & Seq™ platform distinguished phenotypically susceptible from resistant strains and detected genetic resistance determinants in <4 hours.
Figure 12B:
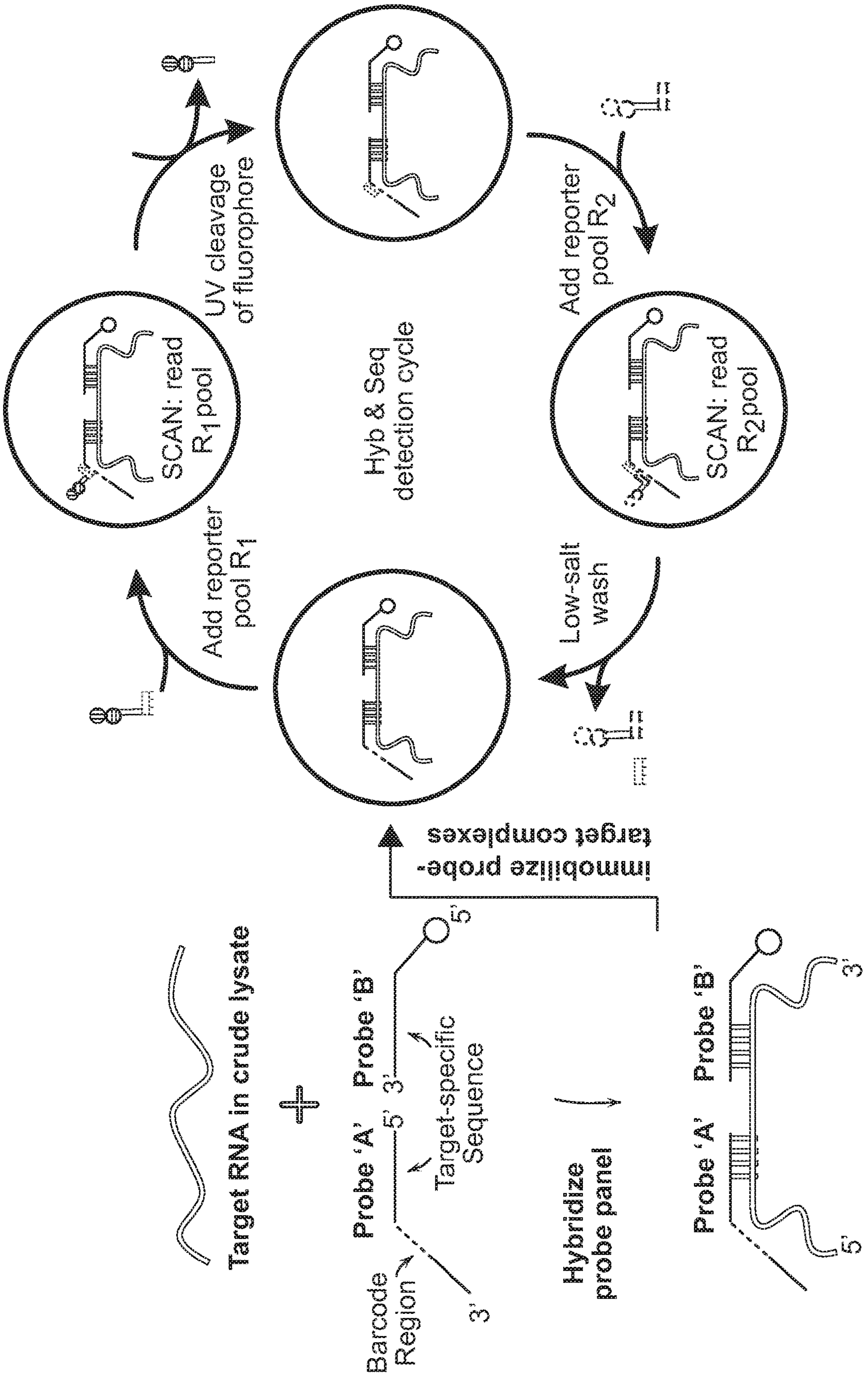
Figure 12B:
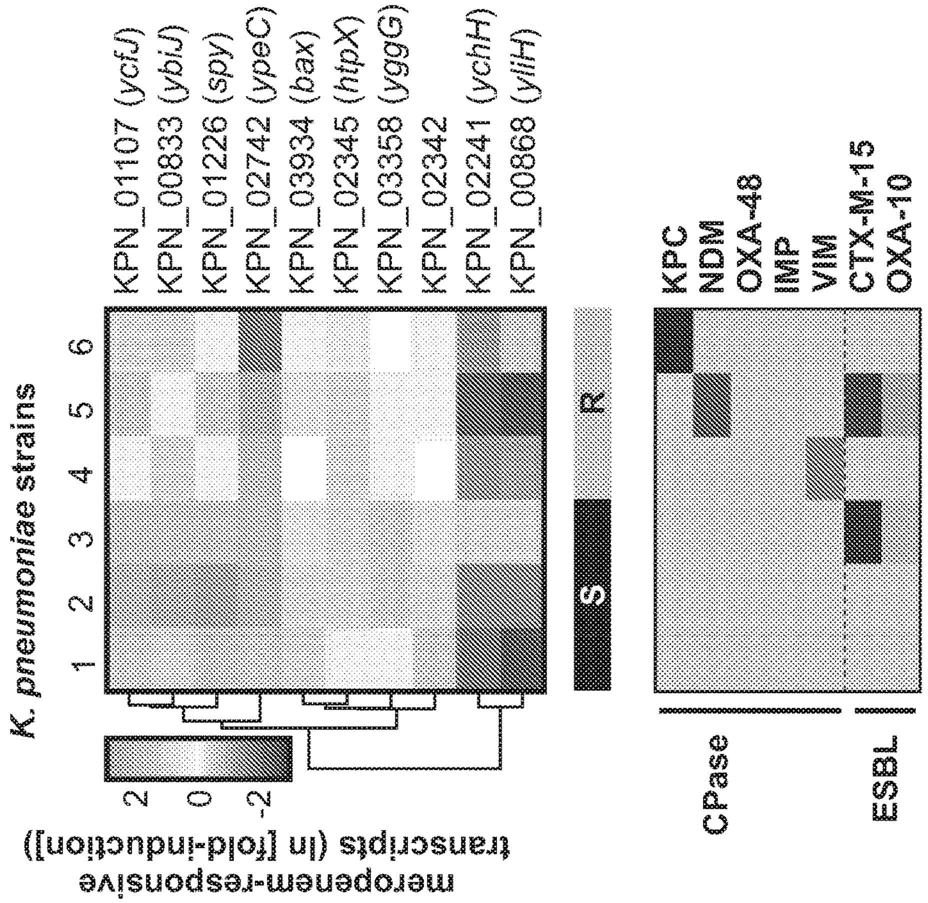
Figure 13A:
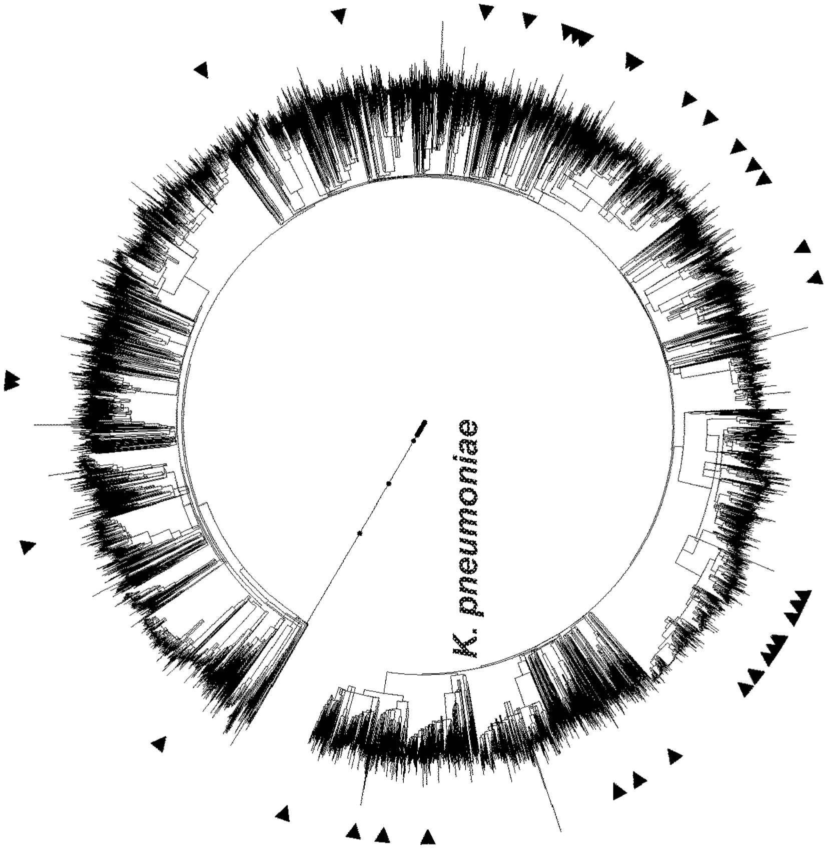
FIGS. 13A-13D show phylogenetic trees that highlight the diversity of strains used in that instant disclosure.
Figure 13B:
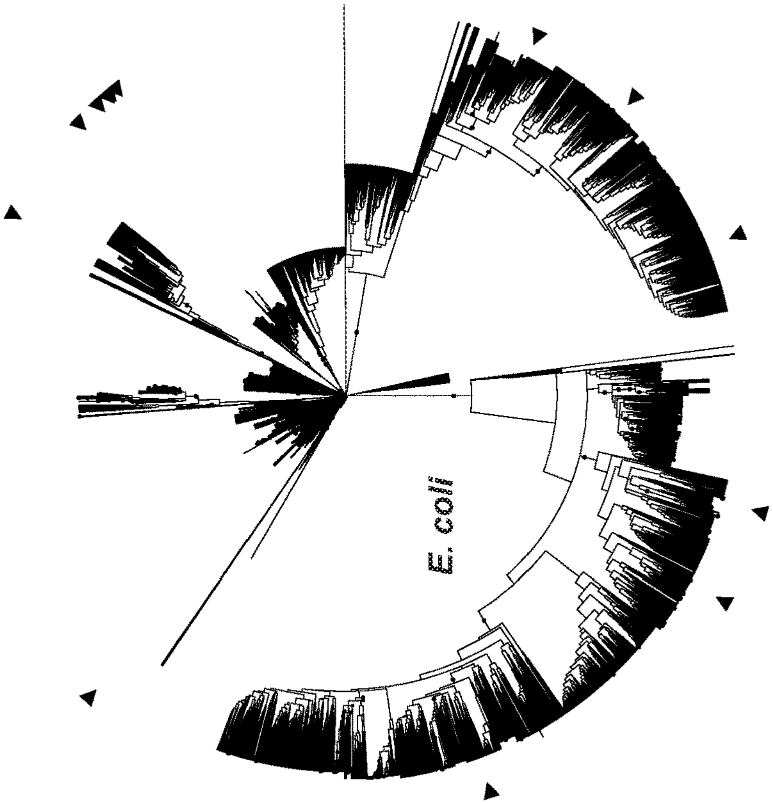
Figure 13D:
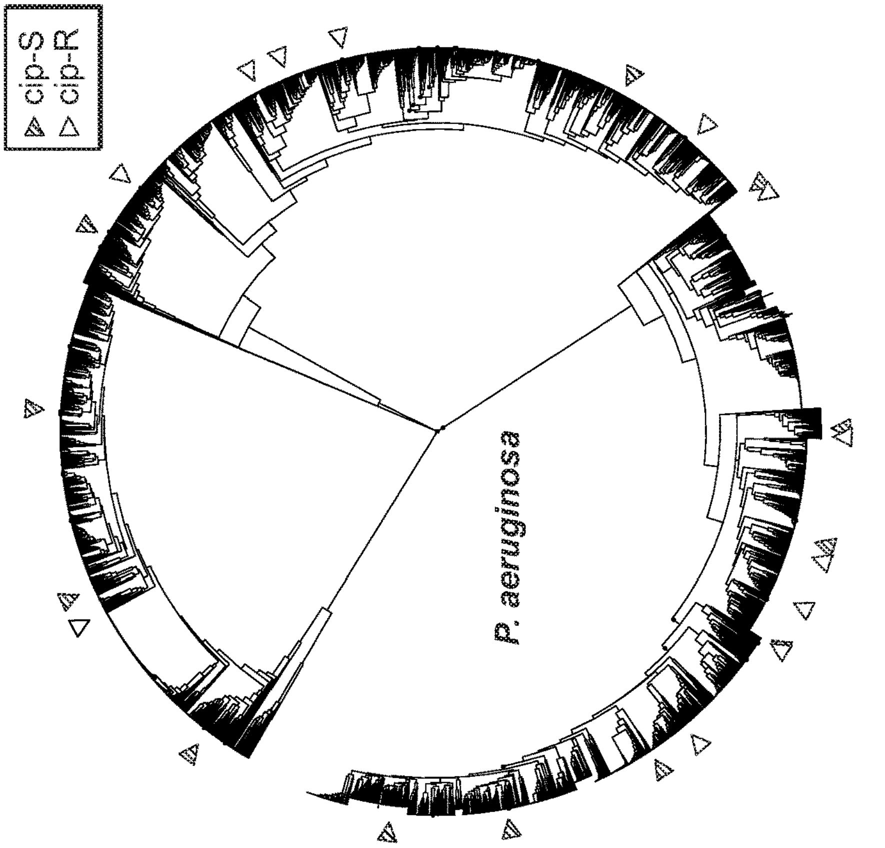
Figure 13C:
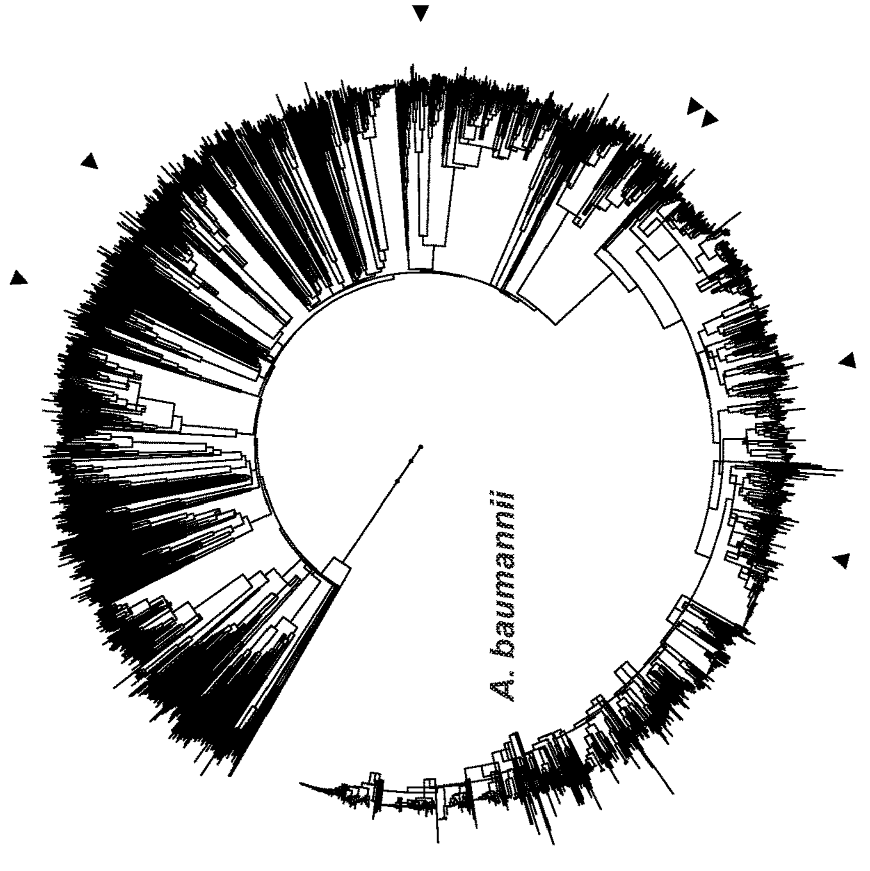

Example 8: A Next-Generation NanoString® Detection Platform, Hyb & Seq™, Accelerates GoPhAST-R to <4 Hours GoPhAST-R was deployed on an exemplary next-generation nucleic detection platform, NanoString® Hyb & Seq™ (J. Beechem, AGBT Precision Health 2017), that features accelerated detection technology, thus enabling AST in <4 hours (FIG. 12A). Relative to the nCounter detection platform, Hyb & Seq™ (FIG. 12B, left panel) enables accelerated hybridization by utilizing unlabeled reporter probes that are far smaller and thus equilibrate far faster than the standard nCounter probes, which are covalently attached to a bulky set of fluorophores during hybridization. Accelerated optical scanning enables fluorescent barcoding of these smaller reporter probes via sequential cycles of binding, detection, and removal of complementary barcoded fluorophores (FIG. 12B, middle panel; see Methods). On a prototype Hyb & Seq instrument, GoPhAST-R can measure expression signatures to determine antibiotic susceptibility in <4 hours, as demonstrated with *K. pneumoniae* for both phenotypic meropenem-responsive transcriptional signatures and detection of carbapenemase and select beta-lactamase genes (FIG. 12B, right panel). A head-to-head time trial on simulated blood culture bottles demonstrated GoPhAST-R results in <4 hours from the time of culture positivity, compared with 28-40 hours in the MGH clinical microbiology laboratory by standard methods, which entailed subculture followed by AST determination on a VITEK-2.

As discussed herein, fast, accurate antibiotic susceptibility testing is a critical need in the battle against escalating antibiotic resistance. Advantageously, the ability of the presently disclosed AST assays to be conducted in hours instead of days can inform decisions on antibiotic administration closer to real-time, which may both improve individual patient outcomes (Kumar et al. 2006) and minimize needless use of broad-spectrum antibiotics for susceptible organisms (Maurer et al.). Growth-based assays are fundamentally limited in speed by the doubling time of the pathogen, and genotypic assays are limited by the inability to comprehensively define the ever-growing diversity and complexity of bacterial antibiotic resistance mechanisms. At least in part by quantifying a refined set of transcripts whose antibiotic-induced expression reflects susceptibility, GoPhAST-R provides a conceptually distinct approach to rapid phenotypic antibiotic resistance detection, agnostic to resistance mechanism and extendable to any antibiotic class, while simultaneously providing select, complementary genotypic information that can both improve the accuracy of phenotypic classification and provide valuable epidemiologic data for identifying the emergence and tracking the spread of resistance. Considering the widespread adoption of rapid pathogen identification by matrix-associated laser desorption and ionization/time-of-flight (MALDI-TOF) mass spectrometry in 2 hours from subcultured colonies streaked from blood culture bottles (Florio et al.; Tanner et al.; Perez et al.), this comparatively more informative AST assay directly from blood culture bottles in <4 hours promises to be transformative. Probes have been designed herein to target regions conserved across all sequenced members of their parent species, thereby allowing each probeset to encode species identity in its reactivity profile. Since the NanoString® platform described herein can multiplex up to 800 probes in a single assay (Geiss et al.), the actual deployed test is expected to combine all 20 probes used for each pathogen-antibiotic pair (Table 9) into a single multi-species probeset for each antibiotic, thereby providing simultaneous pathogen identification along with AST. Alternatively, it is expected that species can be identified prior to AST on the same NanoString® platform using a more sensitive rRNA-based assay (Bhattacharyya et al.). The machine learning approach to strain classification developed for GoPhAST-R provides actionable information in excellent categorical agreement with the gold standard broth microdilution assay and should continue to improve in accuracy as it is trained on an increasing number of strains. Taken all together, omitting carbapenemase-producing strains with ambiguous and likely errant susceptible classification by the gold standard assay, GoPhAST-R correctly classified 100 of 106 strains (94%) in phase 1 and 52 of 54 strains (96%) in phase 2, as well as 71 of 72 (99%) simulated blood cultures, with 8 of the 9 discrepancies occurring on strains within two dilutions of the clinical breakpoint.

By integrating genotypic and early phenotypic information in a single rapid, highly multiplexed RNA detection assay, GoPhAST-R offers several advantages over the current gold standard that are unique among other rapid AST assays under development. First, like other phenotypic assays, it determines susceptibility agnostic to mechanism of resistance, a clear advantage over genotypic AST assays. Second, combining genotypic and phenotypic information enhances AST accuracy over conventional growth-based methods. This combined approach notably improves sensitivity of resistance detection in certain cases such as carbapenemase-producing Enterobacteriaceae that test susceptible by standard methods but may rapidly evolve resistance upon treatment (see e.g., Anderson et al. 2007; Arnold et al. 2011; Centers for Disease and Prevention 2009; Gupta, V. et al. 2018; Nordmann, Cuzon, and Naas 2009; Weisenberg et al. 2009). Third, the identification of carbapenem resistance determinants can guide antibiotic choice for some resistant isolates, as certain novel beta-lactamase inhibitors like avibactam or vaborbactam will overcome some classes of carbapenemases (e.g., KPC) but not others (e.g., metallo-beta-lactamases such as the NDM class) (Lomovskaya et al.; Marshall et al.; van Duin & Bonomo). Solely phenotypic assays would currently require additional, serial testing to provide this level of guidance. Fourth, the ability to track resistance determinants in conjunction with a phenotypic assay enables molecular epidemiology without requiring additional testing for use in local, regional, national, or global tracking. The techniques herein demonstrate this advantage for one major class of high-value resistance determinants, the carbapenemases (Woodworth et al. 2018); this combined approach can be extended readily to other critical emerging resistance determinants, such as mcr genes, plasmid-borne colistin resistance determinants recently found in the Enterobacteriaceae (Caniaux et al. 2017; Liakopoulos et al. 2016; Liu et al. 2016; Sun et al. 2018), or even to detect the presence of key bacterial toxins such as Shiga toxin (Rasko et al. 2011) in seamless conjunction with a phenotypic AST assay. Fifth, strains with unknown mechanism of resistance, such as CREs without carbapenemases, can be immediately identified from a single assay; such isolates could be flagged for further study such as WGS if desired. Sixth, the graded relationship between transcriptional response and MIC (FIGS. 14B and 14E) underscores the biology that underpins the strategy: the more susceptible the strain, the greater its transcriptional response to antibiotic exposure. This relationship allows GoPhAST-R to be informed by clinical breakpoint concentrations, thus leveraging decades of careful study linking in vitro strain behavior to clinical outcomes (CLSI). This relationship also explains why the majority of discrepancies between GoPhAST-R and broth microdilution occurred on strains with MICs close to the breakpoint. By contrast, the inability to map to MIC is considered a liability of genotypic assays, including WGS (Ellington et al.). Finally, as a hybridization-based assay, GoPhAST-R will tolerate mutation in its detection targets more robustly than PCR-based assays (see e.g., Klungthong et al. 2010; Paterson, Harrison, and Holmes 2014). This enables GoPhAST-R to more readily detect resistance determinants with marked sequence variation such as the IMP family of carbapenemases, which is challenging to detect by PCR (Kaase et al. 2012). The phenotypic portion of the assay is particularly robust to sequence variation, both because it incorporates the behavior of multiple targets to provide redundancy, and because it measures fold-induction of the target gene by antibiotic, so a target gene that has mutated beyond recognition would not inform AST classification when registered as absent.

The instant disclosure has therefore provided an important proof of principle of a new approach to AST, for expected application to clinical practice. Genetic diversity within a species poses a fundamental challenge to the generalizability of bacterial molecular diagnostics, including transcription-based assays (Wadsworth et al.). The instant GoPhAST-R technique addresses this crucial challenge in a number of ways. First, for each pathogen-antibiotic pair, GoPhAST-R is trained and tested on a geographically and phylogenetically diverse set of strains: strains in the instant disclosure were obtained from multiple geographic regions that sample across the entire phylogeny of each species (FIGS. 13A-13D), notably including the CDC's Antibiotic Resistance Isolate Bank collection ((www)cdc.gov/ARIsolateBank/) that is intended as a test set for new diagnostic assays. Additionally, by targeting transcripts affected by antibiotics, which by definition affect core bacterial processes required for bacterial survival and whose transcriptional regulation is thus generally conserved (Wadsworth et al.), GoPhAST-R measures responses that are also likely to be conserved and therefore generalizable. Indeed, the fact that GoPhAST-R performed well on test strains that were selected randomly relative to training strains, that the sets of genes selected through iterative phase 1 and 2 training were relatively similar, and that the same classes of antibiotic elicit responses in similar pathways (Table 8) and even homologous genes (Table 9) across different species, all point to the ability of GoPhAST-R to account for the genetic diversity within a species. In addition to accommodating the potential variable transcriptional responses of strains within a species, by focusing on the most conserved regions of core transcripts by imposing a homology screen in the probe design process, GoPhAST-R also takes into account variability in genetic sequence of conserved genes in different strains. The initial sample set described herein attempted to capture significant diversity; yet larger numbers of strains will likely improve the current techniques further. By employing a classification process built on machine-learning algorithms that can be iteratively refined as more strains are tested, GoPhAST-R is able to incorporate new diversity to asymptotically improve performance. With wider testing, while the specific classifiers will improve, the general strategy and approach remains valid. Indeed, the capacity to learn through iterative retraining is one of the strengths of this approach as it is used more broadly. Likewise, extending this assay to more pathogen and antibiotic pairs will be advantageous for widespread clinical utility.

To extend GoPhAST-R in this manner, the entire pathway described herein for signature derivation, from RNA-Seq to iterative phases of NanoString® refinement and validation, are employed and advanced towards implementation in a clinical setting. Some antibiotics elicit responses in predictable pathways, exemplified by fluoroquinolones up-regulating SOS-response transcripts; however, it is expected that applying the instant diagnostic assay to certain new pathogen-antibiotic pairs will be performed with additional rigor to meet clinical performance mandates. For instance, when the instant approach was applied herein to *S. aureus* and *P. aeruginosa* treated with fluoroquinolones, it was identified that experimental derivation resulted in refined transcriptional signatures and control genes that were not predictable from prior assays on related pathogen-antibiotic pairs, often involving hypothetical or uncharacterized ORFs. This observed difficulty in predicting the best-performing responsive and control genes by inference from other species highlights the significance, at least ideally, of individualizing the expression signature for each pathogen-antibiotic pair, a process that is equivalent to the individualization currently employed by CLSI to extend traditional AST assays to new pathogen-antibiotic pairs. Fortunately, the experimental and computational approaches described herein allow for very rapid and conceptually straightforward extension to all pathogen-antibiotic combinations, and it is further noted that advances in RNA-Seq library construction and sequencing, described herein and elsewhere (Shishkin et al.), make a full derivation cycle for GoPhAST-R routine. Underscoring the ready generalizability of this approach, preliminary RNA-Seq data have been generated for 50 additional pathogen-antibiotic pairs, spanning Gram positive, Gram negative, and mycobacteria, that demonstrate early differential transcriptional responses to antibiotics in all cases tested (data not shown). While GoPhAST-R cannot completely overcome the challenge of identifying delayed inducible resistance (though this would be true for any rapid phenotypic test), it is noted that GoPhAST-R is expected to accurately identify at least some of these cases through simultaneous genotypic detection of induced resistance determinants, where known.

Following the approach described herein as a blueprint, it is contemplated that GoPhAST-R can be extended to all other pathogens and antibiotic classes, including those with novel mechanisms of action and as-yet-unknown or newly emerging mechanisms of resistance. Because GoPhAST-R is specifically informed by MIC, it leverages decades of prior studies linking in vitro behavior to clinical outcomes (CLSI), thereby facilitating its extension to new pathogens or antibiotics. It is further contemplated that the instant approach can be expanded to other clinical specimen types, beyond the instant demonstration performed upon cultured blood. Notably, while the application of a next-generation nucleic acid detection platform that can yield an answer in <4 hours has been described herein, a reliable transcriptional signature of susceptibility has actually been described as present in ≤1 hour for each of these key antibiotic classes. Thus, as RNA detection methods become faster and more sensitive, the GoPhAST-R approach is contemplated to offer even more rapid phenotypic AST on timescales that can inform early antibiotic decisions and thus transform infectious disease practice.

Example 9: Materials and Methods

Strain Acquisition and Characterization

All strains in this study (Table 7) were obtained from clinical or reference microbiological laboratories, including both local hospitals and MDRO strain collections from the Centers for Disease Control's Antibiotic Resistance Isolate Bank (see e.g., World Wide Web at (www).cdc.gov/ARIsolateBank/) and the New York State Department of Health. MICs reported from those laboratories were validated by standard broth microdilution assays (Wiegand, Hilpert, and Hancock 2008) in Mueller-Hinton broth; any discrepancies of >1 doubling from reported values were resolved by repeating in triplicate.

Rna-Seq Experimental Conditions

For each bacteria-antibiotic pair, selected clinical isolates (Table 7), two susceptible and two resistant, were grown at 37° C. in Mueller-Hinton broth to early logarithmic phase, then treated with the relevant antibiotic at breakpoint concentrations set by the Clinical Laboratory Standards Institute (CLSI): 2 mg/L for meropenem, 1 mg/L for ciprofloxacin, and 4 mg/L for gentamicin. Total RNA was harvested from paired treated and untreated samples at 0, 10, 30, and 60 minutes. cDNA libraries were made using a variant of the previously described RNAtag-Seq protocol (Shishkin et al. 2015) and sequenced on either an Illumina™ HiSeq or NextSeq. Sequencing reads were aligned using BWA (Li and Durbin 2009) and tabulated as previously described (Shishkin et al. 2015).

Differential Gene Expression Analysis and Selection of Responsive and Control Transcripts Differentially expressed genes were determined using the DESeq2 package (Love, Huber, and Anders 2014), comparing treated vs untreated samples at each timepoint. Fisher's combined probability test was used to select only those genes whose expression after antibiotic treatment was statistically distinguishable from its expression at any timepoint in the untreated samples. Gene ontology (GO) terms were assigned using blast2GO (version 1.4.4), with hypergeometric testing for enrichment. For each pathogen-antibiotic pair, the fold-change threshold in DESeq2 used to test statistical significance was increased to select 60-100 antibiotic-responsive transcripts with maximal stringency, a number readily accommodated by the NanoString® assay format. Control transcripts were also determined with DESeq2 using an inverted hypothesis test as described (Love, Huber, and Anders 2014) to select genes whose expression was expected to be unaffected by antibiotic exposure or growth in both susceptible and resistant isolates, at all timepoints and treatment conditions. As with responsive genes, the fold-change threshold was varied in order to select the top 10-20 control transcripts. The resulting control and responsive gene lists for each pathogen-antibiotic pair, and the fold-change thresholds used to generate them, are shown in Table 9. See Supplemental Methods sections below for further details.

Targeted Transcriptional Response to Antibiotic Exposure

After using BLASTn to identify regions of targeted transcripts with maximal conservation across all RefSeq genomes from that species (see Supplemental Methods), NanoString® probes were designed per manufacturer's standard process (Geiss et al. 2008) to these conserved regions. Strains treated with antibiotic at the CLSI breakpoint concentration, and untreated controls, were lysed via bead-beating at the desired timepoint. The resulting crude lysates were used as input for standard NanoString® (Seattle, WA) assays, which were performed on the nCounter® Sprint platform with variations on the manufacturer's protocol to enhance speed, detailed in Supplemental Methods. Raw counts for each target were extracted and processed as described in Supplemental Methods. Briefly, for each sample, each responsive gene was normalized by control gene expression as a proxy for cell loading using a variation on the geNorm algorithm (Vandesompele et al.), then converted to fold-induction in treated compared with untreated strains. Pilot NanoString® Hyb & Seq™ assays (FIGS. 12A and 12B) were performed on a prototype Hyb&Seq instrument at NanoString®, with 20 minute hybridization time and 5 imaging cycles to detect hybridization probes with two-segment 10-plex barcodes. See Supplemental Methods for more details.

Machine Learning: Feature Selection and Susceptibility Classification

For each pathogen-antibiotic pair, the normalized data were first partitioned, grouping half the strains into a derivation cohort on which the algorithm was trained, reserving the other half for validation (FIGS. 14A-14F), ensuring equivalent representation of susceptible and resistant isolates in each cohort.

In phase 1, implemented for all pathogen-antibiotic pairs, normalized fold-induction data of responsive genes from strains in the training cohort, along with CLSI susceptibility classification for each training strain, were input to the ReliefF algorithm using the CORElearn package (version 1.52.0) to rank the top 10 responsive transcripts that best distinguished susceptible from resistant strains. These 10 features were then used to train a random forest classifier using the caret package (version 6.0-78) in R (version 3.3.3) on the same training strains. Performance of this classifier was then assessed on the testing cohort, to which the classifier had yet to be exposed.

In phase 2, implemented for *K. pneumoniae*+meropenem and ciprofloxacin, all 18-24 strains from phase 1 were combined into a single, larger training set. For each antibiotic, ReliefF was again used to select the 10 most informative responsive transcripts, which were then used to train a random forest classifier on the same larger training set. Transcriptional data were then collected on a test set of 25-30 new strains using a trimmed NanoString® nCounter®

Elements™ probeset containing only probes for these 10 selected transcripts, plus 8-13 control probes. Susceptibility of each strain in this test set was predicted using the trained classifier. See Supplemental Methods for further detail on machine learning strategy and implementation.

For classification of simulated blood cultures, NanoString® data were collected for the top 10 transcripts (selected in phase 1) from 12 strains for each pathogen-antibiotic pair, and analyzed using a leave-one-out cross-validation approach (Efron & Gong), training on 11 strains and classifying the 12$^{th}$, then repeating with each strain omitted once from training and used for prediction.

Blood Culture Processing

Bacteria were isolated from real or simulated blood cultures in a clinical microbiology laboratory, isolated by differential centrifugation, resuspended in Mueller-Hinton broth, and immediately split for treatment with the indicated antibiotics. Lysis and targeted RNA detection were performed as above. Specimens were blinded until all data acquisition and analysis was complete. See Supplemental Methods for more detail. Samples were collected under waiver of patient consent due to experimental focus only on the bacterial isolates, not the patients from which they were derived.

Data Availability

All RNA-Seq data generated and analyzed during this study, supporting the analyses in FIGS. 2A-2D, have been deposited as aligned bam files in the NCBI Sequencing Read Archive under study ID PRJNA518730. All other datasets obtained herein, including raw and processed NanoString® data, are available upon reasonable request.

Code Availability

Custom scripts for transcript selection from RNA-Seq data are available at the World Wide Web at (www)github.com/broadinstitute/gene_select_v3/. Custom scripts for feature selection and strain classification from NanoString® data are available at World Wide Web at (www)github.com/broadinstitute/DecisionAnalysis/.

Example 10: Supplemental Methods

Rna Extraction for RNA-Seq:

After antibiotic treatment as described in the above Materials and Methods section, cells were pelleted, resuspended in 0.5 mL Trizol reagent (ThermoFisher Scientific), transferred to 1.5 mL screw-cap tubes containing 0.25 mL of 0.1 mm diameter Zirconia/Silica beads (BioSpec Products), and lysed mechanically via bead-beating for 3-5 one-minute cycles on a Minibeadbeater-16 (BioSpec) or one 90-second cycle at 10 m/sec on a FastPrep (MP Bio). After addition of 0.1 mL chloroform, each sample tube was mixed thoroughly by inversion, incubated for 3 minutes at room temperature, and centrifuged at 12,000×g for 15 minutes at 4° C. The aqueous phase was mixed with an equal volume of 100% ethanol, transferred to a Direct-zol spin plate (Zymo Research), and RNA was extracted according the Direct-zol protocol (Zymo Research).

Library Construction and RNA-Seq Data Generation:

Illumina cDNA libraries were generated using a modified version of the RNAtag-Seq protocol (Shishkin et al. 2015), RNAtag-Seq-TS, developed during the course of work for the instant disclosure, in which adapters are added to the 3' end of cDNAs by template switching (Zhu et al. 2001) rather than by an overnight ligation, markedly decreasing the time, cost, and minimum input of library construction. Briefly, 250-500 ng of total RNA was fragmented, DNase treated to remove genomic DNA, dephosphorylated, and ligated to DNA adapters carrying 5'-AN8-3' barcodes of known sequence with a 5' phosphate and a 3' blocking group. Barcoded RNAs were pooled and depleted of rRNA using the RiboZero RNA depletion kit (Epicentre). Pools of barcoded RNAs were converted to Illumina cDNA libraries in 2 main steps: with template switching, then library amplification. RNA was reverse transcribed using a primer designed to the constant region of the barcoded adaptor with addition of an adapter to the 3' end of the cDNA by template switching using SMARTScribe (Clontech). Briefly, two primers were added to the reverse transcription reaction to facilitate template switching: primer AR2 (Shishkin et al. 2015), which primes SMARTScribe reverse transcriptase off of the ligated adapter, and primer 3Tr3 (Shishkin et al. 2015), which contains 3 protected G's at the 3' terminus to complement the C's added to the 3' end of newly synthesized cDNA by SMARTScribe and also contains a 5' blocking group to prevent multiple template-switching events. These primers were pre-incubated with rRNA-depleted, adapter-ligated RNA (at 8.33 uM of each primer) at 72° C.×3 min, then 42° C.×2 min, then added directly to a master mix containing SMARTScribe buffer (1×), DTT (2.5 mM), dNTPs (1 mM each; NEB), SUPERase-In RNase inhibitor (1 unit; Invitrogen), and SMARTScribe reverse transcriptase enzyme (final primer concentration in reaction mixture: 5 uM each). This reaction mixture was incubated at 42° C.×60 min, then 70° C.×10 min, followed by addition of Exonuclease I (1 µL) and incubation at 37° C.×30 min. After 1.5×SPRI cleanup, the resulting cDNA library was PCR amplified using primers whose 5' ends target the constant regions of the ligated adapter (3' end of original RNA) and the template-switching oligo (5' end of original RNA) and whose termini contain the full Illumina P5 or P7 sequences. cDNA libraries were sequenced on the Illumina NextSeq 2500 or HiSeq 2000 platform to generate paired end reads.

Rna-Seq Data Alignment:

Sequencing reads from each sample in a pool were demultiplexed based on their associated barcode sequence. Barcode sequences were removed from the first read, as were terminal G's from the second read that may have been added by SMARTScribe during template switching. The resulting reads were aligned to reference sequences using BWA (Li and Durbin 2009), and read counts were assigned to genes and other genomic features as described (Shishkin et al. 2015). For each pathogen-antibiotic pair, a single reference genome was chosen for analysis of all four clinical isolates. This reference genome was selected by aligning a subset of RNA-Seq reads from each of the four isolates to all RefSeq genomes from that species and identifying the genome to which the highest percentage of reads aligned on average across all isolates. Since none of the isolates used for RNA-Seq have reference-quality genome assemblies themselves, and since four different isolates were used, not all genes in each isolate will be represented in the alignment. Yet for this application, any reads omitted due to the absence of a homologue in the reference genome used for alignment (i.e., accessory genes not shared by the reference) were assumed to be unlikely to be generalizable enough for diagnostic use. Using these criteria, the following reference genomes were chosen for alignment of RNA-Seq data for each of the following pathogen-antibiotic pairs: *K. pneumoniae*=NC_016845 for meropenem and ciprofloxacin, and NC_012731 for gentamicin; *E. coli*=NC_020163 for meropenem, and NC_008563 for ciprofloxacin and gentamicin; *A. baumannii*=NC_021726 for meropenem, and NC_017847 for ciprofloxacin and gentamicin. Note that for display purposes in FIGS. 5, 6, 10, 12A, 12B and 14A-14F, all responsive genes were named according to their homologues in the best-annotated reference available (NC_016845 for *K. pneumoniae*, NC_000913 for *E. coli*, and NC_017847 for *A. baumannii*) in order to convey gene names that were as meaningful as possible, instead of simply gene identifiers. Read tables were generated, quality control metrics examined, and coverage plots from raw sequencing reads in the context of genome sequences and gene annotations were visualized using GenomeView (Abeel et al. 2012). Aligned bam files were deposited to the Sequence Read Archive (SRA) under study ID PRJNA518730.

Selecting Candidate Responsive Genes from RNA-Seq Data:

The DESeq2 package (Love, Huber, and Anders 2014) was used to identify differentially expressed genes in treated vs untreated samples at each timepoint, in both susceptible and resistant strains. Analyses from select timepoints are displayed as MA plots in FIGS. 2A-2D. Since no statistically significant changes in transcription were observed in resistant strains, responsive gene selection was only carried out on susceptible isolates.

It was expected that the resulting list of differentially expressed genes would represent both genes that respond primarily to antibiotic exposure, and genes that respond to ongoing growth that may be prevented by antibiotic treatment in susceptible strains, i.e. whose differential expression upon antibiotic exposure is more a secondary effect. As an example of this type secondary effect, consider a gene whose expression is repressed by increasing cell density, or nutrient depletion from the medium, as cells grow. In the presence of antibiotic, cells may never reach that cell density; therefore, this gene would exhibit higher expression in the antibiotic-treated culture (where it is not repressed) than in the untreated culture (where it is repressed). Without any correction, this gene would appear indistinguishable from one whose expression is induced by antibiotic, although this may be entirely a secondary effect. Such "secondarily" regulated genes were reasoned to be more dependent upon precise growth conditions (media type, temperature, cell density, cell state, etc.—in other words, transcripts upregulated by progression towards stationary phase in minimal media will likely look different than that in rich media, etc.), some of which may vary across clinical samples. By contrast, since antibiotics target core cellular processes, it was hypothesized that the "direct" transcriptional response to antibiotic exposure would be more likely to be conserved across strains, which is critical for their success in a diagnostic assay. Therefore, a focus was placed on transcripts whose expression appeared to be a direct result of antibiotic exposure, rather than this indirect result of the effects of an antibiotic on the progression of the strain to different culture densities.

To identify such genes, additional differential expression analyses were carried out using DESeq2 to identify genes whose expression varied in untreated samples over the timecourse of the experiment. Such genes were very common: >10% of the transcriptome was differentially regulated at some timepoints compared with others in the timecourses of *K. pneumoniae* and *E. coli* (though considerably fewer in *A. baumannii* cultures). Therefore, the additional requirement that any candidate responsive gene exhibit a greater degree of differential expression in time-matched antibiotic-treated vs untreated samples at ≥1 timepoint, than it did in any untreated timepoint—in other words, that antibiotics induce a degree of induction or repression that exceeds that which was achieved at any timepoint in the absence of antibiotics—was imposed. To implement this, Fisher's combined probability test was imposed to combine p-values from each pairwise comparison, selecting those genes whose differential expression upon antibiotic treatment at a given timepoint exceeds their differential expression between any pair of points in the untreated timecourse, with adjusted p-value <0.05. As an additional filter for gene selection, in order to be sure to target genes with sufficient abundance to be readily detected in the hybridization assay, only genes in the upper 50% of expression in each condition were considered.

For most pathogen-antibiotic pairs, this analysis resulted in the identification of hundreds of candidate antibiotic-responsive genes. This process (differential expression analysis+Fisher's method) was repeated using progressively higher thresholds for the fold-change threshold used in the statistical test for differential expression, by increasing the lfcThreshold parameter in DESeq2 (for all comparisons, i.e. antibiotic treatment and each pair of untreated timepoints used in Fisher's method) until the resulting list of candidate responsive genes was 60-100 long, the size that was intended to target in phase 1 NanoString® assays. Table 9 shows the fold-change thresholds used to generate the final candidate responsive transcript list for each pathogen-antibiotic pair. This process was executed using custom scripts, available at World Wide Web at (www)github.com/broadinstitute/gene_select_v3/.

Selecting Candidate Control Genes from RNA-Seq Data

To quantitatively compare the transcription of key antibiotic-responsive genes, it is important to normalize for cell loading, lysis efficiency, and other experimental factors that may systematically affect absolute transcript abundance from a given sample. Such invariant transcripts (often referred to as "housekeeping" transcripts in qPCR) are important for scaling candidate responsive genes for comparison across samples, e.g. for comparing treated vs untreated samples. Control transcripts were therefore included in the NanoString® assay in order to normalize for these factors. Candidate control genes were identified by seeking transcripts whose expression did not change in the RNA-Seq timecourses, either upon antibiotic treatment or with over the untreated timecourse. To find such genes, a statistical test was imposed to find transcripts whose expression did not change by more than a certain fold-change threshold in any of the treated or untreated samples by re-running DESeq2 using an inverted hypothesis test (altHypothesis="lessAbs"), tuning the lfcThreshold parameter until the 10-20 best control genes were identified. Table 9 shows the fold-change thresholds used to generate the final candidate control transcript list for each pathogen-antibiotic pair.

Gene Ontology (GO) Term Enrichment:

For GO enrichment analysis, the same protocol was followed for responsive gene selection using DESeq2 and Fisher's method (see "Selecting candidate responsive genes from RNA-Seq data", above), with two exceptions. First, the lfcThreshold parameter (log2 fold change threshold) was set to 0, in order to capture all differentially expressed genes. Second, genes of any expression level were considered, since sensitivity of detection was not a concern. This process produced a list of all genes that were differentially expressed upon antibiotic exposure to a greater extent than at any timepoint in the absence of antibiotic, over the full timecourse tested (0, 10, 30, and 60 min). These differentially expressed genes were named according to the reference genome that best matched the four strains used for RNA-Seq, as described (see "RNA-Seq analysis", above). GO terms were assigned to annotated genes from each reference genome by blasting the peptide sequences for each ORF from that reference genome against a local database of ~120 well-annotated reference strains from NCBI using blast2GO (version 1.4.4; Gotz et al. 2008). GO terms associated with the list of differentially expressed genes was then compared with all GO terms associated with the genome, and hypergeometric testing was deployed to identify GO terms that were enriched to a statistically significant extent among the differentially expressed genes, using the Benjamini-Hochberg correction for multiple hypothesis testing. A false discovery rate threshold of 0.05 was used to generate the list of enriched GO terms in Table 8.

Homology Masking of Selected Responsive and Control Transcripts

Within each candidate responsive or control gene, regions of highest homology to target with NanoString® probes were identified. For each species, all complete reference genomes from RefSeq as of Jan. 1, 2016 were compiled, and BLASTn was run to identify the closest homologue of each desired target from each reference genome, and eliminated targets without an annotated homologue in at least 80% of genomes. A multi-sequence alignment was then constructed and queried each sliding 100mer window to keep only those windows with at least one 100mer region of >97% nucleotide identity across all reference genomes; all sequences failing to meet this homology threshold were "masked", i.e., removed from consideration as targets for probe design. If no such region was found, the homology threshold was relaxed to >95% identity, then to >92% identity; if no region with at least 92% identity was found, the transcript was deemed too variable to reliably target and thus eliminated from consideration entirely. The window size of 100 nucleotides was chosen because NanoString® detection involves targeting with two ~50mer probes that bind consecutive regions (Geiss et al. 2008). The resulting homology-masked sequences, retaining only those regions of intended target transcripts with sufficient homology, were then provided to NanoString® for their standard probe design algorithms (Geiss et al. 2008).

Design of NanoString® Probes for Carbapenemase and Extended-Spectrum Betalactamase Gene Families:

All gene sequences representing each targeted antibiotic resistance gene family (carbapenemases: KPC, NDM, OXA-48, IMP, VIM; ESBLs: CTX-M-15, OXA-10) were collected from representatives reported in three databases of antibiotic resistance genes: Resfinder (Zankari et al. 2012), ArDB (Liu and Pop 2009), and the Lahey Clinic catalog of beta-lactamases on the World Wide Web at (www)lahey.org/Studies. Additional representatives of each family were identified by homology search (BLASTp, E-value <10-10, >80% similarity) against the conceptual translation of genes identified in the genomes of isolates collected as part a multi-institute analysis of carbapenem-resistant Enterobacteriaceae specimens (Cerqueira et al. 2017). All other genes in the pan-genome of that cohort that did not meet the homology search criterion for inclusion as one of the targeted families were consolidated in an outgroup sequence database, which was used to screen for cross-reactivity. This outgroup contains many other non-targeted beta-lactamases, as well as the complete genomes of hundreds of Enterobacteriaceae isolates (Cerqueira et al. 2017). For each targeted antibiotic resistance gene family, target regions for NanoString® probe design were identified as described above (see above section entitled Homology masking of selected responsive and control transcripts) by identifying regions with >95% sequence homology across 150 nucleotides in >90% of homologues within that family. In order to minimize risk of cross-reactivity with undesired targets, these conserved regions of the desired targets were then compared by BLASTn to the outgroup database, and any regions with E-value <10 were discarded. For the IMP gene family, no region of sufficient conservation could be identified due to sequence diversity within the family, consistent with reports that it is difficult to uniformly target by PCR (Kaase et al. 2012). Four different regions were identified that together were predicted to cover all IMP homologs from these databases, i.e., where each IMP homolog contained a stretch of sufficient homology to one or more of the four regions. These regions were submitted to NanoString® for probe design by their standard algorithms (Geiss et al. 2008), including four separate probe pairs for IMP (Table 9). Signal from each of these four IMP probes was combined to yield a single combined total IMP signal (see section entitled "NanoString® data processing, normalization, and visualization" below).

Lysate Preparation for NanoString® Transcriptional Profiling Assays:

Each strain to be tested was grown at 37° C. in Mueller-Hinton broth to mid-logarithmic phase, and split into a treated sample, to which antibiotic was added at the CLSI breakpoint concentration, and an untreated control. Both samples were grown for the specified time (30-60 min), then a 100 μL aliquot of culture was added to 100 μL of RLT buffer (Qiagen) plus 1% beta-mercaptoethanol and mechanically lysed using either the MiniBeadBeater-16 (BioSpec) or the FastPrep (MP Biomedicals). This crude lysate was either used directly for hybridization, or frozen immediately and stored at −80° C., then thawed on ice prior to use.

Nanostring® nCounter® Assays:

All Phase 1 and Phase 2 NanoString® experiments (see FIG. 5) were performed on a NanoString® nCounter® Sprint instrument, with hybridization conditions as per manufacturer's recommendations, including a 10% final volume of crude lysate as input. Phase 1 experiments used probesets made with XT barcoded probe pools and were hybridized for 2 hours at 65° C., while Phase 2 experiments used probesets made with nCounter® Elements™ probe pools plus cognate barcoded TagSets (ref?) and were hybridized for 1 hour at 67° C., rather than the 16-24 hour hybridizations as recommended by the manufacturer's protocol. Including 30-60 min for antibiotic exposure and these hybridizations, plus a 6 hour run for 12 samples, the total run time was under 8 hours for phase 2. Technical replicates for five strains run on separate days resulted in Pearson correlations of 0.95-0.99 for normalized data, consistent with expectations for this assay platform (Geiss et al. 2008), indicating that the shorter hybridization time did not affect reproducibility.

Phylogenetic Analysis of Strains Included in this Study:

The Genome Tree report was downloaded for each species from the National Center for Biotechnology Information (NCBI; ncbi.nlm.nih.gov) in Newick file format and uploaded to the Interactive Tree of Life (iTOL; itol.embl.de; Letunic et al. 2019) for visualization and annotation. Strains from the instant disclosure that were available on NCBI were identified using strain name or other identifying metadata from the NCBI Tree View file, cross-referencing the NCBI ftp server (ftp.ncbi.nlm.nih.gov/pathogen/Results/) as needed to confirm strain identity.

Rapid Transcriptional Profiling with Pilot NanoString® Hyb & Seq™ Assay Platform For the rapid pilot GoPhAST-R experiment on a prototype Hyb & Seq™ instrument at NanoString® (FIGS. 12A and 12B), pairs of capture probes (Probe A and Probe B) were constructed for all targets of interest such that each pair could uniquely bind to one target transcript. For Hyb & Seq™ chemistry (FIG. 12A), each Probe A contained a unique target binding region, a universal purification sequence, and an affinity tag for surface immobilization. Each Probe B contained another unique target binding region, a barcoded sequence for downstream signal detection, and a common purification sequence that was different from that of Probes A. For multiplexed RNA profiling, crude lysates were mixed with all capture and reporter probes in a single hybridization reaction and incubated on a thermocycler with heated lid at 65° C. for 20 min. This hybridization reaction enables formation of unique trimeric complexes between target mRNA, Probe A, and Probe B for each target.

Three sequential steps of post-hybridization purification were then performed to ensure minimal background signal. Briefly, the hybridization product was first purified over magnetic beads coupled to oligonucleotides complementary to the universal sequence contained on every Probe B. The hybridization product was first incubated with the beads in 5×SSPE/60% formamide/0.1% Tween20 at room temperature for 10 min in order to bind all target complexes containing Probes B, along with the free (un-hybridized) Probes B, onto the beads. Bead complexes were then washed with 0.1×SSPE/0.1% Tween20 to remove unbound oligos and complexes without Probes B. The washed beads were then incubated in 0.1×SSPE/0.1% Tween20 at 45° C. for 10 min to elute the bound hybridized complexes off the beads. This second purification was carried out per manufacturer's instructions using Agencourt AMPure XP beads (Beckman Coulter) at a 1.8:1 volume ratio of beads to sample, in order to remove oligos shorter than 100 nt. This size-selective purification recovers the bigger hybridization complexes while removing smaller free capture Probes A and B. Eluates from these AMPure beads were purified over a third kind of magnetic beads coupled to oligonucleotides complementary to the common purification sequence contained on every Probe A, similar to the first bead purification, then eluted at 45° C. These triple-purified samples were driven through a microfluidic flow cell on a readout cartridge by hydrostatic pressure within 20 min. The flow cell was enclosed by a streptavidin-coated glass slide that can specifically bind to the affinity tag (biotin) of each Probe B, allowing the immobilization of purified complexes on the glass surface.

The cartridge with samples loaded was mounted on a Hyb & Seq™ prototype instrument equipped with an LED light source, an automated stage, and a fluorescent microscope. The barcoded region of each Probe A consisted of two short nucleic acid segments, each of which can bind to one of ten available fluorescent bi-colored DNA reporter complexes as dictated by complementarity to the exact segment sequences. To detect each complex captured on the glass surface (FIG. 12B), photocleavable fluorescent color-coded reporters were grouped by their target segment location and introduced into the flow cell one pool at a time. Following each reporter pool introduction, the flow cell was washed with non-fluorescent imaging buffer to remove unbound reporter complexes and scanned by the automated Hyb & Seq prototype. Each field of view (FOV) was scanned at different excitation wavelengths (480, 545, 580 and 622 nm) to generate four images (one for each wavelength) and then exposed to UV (375 nm) briefly to remove the fluorophore on surface-bound reporter probes by breaking a photocleavable linker. The flow cell was then subjected to a second round of probing with a new reporter pool targeting the second segment location on each Probe A. Thus, two rounds of probing, washing, imaging and cleavage completed one Hyb & Seq barcode readout cycle (FIG. 12B). In order to improve signal-to-noise ratio, 5 such cycles were completed for each assay. Between each cycle, the flow cell was incubated with low salt buffer (0.0033×SSPE/0.1% Tween20) to remove all bound reporter complexes without disrupting the ternary complex between Probe A, target mRNA, and Probe B.

A custom algorithm was implemented to process the raw images for each FOV on a FOV-by-FOV basis. This algorithm can identify fluorescent spots and register images between each wavelengths and readout cycles. A valid feature is defined as a spot showing positive fluorescence readout for all barcoded segment locations in the same spatial position of each image after image registration. The molecular identity of each valid feature is determined by the permutation of color codes for individual rounds of barcode segment readout. In this implementation, the maximal degree of available multiplexing for a single assay using 10-plex reporter pools was $10^2$=100 kinds for two-segment barcodes, but up to four-segment barcodes are available, permitting up to $10^4$=10,000 distinct barcodes. This algorithm provides tabulated results for the total raw count of each reporter barcode of interest identified in a single assay. These raw counts are used as input for subsequent data processing, visualization, and further analysis.

Nanostring® Data Processing, Normalization, and Visualization:

For each sample, read counts from each targeted transcript were extracted using nSolver Analysis Software (v4.070, NanoString®, Seattle WA). Raw read counts underwent the following processing steps, all executed in R (version 3.3.3), utilizing the packages dplyr (version 0.7.4), xlsx (version 0.5.7), gplots (version 3.0.1), and DescTools (version 0.99.23):

1. Data aggregation: all data for a given pathogen-antibiotic pair, for a given phase of analysis (eg phase 1 or phase 2), was read in to a single data object so that all subsequent data processing steps were done together.
2. Positive control correction: per manufacturer's protocol, ERCC spike-ins were included in every hybridization at known concentrations, spanning the range of expected target RNA concentrations. For each sample, the geometric mean of counts from positive control probes targeting these ERCC spike-ins was calculated. This geometric mean was used to scale each remaining probe in the sample, in order to standardize across lanes for any systematic variation.
3. Negative control subtraction: per manufacturer's protocol, for each sample, the mean of negative control probes targeting ERCC spike-ins not present in the hybridization reaction were subtracted from the raw read counts for each target.
4. Failed probe removal: any control probe with fewer than 10 reads, or any responsive control with negative reads, after negative control subtraction in any sample was removed from all samples for a given pathogen-antibiotic pair, in order to omit transcripts whose content, sequence, or expression was too variable across strains.
5. Selection of optimal control probes: among the set of candidate control probes, across all strains in a given phase of analysis, the subset of these control probes that performed most consistently across samples was selected using a variation on the geNorm algorithm (Vandesompele et al. 2002). The principle behind this algorithm is that the per-cell expression of ideal control probes will not vary under any experimental conditions, and therefore, the ratio between expression levels of a set of ideal control probes will be constant (reflecting only the difference in cell number in each sample). Accordingly, the coefficient of variation of each control probe with the geometric mean of all control probes was calculated. In the ideal case, this coefficient of variation will be zero. The candidate control probe with the highest coefficient of variation is removed, and the process is repeated with the remaining control probes until the highest coefficient of variation is less than a threshold set to yield an acceptable number of non-operonic control transcripts, typically 4-8. For these experiments, this threshold was adjusted from 0.2 to 0.3 depending on the bacteria-antibiotic pair. Thresholds chosen, and the optimal control probes used at this threshold, are noted in Table 9.

6. Control transcript normalization: the geometric mean of the optimal control probes was calculated for each sample and used to normalize all remaining read counts from that sample, i.e. for candidate responsive transcripts, and for carbapenemase or ESBL genes (if applicable), by dividing these corrected read counts by this geometric mean for each sample.
7. Calculation of fold-induction of normalized responsive transcripts by antibiotic: for each candidate responsive transcript, normalized counts from each antibiotic-treated strain were divided by normalized counts from untreated samples of the same strain. These fold-inductions of normalized expression for each candidate responsive transcript were used as input into machine learning algorithms, both reliefF for feature selection and the caret package for random forest classification.
8. Log-transformation of fold-induction data for responsive transcripts: for visualization, the natural logarithm of fold-inductions of normalized expression for each candidate responsive transcript was calculated and displayed using the heatmap.2 function of the gplots R package (version 3.0.1). For each set of strains, ln(fold induction) for each transcript was clustered using the default hclust function, and strains were ordered by MIC.
9. Combination of IMP probes: because of the variability of gene sequences in the IMP family, four separate IMP probes were designed, one or more of which was expected to recognize all sequenced members of this gene family. Following control gene normalization, signal from the four separate probes was added together to give a single IMP score.
10. Background subtraction for carbapenemase/ESBL gene detection: For each species, the subset of tested strains was identified for which whole-genome-sequencing (WGS) data was available and none of the target beta-lactamase genes was found. From this subset, the arithmetic mean plus two standard deviations of the normalized signal from each probe (step 6) was calculated, and this mean+two standard deviations was subtracted from the normalized signal from each probe across all tested samples. All carbapenemases identified by WGS were detected above background, though the two *A. baumannii* isolates expressing blaNDM were only detected at very low levels. Background-subtracted data were log-transformed for visualization (any probe with a negative value after background-subtraction was set to 0.1 normalized counts for all standard nCounter experiments, or to 0.25 normalized counts for Hyb & Seq experiments, prior to log-transformation).

One-Dimensional Projection of Transcriptional Data Via Squared Projected Distance (SPD) Metric:

Normalized, log-transformed fold-induction data from the ~60-100 responsive were collapsed into a one-dimensional projection referred to as a squared projected distance (SPD), essentially as described (Barczak et al. 2012). Conceptually, the transcriptional response of a test strain is placed on a vector in N-dimensional transcriptional space (where N=number of responsive genes, here ~60-100 per probeset) between the average position (i.e. centroid in transcriptional space) of a derivation set of susceptible strains (defined as SPD=0) and the average position of a derivation set of resistant strains (defined as SPD=1). All vector math was performed exactly as described (Barczak et al. 2012) and implemented in R (version 3.3). For each pathogen-antibiotic pair, the same strains used for RNA-Seq were also used as the derivation set of two susceptible and two resistant strains, in order to ensure that the resulting projections of the remaining strains were not self-determined. In other words, only the strains used to select the transcripts to be used in the NanoString® experiments (based on RNA-Seq) were used to set the average position of susceptible or resistant isolates; any tendency of other isolates to cluster at a similar SPD as these derivation strains, either susceptible or resistant, is thus due to a similarity in their transcriptional profiles. These derivation strains are labeled in Table 7 as “deriv_S” and “deriv_R” for susceptible and resistant strains, respectively. SPD data are plotted by CLSI class (FIG. 4A) and by MIC (FIG. 4B), showing a proportional relationship between MIC and this summative metric of transcriptional response to antibiotic exposure upon treatment at the breakpoint concentration (vertical dashed line).

Approach to Strain Classification Based on NanoString® Data:

In order to select the most distinguishing features and to classify isolates as susceptible or resistant, machine learning algorithms were utilized and implemented in two phases (FIG. 5).

In phase 1, NanoString® XT probesets were designed targeting dozens (60-100) of antibiotic-responsive transcripts (Table 9) selected from RNA-Seq data as described and used to quantify target gene expression from 18-24 isolates of varying susceptibility, both treated and untreated with the antibiotic in question, from which normalized fold-induction data for each responsive gene candidate was determined as described above. These isolates are partitioned into 50% training strains and 50% testing strains, randomly but informed by MIC: isolates are sorted in order of MIC and then alternately assigned to training and testing sets in order to ensure a balanced mix of isolates in each cohort across the full range of MICs represented by the strains in question. The only exceptions to random strain assignments to training vs testing sets in Phase 1 were: (1) intermediate isolates were not used for training, but were assigned to the validation cohort (and were grouped with resistant isolates for accuracy reporting, i.e., “not susceptible”), and (2) the two *E. coli* isolates with large meropenem inoculum effects were noted prior to randomization and deliberately assigned to the validation cohort, given the physiological basis for their discrepant transcriptional response from that of a conventional susceptible strain. From the training (derivation) cohort, the top 10 features were first selected using reliefF (see details below, “Feature selection from NanoString® data”), then a random forest model was trained on this derivation cohort using the caret package, then implemented on the testing (validation) cohort, using only data from these top 10 selected features (see details below, "Random forest classification of strains from NanoString® data"). Accuracy of GoPhAST-R in this phase was assessed by comparing predictions of the random forest model for the strains in the testing cohort, which it had never previously seen, with known susceptibility data for these strains (FIG. 7A; Table 10).

In phase 2, the training and testing cohorts from phase 1 were first combined into a single, larger training set, and selection of the top 10 responsive features were repeated using the same algorithms (reliefF). These represent the best-informed prediction of the 10 responsive probes that most robustly discriminate between susceptible and resistant isolates, and are highlighted in Table 9 for each pathogen-antibiotic combination (column F=either "Phase 2" or "Top feature"). A new NanoString® nCounter® Elements™ probeset was then designed for each pathogen-antibiotic pair, targeting only these 10 transcripts as well as ~10 control probes that performed best in phase 1 (i.e. had the lowest coefficients of variation compared with the geometric mean of all control probes, using the variation on the geNorm algorithm described above; also indicated in Table 9, column F). For *K. pneumoniae*+meropenem and ciprofloxacin, an additional 25-30 strains were tested using these focused phase 2 probesets, again quantifying target gene expression and normalized fold-induction of these responsive genes with and without antibiotic exposure. These data were supplied to the random forest classifier trained on all data from phase 1, and the resulting classifications of phase 2 strains were compared with known susceptibility data for these strains (FIG. 7B; Table 10). Of note, phase 2 deploys GoPhAST-R in exactly the way it was envisioned being deployed on true unknown samples: each of the phase 2 strains was an unknown, considered independently and not used at any point to train the model, only to assess its performance one strain at a time.

Every strain tested was an independent clinical isolate, with two minor exceptions. First, in the case of *A. baumannii*+ciprofloxacin, there were not sufficient numbers of independent ciprofloxacin-susceptible *A. baumannii* isolates to train and test a classifier (only five out of 22 *A. baumannii* isolates). For this bacteria-antibiotic pair, biological replicates of the two susceptible strains used for RNA-Seq, RB197 (three replicates) and RB201 (two replicates) were run. These biological replicates were grown from separate colonies in separate cultures, each split into treated and untreated samples. All three RB197 replicates ended up randomized to the phase 1 training set, while both RB201 replicates were randomized to the phase 1 testing set. Since there was not training on one biological replicate and testing on another, the reported categorical agreement should not be confounded by excessive similarity between replicates. One additional linkage between isolates was that one *A. baumannii* isolate, RB197, exhibited two distinct colony morphotypes upon streaking onto LB plates: a dominant, larger morphotype, and a less abundant, smaller morphotype. The smaller morphotype was renamed RB197s and tested in both the meropenem and ciprofloxacin datasets, randomized to the testing (validation) cohort in both cases.

Feature Selection from NanoString® Data:

For feature selection in both phase 1 and phase 2, the reliefF algorithm (Robnik-Šikonja and Kononenko 2003) was employed using the CORElearn package (version 1.52.0) in R (version 3.3.3) to generate a list of features ranked in order of importance in distinguishing susceptible from resistant strains within the training set. The input to the reliefF algorithm was normalized fold-induction data from all responsive probes, and the CLSI classification, for each training isolate. (For this analysis, CLSI classification was simplified into two classes by grouping intermediate strains with resistant strains, in keeping with common clinical practice to avoid an antibiotic for which an isolate tests intermediate.)

The process by which reliefF generates its ranking has been well-described elsewhere (Robnik-Šikonja and Kononenko 2003). The specific estimator algorithm (lEst parameter) "ReliefFexpRank", which considers the k nearest hits and misses, was chosen with the weight of each hit and miss exponentially decreasing with decreasing rank. This was iterated five times (ltimes parameter=5), with a separate 80% partition of the training data for each iteration, then averaged feature weight across each of these five iterations to generate the final ranked list. The output from this reliefF algorithm is a ranked list of features that best distinguish susceptible from resistant isolates; from this list, and the top 10 features (featureCount parameter=10) were kept. The same parameter values were chosen for feature selection for both phase 1 (i.e., on the half of the phase 1 data assigned to the training set) and phase 2 (i.e., using all of the phase 1 data, for use in designing new probesets for de novo data acquisition in phase 2).

Random Forest Classification of Strains from NanoString® Data:

To build a random forest classifier, the caret (classification and regression training) package (version 6.0-78) in R (version 3.3.3) was employed to classify strains in the testing cohort. Input data for this algorithm are normalized fold-inductions of the top 10 responsive genes selected by reliefF for both training and testing strains, and CLSI classifications for each training strain (again with intermediate and resistant isolates grouped together). This random forest model is a common example of an ensemble classifier (Liaw et al. 2001) that embeds feature selection and weighting in building its models, which should mitigate risk for overtraining from including additional features from reliefF, since features not required for accurate classification need not be considered. It enacts 5-fold cross-validation on the training set, i.e. 80% sampling of the testing data, run 5 times, to optimize parameters including "mtry", "min.node.size", and "splitrule", to build 500 trees (parameter "ntree" set to 500) based on prediction of the omitted training strains. After these hyperparameters are optimized through this cross-validation, an additional 500 trees are built using all of the training data and used to classify strains from the test set, one strain at a time. The resulting output is this classifier model that generates predictions for the classification of each test strain, reported as "probability of resistance" (probR) based on what fraction of trees ended up classifying the strain as resistant. (For instance, a strain with probR of 0.2 was classified as susceptible in 100 trees and as resistant in 400.) For quantitative assessment of accuracy, the prediction of the most likely class as the ultimate classification (i.e., if probR >0.5, the classifier is predicting resistant; if probR <0.5, the classifier is predicting susceptible) was used. One might ultimately choose to set this threshold somewhere other than 0.5: since the cost of misclassifying a resistant isolate as susceptible (a "very major error" in the parlance of the FDA) is greater than the cost of misclassifying a susceptible isolate as resistant, one might wish to label an isolate resistant if its probR is, say, 0.3. However, for simplicity, and to avoid overtraining on the relatively limited number of samples in this manuscript, the default threshold of 0.5 was chosen, accepting the classifier's prediction as to which state is more likely.

Reproducibility of GoPhAST-R Classification:

Phase 2 probesets for meropenem susceptibility were combined with probes for carbapenemase and ESBL gene detection (Table 9). For *K. pneumoniae*+meropenem, in addition to testing all phase 2 strains simultaneously for phenotypic AST and genotypic resistance determinants, 23 of 24 phase 1 strains were retested using the phase 2 probeset in order to capture their carbapenemase and ESBL gene content. This provides a set of effective technical replicates for assessing the robustness of the classifier, since all phase 2 genes are included as a subset of the phase 1 probeset, but all data were regenerated in a new NanoString® experiment using the phase 2 probeset with added genotypic probes.

All 23 retested strains (11 susceptible, 12 resistant) were classified correctly based upon data from the phase 2 probeset; of these 23 strains, 12 (6 susceptible, 6 resistant) were phase 1 training strains (that were therefore not previously classified in phase 1), and 11 (5 susceptible, 6 resistant) were phase 1 testing strains that were classified the same way based upon data from the phase 2 probeset as they had been in phase 1 testing. The probability of resistance (probR) parameters for these 23 replicates from phase 1 (Table 10) versus those from "re-classification" using data from the phase 2 probeset were highly correlated (Pearson correlation coefficient=0.95). Note that because these same strains were used in training the random forest classifier, the results of re-classification of these retested strains are not included in the accuracy statistics reported elsewhere in this manuscript. The 100% concordance observed for re-classification of these 23 strains is thus not a reflection of GoPhAST-R's accuracy, but does speak to its reproducibility.

Blood Culture Processing:

Under Partners IRB 2015P002215, 1 mL aliquots from blood cultures in the MGH clinical microbiology laboratory whose Gram stain demonstrated gram-negative rods were removed for processing. For simulated blood cultures, consistent with clinical microbiology laboratory protocol (Clark et al. 2009), blood culture bottles were inoculated with individual isolates of each pathogen suspended in fetal bovine serum at <10 cfu/mL to simulate clinical samples and incubated in a BD BacTec FX instrument (BD Diagnostics; Sparks, MD) in the clinical microbiology laboratory at Massachusetts General Hospital, or on a rotating incubator at 37° C. in the research laboratory at the Broad Institute. Once the BacTec instrument signaled positive (after 8.5-11.75 hours of growth), or after an equivalent time to reach the same culture density in the research laboratory (confirmed by enumeration of colony-forming units), 1 mL aliquots were removed for processing. Bacteria were isolated by differential centrifugation: 100 xg×10 min to pellet RBCs, followed by 16,000 xg×5 min to pellet bacteria. The resulting pellet was resuspended in 100 μL of Mueller-Hinton broth and immediately split into 5×20 μL aliquots for treatment with the indicated antibiotics (three antibiotics, plus two untreated samples, one for harvesting at 30 min to pair with the ciprofloxacin-treated aliquot and one at 60 min to pair with both meropenem- and gentamicin-treated aliquots). After the appropriate treatment time, 80 μL of RLT buffer+1% beta-mercaptoethanol was added to 20 μL of treated bacterial sample, and lysis via bead-beating followed by NanoString® detection were carried out as above (see "Lysate preparation for NanoString® transcriptional profiling assays" section). For real blood cultures, lysates were stored at −80° C. until organisms were identified in the laboratory by conventional means; only samples containing *E. coli* or *K. pneumoniae* were run on NanoString®. GoPhAST-R results were compared with standard MIC testing in the MGH clinical microbiology laboratory, which were also run on simulated cultures. Specimens were blinded until all data acquisition and analysis was complete. For head-to-head time trial compared with gold standard AST testing in the MGH clinical microbiology laboratory (subculture+VITEK-2), blood culture processing steps were timed in the research laboratory (Boston, MA, USA), then frozen and shipped to NanoString® for transcript quantification on the prototype Hyb & Seq™ platform at NanoString® (Seattle, WA, USA). A timer was restarted when lysates were thawed, and the total time at each site was combined to estimate the complete assay duration.

Blood Culture AST Classification:

Simulated blood cultures were classified using the same random forest approach as cultured strains, using the top 10 features selected during Phase 1 for each pathogen-antibiotic pair. This was implemented using leave-one-out cross-validation (Efron et al. 1983) rather than an even partitioning into training and testing because (1) feature selection was already complete, allowing multiple rounds of classifier training without requiring one unified model, and (2) given this, leave-one-out cross-validation (i.e., iteratively omit each strain once from training, test on the omitted strain, repeat with each strain omitted) allowed for training on the maximum number of strains.

TABLE 7

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | KpMero | | | CRE | | | |
|---|---|---|---|---|---|---|---|---|---|
| STRAIN | Alt name 1 | Alt name 2 | Phase 1 | Phase 2 | mero MIC (mg/L) | Known gene(s) in probeset | Other known bla gene(s) | Source | Comments |
| AR0034 | CarbaNP-03 | | | x | 2 | IMP-4 | TEM-1B; SHV-11 | CDC | ARBank |
| AR0040 | CarbaNP-09 | RB408 | x | (x) | >32 | VIM-27; CTX-M-15 | SHV-11; OXA-1 | CDC | ARBank |
| AR0041 | CarbaNP-10 | RB826 | | x x | 16 | NDM-1; CTX-M-15; OXA-10 | CMY-4; SHV-11 | CDC | ARBank |
| AR0042 | CarbaNP-11 | RB410 | x | (x) | <0.5 | CTX-M15; OXA-10 | TEM-1B; SHV-1; OXA-1 | CDC | ARBank |
| AR0043 | CarbaNP-12 | RB411 | x | | 2 | | SHV-12 | CDC | ARBank |
| AR0044 | CarbaNP-13 | | | x | 4 | CTX-M-15 | OXA-9; TEM-1A; SHV-12; OXA-1 | CDC | ARBank |
| AR0047 | CarbaNP-16 | | | x | 4 | | TEM-1A | CDC | ARBank |
| AR0075 | CarbaNP-44 | RB414 | x | (x) | 8 | CTX-M15 | OXA-232; SHV-1; OXA-1 | CDC | ARBank |
| AR0087 | CarbaNP-56 | RB417 | x | (x) | 1 | | SHV-12 | CDC | ARBank |
| AR0135 | CRE-24 | | | x | 8 | VIM-1 | OXA-9; TEM-1A; SHV-12 | CDC | ARBank |
| AR0139 | CRE-28 | | | x x | 32 | NDM-1; CTX-M-15; OXA-10 | CMY-4; SHV-11 | CDC | ARBank |
| BAA2524 | RB554 | | | x | 0.5* | OXA-48 | | ATCC | |
| BIDMC_14 | RB289 | | | x | 16 | KPC-3 | SHV-134; | BIDMC<br>TEM-1 | Cerqueira et al, PNAS 2017 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | |
|---|---|---|---|---|---|---|---|---|
| BIDMC_21 | RB563 | | | | | | BIDMC | Cerqueira et al, PNAS 2017 |
| BIDMC_22 | RB564 | | x | 0.25 | | SHV-134 | BIDMC | Cerqueira et al, PNAS 2017 |
| BIDMC_31 | RB565 | | x | 0.125 | | SHV-38 | BIDMC | Cerqueira et al, PNAS 2017 |
| BIDMC_35 | RB552 | x | (x) | >32 | OXA-10 | SHV-134 | BIDMC | Cerqueira et al, PNAS 2017 |
| BIT-03 | RB400 | x | (x) | 8 | KPC (unknown type) | | CDC | precursor to ARBank strain collection, shared by J. Patel |
| BIT-04 | RB401 | x (deriv_R) | x (deriv_R) | 32 | KPC (unknown type) | | CDC | precursor to ARBank strain collection, shared by J. Patel |
| BIT-05 | RB402 | x | (x) | >32 | KPC (unknown type) | | CDC | precursor to ARBank strain collection, shared by J. Patel |
| BIT-12 | RB404 | x | (x) | <0.5 | | | CDC | precursor to ARBank strain collection, shared by J. Patel |
| BIT-16 | RB405 | x | (x) | ≤0.5 | | | CDC | precursor to ARBank strain collection, shared by J. Patel |
| BWH_15 | RB268 | x | (x) | 8 | KPC-4 | SHV-134; TEM-1 | BWH | Cerqueira et al, PNAS 2017 |
| BWH_2 | RB551 | | x | 16 | CTX-M-15; OXA-48 | OXA-30; OXA-9; SHV-38; TEM-1 | BWH | Cerqueira et al, PNAS 2017 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | |
|---|---|---|---|---|---|---|---|---|
| BWH_30 | RB270 | x | (x) | ≤0.5 | | SHV-134 | BWH | Cerqueira et al, PNAS 2017 |
| BWH_36 | RB271 | x | (x) | 16 | KPC-3 | SHV-134; TEM-1 | BWH | Cerqueira et al, PNAS 2017 |
| CDC_1500610 | RB419 | x | (x) | ≤0.5 | | | CDC | precursor to ARBank strain collection, shared by J. Patel |
| IDR1200023303 | RB596 | x | (x) | >32 | | SHV-38 | NYDOH | shared by K. Musser |
| IDR1600031102-01-00 | RB579 | x | (x) | >32 | NDM-1; CTX-M15 | | NYDOH | shared by K. Musser |
| IDR1600037310 | RB587 | x | (x) | 1 | CTX-M-15 | | NYDOH | shared by K. Musser |
| IDR1600057468-01-00 | RB584 | | x | 4 | CTX-M-15 | | NYDOH | shared by K. Musser |
| MGH_17 | RB273 | | x | ≤0.5 | | SHV-134 | MGH | Cerqueira et al, PNAS 2017 |
| MGH_18 | RB274 | x (deriv_S) | x (deriv_S) | ≤0.5 | | SHV-134 | MGH | Cerqueira et al, PNAS 2017 |
| MGH_19 | RB275 | x | (x) | ≤0.5 | | SHV-134 | MGH | Cerqueira et al, PNAS 2017 |
| MGH_20 | RB276 | | x | ≤0.5 | | SHV-134 | MGH | Cerqueira et al, PNAS 2017 |
| MGH_31 | RB291 | | x | 8 | | SHV-134 | MGH | Cerqueira et al, PNAS 2017 |
| MGH_35 | RB543 | | x | 2 | CTX-M-15 | OXA-30; SHV-134; TEM-1 | MGH | Cerqueira et al, PNAS 2017 |
| MGH_36 | RB280 | | x | ≤0.5 | | SHV-38 | MGH | Cerqueira et al, PNAS 2017 |
| MGH_39 | RB780 | | x | 2 | KPC-3 | OXA-9; SHV-38; TEM-1 | MGH | Cerqueira et al, PNAS 2017 |
| MGH_48 | RB284 | | x | ≤0.5 | | SHV-134 | MGH | Cerqueira et al, PNAS 2017 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | |
|---|---|---|---|---|---|---|---|---|
| MGH_71 | RB462 | | x | 32 | KPC-2; OXA-10 | SHV-134; TEM-1 | MGH | Cerqueira et al, PNAS 2017 |
| RB039 | | x (deriv_S) | x (deriv_S) | ≤0.5 | | | BWH | this paper |
| RB041 | | | x | ≤0.5 | | | BWH | this paper |
| RB042 | | | x | ≤0.5 | | | BWH | this paper |
| UCI_19 | RB285 | x (deriv_R) | x (deriv_R) | >32 | KPC-2 | SHV-134; TEM-1 | UCI | Cerqueira et al, PNAS 2017 |
| UCI_37 | RB290 | x | (x) | 32 | KPC-3 | OXA-9; SHV-38; TEM-1 | UCI | Cerqueira et al, PNAS 2017 |
| UCI_38 | RB288 | x | (x) | ≤0.5 | | SHV-134 | UCI | Cerqueira et al, PNAS 2017 |
| UCI_44 | RB483 | | x | 0.25 | | OXA-9; TEM-1 | UCI | Cerqueira et al, PNAS 2017 |
| UCI_61 | RB480 | | x | 32 | KPC-2 | SHV-134; TEM-1 | UCI | Cerqueira et al, PNAS 2017 |
| UCI_64 | RB541 | | x | 0.25 | | SHV-134 | UCI | Cerqueira et al, PNAS 2017 |
| UCI_7 | RB540 | | x | 0.25 | | SHV-134 | UCI | Cerqueira et al, PNAS 2017 |

| | | | KpCip | | | | |
|---|---|---|---|---|---|---|---|
| STAIN | Alt name 1 | Alt name 2 | Phase 1 | Phase 2 | cip MIC (mg/L) | Source | Comments |
| AR0034 | CarbaNP-03 | | | x | 1 | CDC | ARBank |
| AR0040 | CarbaNP-09 | RB408 | | x | 128 | CDC | ARBank |
| AR0076 | CarbaNP-45 | RB415 | x | | 0.5 | CDC | ARBank |
| AR0080 | CarbaNP-49 | RB416 | x | | <0.03 | CDC | ARBank |
| AR0126 | CRE-15 | | | x | 0.125 | CDC | ARBank |
| AR0160 | CRE-49 | | | x | 0.06 | CDC | ARBank |
| BAC0800005950 | RB592 | | x | | 0.25 | NYDOH | shared by K. Musser |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | |
|---|---|---|---|---|---|---|
| BIDMC_21 | RB563 | | x | 64 | BIDMC | Cerqueira et al, PNAS 2017 |
| BIDMC_22 | RB564 | | x | 0.03 | BIDMC | Cerqueira et al, PNAS 2017 |
| BIDMC_31 | RB565 | | x | 0.125 | BIDMC | Cerqueira et al, PNAS 2017 |
| BIT-03 | RB400 | x | | 32 | CDC | precursor to ARBank strain collection, shared by J. Patel |
| BIT-04 | RB401 | x | | 16 | CDC | precursor to ARBank strain collection, shared by J. Patel |
| BIT-05 | RB402 | x | | 128 | CDC | precursor to ARBank strain collection, shared by J. Patel |
| BIT-10 | RB403 | x | | | CDC | precursor to ARBank strain collection, shared by J. Patel |
| BIT-16 | RB405 | x | | 0.5 | CDC | precursor to ARBank strain collection, shared by J. Patel |
| BWH_15 | RB268 | x | | 0.125 | BWH | Cerqueira et al, PNAS 2017 |
| BWH_22 | RB287 | | x | 64 | BWH | Cerqueira et al, PNAS 2017 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | |
|---|---|---|---|---|---|---|
| CDC_1500476 | RB418 | x | | 1 | CDC | precursor to ARBank strain collection, shared by J. Patel |
| CDC_1500610 | RB419 | | x | 16 | CDC | precursor to ARBank strain collection, shared by J. Patel |
| IDR1200022727 | RB595 | x | | >32 | NYDOH | shared by K. Musser |
| IDR1600031102-01-00 | RB579 | | x | 64 | NYDOH | shared by K. Musser |
| IDR1600037319-01-00 | RB582 | | x | >32 | NYDOH | shared by K. Musser |
| IDR1600039511-01-00 | RB578 | x | | >32 | NYDOH | shared by K. Musser |
| IDR1600053363-01-00 | RB583 | | x | 16 | NYDOH | shared by K. Musser |
| MGH_18 | RB274 | | x | 0.125 | MGH | Cerqueira et al, PNAS 2017 |
| MGH_21 | RB277 | | x | 0.125 | MGH | Cerqueira et al, PNAS 2017 |
| MGH_35 | RB543 | | x | 64 | MGH | Cerqueira et al, PNAS 2017 |
| MGH_39 | RB780 | | x | 0.06 | MGH | Cerqueira et al, PNAS 2017 |
| MGH_74 | RB572 | | x | 0.03 | MGH | Cerqueira et al, PNAS 2017 |
| RB013 | | x (deriv_R) | x (deriv_R) | 128 | BWH | this paper |
| RB039 | | x (deriv_R) | x (deriv_R) | 128 | BWH | this paper |
| RB040 | | x (deriv_S) | x (deriv_S) | <0.03 | BWH | this paper |
| RB041 | | x (deriv_S) | x (deriv_S) | <0.03 | BWH | this paper |
| RB122 | | x | | 2 | BWH | this paper |
| RB123 | | x | | <0.03 | BWH | this paper |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | |
|---|---|---|---|---|---|
| UCI_20 | RB568 | x | 0.06 | UCI | Cerqueira et al, PNAS 2017 |
| UCI_22 | RB569 | x | 64 | UCI | Cerqueira et al, PNAS 2017 |
| UCI_37 | RB290 | x | 64 | UCI | Cerqueira et al, PNAS 2017 |
| UCI_56 | RB571 | x | 0.125 | UCI | Cerqueira et al, PNAS 2017 |

| STRAIN | Alt name 1 | Alt name 2 | KpGent Phase 1 | KpGent gent MIC (mg/L) | Source | Comments |
|---|---|---|---|---|---|---|
| AR0042 | CarbaNP-11 | RB410 | x | 32 | CDC | ARBank |
| AR0043 | CarbaNP-12 | RB411 | x | 1 | CDC | ARBank |
| AR0076 | CarbaNP-45 | RB415 | x | 32 | CDC | ARBank |
| AR0080 | CarbaNP-49 | RB416 | x | 2 | CDC | ARBank |
| ATCC 700721 | RB435 | | x | >32 | ATCC | |
| BAC0800007138 | RB594 | | x | 0.5 | NYDOH | shared by K. Musser |
| BIDMC_2A | RB469 | | x | 2 | BIDMC | Cerqueira et al, PNAS 2017 |
| BIDMC_34 | RB456 | | x | 32 | BIDMC | Cerqueira et al, PNAS 2017 |
| BIT-10 | RB403 | | x | 4 | CDC | precursor to ARBank strain collection, shared by J. Patel |
| BWH_15 | RB268 | | x | 4 | BWH | Cerqueira et al, PNAS 2017 |
| IDR1600031102-01-00 | RB579 | | x | >32 | NYDOH | shared by K. Musser |
| IDR1600039511-01-00 | RB578 | | x | 0.5 | NYDOH | shared by K. Musser |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| STRAIN | Alt name 1 | Alt name 2 | EcMero Phase 1 | EcMero mero MIC (mg/L) | CRE Known gene(s) in probeset | CRE Other known bla gene(s) | Source | Comments |
|---|---|---|---|---|---|---|---|---|
| MGH_30 | RB278 | | x | 1 | | | MGH | Cerqueira et al, PNAS 2017 |
| MGH_35 | RB543 | | x | >16 | | | MGH | Cerqueira et al, PNAS 2017 |
| MGH_63 | RB545 | | x | >16 | | | MGH | Cerqueira et al, PNAS 2017 |
| RB012 | | | x (deriv_R) | 32 | | | BWH | this paper |
| RB040 | | | x (deriv_S) | 0.5 | | | BWH | this paper |
| RB042 | | | x | 2 | | | BWH | this paper |
| RB121 | | | x (deriv_S) | 1 | | | BWH | this paper |
| RB122 | | | x (deriv_R) | 128 | | | BWH | this paper |
| UCI_13 | RB487 | | x | 0.5 | | | UCI | Cerqueira et al, PNAS 2017 |
| UCI_37 | RB290 | | x | 16 | | | UCI | Cerqueira et al, PNAS 2017 |
| UCI_63 | RB481 | | x | 4 | | | UCI | Cerqueira et al, PNAS 2017 |
| UCI_67 | RB484 | | x | 8 | | | UCI | Cerqueira et al, PNAS 2017 |
| UCI_7 | RB540 | | x | 0.5 | | | UCI | Cerqueira et al, PNAS 2017 |
| AR0048 | CarbaNP-17 | RB420 | x (deriv_R) | 32 | NDM-1; CTX-M-15 | TEM-1B; CMY-6; OXA-1 | CDC | ARBank |
| AR0055 | CarbaNP-24 | | x | 8 | NDM-1 | CMY-6; OXA-1 | CDC | ARBank |
| AR0058 | CarbaNP-27 | | x | 0.25 | | TEM-52B | CDC | ARBank |
| AR0061 | CarbaNP-30 | | x | 8 | KPC-3 | OXA-9; TEM-1A | CDC | ARBank |
| AR0069 | CarbaNP-38 | RB421 | x (deriv_R) | 16 | NDM-1 | TEM-1B; CMY-6 | CDC | ARBank |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | |
|---|---|---|---|---|---|---|---|---|
| AR0077 | CarbaNP-46 | | x | 0.5 | | | CDC | ARBank |
| AR0089 | CarbaNP-58 | | x | 0.5 | | CMY-2 | CDC | ARBank |
| AR0104 | CarbaNP-73 | | x | 1* | KPC-4 | TEM-1A | CDC | ARBank |
| BAA2469 | RB557 | | x | 16 | NDM-1 | | ATCC | |
| BAA2523 | RB553 | | x | 0.5* | OXA-48 | | ATCC | |
| BIDMC_77 | RB827 | | x | 0.5 | CTX-M-15 | CFE-1; OXA-30 | BIDMC | Cerqueira et al, PNAS 2017 |
| IDR1200024571 | RB597 | | x | >32 | | CMY-2 | NYDOH | shared by K. Musser |
| IDR1200039757 | RB598 | | x | >32 | | CMY-2 | NYDOH | shared by K. Musser |
| IDR1300027657 | RB602 | | x | 1 | | CMY-2 | NYDOH | shared by K. Musser |
| IDR1600029769 | RB585 | | x | 8 | OXA-48 | | NYDOH | shared by K. Musser |
| IDR1600035372 | RB586 | | x | 0.5 | CTX-M-15 | | NYDOH | shared by K. Musser |
| IDR1600043633 | RB589 | | x | 2 | CTX-M-15 | | NYDOH | shared by K. Musser |
| MGH_57 | RB544 | | x | 4 | CTX-M-15 | CFE-1; TEM-1 | MGH | Cerqueira et al, PNAS 2017 |
| RB001 | | | x (deriv_S) | 0.25 | | | BWH | this paper |
| RB002 | | | x (deriv_S) | 0.25 | | | BWH | this paper |
| RB076 | | | x | ≤0.5 | | | BWH | this paper |
| RB156 | | | x | 1 | | | BWH | this paper |
| RB765 | | | x | >32 | NDM; KPC | | MGH | this paper |
| RB767 | | | x | >32 | NDM | | MGH | this paper |
| UCI_51 | RB828 | | x | 4 | CTX-M-15 | bl1_ec; OXA-30; TEM-1 | UCI | Cerqueira et al, PNAS 2017 |

| | | | EcCip | | | |
|---|---|---|---|---|---|---|
| STRAIN | Alt name 1 | Alt name 2 | Phase 1 | cip MIC (mg/L) | Source | Comments |
| AR0061 | CarbaNP-30 | | x | 0.25 | CDC | ARBank |
| AR0081 | CarbaNP-50 | | x | 16 | CDC | ARBank |
| AR0085 | CarbaNP-54 | | x | 16 | CDC | ARBank |
| AR0089 | CarbaNP-58 | | x | 0.25 | CDC | ARBank |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | |
|---|---|---|---|---|---|
| AR0104 | CarbaNP-73 | x | 32 | CDC | ARBank |
| BAA2469 | RB557 | x | 64 | ATCC | |
| BAA2523 | RB553 | x | 0.5 | ATCC | |
| BAC0800005647 | RB591 | x | 64 | NYDOH | shared by K. Musser |
| IDR1200024571 | RB597 | x | 0.5 | NYDOH | shared by K. Musser |
| IDR1300034680 | RB603 | x | 0.03 | NYDOH | shared by K. Musser |
| RB001 | | x (deriv_S) | 0.03 | BWH | this paper |
| RB025 | | x | 0.25 | BWH | this paper |
| RB051 | | x (deriv_R) | 64 | BWH | this paper |
| RB057 | | x (deriv_R) | 64 | BWH | this paper |
| RB075 | | x (deriv_S) | 0.03 | BWH | this paper |
| RB077 | | x | 1 | BWH | this paper |
| RB086 | | x | 64 | BWH | this paper |
| RB110 | | x | 8 | BWH | this paper |

| | | | EcGent | | | |
|---|---|---|---|---|---|---|
| STRAIN | Alt name 1 | Alt name 2 | Phase 1 | gent MIC (mg/L) | Source | Comments |
| AR0055 | CarbaNP-24 | | x | 64 | CDC | ARBank |
| AR0061 | CarbaNP-30 | | x | 32 | CDC | ARBank |
| AR0081 | CarbaNP-50 | | x | 0.5 | CDC | ARBank |
| AR0084 | CarbaNP-53 | | x | 0.5 | CDC | ARBank |
| AR0085 | CarbaNP-54 | | x | 2 | CDC | ARBank |
| BAA2469 | RB557 | | x | 64 | ATCC | |
| BAC0800005647 | RB591 | | x | 1 | NYDOH | shared by K. Musser |
| IDR1300027657 | RB602 | | x | 64 | NYDOH | shared by K. Musser |
| IDR1300034680 | RB603 | | x | 1 | NYDOH | shared by K. Musser |
| IDR1600047120 | RB590 | | x | 64 | NYDOH | shared by K. Musser |
| MGH_57 | RB544 | | x | 0.5 | MGH | Cerqueira et al, PNAS 2017 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | |
|---|---|---|---|---|
| RB001 | x (deriv_S) | 1 | BWH | this paper |
| RB051 | x (deriv_R) | 256 | BWH | this paper |
| RB057 | x (deriv_R) | 256 | BWH | this paper |
| RB075 | x (deriv_S) | 0.5 | BWH | this paper |
| RB076 | x | 1 | BWH | this paper |
| RB765 | x | 64 | MGH | this paper |

| | | | AbMero | | CRE | | | |
|---|---|---|---|---|---|---|---|---|
| STRAIN | Alt name 1 | Alt name 2 | Phase 1 | mero MIC (mg/L) | Known gene(s) in probeset | Other known bla gene(s) | Source | Comments |
| ATCC 17978 | RB651 | | x | <0.5 | | OXA-95 | ATCC | |
| AR0033 | CarbaNP-02 | RB389 | x | >32 | NDM-1 | OXA-94 | CDC | ARBank |
| AR0035 | CarbaNP-04 | RB390 | x | >32 | | TEM-1D; ADC-25; OXA-66; OXA-72 | CDC | ARBank |
| AR0036 | CarbaNP-05 | RB425 | x | 16 | | OXA-65; OXA-24 | CDC | ARBank |
| AR0037 | CarbaNP-06 | RB391 | x | >32 | NDM-1 | OXA-94 | CDC | ARBank |
| AR0045 | CarbaNP-14 | RB392 | x | 32 | | TEM-1D; OXA-23; OXA-69 | CDC | ARBank |
| AR0052 | CarbaNP-21 | RB393 | x | 2 | | OXA-58; OXA-100 | CDC | ARBank |
| AR0056 | CarbaNP-25 | RB394 | x | >32 | | OXA-23; OXA-66 | CDC | ARBank |
| AR0063 | CarbaNP-32 | RB395 | x | 4 | | OXA-23; OXA-24; OXA_65 | CDC | ARBank |
| AR0070 | CarbaNP-39 | RB396 | x | 16 | | OXA-58; OXA-100 | CDC | ARBank |
| AR0078 | CarbaNP-47 | RB397 | x | >32 | | ADC-25; SHV-5; OXA-71 | CDC | ARBank |
| AR0101 | CarbaNP-70 | RB398 | x | >32 | | OXA-65; OXA-24 | CDC | ARBank |
| AR0102 | CarbaNP-71 | RB399 | x | 4 | | ADC-25; OXA-66 | CDC | ARBank |
| RB197 | | | x (deriv_S) | <0.5 | | | BWH | this paper |
| RB197s | | | x | ≤0.5 | | | BWH | this paper, small colony morphotype of RB197 |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | |
|---|---|---|---|---|---|---|
| RB198 | | | x | 8 | BWH | this paper |
| RB200 | | | x (deriv_R) | >32 | BWH | this paper |
| RB201 | | | x (deriv_S) | 0.25 | BWH | this paper |
| RB202 | | | x | 32 | BWH | this paper |
| RB203 | | | x (deriv_R) | >32 | BWH | this paper |
| RB204 | | | x | 16 | BWH | this paper |
| RB205 | | | x | 1 | BWH | this paper |
| RB206 | | | x | 1 | BWH | this paper |

| | | | AbCip | | | |
|---|---|---|---|---|---|---|
| STRAIN | Alt name 1 | Alt name 2 | Phase 1 | cip MIC (mg/L) | Source | Comments |
| ATCC 17978 | RB651 | | x | 0.5 | ATCC | |
| AR0033 | CarbaNP-02 | RB389 | x | >32 | CDC | ARBank |
| AR0035 | CarbaNP-04 | RB390 | x | >32 | CDC | ARBank |
| AR0036 | CarbaNP-05 | RB425 | x | >32 | CDC | ARBank |
| AR0037 | CarbaNP-06 | RB391 | x | >32 | CDC | ARBank |
| AR0045 | CarbaNP-14 | RB392 | x | >32 | CDC | ARBank |
| AR0052 | CarbaNP-21 | RB393 | x | 4 | CDC | ARBank |
| AR0056 | CarbaNP-25 | RB394 | x | >32 | CDC | ARBank |
| AR0063 | CarbaNP-32 | RB395 | x | 8 | CDC | ARBank |
| AR0070 | CarbaNP-39 | RB396 | x | 8 | CDC | ARBank |
| AR0078 | CarbaNP-47 | RB397 | x | >32 | CDC | ARBank |
| AR0101 | CarbaNP-70 | RB398 | x | >32 | CDC | ARBank |
| AR0102 | CarbaNP-71 | RB399 | x | >32 | CDC | ARBank |
| RB197 | | | x x x (deriv_S) | 0.25 | BWH | this paper |
| RB197s | | | x | 0.25 | BWH | this paper; small colony morphotype of RB197 |
| RB198 | | | x (deriv_R) | >32 | BWH | this paper |
| RB201 | | | x x (deriv_S) | 0.25 | BWH | this paper |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| STRAIN | Alt name 1 | Alt name 2 | AbGent Phase 1 | AbGent gent MIC (mg/L) | Source | Comments |
|---|---|---|---|---|---|---|
| RB202 | | | x (deriv_R) | >32 | BWH | this paper |
| RB203 | | | x | >32 | BWH | this paper |
| RB204 | | | x | >32 | BWH | this paper |
| RB205 | | | x | 1 | BWH | this paper |
| RB206 | | | x | >32 | BWH | this paper |
| ATCC 17978 | RB651 | | x | ≤0.5 | ATCC | |
| AR0033 | CarbaNP-02 | RB389 | x | 32 | CDC | ARBank |
| AR0035 | CarbaNP-04 | RB390 | x | 16 | CDC | ARBank |
| AR0037 | CarbaNP-06 | RB391 | x | >32 | CDC | ARBank |
| AR0045 | CarbaNP-14 | RB392 | x | >32 | CDC | ARBank |
| AR0052 | CarbaNP-21 | RB393 | x | 32 | CDC | ARBank |
| AR0056 | CarbaNP-25 | RB394 | x | >32 | CDC | ARBank |
| AR0063 | CarbaNP-32 | RB395 | x | 4 | CDC | ARBank |
| AR0070 | CarbaNP-39 | RB396 | x | >32 | CDC | ARBank |
| AR0078 | CarbaNP-47 | RB397 | x | >32 | CDC | ARBank |
| AR0101 | CarbaNP-70 | RB398 | x | 8 | CDC | ARBank |
| AR0102 | CarbaNP-71 | RB399 | x | >32 | CDC | ARBank |
| RB197 | | | x (deriv_S) | ≤0.5 | BWH | this paper |
| RB198 | | | x | >32 | BWH | this paper |
| RB200 | | | x (deriv_R) | >32 | BWH | this paper |
| RB201 | | | x | 1 | BWH | this paper |
| RB202 | | | x | >32 | BWH | this paper |
| RB203 | | | x | 4 | BWH | this paper |
| RB204 | | | x (deriv_R) | >32 | BWH | this paper |
| RB205 | | | x (deriv_S) | 2 | BWH | this paper |
| RB206 | | | x | >32 | BWH | this paper |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | KpMero | | | CRE | | | | KpGent | | |
|---|---|---|---|---|---|---|---|---|---|---|
| STRAIN | Phase 1 | Phase 2 | mero MIC (mg/L) | Run? | Known gene(s) in probset | Other known bla gene(s) | Found by | Phase 1 | gent MIC (mg/L) | Used in blood cultures? |
| AR0034 | | x | 2 | + | IMP-4 | TEM-1B; SHV-11 | WGS | | | |
| AR0040 | x | (x) | >32 | + | VIM-27; CTX-M-15 | SHV-11; OXA-1 | WGS | | | |
| AR0041 | | x x | 16 | + | NDM-1; CTX-M-15; OXA-10 | CMY-4; SHV-11 | WGS | | | |
| AR0042 | x | (x) | ≤0.5 | + | CTX-M15; OXA-10 | TEM-1B; SHV-1; OXA-1 | WGS | x | 32 | |
| AR0043 | x | | 2 | – | | SHV-12 | WGS | x | 1 | |
| AR0044 | | x | 4 | + | CTX-M-15 | OXA-9; TEM-1A; SHV-12; OXA-1 | WGS | | | |
| AR0047 | | x | 4 | + | | TEM-1A | WGS | | | |
| AR0075 | x | (x) | 8 | + | CTX-M15 | OXA-232; SHV-1; OXA-1 | WGS | | | x |
| AR0076 | | | | | | | | x | 32 | |
| AR0080 | | | | | | | | x | 2 | x |
| AR0087 | x | (x) | 1 | + | | SHV-12 | WGS | | | |
| AR0126 | | | | | | | | | | |
| AR0135 | | x | 8 | + | VIM-1 | OXA-9; TEM-1A; SHV-12 | WGS | | | |
| AR0139 | | | | | | | | | | |
| AR0160 | | x x | 32 | + | NDM-1; CTX-M-15; OXA-10 | CMY-4; SHV-11 | WGS | | | |
| ATCC 700721 | | | | | | | | x | <32 | |
| BAA2524 | | x | 0.5* | + | OXA-48 | | unknown | | | |
| BAC0800005950 | | | | | | | | | | |
| BAC0800007138 | | | | | | | | x | 0.5 | |
| BIDMC_14 | | x | 16 | + | KPC-3 | SHV-134; TEM-1 | WGS | | | x |
| BIDMC_21 | | | | | | | | | | |
| BIDMC_22 | | x | 0.25 | + | | SHV-134 | WGS | | | |
| BIDMC_2A | | | | | | | | x | 2 | |
| BIDMC_31 | | x | 0.125 | + | | SHV-38 | WGS | | | |
| BIDMC_34 | | | | | | | | x | 32 | x |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | | | |
|---|---|---|---|---|---|---|---|---|---|---|
| BIDMC_35 | x | (x) | >32 | + | OXA-10 | SHV-134 | WGS | | | |
| BIT-03 | x | (x) | 8 | + | KPC (unknown type) | | unknown | | | |
| BIT-04 | x (deriv_R) | x (deriv_R) | 32 | + | KPC (unknown type) | | unknown | | | |
| BIT-05 | x | (x) | >32 | − | KPC (unknown type) | | unknown | | | |
| BIT-10 | | | | | | | | x | 4 | |
| BIT-12 | x | (x) | ≤0.5 | + | | | unknown | | | |
| BIT-16 | x | (x) | ≤0.5 | + | | | unknown | | | x |
| BWH_15 | x | (x) | 8 | + | KPC-4 | SHV-134; TEM-1 | WGS | x | 4 | |
| BWH_2 | | x | 16 | + | CTX-M-15; OXA-48 | OXA-30; OXA-9; SHV-38; TEM-1 | WGS | | | |
| BWH_22 | | | | | | | | | | x |
| BWH_30 | x | (x) | ≤0.5 | − | | SHV-134 | WGS | | | |
| BWH_36 | x | (x) | 16 | + | KPC-3 | SHV-134; TEM-1 | WGS | | | |
| CDC_1500476 | | | | | | | | | | |
| CDC_1500610 | x | (x) | ≤0.5 | + | | | (no data) | | | |
| IDR1200022727 | | | | | | | | | | |
| IDR1200023303 | x | (x) | >32 | + | | SHV-38 | WGS | | | |
| IDR1600031102-01-00 | x | (x) | >32 | + | NDM-1; CTX-M15 | | WGS | x | >32 | |
| IDR1600037310 | x | (x) | 1 | + | CTX-M-15 | | WGS | | | |
| IDR1600037319-01-00 | | | | | | | | | | |
| IDR1600039511-01-00 | | | | | | | | x | 0.5 | |
| IDR1600053363-01-00 | | | | | | | | | | |
| IDR1600057468-01-00 | | x | 4 | + | CTX-M-15 | | WGS | | | |
| MGH_17 | | x | ≤0.5 | + | | SHV-134 | WGS | | | |
| MGH_18 | x (deriv_S) | x (deriv_S) | ≤0.5 | + | | SHV-134 | WGS | | | |
| MGH_19 | x | (x) | ≤0.5 | + | | SHV-134 | WGS | | | |
| MGH_20 | | x | ≤0.5 | + | | SHV-134 | WGS | | | |
| MGH_21 | | | | | | | | | | |
| MGH_30 | | | | | | | | x | 1 | |
| MGH_31 | | x | 8 | + | | SHV-134 | WGS | | | |
| MGH_35 | | x | 2 | + | CTX-M-15 | OXA-30; SHV-134; TEM-1 | WGS | x | >16 | |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | | | | | | | | | | |
|---|---|---|---|---|---|---|---|---|---|---|
| MGH_36 | | x | ≤0.5 | + | | SHV-38 | WGS | | | |
| MGH_39 | | x | 2 | + | KPC-3 | OXA-9; SHV-38; TEM-1 | WGS | | | |
| MGH_48 | | x | ≤0.5 | + | | SHV-134 | WGS | | | |
| MGH_63 | | | | | | | | x | >16 | x |
| MGH_71 | | x | 32 | + | KPC-2; OXA-10 | SHV-134; TEM-1 | WGS | | | |
| MGH_74 | | | | | | | | | | x |
| RB012 | | | | | | | | x (deriv_R) | 32 | |
| RB013 | | | | | | | | | | |
| RB039 | x (deriv_S) | x (deriv_S) | ≤0.5 | + | | | (no data) | | | |
| RB040 | | | | | | | | x (deriv_S) | 0.5 | |
| RB041 | | x | ≤0.5 | + | | | (no data) | | | x |
| RB042 | | x | ≤0.5 | + | | | (no data) | x | 2 | |
| RB121 | | | | | | | | x (deriv_S) | 1 | |
| RB122 | | | | | | | | x (deriv_R) | 128 | |
| RB123 | | | | | | | | | | x |
| UCI_13 | | | | | | | | x | 0.5 | |
| UCI_19 | x (deriv_R) | x (deriv_R) | >32 | + | KPC-2 | SHV-134; TEM-1 | WGS | | | |
| UCI_20 | | | | | | | | | | |
| UCI_22 | | | | | | | | | | |
| UCI_37 | x | (x) | 32 | + | KPC-3 | OXA-9; SHV-38; TEM-1 | WGS | x | 16 | |
| UCI_38 | x | (x) | ≤0.5 | + | | SHV-134 | WGS | | | |
| UCI_44 | | x | 0.25 | + | | OXA-9; TEM-1 | WGS | | | |
| UCI_56 | | | | | | | | | | |
| UCI_61 | | x | 32 | + | KPC-2 | SHV-134; TEM-1 | WGS | | | |
| UCI_63 | | | | | | | | x | 4 | |
| UCI_64 | | x | 0.25 | + | | SHV-134 | WGS | | | x |
| UCI_67 | | | | | | | | x | 8 | x |
| UCI_7 | | x | 0.25 | + | | SHV-134 | WGS | x | 0.5 | |

TABLE 7-continued

Strains used in this study (including origin, and which assay(s) they were used in), with MIC measurements. Highlight those used for RNA-Seq, and which were used for which NSTG assay, and which were used as "derivation" or "validation" in ML algorithms and for SPD.

| | EcCip | | EcGent | | |
|---|---|---|---|---|---|
| STRAIN | Phase 1 | cip MIC (mg/L) | Phase 1 | gent MIC (mg/L) | Used in blood cultures? |
| AR0048 | | | | | |
| AR0055 | | | x | 64 | x |
| AR0058 | | | | | |
| AR0061 | x | 0.25 | x | 32 | x |
| AR0077 | | | | | x |
| AA0081 | x | 16 | x | 0.5 | |
| AA0084 | | | x | 0.5 | |
| AR0085 | x | 16 | x | 2 | |
| AR0089 | x | 0.25 | | | x |
| AR0104 | x | 32 | | | |
| BAA2469 | x | 64 | x | 64 | |
| BAA2523 | x | 0.5 | | | |
| BAC08000005647 | x | 64 | x | 1 | x |
| BIDMC_77 | | | | | |
| IDR1200024571 | x | 0.5 | | | |
| IDR1200039757 | | | | | |
| IDR1300027657 | | | x | 64 | |
| IDR1300034680 | x | 0.03 | x | 1 | x |
| IDR1600029769 | | | | | |
| IDR1600035372 | | | | | |
| IDR1600043633 | | | | | |
| IDR1600047120 | | | x | 64 | |
| MGH_57 | | | x | 0.5 | |
| RB001 | x (deriv_S) | 0.03 | x (deriv_S) | 1 | |
| RB002 | | | | | |
| RB025 | x | 0.25 | | | |
| RB051 | x (deriv_r) | 64 | x (deriv_R) | 256 | x |
| RB057 | x (deriv_r) | 64 | x (deriv_R) | 256 | x |
| RB075 | x (deriv_S) | 0.03 | x (deriv_S) | 0.5 | |
| RB076 | | | x | 1 | x |
| RB077 | x | 1 | | | |
| RB086 | x | 64 | | | x |
| RB110 | x | 8 | | | |
| RB156 | | | | | x |
| RB765 | | | x | 64 | |
| RB767 | | | | | |
| UCI_51 | | | | | |
| BAA2471 | | | | | x |

| | EcCip | | EcGent | | |
|---|---|---|---|---|---|
| STRAIN | Phase 1 | cip MIC (mg/L) | Phase 1 | gent MIC (mg/L) | Used in blood cultures? |
| AR0048 | | | | | |
| AR0055 | | | x | 64 | x |
| AR0058 | | | | | |
| AR0061 | x | 0.25 | x | 32 | x |
| AR0069 | | | | | x |
| AR0077 | | | | | |
| AR0081 | x | 16 | x | 0.5 | |
| AR0084 | | | x | 0.5 | |
| AR0085 | x | 16 | x | 2 | |
| AR0089 | x | 0.25 | | | x |
| AR0104 | x | 32 | | | |
| BAA2469 | x | 64 | x | 64 | |
| BAA2523 | x | 0.5 | | | |
| BAC0800005647 | x | 64 | x | 1 | x |
| BIDMC_77 | | | | | |
| IDR1200024571 | x | 0.5 | | | |
| IDR1200039757 | | | | | |
| IDR1300027657 | | | x | 64 | |
| IDR1300034680 | x | 0.03 | x | 1 | x |
| IDR1600029769 | | | | | |
| IDR1600035372 | | | | | |
| IDR1600043633 | | | | | |
| IDR1600047120 | | | x | 64 | |
| MGH_57 | | | x | 0.5 | |
| RB001 | x<br>(deriv_S) | 0.03 | x<br>(deriv_S) | 1 | |
| RB002 | | | | | |
| RB025 | x | 0.25 | | | |
| RB051 | x<br>(deriv_R) | 64 | x<br>(deriv_R) | 256 | x |
| RB057 | x<br>(deriv_R) | <br>64 | x<br>(deriv_R) | 256 | x |
| RB075 | x<br>(deriv_S) | <br>0.03 | x<br>(deriv_S) | 0.5<br>1 | <br>x |
| RB076 | | | x | | |
| RB077 | x | 1 | | | |
| RB086 | x | 64 | | | x |
| RB110 | x | 8 | | | |
| RB156 | | | | | x |
| RB765 | | | x | 64 | |
| RB767 | | | | | |
| UCl_51 | | | | | |
| BAA2471 | | | | | x |

| | AbCip | | AbGent | |
|---|---|---|---|---|
| STRAIN ATCC | Phase 1 | cip MIC (mg/L) | Phase 1 | gent MIC (mg/L) |
| 17978 | x | 0.5 | x | ≤0.5 |
| AR0033 | x | >32 | x | 32 |
| AR0035 | x | >32 | x | 16 |
| AR0036 | x | >32 | x | |
| AR0037 | x | >32 | x | >32 |
| AR0045 | x | >32 | x | >32 |
| AR0052 | x | 4 | x | 32 |
| AR0056 | x | >32 | x | >32 |
| AR0063 | x | 8 | x | 4 |
| AR0070 | x | 8 | x | >32 |
| AR0078 | x | >32 | x | >32 |
| AR0101 | x | >32 | x | 8 |
| AR0102 | x | >32 | x | >32 |
| RB197 | xxx<br>(deriv_S) | 0.25 | x<br>(deriv_S) | ≤0.5 |
| RB197s | x | 0.25 | | |
| RB198 | x<br>(deriv_R) | >32 | x | 32 |

-continued

| | AbCip | | AbGent | |
|---|---|---|---|---|
| STRAIN ATCC | Phase 1 | cip MIC (mg/L) | Phase 1 | gent MIC (mg/L) |
| RB200 | | | x<br>(deriv_R) | >32 |
| RB201 | xx<br>(deriv_S) | 0.25 | x | 1 |
| RB202 | x<br>(deriv_R) | >32 | x | >32 |
| RB203 | x | >32 | x | 4 |
| RB204 | x | >32 | x<br>(deriv_R) | >32 |
| RB205 | x | 1 | x<br>(deriv_S) | 2 |
| RB206 | x | >32 | x | >32 |

| STRAIN | Alt name 1 | PaCip Phase 1 | PaCip cip MIC (mg/L) | Source | Comments |
|---|---|---|---|---|---|
| BL01 | RB918 | x | 0.125 | B&L | eye isolate |
| BL03 | RB919 | x | 16 | B&L | eye isolate |
| BL08 | RB920 | x | 0.06 | B&L | eye isolate |
| BL11 | RB921 | x | 0.125 | B&L | eye isolate |
| BL17 | RB922 | x | 16 | B&L | eye isolate |
| BL22 | RB923 | x | 0.5 | B&L | eye isolate |
| BWHPSA003 | RB294 | x | 16 | BWH | clinical pulmonary isolate |
| BWHPSA006 | RB925 | x | 16 | BWH | clinical pulmonary isolate |
| BWH029 | RB926 | x | 0.03 | BWH | clinical pulmonary isolate |
| BWH033 | RB927 | x | 0.06 | BWH | clinical urinary isolate |
| BWHPSA041 | RB928 | x | 2 | BWH | clinical wound isolate |
| BWHPSA043 | RB929 | x | 0.06 | BWH | clinical wound isolate |
| BWHPSA046 | RB930 | x | 0.06 | BWH | clinical pulmonary isolate |
| BWHPSA048 | RB931 | x | 8 | BWH | clinical urinary isolate |
| BWH049 | RB932 | x | 16 | BWH | clinical urinary isolate |
| BWH050 | RB933 | x | 0.25 | BWH | clinical blood isolate |
| BWH053 | RB934 | x | 16 | BWH | clinical blood isolate |
| BWH055 | RB935 | x | 0.125 | BWH | clinical urinary isolate |
| CF5 | RB936 | x | 8 | Lory lab | respiratory isolate from CF patient from Lory lab via Aussubel lab |
| CF18 | RB937 | x | 0.06 | Lory lab | respiratory isolate from CF patient from Lory lab via Aussubel lab |
| CF27 | RB938 | X | 1 | Lory lab | respiratory isolate from CF patient from Lory lab via Aussubel lab |
| UDL | RB939 | x | 0.125 | Lory lab | urinary isolate from Lory lab via Aussubel lab |
| X13273 | RB940 | x | 8 | Lory lab | blood isolate from Lory lab via Aussubel lab |
| X24509 | RB941 | x | 64 | Lory lab | urinary isolate from Lory lab via Aussubel lab |

| STRAIN | SaLevo Phase 1 | SaLevo levo MIC (mg/L) | Source | Comments |
|---|---|---|---|---|
| RB003 | x | 0.125 | BWH | clinical isolate from BWH |
| RB004 | x | 32 | BWH | clinical isolate from BWH |
| RB006 | x | 0.06 | BWH | clinical isolate from BWH Crimson Core |
| RB007 | x | 16 | BWH | clinical isolate from BWH Crimson Core |
| RB010 | x | >32 | BWH | clinical isolate from BWH Crimson Core |
| RB045 | x | 32 | BWH | clinical isolate from BWH Crimson Core |
| RB047 | x | >32 | BWH | clinical isolate from BWH Crimson Core |
| RB064 | x | 8 | BWH | clinical isolate from BWH Crimson Core |
| RB065 | x | 0.06 | BWH | clinical isolate from BWH Crimson Core |
| RB066 | x | 0.06 | BWH | clinical isolate from BWH Crimson Core |
| RB067 | x | 0.13 | BWH | clinical isolate from BWH Crimson Core |
| RB0069 | x | 0.13 | BWH | clinical isolate from BWH Crimson Core |
| RB072 | x | 4 | BWH | clinical isolate from BWH Crimson Core |
| RB074 | x | 32 | BWH | clinical isolate from BWH Crimson Core |
| RB090 | x | 32 | BWH | clinical isolate from BWH Crimson Core |
| RB095 | x | 32 | BWH | clinical isolate from BWH Crimson Core |

-continued

| STRAIN | SaLevo Phase 1 | SaLevo levo MIC (mg/L) | Source | Comments |
|---|---|---|---|---|
| RB096 | x | 0.13 | BWH | clinical isolate from BWH Crimson Core |
| RB098 | x | 0.13 | BWH | clinical isolate from BWH Crimson Core |
| RB211 | x | 16 | BWH | clinical isolate from BWH Crimson Core |
| RB219 | x | 32 | BWH | clinical isolate from BWH Crimson Core |
| RB221 | x | 0.13 | BWH | clinical isolate from BWH Crimson Core |
| RB223 | x | 0.13 | BWH | clinical isolate from BWH Crimson Core |
| RB245 | x | 0.25 | BWH | clinical isolate from BWH |
| RB247 | x | 0.5 | BWH | clinical isolate from BWH |

KEY/ABBREVIATIONS:

* large inoculum effect for meropenem MIC (RB554: MIC 0.5 at 1e5 cfu/mL, MIC 32 at 1e7 cfu/mL)

ATCC American Type Culture Collection

BWH Brigham and Women's Hospital, Boston MA USA

CDC United States Centers for Disease Control deriv_S susceptible strain used in RNA-Seq for derivation of responsive and control genes, and for derivation of "centroid" of susceptible strains for SPD calculations, defined as SPD := 0 (see Barczak, Gomez et al, PNAS 2012).

deriv_R resistant strain used in RNA-Seq for derivation of control genes, and for derivation of "centroid" of resistant strains for SPD calculations, defined as SPD := 0 (see Barczak, Gomez et al, PNAS 2012).

MGH Massachusetts General Hospital, Boston MA USA

NYDOH New York Department of Health (aka Wadsworth laboratories)

UCI Universities of California at Irvine, USA (x) non-derivation strain from phase 1 that was rerun in phase 2

Table 8: GO term enrichment summary (bold = enriched in two bacteria for the same drug; bold/red = enriched in all three bacteria for the same drug)

| **KpMero:** | category | over_represented_pvalue | under_represented_pvalue | numDEInCat | numInCat | term | ontology | BH.adjusted.pvalue |
|---|---|---|---|---|---|---|---|---|
| | GO:0009432 | 2.30E-07 | 1 | 13 | 30 | SOS response | BP | 6.75E-05 |
| | GO:0009245 | 7.11E-05 | 0.9999908 | 9 | 24 | lipid A biosynthetic process | BP | 0.010445386 |
| | GO:0009103 | 0.0002335 | 0.9999686 | 8 | 22 | **lipopolysaccharide biosynthetic process** | BP | 0.022882608 |
| | | | | | | | | |
| **KpCip:** | | | | | | | | |
| | GO:0009432 | 1.20E-11 | 1 | 19 | 30 | **SOS response** | BP | 3.52E-09 |
| | GO:0009246 | 7.42E-06 | 0.9999995 | 9 | 15 | enterobacterial common antigen biosynthetic process | BP | 0.001090988 |
| | GO:0045272 | 0.0002088 | 0.9999808 | 7 | 13 | **plasma membrane respiratory chain complex I** | CC | 0.020461935 |

| | | | | | | | | |
|---|---|---|---|---|---|---|---|---|
| **KpGent:** | | | | | | | | |
| | GO:0005829 | 4.52E-08 | 1 | 354 | 804 | cytosol | CC | 1.29E-05 |
| | GO:0042802 | 4.46E-07 | 1 | 139 | 279 | **identical protein binding** | MF | 6.38E-05 |
| | GO:0003677 | 1.42E-06 | 1 | 162 | 339 | DNA binding | MF | 0.0001353 |
| | GO:0006094 | 3.72E-05 | 1 | 12 | 13 | gluconeogenesis | BP | 0.0021253 |
| | GO:0045272 | 3.72E-05 | 1 | 12 | 13 | plasma membrane respiratory chain complex I | CC | 0.0021253 |
| | GO:0006096 | 0.0004 | 0.99993 | 15 | 20 | glycolytic process | BP | 0.015156 |
| | GO:0008137 | 0.0004 | 0.99993 | 15 | 20 | **NADH dehydrogenase (ubiquinone) activity** | MF | 0.015156 |
| | GO:0009246 | 0.00042 | 0.99996 | 11 | 13 | **enterobacterial common antigen biosynthetic process** | BP | 0.015156 |

| | | | | | | | | |
|---|---|---|---|---|---|---|---|---|
| | GO:0048038 | 0.00073 | 0.99989 | 13 | 17 | quinone binding | MF | 0.0232089 |
| | GO:0003700 | 0.00088 | 0.99944 | 116 | 257 | **transcription factor activity, sequence-specific DNA binding** | MF | 0.0232221 |
| | GO:0005515 | 0.00089 | 0.99935 | 247 | 594 | protein binding | MF | 0.0232221 |
| | GO:0051082 | 0.00195 | 0.99955 | 15 | 22 | unfolded protein binding | MF | 0.0465668 |
| | GO:0009252 | 0.00218 | 0.99921 | 25 | 43 | peptidoglycan biosynthetic process | BP | 0.0479236 |
| | GO:0006355 | 0.00245 | 0.99838 | 114 | 258 | **regulation of transcription, DNA-templated** | BP | 0.0499734 |
| | | | | | | | | |
| **EcMero:** | category | over_represented_pvalue | under_represented_pvalue | numDEInCat | numInCat | term | ontology | BH.adjusted.pvalue |

| | | | | | | | | |
|---|---|---|---|---|---|---|---|---|
| | GO:0045228 | 1.63E-10 | 1 | 10 | 10 | slime layer polysaccharide biosynthetic process | BP | 4.84E-08 |
| | GO:0009103 | 1.53E-08 | 1 | 18 | 39 | **lipopolysaccharide biosynthetic process** | BP | 2.26E-06 |
| | GO:0000160 | 1.20E-05 | 0.9999968 | 21 | 73 | phosphorelay signal transduction system | BP | 0.001179541 |
| | GO:0003700 | 8.05E-05 | 0.9999668 | 34 | 165 | transcription factor activity, sequence-specific DNA binding | MF | 0.005950885 |
| | GO:0000155 | 0.0001407 | 0.9999748 | 11 | 30 | phosphorelay sensor kinase activity | MF | 0.005950885 |
| | GO:0018106 | 0.0001407 | 0.9999748 | 11 | 30 | peptidyl-histidine phosphorylation | BP | 0.005950885 |

| | | | | | | | | |
|---|---|---|---|---|---|---|---|---|
| | GO:0023014 | 0.0001407 | 0.9999748 | 11 | 30 | signal transduction by protein phosphorylation | BP | 0.005950885 |
| | GO:0009408 | 0.000194 | 0.9999563 | 13 | 41 | **response to heat** | BP | 0.007176356 |
| | GO:0009242 | 0.0007007 | 0.9999106 | 7 | 16 | colanic acid biosynthetic process | BP | 0.023043956 |
| | GO:0042802 | 0.0010501 | 0.9994156 | 51 | 316 | identical protein binding | MF | 0.031083956 |
| | GO:0009097 | 0.0012302 | 0.9998603 | 6 | 13 | isoleucine biosynthetic process | BP | 0.033102869 |
| | GO:0006355 | 0.0016 | 0.9992615 | 28 | 149 | regulation of transcription, DNA-templated | BP | 0.039467343 |
| | | | | | | | | |
| **EcCip:** | | | | | | | | |
| | GO:0005829 | 5.89E-14 | 1 | 259 | 838 | cytosol | CC | 1.77E-11 |
| | GO:0045272 | 8.23E-08 | 1 | 12 | 13 | plasma membrane respiratory chain complex I | CC | 8.45E-06 |

| | | | | | | | | |
|---|---|---|---|---|---|---|---|---|
| | GO:0009432 | 1.04E-07 | 1 | 22 | 35 | SOS response | BP | 8.45E-06 |
| | GO:0048038 | 1.12E-07 | 1 | 13 | 15 | quinone binding | MF | 8.45E-06 |
| | GO:0005524 | 4.95E-07 | 0.9999997 | 142 | 468 | ATP binding | MF | 2.98E-05 |
| | GO:0042802 | 7.52E-06 | 0.9999959 | 98 | 312 | identical protein binding | MF | 0.000377223 |
| | GO:0005515 | 2.15E-05 | 0.999986 | 185 | 678 | protein binding | MF | 0.0008179 |
| | GO:0008137 | 2.17E-05 | 0.9999981 | 11 | 15 | **NADH dehydrogenase (ubiquinone) activity** | MF | 0.0008179 |
| | GO:0009060 | 7.64E-05 | 0.9999928 | 10 | 14 | **aerobic respiration** | BP | 0.002554494 |
| | GO:0009408 | 0.0001178 | 0.9999698 | 19 | 39 | response to heat | BP | 0.003544968 |
| | GO:0005737 | 0.0004105 | 0.9997398 | 107 | 379 | cytoplasm | CC | 0.011232616 |
| | GO:0003924 | 0.0010496 | 0.9997509 | 13 | 26 | GTPase activity | MF | 0.025792402 |
| | GO:0000287 | 0.001114 | 0.9993795 | 56 | 181 | magnesium ion binding | MF | 0.025792402 |
| | GO:0000049 | 0.0012322 | 0.9996029 | 18 | 42 | tRNA binding | MF | 0.026492746 |
| | GO:0006281 | 0.0013993 | 0.9995073 | 20 | 49 | DNA repair | BP | 0.028079213 |
| | GO:0006094 | 0.0018422 | 0.9997384 | 8 | 13 | gluconeogenesis | BP | 0.033095829 |
| | GO:0005525 | 0.0019593 | 0.9992409 | 22 | 57 | GTP binding | MF | 0.033095829 |

| | | | | | | | | |
|---|---|---|---|---|---|---|---|---|
| | GO:0008270 | 0.0019792 | 0.9989393 | 45 | 142 | zinc ion binding | MF | 0.033095829 |
| | | | | | | | | |
| | | | | | | | | |
| **EcGent:** | | | | | | | | |
| | GO:0005829 | 1.10E-10 | 1 | 292 | 838 | cytosol | CC | 3.32E-08 |
| | GO:0045272 | 9.19E-07 | 1 | 12 | 13 | plasma membrane respiratory chain complex I | CC | 0.000138358 |
| | GO:0048038 | 1.46E-06 | 0.9999999 | 13 | 15 | quinone binding | MF | 0.000146098 |
| | GO:0009408 | 2.88E-06 | 0.9999994 | 24 | 39 | response to heat | BP | 0.000216511 |
| | GO:0009060 | 4.90E-06 | 0.9999997 | 12 | 14 | **aerobic respiration** | BP | 0.000295219 |
| | GO:0000976 | 0.0001515 | 0.9999613 | 20 | 36 | **transcription regulatory region sequence-specific DNA binding** | MF | 0.007180246 |

| | | | | | | | | |
|---|---|---|---|---|---|---|---|---|
| | GO:0008137 | 0.000167 | 0.9999813 | 11 | 15 | **NADH dehydrogenase (ubiquinone) activity** | MF | 0.007180246 |
| | GO:0009246 | 0.0004784 | 0.9999418 | 10 | 14 | **enterobacterial common antigen biosynthetic process** | BP | 0.015360219 |
| | GO:0000160 | 0.0005103 | 0.9997895 | 33 | 75 | phosphorelay signal transduction system | BP | 0.015360219 |
| | GO:0045893 | 0.0005103 | 0.9997895 | 33 | 75 | **positive regulation of transcription, DNA-templated** | BP | 0.015360219 |
| | GO:0045892 | 0.000689 | 0.9996804 | 40 | 97 | **negative regulation of transcription, DNA-templated** | BP | 0.018272272 |

| | | | | | | | | |
|---|---|---|---|---|---|---|---|---|
| | GO:0042802 | 0.0007285 | 0.9995352 | 106 | 312 | **identical protein binding** | MF | 0.018272272 |
| | GO:0032993 | 0.0011444 | 0.9996019 | 22 | 46 | protein-DNA complex | CC | 0.025110664 |
| | GO:0005524 | 0.0011679 | 0.9991888 | 150 | 468 | **ATP binding** | MF | 0.025110664 |
| | GO:0051082 | 0.0018124 | 0.9995693 | 13 | 23 | unfolded protein binding | MF | 0.036369052 |
| | GO:0001216 | 0.0024028 | 0.9994473 | 12 | 21 | **bacterial-type RNA polymerase transcriptional activator activity, sequence-specific DNA binding** | MF | 0.045203227 |
| | GO:0000156 | 0.0026702 | 0.9992241 | 15 | 29 | phosphorelay response regulator activity | MF | 0.047278898 |
| | | | | | | | | |
| **AbMero:** | category | over_represented_pvalue | under_represented_pvalue | numDEInCat | numInCat | term | ontology | BH.adjusted.pvalue |

| | | | | | | | | |
|---|---|---|---|---|---|---|---|---|
| | GO:0003735 | 6.18E-25 | 1 | 38 | 56 | structural constituent of ribosome | MF | 9.02E-23 |
| | GO:0006412 | 1.02E-21 | 1 | 37 | 61 | translation | BP | 7.42E-20 |
| | GO:0022625 | 2.06E-19 | 1 | 26 | 34 | cytosolic large ribosomal subunit | CC | 1.00E-17 |
| | GO:0010124 | 1.12E-11 | 1 | 14 | 17 | phenylacetate catabolic process | BP | 4.07E-10 |
| | GO:0019843 | 5.58E-10 | 1 | 18 | 33 | rRNA binding | MF | 1.63E-08 |
| | GO:0000027 | 1.20E-09 | 1 | 15 | 24 | ribosomal large subunit assembly | BP | 2.93E-08 |
| | GO:0008137 | 2.95E-07 | 1 | 9 | 12 | NADH dehydrogenase (ubiquinone) activity | MF | 5.39E-06 |
| | GO:0045272 | 2.95E-07 | 1 | 9 | 12 | plasma membrane respiratory chain complex I | CC | 5.39E-06 |
| | GO:0022627 | 7.15E-06 | 0.9999993 | 10 | 19 | cytosolic small ribosomal subunit | CC | 0.000115922 |

| | | | | | | | | |
|---|---|---|---|---|---|---|---|---|
| | GO:0005515 | 2.53E-05 | 0.9999893 | 43 | 216 | protein binding | MF | 0.000368873 |
| | GO:0009408 | 0.000156 | 0.9999865 | 7 | 13 | **response to heat** | BP | 0.002069898 |
| | GO:0009060 | 0.001353 | 0.999844 | 6 | 13 | aerobic respiration | BP | 0.016461583 |
| | GO:0005887 | 0.0015257 | 0.9993957 | 21 | 99 | integral component of plasma membrane | CC | 0.01713523 |
| | GO:0006635 | 0.0032705 | 0.9995175 | 6 | 15 | fatty acid beta-oxidation | BP | 0.031887682 |
| | GO:0000049 | 0.0032761 | 0.999218 | 9 | 30 | tRNA binding | MF | 0.031887682 |
| | GO:0048038 | 0.0038197 | 0.9995601 | 5 | 11 | quinone binding | MF | 0.034855201 |
| | | | | | | | | |
| **AbCip:** | | | | | | | | |
| | GO:0005887 | 4.48E-07 | 0.9999999 | 27 | 99 | integral component of plasma membrane | CC | 6.64E-05 |
| | GO:0045272 | 4.54E-05 | 0.999997 | 7 | 12 | plasma membrane respiratory chain complex I | CC | 0.002664886 |

| | | | | | | | | |
|---|---|---|---|---|---|---|---|---|
| | GO:0008137 | 9.00E-05 | 0.9999929 | 7 | 13 | **NADH dehydrogenase (ubiquinone) activity** | MF | 0.002664886 |
| | GO:0009060 | 9.00E-05 | 0.9999929 | 7 | 13 | **aerobic respiration** | BP | 0.002664886 |
| | GO:0009432 | 9.00E-05 | 0.9999929 | 7 | 13 | SOS response | BP | 0.002664886 |
| | GO:0099132 | 0.0015503 | 0.999864 | 5 | 10 | ATP hydrolysis coupled cation transmembrane transport | BP | 0.038240038 |
| | | | | | | | | |
| **AbGent:** | | | | | | | | |
| | GO:0045272 | 6.71E-08 | 1 | 12 | 12 | plasma membrane respiratory chain complex I | CC | 9.93E-06 |
| | GO:0008137 | 1.24E-05 | 0.9999993 | 11 | 13 | NADH dehydrogenase (ubiquinone) activity | MF | 0.000685478 |

| | | | | | | | | |
|---|---|---|---|---|---|---|---|---|
| | GO:0051082 | 1.39E-05 | 0.999999 | 12 | 15 | unfolded protein binding | MF | 0.000685478 |
| | GO:0005829 | 8.20E-05 | 0.999951 | 118 | 348 | cytosol | CC | 0.003034026 |
| | GO:0048038 | 0.0001397 | 0.999991 | 9 | 11 | quinone binding | MF | 0.003461981 |
| | GO:0009060 | 0.0001404 | 0.9999876 | 10 | 13 | **aerobic respiration** | BP | 0.003461981 |
| | GO:0051537 | 0.0006792 | 0.9998184 | 17 | 32 | 2 iron, 2 sulfur cluster binding | MF | 0.014360095 |
| | GO:0005524 | 0.0011434 | 0.9993209 | 76 | 221 | **ATP binding** | MF | 0.021153405 |
| | GO:0006099 | 0.0018825 | 0.9995827 | 12 | 21 | tricarboxylic acid cycle | BP | 0.030956723 |
| | GO:0051301 | 0.0027479 | 0.9992393 | 14 | 27 | cell division | BP | 0.040669255 |
| | GO:0016226 | 0.0038105 | 0.999543 | 7 | 10 | iron-sulfur cluster assembly | BP | 0.046996546 |
| | GO:0099132 | 0.0038105 | 0.999543 | 7 | 10 | ATP hydrolysis coupled cation transmembrane transport | BP | 0.046996546 |
| | | | | | | | | |
| **PaCip:** | | | | | | | | |
| | GO:0005829 | 1.5411E-10 | 1 | 88 | 596 | cytosol | CC | 4.6387E-08 |

| | | | | | | | | |
|---|---|---|---|---|---|---|---|---|
| | GO:0005515 | 1.6401E-05 | 0.99999256 | 49 | 349 | protein binding | MF | 0.00246842 |
| | GO:0016226 | 3.2454E-05 | 0.9999985 | 6 | 10 | iron-sulfur cluster assembly | BP | 0.00325621 |
| | GO:0005737 | 0.00011236 | 0.99994478 | 48 | 365 | cytoplasm | CC | 0.00845502 |
| | GO:0001896 | 0.00021704 | 0.99998253 | 6 | 13 | autolysis | BP | 0.01306574 |
| | GO:0009432 | 0.00094306 | 0.99985892 | 7 | 22 | SOS response | BP | 0.04355305 |
| | GO:0000049 | 0.00101286 | 0.99979112 | 9 | 35 | tRNA binding | MF | 0.04355305 |
| | | | | | | | | |
| **SaLevo:** | | | | | | | | |
| | GO:0009432 | 3.67E-05 | 0.9999973 | 7 | 15 | SOS response | BP | 0.00433248 |
| | GO:0006096 | 1.51E-04 | 0.99998479 | 7 | 18 | glycolytic process | BP | 0.00888559 |

TABLE 9 displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_mero GeneID = NC_ 009648 | KPN_00050 | 1178-1277 | AGATCGTGCTTACCGCATGCTGATGAACCGCAAATTCTCTGAAGAAGCGG CAACCTGGATGCAGGAACAGCGCGCCAGTGCGTATGTTAAAATTCTGAGC | SEQ ID NO: 140 | C | | x |
| Kp_mero | KPN_00098 | 523-622 | GGAACGTTGTGGTCTGAAAGTTGACCAACTTATTTTCGCCGGGTTAGCGG CCAGTTATTCGGTATTAACAGAAGACGAACGTGAGCTGGGCGTCTGCGTT | SEQ ID NO: 141 | C | | x |
| Kp_mero | KPN_00100 | 635-734 | TCGATTGTGCCATCGTTGTTGACGATTATCGCGTACTGAACGAAGACGGT CTGCGCTTTGAAGACGAATTTGTTCGCCACAAAATGCTGGATGCGATCGG | SEQ ID NO: 142 | C | | x |
| Kp_mero | KPN_00945 | 637-736 | AGTGCTGTGGTATGGCGAGAAAATCCATGTCGCCGTGGCGGCCGAAGTGC CCGGCACCGGCGTGGATACCCCGGAAGATCTGGAGCGCGTCCGCGCTGAG | SEQ ID NO: 143 | C | | |
| Kp_mero | KPN_00949 | 157-256 | GTGGATGCGTTCCGCCACGTCAGTGATGCGTTTGAGCAGACCAGCGAAAC CATCAGCCAGCGCGCCAATAACGCGATCAACGATTTGGTGCGCCAGCGTC | SEQ ID NO: 144 | C | | |
| Kp_mero | KPN_00950 | 61-160 | GTTAAGCTGGCGCAGGCGTTGGCCAATCCGTTATTTCCGGCGCTGGACAG CGCCCTGCGCGCGGGCCGTCATATCGGTCTCGACGAGCTGGATAATCACG | SEQ ID NO: 145 | C | | |
| Kp_mero | KPN_01276 | 1-100 | ATGCTGGAGTTGTTGTTTCTGCTTTTACCCGTTGCCGCCGCTTACGGCTG GTACATGGGGCGCAGAAGTGCACAACAGTCCAAACAGGACGATGCGAGCC | SEQ ID NO: 146 | C | | x |
| Kp_mero | KPN_02357 | 679-778 | TGATCAAATGTGCGCTGGTCGCCGGGATGGTGGTAATTGCGTTAGTGAAC AGGTATGTTCTGGTACCGCGCATGTCGGCAAGCGGTTCGCAGGCGGAAAG | SEQ ID NO: 147 | C | | |
| Kp_mero | KPN_02805 | 81-180 | GTTAATGATTGAACGCCTGCGTGCGATCGGCTTTACCGTTGAACCGATGG ATTTCGGCGATACGCAGAATTTCTGGGCCTGGCGCGGCCACGGCGAGACG | SEQ ID NO: 148 | C | | |
| Kp_mero | KPN_02846 | 732-831 | GCGCAGGATCTGGTGATGAACTTTTCCGCCGACTGCTGGCTGGAAGTGAG CGATGCCACCGGTAAAAAACTGTTCAGCGGCCTGCAGCGTAAAGGCGGTA | SEQ ID NO: 149 | C | | x |
| Kp_mero | KPN_02864 | 527-626 | CCGTACCCGCTGGTGGACGATCTGGAGCGATTCTACGACCATCTTGAGCA GACGCTGCTGGCGACGGGCTTTATCCGCCCGAATCATCCGGGGCAGGTGA | SEQ ID NO: 150 | C | | |
| Kp_mero | KPN_03230 | 100-199 | ATCCGCAAAAGCGAAAAAGATACGCGTCAGTATCAGGCGATCCGCCTTGA TAACGACATGGTCGTGCTGCTGGTTTCCGATCCGCAGGCGGTGAAATCGC | SEQ ID NO: 151 | C | | |
| Kp_mero | KPN_03317 | 34-133 | ATGGCCGGGGAACACGTCATTTTGCTGGATGAGCAGGATCAGCCTGCCGG TATGCTGGAGAAGTATGCCGCCCATACGTTTGATACCCCTTTACATCTCG | SEQ ID NO: 152 | C | | x |
| Kp_mero | KPN_03628 | 256-355 | CCGCCGTTAATGCCGGTTTATCCGGTGGCGCGTGGTGAAAGCCGCCTGTA TATGCAACGTATCGAGAAGGACTGGTATTCGCTGATGAACACCATCCAGA | SEQ ID NO: 153 | C | | |
| Kp_mero | KPN_03634 | 656-755 | AGCAATGACGGCGAAACGCCGGAAGGCATTGGCTTTGCGATCCCGTTCCA GTTAGCGACCAAAATTATGGATAAACTGATCCGCGATGGCCGGGTGATCC | SEQ ID NO: 154 | C | | x |
| Kp_mero | KPN_04331 | 423-522 | TCTGAAGGAGAATGGCAAAGAGGTGGTGATCAAGGTTATCCGCCCGGATA TTTTGCCGATCATTAAAGCGGACATGAAGCTCATCTACCGCCTGGCGCGC | SEQ ID NO: 155 | C | | |
| Kp_mero | KPN_04429 | 49-148 | CAGGTGCTGGTAAAAAGCAAGTCTATTCCGGCAGAGCCTGCCCAGGAATT AGGACTCGATACCTCGCGTCCGGTCATGTACGTCCTGCCCTATAATTCGA | SEQ ID NO: 156 | C | | |
| Kp_mero | KPN_04616 | 1272-1371 | TCATCGTGATGCAGGCCCAGGACGTCTGGATCCGTACCCTCTATGACCGC CACCGCTTTGTGGTGCGCGGCAACCTTGGCTGGATCGAAGCGGACAACTT | SEQ ID NO: 157 | C | | |
| Kp_mero | KPN_04617 | 3455-3554 | CGATAGCGCCGCGATGACCTCAATGCTTATTGGTATGGGGGTTGCACAAA GTGGTCAGGTTGTGGGTAAAATCGGCGAGACGTTTGGCGTAAGCAACTTG | SEQ ID NO: 158 | C | | |
| Kp_mero | KPN_04663 | 1199-1298 | ATTCAGTTCGTGCCGAAGCAGTACGAAAATATGTACTTCTCCTGGATGCG CGATATTCAGGACTGGTGTATCTCCCGTCAGCTGTGGTGGGGTCACCGCA | SEQ ID NO: 159 | C | | |
| Kp_mero | KPN_04666 | 450-549 | CAGGCCAGCGATGGTAACGCGGTGATGTTTATCGAAAGCGTCAACGGCAA CCGCTTCCATGACGTCTTCCTTGCCCAGCTGCGTCCGAAAGGCAATGCGC | SEQ ID NO: 160 | C | | x |
| Kp_mero | KPN_00055 | 496-595 | CCCGATGCTGTGCGGCGAAGTGGTCGGCATGCTGGTGGGCATCGGCGTCG GCACGCTGCTGGGCATGGAGCCGTTCCAGGTGTTCTTCTTTATCGTGCTG | SEQ ID NO: 161 | R | dn | |
| Kp_mero | KPN_00499 | 331-430 | TCTTCCCAATTTTAAATAACCCGGTGCCAGCAGGTATTGCCTGTATTGCC ATCGTGTGGATCTTTACTTTCGTTAATATGCTCGGCGGGACCTGGGTCAG | SEQ ID NO: 162 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_mero | KPN_00681 | 452-551 | CTTCTCCGATACCATCTTCGTGGTCGGTACCCGTCTGCTGGTGAAGAAAGGCGGTCCGATCAAAGATTTCCCGGACCTGAAGGATAAAGCGGTCGTCGTC | SEQ ID NO: 163 | R | dn | |
| Kp_mero | KPN_00699 | 295-394 | TCCGGCAGAAAATATCAACCTGCTGAATGGTAACGCGCCGGACATCGATGCGGAATGCCGTCGCTATGAAGAAAAAATTCGTTCCTACGGTAAAATCCAC | SEQ ID NO: 164 | R | dn | |
| Kp_mero | KPN_00840 | 385-484 | GACATCAAAGATGTCAAAGATCTGAACGGTAAAGTGGTCGCGGTGAAGAGCGGCACCGGCTCCGTTGACTACGCGAAAGCCAATATCAAAACCAAAGATC | SEQ ID NO: 165 | R | dn | |
| Kp_mero | KPN_00868 | 110-209 | TGCAACTGCGAAAGGCCAAAGGCTACATGTCAGTCAGCGAAAATGACCATCTGCGTGATAACTTGTTTGAGCTTTGCCGTGAAATGCGTGCGCAGGCGCC | SEQ ID NO: 166 | R | dn | x |
| Kp_mero | KPN_00956 | 570-669 | CTTCAGCACCGCAGCCACCTACGCGTTCGACAACGGTATCGCACTGTCTGCAGGCTACTCCAGCTCTAACCGTAGCGTCGATCAGAAAGCTGACGGCAAT | SEQ ID NO: 167 | R | dn | |
| Kp_mero | KPN_01105 | 326-425 | AGCGGATTGGTTTTCTGTGCGATATCCGCCAGGCGGTGTTCAATCCAAACCTGTTTCCGCATGAGAACATGGAAGGCAAAATCGACCGACCGGAAGAGTA | SEQ ID NO: 168 | R | dn | |
| Kp_mero | KPN_01164 | 1059-1158 | GGAAGCCTTACAGATTATGGAAGCGGATGTTATAAATGGCGCTCTGGATAGCGATGTCTTCCTCGTTTTGCGCCACCATGCGGAAACGCTACACGCCATC | SEQ ID NO: 169 | R | dn | |
| Kp_mero | KPN_01172 | 834-933 | CTGTGCGGCGTCTACTTCCTCGGCGAACAGCGTATCGACTATGAGGGCGCCAGCTTCGGGGTGGTCACCTGCGATCCGCAGAGTATCGATGTTGAAGCGG | SEQ ID NO: 170 | R | dn | |
| Kp_mero | KPN_01229 | 3-102 | GAACAAAAGCTTAGCAGGAATACTGGGCGTCACCGTCGCGTTAACCTTACTGGCGGGCTGTACCGCTTACGATCGTACCAAAGACCAGTTTACCCAGCCG | SEQ ID NO: 171 | R | dn | |
| Kp_mero | KPN_01529 | 69-168 | AGCGGTGTACCTGCACCAACGGATTGGTGGACGCATCAAAGCCTTTTTGCCGATCTATGATTTTTCCTATGAAATGACCACCCTGCTGTCGCCGGACGAG | SEQ ID NO: 172 | R | dn | |
| Kp_mero | KPN_01553 | 610-709 | AGGCAGATCGTCAATATGCTGACAACCGGACTCGCCATCCGTGACGGTCGGGTGTACAGCAATTTGCGGGTGGACGTGCAGGCTGACAATTCGCACTGGG | SEQ ID NO: 173 | R | dn | |
| Kp_mero | KPN_02241 | 71-170 | GGGTAGGTTACTCCATTCTGAACCAGCTTCCGCAGCTTAACCTGCCACAATTCTTTGCGCATGGCGCAATCCTAAGCATCTTCGTTGGCGCAGTGCTCTG | SEQ ID NO: 174 | R | dn | x |
| Kp_mero | KPN_02411 | 1592-1691 | CGCGATGAATCGCACGATCATGCGATCTCCGGGCATCGCAAAAAACGGGCGAAAGTGAAGAGCACCAGCTCGCTTGAGACTATCGAGGGGGTGGGGCCGA | SEQ ID NO: 175 | R | dn | |
| Kp_mero | KPN_02412 | 177-276 | GTGCCGGGCTAATTCCGCAGATGTCGTCCTGATGGACATGAACATGCCTGGGATCGGTGGTCTTGAAGCGACGCGCAAAATCGCGCGCTCCGTGGCGGGC | SEQ ID NO: 176 | R | dn | |
| Kp_mero | KPN_02563 | 150-249 | TCGCCTGCCGCACAAGCTGCTGTGCTACGTCACCTTCTCCATTTTCTGCATTATGGGGACCTATTTCGGTCTGCATATCGAAGACTCCATCGCCAACACC | SEQ ID NO: 177 | R | dn | |
| Kp_mero | KPN_02725 | 174-273 | GTTAAGCGAAAAAGCCCGCAATGTCGAATCTGAGCCGTGCCAAATTAACCCAACCTTCACTGACGTTGACGGCGGTGTGCAGCTGGATATCGATTTTGTT | SEQ ID NO: 178 | R | dn | |
| Kp_mero | KPN_02907 | 1176-1275 | CGCGCGGTAAATATGTCACCGTGCTGACCAACTGGTGCGGCGAATTTTCCTCGCAGGAAGCGCGACGTTTATTCAGCGATGCCGGCCTCCCTACCTACCG | SEQ ID NO: 179 | R | dn | |
| Kp_mero | KPN_02919 | 100-199 | GTCGCAGACCGTCTCGCCAAACTGGATAAGTGGCAAACTCATTTAATCAACCCGCACATCATTCTGTCTAAGGAGCCGCAGGGTTTTATCGCTGATGCAA | SEQ ID NO: 180 | R | dn | |
| Kp_mero | KPN_03396 | 15-114 | GCAGCTCAAAATACTGTCGTTCCTGCAGTTCTGCCTTTGGGGGAGCTGGCTCACCACGCTTGGCTCGTACATGTTTGTCACGCTGAAGTTTGACGGCGCG | SEQ ID NO: 181 | R | dn | |
| Kp_mero | KPN_04155 | 512-611 | GATCCCGACGCCGGTATGGATCATGGCGATTGTCTTCCTGGCGGCCTGGTACATGCTGCACCATACTCGCCTGGGCCGTTATATTTATGCCCTGGGCGGT | SEQ ID NO: 182 | R | dn | |
| Kp_mero | KPN_04160 | 539-638 | TCATTCGGTCTACCACACCTACTTCACGTCGATTACGCAAAATGAAGTGGTGAAGCTCGATCTCCACCAGGCGATTGTCGATGCCATTCTTAACAGTGAT | SEQ ID NO: 183 | R | dn | |
| Kp_mero | KPN_04423 | 109-208 | ATTAACGGCGACAAAGGCTACAACGGCCTCGCTGAAGTGGGTAAAAAGTTTGAAAAAGACACCGGCATTAAAGTTTCCGTAGAACACCCGGACAAGCTGG | SEQ ID NO: 184 | R | dn | |
| Kp_mero | KPN_04425 | 402-501 | TCATGACGTTCACATGATCGACTTCTACTACTGGGATATCTCCGGCCCGGGTGCAGGTCTGGAAAACGTTGACCTTGGCTTCGGTAAGCTCTCTCTGGCC | SEQ ID NO: 185 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_mero | KPN_04553 | 452-551 | CGCTTTGACGAACATTTCGTCCTTGACCTGCTGGTCGATGACGGGCAGGC CCGCGGCCTGGTGGCGATGAATATGATGGAAGGCACCCTGGTGCAGATCC | SEQ ID NO: 186 | R | dn | |
| Kp_mero | KPN_04582 | 56-155 | GCGCCCTGCAGGGAACGCCGGAAGCCCCGCCGCCCGCCACCGACCATCCG CAGGAGATCCAGCGCTACCAGACGGCTGGCCTGCAGAAAATGGCCACGGT | SEQ ID NO: 187 | R | dn | |
| Kp_mero | KPN_04672 | 183-282 | TTTTGCCAACGCCTTCGGCTTCAGCGGCTTTAACGAAATGAAACAGATGT TCAAGCAACATTTGATGGAAGAGACCGCCAACTATACCGAGCGCGCCCGT | SEQ ID NO: 188 | R | dn | |
| Kp_mero | KPN_04814 | 230-329 | CGCAAAAATGTCGATCGCGGCATTAATATGCATGTGGTGACGGAAGTGCA GCACATTGTGATCCTCGCCGAGCATAAGCTGCTGGACTATCGCGACGTCG | SEQ ID NO: 189 | R | dn | |
| Kp_mero | KPN_00016 | 501-600 | TGAAGATTTTCCTGATGGCGCTGGCGATTATTGATGACCTCGGGGCTATC GTGATTATCGCGCTGTTTTATACCCACGACCTGTCCATGCTCTCGCTGGG | SEQ ID NO: 190 | R | up | |
| Kp_mero | KPN_00017 | 403-502 | TGGAGCAGCTGAGCCAGCATAAGCTCGACATGATTATCTCTGACTGCCCG ATCGACTCGACGCAGCAGGAAGGGCTATTTTCGGTGAAGATCGGCGAGTG | SEQ ID NO: 191 | R | up | |
| Kp_mero | KPN_00043 | 139-238 | GCCGCCGAGCAGGCGGCGCTGGCCCGTGCCGATCTGGTTATCTGGCAGCA TCCTATGCAGTGGTATAGCGTACCGCCGCTGCTCAAGCTGTGGATGGACA | SEQ ID NO: 192 | R | up | |
| Kp_mero | KPN_00078 | 682-781 | AAAGCGGGCCTGGTCGCGCCGGACGAAACCACCTTCAATTACGTACGCGG CCGTCTGCATGCGCCGAAAGGCAAAGATTTTGACGATGCCGTAGCGTACT | SEQ ID NO: 193 | R | up | |
| Kp_mero | KPN_00164 | 208-307 | GCTGTGGCTGCTGGTCAAGCTGGGGATTGTCTTCGCGGTGCTGATTGCCG CCTATGGCGTCTACCTCGACCAGAAAATCCGCAGCCGCATTGACGGTAAA | SEQ ID NO: 194 | R | up | |
| Kp_mero | KPN_00176 | 597-696 | GCAACCCGTTCGGTCTGGGCGAAACCGTGACCTCCGGGATTGTCTCCGCG CTGGGCCGTAGCGGCCTCAACGTGGAAAACTACGAAAACTTTATCCAGAC | SEQ ID NO: 195 | R | up | |
| Kp_mero | KPN 00200 | 1-100 | ATGCTGGGTTTGAAACGGGTTCACCATATTGCCATCATTGCGACCGACTA CGCCCGCAGTAAAGCGTTCTATTGCGATATTCTGGGGTTTACGCTGCAAA | SEQ ID NO: 196 | R | up | |
| Kp_mero | KPN_00320 | 351-450 | CATTCCGCCGTTTCTGGTCCATACCGCGCTGAAGATCACCTCGCCAAACG GTAAAAGCTATAGCGACCGTCTGGACAATGTGAAGACGGAAAAGCAGTTG | SEQ ID NO: 197 | R | up | |
| Kp_mero | KPN_00331 | 478-577 | GCGTGGTGCTGGGCAATATGCTGACCAATATGTTCAGCGGCTCGCACCCG CAGGAGATAGTCAATATCATCGAAGAGAAGCCGCAGCCTGATGCCGCCTC | SEQ ID NO: 198 | R | up | |
| Kp_mero | KPN_00341 | 205-304 | CGCGGCAGTTGGGAGCCGCTGCTGTATGGTCTGCACCAGATGCAGATGCG TAATAAAAAGCGTCGGCGCGAGCTGGGAAGCCTGATTAAACGCTTTCGCA | SEQ ID NO: 199 | R | up | |
| Kp_mero | KPN_00560 | 917-1016 | GTGCTGAAGCCGGACCACACCGCCGGGCAGCGTCGTCTGACCCTCGCGGG GCAGCAGGGGCAGCAGTTTGCGGTCGAGAAAGGGCTGCAGGCGGGCGAGC | SEQ ID NO: 200 | R | up | |
| Kp_mero | KPN_00833 | 134-233 | AACCACTTTAGATGGTCTGGAAGCAAAACTGGCTGCTAAAGCCGAAGCCG CTGGCGCGACCGGCTACAGCATTACTTCCGCTAACACCAACAACAAACTG | SEQ ID NO: 201 | R | up | x |
| Kp_mero | KPN_01006 | 184-283 | CTGATGTTCCTGACCTACAAAACGGCGAATAAACCCACCGGGATTATTTC CGCCTTCGCCTTCACCGGGTTCCTCGGCTATATCCTTGGGCCGATGCTGA | SEQ ID NO: 202 | R | up | |
| Kp_mero | KPN_01107 | 100-199 | GCTGTCGCTGGTCTCAACGTGTTGGATCGCGGCCCGCAGTATGCGCAAGT GGTCTCCAGTACACCGATTAAAGAAACCGTGAAAACGCCGCGTCAGGAAT | SEQ ID NO: 203 | R | up | x |
| Kp_mero | KPN_01111 | 722-821 | GATCAAGGCGTCGGTTGAGCCGGATGGCCGCCGTCTGGTTGAGGTCCATC AGCCGCTGTCTGAGCATATCGATGACGACCCGCAGACCCTGCCCATTACG | SEQ ID NO: 204 | R | up | |
| Kp_mero | KPN_01183 | 88-187 | GCTCAGGACTATGTTGAGAAGCGAATCGACCTCAACGAGCTGCTGGTGCA GCATCCCAGCGCGACCTATTTTGTCAAAGCCGCTGGCGACAGCATGATCG | SEQ ID NO: 205 | R | up | |
| Kp_mero | KPN_01184 | 273-372 | CCCGCGCTGCGAAATTTACAGTATCGATGAGGCCTTTTGCGATGTCAGCG GTGTGCGTCATTGCAGAGATCTGACCGATTTTGGCCGCGAAATCCGCGCC | SEQ ID NO: 206 | R | up | |
| Kp_mero | KPN_01226 | 253-352 | GCGCGATGCACGATCTGATCGCCAGCGACACCTTCGATAAGGCGAAGGCG GAAGCGCAGATCGATAAGATGGAAGCGCAGCATAAAGCGATGGCGCTGTC | SEQ ID NO: 207 | R | up | x |
| Kp_mero | KPN_01266 | 19-118 | CGCGAACGCCAGCAGCGGCTGAAAGATAAAGTTGACGCCCGGGTGGCGGC GGCCCAGGACGAGCGCGGCATTGTGATGGTCTTTACCGGCAACGGCAAAG | SEQ ID NO: 208 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Kp_mero | KPN_01448 | 49-148 | TCCGGCTGTGTCTATAACAGTAAGGTGTCCACCGGTGCGGAACAGCTGCA GCATCATCGCTTCGTGCTGACCAGCGTCAACGGCCAGGCGGTCAACGCCA | SEQ ID NO: 209 | R | up | |
| Kp_mero | KPN_01624 | 130-229 | CAACGTATGTTTAAGAAAGAGACCGGCCATTCCCTCGGCCAGTACATCCG CAGCCGCAAGCTGACGGAGATTGCGCAGAAGCTCAAGCAGAGCAATGAGC | SEQ ID NO: 210 | R | up | |
| Kp_mero | KPN_01625 | 65-164 | ACCAGAAAAAAGATCGCCTGCTCAATGACTACCTCTCACCTATGGATATT ACCGCGACCCAGTTTCGCGTGCTCTGCTCCATTCGTTGCGAAGTATGTAT | SEQ ID NO: 211 | R | up | |
| Kp_mero | KPN_02024 | 277-376 | CACGGGCGCGCTCCCTTGCCGTGAACTACGGTCTGGTCGGCTATCAGGCG CTGCCGCCGGGTATCGCCAAAAATGTCGCCCGCGGCAAACCGCTCCCTCC | SEQ ID NO: 212 | R | up | |
| Kp_mero | KPN_02342 | 67-166 | TATGGGGTGTTATTCCACAGTGAGGAAAACGTCGGCGGTCTGGGTCTTAA GTGCCAATACCTCACCGCCCGCGGAGTCAGCACCGCACTTTATGTTCATT | SEQ ID NO: 213 | R | up | x |
| Kp_mero | KPN_02345 | 4-103 | ATGCGAATCGCGCTTTTCCTGCTGACGAACCTGGCAGTGATGGTCGTGTT CGGGCTGGTGTTAAGCCTCACGGGGATCCAATCCAGCAGCATGACCGGTC | SEQ ID NO: 214 | R | up | x |
| Kp_mero | KPN_02394 | 556-655 | CGGATTATTACTAAACAAAACCACCTTTGGCCGTAATACGCTGGCTATTG GCGGCAATGAAGAGGCGGCGCGCCTGGCCGGCGTCCCGGTGGTGCGCACC | SEQ ID NO: 215 | R | up | |
| Kp_mero | KPN_02742 | 97-196 | CAAATAGGCGATCGTGACAATTACGGTAACTACTGGGACGGTGGCAGCTG GCGCGACCGTGATTACTGGCGTCGTCACTATGAATGGCGTGATAACCGTT | SEQ ID NO: 216 | R | up | x |
| Kp_mero | KPN_02800 | 75-174 | GCAGCGCTTCAACGACTGGCTGGTCACCTGTAACAACCAAAATTTCTGCG TCACCCGTAACGTGGGGCTGCATCATGGCCTGGTGATGACCCTCAGCCGC | SEQ ID NO: 217 | R | up | |
| Kp_mero | KPN_02938 | 121-220 | GCGCTGGGGCTGTGCCTCGGCGGCAGAGCGGAAGCCGACATGGTGCGTCG CGGCGCCACCCGTGCCGACCTGTGCGCGCGCTTCGCGCTGAAAGATACCC | SEQ ID NO: 218 | R | up | |
| Kp_mero | KPN_03000 | 89-188 | GCCGCGGCGATAATTATGTTTATGTGAACCGCGAAGCGCGCATGGGGCGA ACAGCGTTAGTTATTCATCCN | SEQ ID NO: 219 | R | up | |
| Kp_mero | KPN_03270 | 1-100 | ATGCAACAGACCCCACATCAGCGCAAGACGCTCACCGAACGCGTTATCCA CGCCATCACCTTCGAAGGACTGGCGACGCTGATCCTCGCCCCTACCGCCG | SEQ ID NO: 220 | R | up | |
| Kp_mero | KPN_03358 | 539-638 | GGGCGAAAAACTGGTGAACTCGCAGTTCTCCCAGCGTCAGGAATCGGAAG CGGATGACTACTCTTACGACCTGCTGCGTAAGCGCGGTATCAATCCGTCG | SEQ ID NO: 221 | R | up | x |
| Kp_mero | KPN_03458 | 362-461 | CCGCGGGCCAGTTGCTGAACATTTATTACGAAACCGCCGATAACTGGCTG CGTCGTCACGATATGGGGCTGCGCATCCGCGGCGATCAGGGGCGTTATGA | SEQ ID NO: 222 | R | up | |
| Kp_mero | KPN_03844 | 749-848 | CATGGCGGCGGAAGAAGAAATTCAGTTTTGCCCACTGAGCCAGCTGCTGC CCGCTGACTTTAGCGAGCTGCCCTCAGGCAAAGTGGTTCGTGGTGAACTG | SEQ ID NO: 223 | R | up | |
| Kp_mero | KPN_03846 | 100-199 | TGCGCCACCCTGGGGCGGCAATATGAAATTCTGTTGATCGACGATGGCAG CAGCGACGATTCCGCGCGCATGCTCACCGAAGCCGCCGAGGCGGAAGGCA | SEQ ID NO: 224 | R | up | |
| Kp_mero | KPN_03847 | 229-328 | GAAGTCATTACGCCGTCCCAGACCTGGGTCTCCACTCTCAATATGATCTG CCTGCTGGGCGCCACGCCGGTGATGATCGATGTCGATAACGACAATCTGA | SEQ ID NO: 225 | R | up | |
| Kp_mero | KPN_03856 | 895-994 | TAAGCGGATCGGCATTGACCCGGCGGTAGTTTCCGCGCCGTTTATCGCCA CGCTGATTGATGGCACCGGGCTAATTATCTATTTCAAAATCGCCCAGTAT | SEQ ID NO: 226 | R | up | |
| Kp_mero | KPN_03903 | 141-240 | GACCAGCCAGTTCCTGCTGGCCTGTAAATACGATGCGCCAGCGACGATCG CAGCCATGCTGGATAACGGCATTGATGTGGATGGTCAGGATAAAACCGGC | SEQ ID NO: 227 | R | up | |
| Kp_mero | KPN_03934 | 257-356 | TGCCTTATATTACCAAGCAGAATCAGGCGATTACTGCGGATCGTAACTGG CTTATTTCCAAGCAGTACGATGCTCGCTGGTCGCCGACTGAGAAGGCGCG | SEQ ID NO: 228 | R | up | x |
| Kp_mero | KPN_03993 | 558-657 | TGGCGGCGGTCTATAACGTCCCGCTGGCCGGGGCGTTGTTCAGCCTTGAG GTCATGCTGCTGTCGTTTAGCTGGGAAAAAACGCTGGCGGCGATAATGAC | SEQ ID NO: 229 | R | up | |
| Kp_mero | KPN_04036 | 1361-1460 | CTCGACTACCTCGACGCCTTCGGCGCGGCGATCCACGCGGCGTTTCTGAT GGCGGCCGGCATTATGGCGGTGGCGTTTGTCCTCTCATGGCTGTTAAAGG | SEQ ID NO: 230 | R | up | |
| Kp_mero | KPN_04037 | 309-408 | GATGATGGTCGAGACGCTGGGGCATATGGCGGAGAAAAACGCCTGGTTCG CGCCGCTGTGGATGCAGGAGATCATCGGCGAGATGCCGATTCTGCGCCAG | SEQ ID NO: 231 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_mero | KPN_04077 | 10-109 | ACCGTATTCTGCATTTTGCTGTTCGCCGCCCTGCTGCACGCCAGCTGGAA CGCTATCGTCAAAGCCAGCGGCGATAAAATGTACGCGGCGATCGGCGTCA | SEQ ID NO: 232 | R | up | |
| Kp_mero | KPN_04129 | 387-486 | CGCTGGGCCGCCACACGGTGCAGATGCTGCATGACGTACTGGATGCGTTT GCGCGTATGGATCTCGACGAAGCGGTACGTATCTATCGCGAAGATAAGAA | SEQ ID NO: 233 | R | up | |
| Kp_mero | KPN_04131 | 431-530 | GGTGGCGCAGATGCAGCACTTCTCGGGCTGGGCGGGCGTTATCGCGCTGG CGCTGCTGCAGGTGCCTATCGTTATTCGTACCACCGAAAACATGCTGAAG | SEQ ID NO: 234 | R | up | |
| Kp_mero | KPN_04132 | 48-147 | CATGATTTTCAGTGCGCTGGTAAAACTGGCTGCGCTGATTGTGCTATTGA TGCTGGGCGGCATCATCGTTTCCCTGATCATCTCTTCCTGGCCGAGCATT | SEQ ID NO: 235 | R | up | |
| Kp_mero | KPN_04133 | 160-259 | AATAAAGTGAACTACCAGGGTATTGGTTCCTCTGGTGGCGTTAAGCAGAT TATTGCCAACACCGTTGATTTCGGTGCTTCTGATGCTCCGCTGGCTGATG | SEQ ID NO: 236 | R | up | |
| Kp_mero | KPN_04244 | 253-352 | CCCGGCGGCAAGAGCGTGGAGGAGTATCGCGCCTATTATAAGAAGGGCTA CGCCACCGATGTGGAGCAGATTGGCATTGAAGATGACGTGATTGAGTTCC | SEQ ID NO: 237 | R | up | |
| Kp_cip GeneID = NC_ 016845 | KPHS_08300 (KPN_00111 (nadC)) | 141-240 | GCAATTATTGCCGCAGGATGCACGCTCCCATGCGGTGGTCATTACTCGTG AAGATGGCGTCTTCTGTGGCAAACGCTGGGTGGAAGAGGTCTTTATTCAG | SEQ ID NO: 238 | C | | x |
| Kp_cip | KPHS_08670 (KPN_00140 (panC)) | 82-181 | CCGACGATGGGCAACCTGCATGATGGTCATATGAAGCTGGTTGATGAAGC CAAAGCCAGTGCGGACGTGGTGGTGGTCAGTATTTTCGTCAATCCGATGC | SEQ ID NO: 239 | C | | x |
| Kp_cip | KPHS_15300 (KPN_00697 (nagC)) | 347-446 | CTGCCCGAGCGCACCCAGGAAACGCTGGAACACGCCCTGCTGAATATCAT CGCCACCTTTATCGAAAACTGTCAGCGCAAAATTCGCGAGCTGATCGCTA | SEQ ID NO: 240 | C | | x |
| Kp_cip | KPHS_20110 (KPN_01134 (ycfD)) | 20-119 | TGGATTATCAATTAACGCTTAACTGGCCCGACTTTATCGAACGCTACTGG CAAAAACGGCCGGTGGTATTGAAGCGCGGCTTCGCCAATTTTATCGACCC | SEQ ID NO: 241 | C | | x |
| Kp_cip | KPHS_29220 (KPN_01944 (ydcG)) | 60-159 | TGTTGCCGCCGTATGCGGAACGTCAGGAGTCGCTTCCTTATTCAGTCAGG CCGCTTTTGCCGAAGACGCGGGCATTGCCGACGGGCAAACGCGTCGTTTT | SEQ ID NO: 242 | C | | x |
| Kp_cip | KPHS_33420 (KPN_02329 (yeaB)) | 80-179 | TCAATCAGCGGCAGGCGGCGGTGCTGGTGCCGATCGTGCGCGCCGGCCGCAG CCCGGCCTGCTGCTGACCCAGCGTTCGCCCGCTGCTGCGCAAGCACGCCGG | SEQ ID NO: 243 | C | | x |
| Kp_cip | KPHS_34080 (KPN_02387 (yecM)) | 100-199 | GCGCGACTGGGACTGGAGATCGCCGGGCTCGACGCCGACCATATCTCCCT GCGCTGTCATCAGAATACCACTGCGGAACGCTGGCGCCGCGGTCTGGAGC | SEQ ID NO: 244 | C | | x |
| Kp_cip | KPHS_37030 (KPN_02637 (yojN)) | 2443-2542 | AGATTGTATACTGAAATCGAAGCGGGCGATTTTGCTGCTCTGGCGCAAAC CGCCCACCGCCTCAAAGGGGCATTTGCTATGCTTAATCTGATACCCGGCA | SEQ ID NO: 245 | C | | x |
| Kp_cip | KPHS_42920 (KPN_03229 (recB)) | 350-449 | GAACGGCAGATGGACGAGGCGGCGGTATTCACCATCCACGGCTTTTGCCA ACGGATGCTGAGCCTTAACGCCTTCGAGTCGGGCATGCTGTTCGAGCAAC | SEQ ID NO: 246 | C | | x |
| Kp_cip | KPHS_44560 (KPN_03386 (yggT)) | 143-242 | TCGGACCGCTGCGCCGGATTATCCCGGCAATGGGGCCGATTGACAGCGCC TCGCTGCTGGTGGCATTTATTCTCTGCGTCATCAAAGCGATCGTGCTGTT | SEQ ID NO: 247 | C | | x |
| Kp_cip | KPHS_47740 (KPN_03634 (degS)) | 617-716 | GGCGAGCTGATGGGGATTAACACCCTCTCCTTTGACAAGAGCAATGACGG CGAAACGCCGGAAGGCATTGGCTTTGCGATCCCGTTCCAGTTAGCGACCA | SEQ ID NO: 248 | C | | x |
| Kp_cip | KPHS_01170 | 77-176 | GAATGACCGATGCCGATTTCGGCAAACCGATTATCGCCGTCGTTAACTCC TTTACCCAGTTTGTCCCCGGGCACGTGCACCTGCGCGATCTCGGCAAACT | SEQ ID NO: 249 | R | dn | |
| Kp_cip | KPHS_01380 | 2-101 | TGATCCCATTTAACGCGCCGCCGGTGGTTGGAACCGAGCTTGATTACATG CAGTCTGCGATGAACAGCGGCAAGCTGTGCGGCGACGGCGGCTTTACGCG | SEQ ID NO: 250 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_cip | KPHS_01410 | 1140-1239 | CTGCACAGTTTCTGTTTCGGCGCTATCTTCAACATGATAGTGCTGGCGCG<br>CGAGGGGCTGGATTCGTTCGGCTCCCGCGTGGTGTTTTTCCTCGTGATCT | SEQ ID NO: 251 | R | dn | |
| Kp_cip | KPHS_01420 | 475-574 | CGACAGCGGGGCGAAAATCGTCACCGTCGCGATGGGGTCGCCGCGCCAGG<br>AGATCTTTATGCGCGACTGCCGGCGCCTGTATCCGCACGCGCTGTATATG | SEQ ID NO: 252 | R | dn | |
| Kp_cip | KPHS_01930 | 151-250 | GAAGAGGTTGCCGAGATCTATTTGCCGCTGTCGCGTTTGCTCAACTTCTA<br>TATCAGTTCTAACCTGCGTCGCCAGGCTGTTCTCGAACAATTTCTTGGCA | SEQ ID NO: 253 | R | dn | |
| Kp_cip | KPHS_07120 | 1767-1866 | CAAAAAGGCCAATACCTCTTCGCTGGATTACTATCACCAGCTGCGCCATG<br>CGGCCAGCAGCTCGCGGCGTAAGTTCCTCTATGACACTAACGTTGGCGCG | SEQ ID NO: 254 | R | dn | |
| Kp_cip | KPHS_07560 | 587-686 | CCTTGGGCGCTATCTGACCCGCCCGCTGCTGCGCTTTGTCGCCCGTTCCG<br>GCCTGCGCGAAGTGTTCAGCGCCGTGGCCCTGTTCCTGGTCTTCGGCTTT | SEQ ID NO: 255 | R | dn | |
| Kp_cip | KPHS_13260 | 412-511 | TGGGCAACCAGGCCGACACCTATGTGGAAATGAACCTCGAACATAAACAG<br>ACCCTGGACAACGGGGCGACCACCCGTTTCAAAGTGATGGTGGCCGACGG | SEQ ID NO: 256 | R | dn | |
| Kp_cip | KPHS_15900 | 291-390 | GAGATCGTCATGCGGGTCTATTTTGAAAAACCGCGCACCACCGTCGGCTG<br>GAAAGGGCTCATCAACGATCCCCATATGGATAACAGCTTCCGCATCAACG | SEQ ID NO: 257 | R | dn | |
| Kp_cip | KPHS_18320 | 1319-1418 | GAGTGGCTGGAAACCTTCCAGGCGAAAGAGCAGGAAGCGACGGAGAAAAT<br>GCTGTCGCTGGAACAGAAAATGAGCGTGGCGCAAACCGCGCACAGCCAGT | SEQ ID NO: 258 | R | dn | |
| Kp_cip | KPHS_18370 | 563-662 | GCGACGGCTTCAGCACCGCAGCCACCTACGCGTTCGACAACGGTATCGCA<br>CTGTCTGCAGGCTACTCCAGCTCTAACCGTAGCGTCGATCAGAAAGCTGA | SEQ ID NO: 259 | R | dn | |
| Kp_cip | KPHS_18380 (KPN_00956 (ompF)) | 39-138 | CCTGCTGGTAGCCGGTGCAGCCAACGCTGCAGAAATCTATAACAAAAACG<br>GCAACAAACTGGACTTCTATGGAAAAATGGTCGGCGAGCACGTCTGGACC | SEQ ID NO: 260 | R | dn | |
| Kp_cip | KPHS_18600 | 972-1071 | GGAGTTCCGCGGTATCCGTCTGGGCACCGTCGGCAAAGTGCCGTTCTTTA<br>TTCCGGGGCTGAAGCAGCGTTTGAACGATGACTATCGTATTCCAGTGGAA | SEQ ID NO: 261 | R | dn | |
| Kp_cip | KPHS_19780 | 857-956 | CCGCGCTGACCTCGTTCCTGACCGGTATCACCGAGCCGATCGAGTTCTCG<br>TTCATGTTCGTGGCGCCGATCCTGTACGTTATCCATGCCATTCTGGCGGG | SEQ ID NO: 262 | R | dn | |
| Kp_cip | KPHS_29510 | 1162-1261 | GCTGCAGTCTATCGGTGAACTGATGATTTCCGGCCTCGGCCTGGCGATGG<br>TCGCTCAGCTGGTTCCTCAGCGTCTGATGGGCTTCATCATGGGCAGCTGG | SEQ ID NO: 263 | R | dn | |
| Kp_cip | KPHS_31980 | 181-280 | TACCGTGAAATGCTGATTGCTGACGGTATTGATCCGAATGAACTGCTGAG<br>CACCATGGCTGCCGTTAAAGCCGGTACCAAAACCAAGCGTGCTGCACGTC | SEQ ID NO: 264 | R | dn | |
| Kp_cip | KPHS_37120 | 220-319 | ATCGCCTATGGATTTTCGAAATTCATCATGGGATCGGTCTCTGACCGCTC<br>GAATCCGCGCATTTTCCTGCCGGCTGGCTTGATCCTCGCCGCGCTGGTGA | SEQ ID NO: 265 | R | dn | |
| Kp_cip | KPHS_37330 | 234-333 | TGGTGCTGCTGGCGAGCCTCGCGACCTGTACTTTCGCCTACCCGTGGCTT<br>GAGGGTTACAAGGACAACAAAGAAGAGTTCTACCTGCTGGTGCTGATCGC | SEQ ID NO: 266 | R | dn | |
| Kp_cip | KPHS_49400 | 898-997 | GCTGGAGGAGATCGAACGCCAGGGGCTGTTCCTGCAGCGGATGGATGATT<br>CCGGCGAATGGTTCCGCTATCACCCGCTGTTTGGCAGCTTCCTGCGCCAG | SEQ ID NO: 267 | R | dn | |
| Kp_cip | KPHS_02660 | 110-209 | TCCGTTCCCCAAACGCGGCGGAAGAACACCTGAAAGCGCTGGCGCGTAAA<br>GGCGCGATCGAGATCGTCTCCGGCGCTTCTCGCGGTATTCGCCTGCTGAC | SEQ ID NO: 268 | R | up | |
| Kp_cip | KPHS_02670 | 624-723 | CGCGGAGTACGCCACCCTCATTATTGGCCTGCTGATGGCGAAGCGGGTGC<br>TGACGCTGCGCGGCGTGTCGCTGGCGATGCTGAAAAACGCCTGGCGCGGG | SEQ ID NO: 269 | R | up | |
| Kp_cip | KPHS_02820 (KPN_04445 (uvrA)) | 2299-2398 | CTATAACCGCGAAACGCTGGAGATTAAGTACAAGGGTAAGACCATCCACG<br>AAGTGCTGGATATGACCATTGAAGAGGCGCGTGAATTCTTTGATGCCGTA | SEQ ID NO: 270 | R | up | x |
| Kp_cip | KPHS_02830 (KPN_04446 (ssb)) | 114-213 | CGAATCCTGGCGTGACAAGCAGACCGGCGAAATGAAAGAGCAGACCGAGT<br>GGCACCGCGTTGTGCTGTTCGGCAAACTGGCGGAAGTCGCTGGTGAGTAT | SEQ ID NO: 271 | R | up | x |
| Kp_cip | KPHS_03430 | 325-424 | TGTCGGTGCTGCGCCCCGCCAGCGCCCATGTCGCCGAGGCCTTTGGCATC<br>AATGAGGGCGAGAACGTGATCCACCTGCGTACCCTGCGCCGGGTCAATGG | SEQ ID NO: 272 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_cip | KPHS_03440 | 498-597 | ATTGAGATGGCCTGGCAGGAAACCTTCTGGGCCCACGGCTTCGGCAAAGT CGTCGACCGCTTTGGCGTCCCCTGGATGATCAACGTGGTCAAACAAGGCT | SEQ ID NO: 273 | R | up | |
| Kp_cip | KPHS_03450 (KPN_04502 (phnA)) | 145-244 | AGCGACATTCTGATCGTTAAAGATGCCAATGGCAATTTACTGGCCGATGG CGACAGCGTTACCGTCGTGAAAGATCTGAAGGTTAAAGGCAGCTCTTCGA | SEQ ID NO: 274 | R | up | x |
| Kp_cip | KPHS_04910 | 1699-1798 | ACCGACAAAGGTTACTACACCAACAGCTTCCACCTCGACGTGGAGAAGAA GGTCAACCCGTACGACAAGATCGATTTCGAAGCGCCGTACCCGCCGCTGG | SEQ ID NO: 275 | R | up | |
| Kp_cip | KPHS_07720 | 2271-2370 | CCAGCAGTCGCCGCTCGATTACGATCACTATTTAACAAAGCAGTTGCAGC CGGTGGCGGAAGGGATCCTGCCCTTCGTCAACGATGACTTTGCTACAATA | SEQ ID NO: 276 | R | up | |
| Kp_cip | KPHS_07860 | 913-1012 | TGTTGAAGCGAACCGGCTCCGTCAACATCAGTCGAAAGTTACCAATAATT TCCGGTTTATTGCTGTCCAGCTGTATTATCGCGGCGAATTGGGTAAGCGC | SEQ ID NO: 277 | R | up | |
| Kp_cip | KPHS_09730 | 671-770 | AGCGCTTCGGTAAATTCGGGCGTATTCTGTGGGAGCGCAGCCACGGGATT GATGAGCGGGAAATTCATAACGATCGGCAGCGTAAATCGGTGGGCGTGGA | SEQ ID NO: 278 | R | up | |
| Kp_cip | KPHS_10170 | 341-440 | CTTGGCGCCCTGTACGACGTGGAAGCCTGGACCGATATGTTCCCGGAATT CGGCGGCGATTCCTCTGCCCAGACCGATAACTTTATGACCAAGCGCGCCA | SEQ ID NO: 279 | R | up | |
| Kp_cip | KPHS_10780 | 308-407 | TCACCAAGCCTTTCTCTCCGAAAGAGCTGGTGGCGCGAATCAAAGCGGTG ATGCGCCGTATTTCACCGATGGCGGTGGAAGAGGTGATCGAAATGCAGGG | SEQ ID NO: 280 | R | up | |
| Kp_cip | KPHS_16320 | 1399-1498 | GAGCACGGCGAGCGCGTGCGCTATCTGCACTCGGATATCGACACCGTCGA GCGCATGGAAATCATCCGCGACCTGCGTCTTGGCGAGTTTGACGTGCTGG | SEQ ID NO: 281 | R | up | |
| Kp_cip | KPHS_16630 | 125-224 | GCAAGGCGCAACCACTTTAGATGGTCTGGAAGCAAAACTGGCTGCTAAAG CCGAAGCCGCTGGCGCGACCGGCTACAGCATTACTTCCGCTAACACCAAC | SEQ ID NO: 282 | R | up | |
| Kp_cip | KPHS_19930 | 157-256 | CAGCTGGCGCAGAAAGCGGATGAGATGGGCGCCACTTCATACCGTATTAC TTCGGTAACCGGTCCGAATACCCTTCACGGTACCGCCGTTATCTACAAGT | SEQ ID NO: 283 | R | up | |
| Kp_cip | KPHS_20630 | 80-179 | CCAAACGCATGCAGCGCATTTTCCCGGAGGCGGAAGTGCGGGTGAAGCCG ATGATGACGCTGCCGGCGATCAACACCGACGCCAGCAAGCATGAAAAAGA | SEQ ID NO: 284 | R | up | |
| Kp_cip | KPHS_20650 | 68-167 | AGTGCGGCTTTCCCAGCCCGGCTCAGGACTATGTTGAGAAGCGAATCGAC CTCAACGAGCTGCTGGTGCAGCATCCCAGCGCGACCTATTTTGTCAAAGC | SEQ ID NO: 285 | R | up | |
| Kp_cip | KPHS_20660 | 276-375 | GCGCTGCGAAATTTACAGTATCGATGAGGCCTTTTGCGATGTCAGCGGTG TGCGTCATTGCAGAGATCTGACCGATTTTGGCCGCGAAATCCGCGCCACG | SEQ ID NO: 286 | R | up | |
| Kp_cip | KPHS_21250 | 277-376 | TGCTGGAGGCGCGGTTGATTAAAGAGCAGCAGCCGCTGTTTAACAAGCGG CTACGGCGTAACAAGCAGCTCTGCGCCTGGCTACTTGCGGACGACCGGCC | SEQ ID NO: 287 | R | up | |
| Kp_cip | KPHS_21390 | 187-286 | AGCCCGTGGCGCGGGCCTTTGGCCACCGCGGCTTCACCCACAGCCTGCTG GCCGTCTTTGGCGCGCTGACGCTGTTCTATCTGAAAGTGCCTGACAGCTG | SEQ ID NO: 288 | R | up | |
| Kp_cip | KPHS_27890 | 610-709 | ACCGTCTCCCTCGACGATTTTGACCAGACCGAGCTGGTGATCTCCATCGG CCATAATCCGGGCACCAACCACCCGCGGATGATGGGCACCCTGCATGAGC | SEQ ID NO: 289 | R | up | |
| Kp_cip | KPHS_31130 | 5-104 | TGCGCTCTATCGCCACCGTTTCGATTTCCGGCACCCTGCCTGAGAAGCTG CACGCTATTGCGGCGGCGGGGTATCAGGGGGTGGAAATTTTCGAGAACGA | SEQ ID NO: 290 | R | up | |
| Kp_cip | KPHS_31630 | 182-281 | TGATCGGCGTTGATATTGTGCTGGCGGTCATCTCCTCGATTATTATCGCC ATGATAATGACCTCGACCGGCCTGCCGGAAATGGGCACGATGCTGGCGAA | SEQ ID NO: 291 | R | up | |
| Kp_cip | KPHS_33810 (KPN_02363 (yebG)) | 4-103 | GCGGTTGAAATTAAATATGTGGTGATCCGCGAAGGTGAGGAAAAAATGTC TTTTGCCAGCAAAAAAGAGGCCGACGCTTACGACAAAATGCTCGATCTGG | SEQ ID NO: 292 | R | up | x |
| Kp_cip | KPHS_34140 | 622-721 | TCGTTAATCAACTGCAGGGAATGTCGGTAAAAGTTGGCGCCGGGGAAACT CAGGCGCATTGGCGGTTGGCGGATGCCGCCGCTGTAAGGACGTGGTTGCA | SEQ ID NO: 293 | R | up | |
| Kp_cip | KPHS_37080 (KPN_02642 (nrdA)) | 2010-2109 | AACAACGACGGTTATCTGCAGCTGGTGGGTATCATGCAGAAGTTTATCGA CCAGTCGATCTCTGCCAACACTAACTACGATCCGACGCGCTTCCCGTCCG | SEQ ID NO: 294 | R | up | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Kp_cip | KPHS_37090 (KPN_02643 (nrdB)) | 805-904 | GCTGAACCTGCTGCGCTCCGGCAGCGACGATCCGGAAATGGCGGAAATCG CCGAAGAGTGCAAGCAGGAGTGCTATGACCTGTTCGTGCTGGCGGCGCAG | SEQ ID NO: 295 | R | up | x |
| Kp_cip | KPHS_39770 | 256-355 | CGTTTTGTGAAAGTCAACACCGAAGCGGAACGTGAGCTTAGCGCCCGGTT TCGTATCCGCAGCATCCCGACCATTATGATGTTCAAAAATGGCGAAGTGA | SEQ ID NO: 296 | R | up | |
| Kp_cip | KPHS_40560 | 121-220 | GCGCTGGGGCTGTGCCTCGGCGGCAGAGCGGAAGCCGACATGGTGCGTCG CGGCGCCACCCGTGCCGACCTGTGCGCGCGCTTCGCGCTGAAAGATACCC | SEQ ID NO: 297 | R | up | |
| Kp_cip | KPHS_40580 | 62-161 | CCACTCTGGAACGAGTGGTTTACCGTCCTGACATCAACCAGGGTAACTAT CTGGCACCAAACGATGTAGCAAAAATTCGTGTCGGTATGACGCAACAGCA | SEQ ID NO: 298 | R | up | |
| Kp_cip | KPHS_41010 (KPN_03030 (recX)) | 380-479 | ACAGCGTAAATACGGCGAACCGTTACCTTCCGCCTTTACTGAAAAAGTGA AAGTTCAGCGATTCCTGCTTTACCGCGGCTACCTGATGGAAGATATCCAG | SEQ ID NO: 299 | R | up | x |
| Kp_cip | KPHS_41020 (KPN_03031 (recA)) | 539-638 | CGGGTAACCTGAAGCAGTCCAACACGCTGCTGATCTTTATCAACCAGATC CGTATGAAAATTGGCGTGATGTTCGGTAACCCGGAAACCACTACCGGTGG | SEQ ID NO: 300 | R | up | x |
| Kp_cip | KPHS_52230 | 272-371 | TGCTGCAGGCGGCGGAAGCGCTCAATTACCGGCCAAACATGATAGCCCAG TCGTTGCTCAGCCAGTCCACCGGCTGCATCGGCGTCATCTGCGCCCAGGA | SEQ ID NO: 301 | R | up | |
| Kp_cip | KPHS_52480 | 80-179 | AAAGCCTTGAACAGCATTTCAATATGCTGCGCCGCCTGGCGGAAAACTGG CAGAGCGGCAAAAACCGCTTTAACGCGCCGGGCGAAACGCTGCTGGGCGC | SEQ ID NO: 302 | R | up | |
| Kp_cip | KPHS_52490 | 10-109 | ACCGTATTCTGCATTTTGCTGTTCGCCGCCCTGCTGCACGCCAGCTGGAA CGCTATCGTCAAAGCCAGCGGCGATAAAATGTACGCGGCGATCGGCGTCA | SEQ ID NO: 303 | R | up | |
| Kp_cip | KPHS_53000 (KPN_04133 (pstS)) | 160-259 | AATAAAGTGAACTACCAGGGTATTGGTTCCTCTGGTGGCGTTAAGCAGAT TATTGCCAACACCGTTGATTTCGGTGCTTCTGATGCTCCGCTGGCTGATG | SEQ ID NO: 304 | R | up | x |
| Kp_gent GeneID = NC_ 012731 | KP1_0027 (KPN_04175 (hemN)) | 189-288 | TTGCCATAAGCTGTGTTATTTCTGCGGCTGCAATAAGATAGTCACCCGCC AGCAGCATAAGGCCGATCAATATCTCGATGTCCTTGAACAGGAGATCATC | SEQ ID NO: 305 | C | | x |
| Kp_gent | KP1_0117 (KPN_04252 (yijC)) | 397-496 | CGGAACTCGCCGACTATTTAGAACTCGAAAACCATATGCCGCGCGCCTTT ACCGAAGCGCAGGCTGAAGCTATGGTCACCATCGTTTTTAGCGCTGGCGC | SEQ ID NO: 306 | C | | x |
| Kp_gent | KP1_0163 | 262-361 | AAGATGTGCCGGTGGAATTCCCGGAGGGCCTGGGGCTGGTGACTATCTGC GAGCGCGACGATCCGCGCGACGCGTTTGTCTCCAATCGCTATGCCTCGAT | SEQ ID NO: 307 | C | | |
| Kp_gent | KP1_0191 (KPN_04329 (ubiE)) | 346-445 | AACGTTGAGTATGTTCAGGCCAACGCGGAAGCCCTGCCTTTTGCTGATAA TACCTTTGACTGCATCACCATCTCTTTCGGTCTGCGTAACGTGACCGACA | SEQ ID NO: 308 | C | | x |
| Kp_gent | KP1_0437 | 161-260 | AGGGTAAACGTCTGGTGGCGCTGGATATCAAGCAGACCGGCGTATTGCAG GGACTACCGCTGCAGTTTAGCGGCAGCAACCTGGTGAAGAGTATTCGCGC | SEQ ID NO: 309 | C | | |
| Kp_gent | KP1_0490 (KPN_04616 (ytfM)) | 1254-1353 | GGGGCTCGGACATCAACTTCATCGTGATGCAGGCCCAGGACGTCTGGATC CGTACCCTCTATGACCGCCACCGCTTTGTGGTGCGCGGCAACCTTGGCTG | SEQ ID NO: 310 | C | | x |
| Kp_gent | KP1_0974 (KPN_00146 (sfsA)) | 370-469 | TACAGGCAGATGACCGACAAAACTGCTATATTGAAGTGAAATCGGTTACG TTGGCGGAGAAAGAATACGGTTATTTTCCCGATGCGGTGACCACGCGCGG | SEQ ID NO: 311 | C | | x |
| Kp_gent | KP1_1702 (KPN_00744 (tolB)) | 1066-1165 | GCACATTGCCAAACAAGATCTGGAAACGGGTGGTGTACAGGTTCTGTCAT CAACGTTTTTAGACGAAACGCCAAGTCTGGCACCTAACGGCACTATGGTA | SEQ ID NO: 312 | C | | x |
| Kp_gent | KP1_1918 | 641-740 | CTGTGGTATGGCGAGAAAATCCATGTCGCCGTGGCGGCCGAAGTGCCCGG CACCGGCGTGGATACCCCGGAAGATCTGGAGCGCGTCCGCGCTGAGCTGC | SEQ ID NO: 313 | C | | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_gent | KP1_4363 | 829-928 | AGATCACCCAGAATCTGGCCGGCGGCACCGACAACACCCTGGCCTCGGTACTCGACTGTACGGTGACGCCGATGGGTAGCCGGATGCTCAAGCGCTGGCT | SEQ ID NO: 314 | C | | |
| Kp_gent | KP1_4377 (KPN_03107 (ygbO)) | 317-416 | CGAGGGCTGCCAGGTACTGGAATATGCTCGCCATAAGCGTAAGCTGCGTTTAGGCGCGCTGAAAGGCAACCAGTTTACCGTGATCCTGCGCGAGATTAGC | SEQ ID NO: 315 | C | | x |
| Kp_gent | KP1_4445 (KPN_03164 (mltA)) | 512-611 | TCGTTGATGGATAACTTCATCATGGACGTGCAGGGCAGCGGCTATATCGACTTTGGCGATGGTTCGCCGCTCAACTTCTTTAGCTATGCCGGGAAAAACG | SEQ ID NO: 316 | C | | x |
| Kp_gent | KP1_0041 | 225-324 | GTCATGGACGGTCATGCGCTTCTCGGAGGTGGAACAAAACGACAAGCTGGAATGGCTCATCCGCAAGGATGGCTGCATGCACTGCGCGGACCCGGGCTGC | SEQ ID NO: 317 | R | dn | |
| Kp_gent | KP1_0276 | 987-1086 | CGACGTGGTGTTGGTAGAAGAGGGAGCCACATTCGCTATCGGTTTGCCGCCAGAACGTTGCCATTTATTCCGTGAGGATGGCACCGCTTGTCGTCGGCTG | SEQ ID NO: 318 | R | dn | |
| Kp_gent | KP1_0395 | 1-100 | ATGTTAAACAACATTCGTATCGAAGAAGATCTGTTGGGCACCAGGGAAGTTCCCGCGGACGCTTACTACGGCGTTCATACTCTGCGAGCGATTGAAAACT | SEQ ID NO: 319 | R | dn | |
| Kp_gent | KP1_0425 | 974-1073 | GAGCGTCTGCCGTTTATCTGTGAACTGGCGAAAGCCTACGTCGGCGTCGATCCGGTGAAAGAGCCGATCCCGGTGCGCCCGACCGCGCACTACACCATGG | SEQ ID NO: 320 | R | dn | |
| Kp_gent | KP1_0908 | 1213-1312 | GAACATTTTAACGATAAAGCCGCCGTGGTGGCTCGCCTGCGCGAGCTGCTGGCGGAGCACAAAATAATGACCATTTTAGTGAAGGGTTCACGTAGTGCCG | SEQ ID NO: 321 | R | dn | |
| Kp_gent | KP1_0909 | 59-158 | CATATCTGACGTTTCGCGCCATCGTCAGCCTGCTGACCGCGCTGTTCATCTCGTTGTGGATGGGCCCGCGCATGATCGCCCGTCTGCAAAAACTCGCCTT | SEQ ID NO: 322 | R | dn | |
| Kp_gent | KP1_0910 | 507-606 | GCAGGCGGTGGCGGCAACCATCCTCAACGTGACTGAGGACCATATGGACCGCTACCCGCTGGGGCTGCAGCAGTATCGCGCGGCGAAGCTGCGGATTTAC | SEQ ID NO: 323 | R | dn | |
| Kp_gent | KP1_1258 | 364-463 | CTGGCCTGCTGGCTGGGGGTGATGGGGTTCGTGGTTTATGTCGGCGTCTACAGCCTGTACATGAAACGCCACTCCGTCTACGGCACGCTGATTGGCTCAC | SEQ ID NO: 324 | R | dn | |
| Kp_gent | KP1_1259 | 127-226 | CATGCGGTTATCCTTGGCACCATTCTGGTGACCGCTGTGGTGCAGATCGTGGTACACCTCGTGTACTTCCTGCATATGAACAGCAAGTCCGATGAAGGTT | SEQ ID NO: 325 | R | dn | |
| Kp_gent | KP1_1260 | 467-566 | CGGTGCTGATGTTCCAGGTTTCACGTCGTGGCCTGACCAGCACTAACCGCACGCGTATCCTGTGCCTGAGCCTGTTCTGGCACTTCCTGGACGTCGTGTG | SEQ ID NO: 326 | R | dn | |
| Kp_gent | KP1_1409 | 690-789 | GGTATCGTCTACATCGCCGCGACTCAGGTTATCGCCGGTATGTATCCTGCTTCTCAGATGGCCGCGTCCGGTGCGCCGTTCGCAATTAGCGCCTCTACCA | SEQ ID NO: 327 | R | dn | |
| Kp_gent | KP1_1410 | 540-639 | GATATCTCCATTTCGGTTTCTGAACTGGGTTCCCTGCTGGACCACAGCGGCCCGCACAAAGAAGCGGAAGAGTATATCGCTCGCGTGTTTAACGCAGAAC | SEQ ID NO: 328 | R | dn | |
| Kp_gent | KP1_1694 | 256-355 | TTCTATGTGGCGATGATTCTGGTGCTGGCCTCGCTGTTCTTCCGTCCGGTCGGTTTTGACTACCGTTCCAAGATCGAGGACACCCGCTGGCGCAACATGT | SEQ ID NO: 329 | R | dn | |
| Kp_gent | KP1_1902 | 764-863 | ATTCAGTGGACCTACTTCGGTTACCTGGCTGCCGTGAAATCTCAGAACGGCGCGGCAATGTCCTTCGGTCGTACCTCCAGCTTCCTGGATATCTACATCG | SEQ ID NO: 330 | R | dn | |
| Kp_gent | KP1_1903 | 473-572 | ATACTTTTGTGGAGGCCGTGAGCCTGGGTATCCTCGCTAACCTGATGGTTTGTCTCGCCGTATGGATGAGCTATTCCGGTCGTAGCCTGATGGATAAAGC | SEQ ID NO: 331 | R | dn | |
| Kp_gent | KP1_3311 (KPN_02199 (adhE)) | 1193-1292 | TTCTCAGGGTGGTATCGGTGACCTGTACAACTTCAAACTCGCGCCTTCCCTGACTCTGGGTTGTGGTTCCTGGGGTGGTAACTCCATCTCTGAAAACGTT | SEQ ID NO: 332 | R | dn | x |
| Kp_gent | KP1_3327 | 1095-1194 | TCCACCTTCCAGATGATCTCCGTGATCTTCCGTAAGCTGACTATGGACCGCGTGAAGGCCCAGGGCGGCAGCGAAGCGCAGGCGATGCGCGAGGCGGCGA | SEQ ID NO: 333 | R | dn | |
| Kp_gent | KP1_3445 | 45-144 | TAATATTGCGAAAGAACGCCTGCAAATCATCGTCGCCGAGCGCCGCCGCGGAGACGCGGAGCCGCATTACCTGCCGCAGTTACGCAAAGATATCCTGGAA | SEQ ID NO: 334 | R | dn | |
| Kp_gent | KP1_3458 | 749-848 | CGTATCGTCGAGGGCGGCGTGAAAATCACCAGCGTCAACATCGGCGGTATGGCGTTCCGCCAGGGTAAAACCCAGGTTAACAACGCGATTTCAGTCGATG | SEQ ID NO: 335 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_gent | KP1_3878 | 66-165 | ATACACCACTTTTTCACAGACGAAAAACGATCAGCTGCTGGAACCCATGT TTTTTGGCCAGCCGGTTAACGTGGCCCGCTACGATCAGCAAAAATACGAC | SEQ ID NO: 336 | R | dn | |
| Kp_gent | KP1_3908 | 32-131 | TGCTACCGCTGCTGATCGTCGGCTTGACGGTGGTGGTTGTGATGCTCTCC ATTGCGTGGCGACGCAATCATTTTCTCAATGCCACGCTGTCGGTTCTTGG | SEQ ID NO: 337 | R | dn | |
| Kp_gent | KP1_3909 | 319-418 | CGTGAAATCGAAAAATACCAGGGCTTCTTCCACCTCAACCTGATGTGGAT CCTGGGCGGCGTTATCGGCGTGTTCCTCGCCATCGACATGTTCCTGTTCT | SEQ ID NO: 338 | R | dn | |
| Kp_gent | KP1_3910 (KPN_02668 (nuoL)) | 1552-1651 | TCCATCGCCAACAGTGCGCCTGGCCGCTTCTTCGGTACCTGGTGGTTCCA TGCCTGGGGCTTCGACTGGTTATACGACAAGGTGTTCGTAAAACCATTCC | SEQ ID NO: 339 | R | dn | x |
| Kp_gent | KP1_3913 | 315-414 | GGTTATCGTTTACGCCATCCTGGGCATTAACGACCAGGGTATCGACGGTG CGGCGATTAACGCCAAAGAAGTGGGCATTGCGCTGTTTGGGCCGTACGTC | SEQ ID NO: 340 | R | dn | |
| Kp_gent | KP1_3914 | 14-113 | TAAAAGAATTATTGGTGGGGTTCGGCACCCAGGTCCGTAGTATCTGGATG ATTGGCCTGCATGCCTTCGCCAAACGTGAAACCCGGATGTATCCGGAAGA | SEQ ID NO: 341 | R | dn | |
| Kp_gent | KP1_3915 | 206-305 | TTAAAGAGGACTGGATCCCGCGCTTCTCCGATCGCGTGATCTTTACTCTG GCGCCGGTTATCGCCTTTACCTCGCTGCTGCTGGCCTTCGCTATCGTGCC | SEQ ID NO: 342 | R | dn | |
| Kp_gent | KP1_3916 | 366-465 | CATAGCTTCCGCCGCTATCGTTTCACCAAGCGTACCCACCGCAATCAGGA TCTGGGGCCGTTTATTTCGCACGAAATGAACCGCTGCATCGCCTGCTACC | SEQ ID NO: 343 | R | dn | |
| Kp_gent | KP1_3917 | 687-786 | CCAACGGCGTCGAGTGGTACCAGAACATTTCCACCAGCAAAGATGCTGGC ACCAAGCTGATGGGCTTCTCCGGCCGGGTGAAGAATCCGGGCGTCTGGGA | SEQ ID NO: 344 | R | dn | |
| Kp_gent | KP1_3919 (KPN_02675 (nuoE)) | 379-478 | ACCCTGCTGCCGACCTGCTGCCTGGGTAACTGCGACAAGGGACCGACCAT GATGATTGATGAGGATACTCACAGCCATCTGACGCCGGAGGCAATTCCTG | SEQ ID NO: 345 | R | dn | x |
| Kp_gent | KP1_4642 | 714-813 | CCGACCATCCTGCGCGACTCTCAGGAATATGTTTCCAAGAAACACAACCT GCCGCACAACAGCCTGAACTTCGTGTTCCACGGCGGTTCCGGTTCTTCCG | SEQ ID NO: 346 | R | dn | |
| Kp_gent | KP1_4873 | 89-188 | ATGACACCAACGCCCGCCACTTTGCCGGCCTTAATTTCACCGAAAAGAAA CTGCAGGAAGCCGTCAGCTTTGTGCATCAGCACCGTCGTAAGCTGCATAT | SEQ ID NO: 347 | R | dn | |
| Kp_gent | KP1_5122 | 390-489 | ATCTGATCAATAATCCGGTGATCCATGACGCGATGCGCTTTTTCCTGCGC CATCAGCCGGAGAATATGACCCTGGTGGTCCTGTCGCGTAACCTGCCGCA | SEQ ID NO: 348 | R | dn | |
| Kp_gent | KP1_5513 | 63-162 | CGAAAAAATCCAGGTAACGGGTAGCGAAGGTGAACTGGGTATTTACCCGG GCCACGCGCCGCTGCTCACCGCCATTAAGCCTGGTATGATTCGCATCGTT | SEQ ID NO: 349 | R | dn | |
| Kp_gent | KP1_5514 | 672-771 | CTGACCATGGCTGAGAAATTCCGTGACGAAGGTCGTGACGTACTGCTGTT CGTCGATAACATCTATCGTTACACCCTGGCCGGTACTGAAGTATCCGCGC | SEQ ID NO: 350 | R | dn | |
| Kp_gent | KP1_5515 | 425-524 | TAACCCATCCCTGTCCGAACTGATCGGCCCGGTAAAAGTGATGTTGCAGG CCTATGATGAAGGCCGTCTGGACAAGCTGTACGTTGTCAGCAACAAATTT | SEQ ID NO: 351 | R | dn | |
| Kp_gent | KP1_0325 (KPN_04462 (soxS)) | 1-100 | ATGTCCCATCAGGATATTATTCAAACTTTGATTGAATGGATTGATGAACA TATCGATCAACCACTTAACATTGATATAGTCGCCAGAAAGTCAGGATACT | SEQ ID NO: 352 | R | up | x |
| Kp_gent | KP1_0533 | 2300-2399 | CGCTGGAACCCGGCCGATCTCGGGCGCTTTATGGTCTTCTTTGGACCGAT CAGCTCGATTTTCGATATCCTCACCTTCGGCCTGATGTGGTGGGTGTTCC | SEQ ID NO: 353 | R | up | |
| Kp_gent | KP1_0837 (KPN_00016 (nhaA)) | 468-567 | TGGCGCTGTTAGGTAGCCGGGTCCCGACGGCGCTGAAGATTTTCCTGATG GCGCTGGCGATTATTGATGACCTCGGGGCTATCGTGATTATCGCGCTGTT | SEQ ID NO: 354 | R | up | x |
| Kp_gent | KP1_0838 (KPN_00017 (nhaR)) | 403-502 | TGGAGCAGCTGAGCCAGCATAAGCTCGACATGATTATCTCTGACTGCCCG ATCGACTCGACGCAGCAGGAAGGGCTATTTTCGGTGAAGATCGGCGAGTG | SEQ ID NO: 355 | R | up | x |
| Kp_gent | KP1_2104 | 107-206 | TAGGCACCATCTCTGCTTCTGCCGGGACTAACCTGGGCTCGCTGGAAGAC CAGCTGGCGCAGAAAGCGGATGAGATGGGCGCCACTTCATACCGTATTAC | SEQ ID NO: 356 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Kp_gent | KP1_2658 (KPN_01624 (marA)) | 107-206 | CCGGTTACTCTAAGTGGCACCTGCAACGTATGTTTAAGAAAGAGACCGGC CATTCCCTCGGCCAGTACATCCGCAGCCGCAAGCTGACGGAGATTGCGCA | SEQ ID NO: 357 | R | up | x |
| Kp_gent | KP1_2659 | 65-164 | ACCAGAAAAAAGATCGCCTGCTCAATGACTACCTCTCACCTATGGATATT ACCGCGACCCAGTTTCGCGTGCTCTGCTCCATTCGTTGCGAAGTATGTAT | SEQ ID NO: 358 | R | up | |
| Kp_gent | KP1_2873 | 406-505 | GAGGCGGCGCAGCGCATTCATGCCTTGCCGGGGGCCGGTGACGAAGAGAA ACGCTATGTCTTACGCGTCACCTGTCTGCGCGAACATGAAAATGCCGTAC | SEQ ID NO: 359 | R | up | |
| Kp_gent | KP1_3472 (KPN_02345 (htpX)) | 1-100 | ATGATGCGAATCGCGCTTTTCCTGCTGACGAACCTGGCAGTGATGGTCGT GTTCGGGCTGGTGTTAAGCCTCACGGGGATCCAATCCAGCAGCATGACCG | SEQ ID NO: 360 | R | up | x |
| Kp_gent | KP1_4962 | 121-220 | GCTGATATTATCAACAGCGAGCAGGCCCAGGGCCGCGAGGCCATCGGCAC GGTTTCCGTCGGCGCGGTAGCATCTTCCCCGATGGATATGCATGAAATGC | SEQ ID NO: 361 | R | up | |
| Kp_gent | KP1_5196 | 893-992 | CTTAAGCGGATCGGCATTGACCCGGCGGTAGTTTCCGCGCCGTTTATCGC CACGCTGATTGATGGCACCGGGCTAATTATCTATTTCAAAATCGCCCAGT | SEQ ID NO: 362 | R | up | |
| Kp_gent | KP1_5423 | 232-331 | AGCGGCTCACGTGGCGTGAAGGAAGCCAGTCGTCAGGCGGTGCTGCAGGC GGCGGAAGCGCTCAATTACCGGCCAAACATGATAGCCCAGTCGTTGCTCA | SEQ ID NO: 363 | R | up | |
| Kp_gent | KP1_5452 | 101-200 | ATATGCTGCGCCGCCTGGCGGAAAACTGGCAGAGCGGCAAAAACCGCTTT AACGCGCCGGGCGAAACGCTGCTGGGCGCCTTCGTCAACCACCAGCTGGT | SEQ ID NO: 364 | R | up | |
| Kp_gent | KP1_5467 (KPN_04090 (ibpB)) | 180-279 | TATTCAACTGGAAGGCACCCGTCTGGTGGTGAAAGGCACGCCGCAGCAGC CGGAAAAAGAGACCACATGGCTGCACCAGGGGTTGGTGAGCCAGGCCTTC | SEQ ID NO: 365 | R | up | x |
| Kp_gent | KP1_5468 (KPN_04091 (ibpA)) | 130-229 | CAGAGCAACGGCGGCTACCCTCCGTATAACGTCGAGCTGGTAGACGAAAA CCACTATCGCATCGCTATCGCGGTGGCTGGCTTTGCTGAAAGCGAGCTGG | SEQ ID NO: 366 | R | up | x |
| Ec_mero GeneID = NC_ 008563 (alt GeneID = NC_ 000913) | APECO78_ 00485 (b3940: metL) | 1-100 | ATGAGTGTGATTGCGCAGGCAGGGGCGAAAGGTCGTCAGCTGCATAAATT TGGTGGCAGTAGTCTGGCTGATGTGAAGTGTTATTTGCGTGTCGCGGGCA | SEQ ID NO: 367 | C | | x |
| Ec_mero | APECO78_ 02145 (b4235: pmbA) | 51-150 | TCTGGAAGAAGCAGTTTCCACTGCGCTGGAGTTGGCCTCAGGCAAATCGG ACGGTGCGGAAGTTGCCGTCAGCAAGACCACCGGCATTAGCGTAAGCACG | SEQ ID NO: 368 | C | | x |
| Ec_mero | APECO78_ 03915 | 656-755 | TTGGCTCGCTTTGTAGAACTTTATCCGGTTTTACAGCAGCAGGCGCAAAC CGATGGCAAACGGATTAGCTACGTTGATTTGCGTTATGACTCTGGAGCGG | SEQ ID NO: 369 | C | | |
| Ec_mero | APECO78_ 03920 (b0094: ftsA) | 624-723 | GATATCGGTGGTGGTACAATGGATATCGCCGTTTATACCGGTGGGGCATT GCGCCACACTAAGGTAATTCCTTATGCTGGCAATGTCGTGACCAGTGATA | SEQ ID NO: 370 | C | | x |
| Ec_mero | APECO78_ 05580 | 362-461 | GTCAGCCACGGGCTGATGATGAGTGAAGCCGAGCAATTGAATAAAGGCTT TCTCAAGCGGATGCGCACCGGCTTTCCTTATATTCAGTTAAAACTTGGCG | SEQ ID NO: 371 | C | | |
| Ec_mero | APECO78_ 05715 (b0438: clpX) | 935-1034 | AACGTTGAATGAACTGAGCGAAGAAGCTCTGATTCAGATCCTCAAAGAGC CGAAAAACGCCCTGACCAAGCAGTATCAGGCGCTGTTTAATCTGGAAGGC | SEQ ID NO: 372 | C | | x |
| Ec_mero | APECO78_ 09610 | 170-269 | AGGACGGTCTGTCACTGATTCGCCGCTGGCGTAGCAATGATGTTTCACTG CCGATTCTGGTATTAACCGCCCGTGAAAGCTGGCAGGACAAAGTCGAAGT | SEQ ID NO: 373 | C | | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Ec_mero | APECO78_ 13105 | 190-289 | AACGGAAAACTGCGCATCGGCTATGTACCGCAGAAGCTGTATCTCGACAC CACGTTGCCACTGACCGTAAACCGTTTTTTACGCTTACGCCCTGGTACAC | SEQ ID NO: 374 | C | | |
| Ec_mero | APECO78_ 16235 (b2502: ppx) | 987-1086 | GAACAGGCCCGACGGGTGCTGGATACCACTATGCAAATGTACGAACAGTG GCGGGAACAGCAACCGAAGCTGGCGCATCCGCAACTGGAGGCGCTACTGC | SEQ ID NO: 375 | C | | x |
| Ec_mero | APECO78_ 16510 | 1353-1452 | AGGGCAGCGGTCTGGGATTAAGCATTGCCAGGGATTGTATTCGCCGTATG CAAGGGGAACTGTATCTGGTCGACGAGAGCGGGCAAGACGTTTGTTTCCG | SEQ ID NO: 376 | C | | |
| Ec_mero | APECO78_ 17535 (b2784: relA) | 289-388 | GAGAGCGTCGGTAAGTCGGTCGTTAACCTTATTCACGGCGTGCGTGATAT GGCGGCGATCCGCCAGCTGAAAGCGACGCACACTGATTCTGTTTCCTCCG | SEQ ID NO: 377 | C | | x |
| Ec_mero | APECO78_ 19825 (b3197: kdsD) | 645-744 | ATGCATACGGGCGATGAGATCCCGCATGTTAAGAAAACGGCCAGTCTGCG TGACGCATTGCTGGAAGTTACCCGCAAAAATCTTGGTATGACTGTCATTT | SEQ ID NO: 378 | C | | x |
| Ec_mero | APECO78_ 19830 | 186-285 | CGTTGTGCGCTCACCTCTGATATTGAAGTCGCTATCATTACCGGGCGAAA GGCTAAACTGGTAGAAGATCGTTGTGCCACATTGGGGATCACTCACTTGT | SEQ ID NO: 379 | C | | |
| Ec_mero | APECO78_ 20780 (b3398: yrfF) | 1327-1426 | ACAAAGCGACGGCATTGACTGAAGCAGTTAATCGCCAGCTGCACCCTAAA CCGGAAGATGAATCTCGCGTCAGTGCCTCATTACGTTCAGCAATTCAAAA | SEQ ID NO: 380 | C | | x |
| Ec_mero | APECO78_ 21435 | 1011-1110 | GTCAGCAAGTGCTCACTATCATGAGCGAGCGCCTGCCGATTGAACGTATT CAACTCCGTCCGCACTGTAGCATTGGCGTGGCGATGTTCTACGGCGATCT | SEQ ID NO: 381 | C | | |
| Ec_mero | APECO78_ 01050 | 279-378 | TCTGCAGGATGGCGCTATCAGCGCTTATGATCTGCTTGATTTGCTGCGCG AAGCTGAACCGCAAGCCAAGCCGCCAACGGTTTATCGCGCGCTGGATTTT | SEQ ID NO: 382 | R | dn | |
| Ec_mero | APECO78_ 08635 | 844-943 | TGCGCAATACCAGTTCGATTTCGGTCTGCGTCCGTCCATCGCTTACACCA AATCTAAAGCGAAAGACGTAGAAGGTATCGGTGATGTTGATCTGGTGAAC | SEQ ID NO: 383 | R | dn | |
| Ec_mero | APECO78_ 12200 | 1-100 | ATGAAAGCTACTAAACTGGTACTGGGCGCGGTAATCCTGGGTTCTACTCT GCTGGCAGGTTGCTCCAGCAACGCTAAAATCGATCAGCTGTCTTCTGACG | SEQ ID NO: 384 | R | dn | |
| Ec_mero | APECO78_ 16640 | 267-366 | AAGATGCAGTTAAGCATCCGGAAAAAATATCCGCAGCTGACCATCCGTGTA TCCGGTTATGCAGTTCGCTTTAACTCTCTGACTCCGGAACAGCAGCGCGA | SEQ ID NO: 385 | R | dn | |
| Ec_mero | APECO78_ 22630 | 277-376 | CAGCTGCAAAAACACCAGGGAAATACCATTGAAATTCGTTACACCACGCA TGAACAATTCAAACAACAAACCGCAGAAAGTCAGGCGGTAATTCGCAGCG | SEQ ID NO: 386 | R | dn | |
| Ec_mero | APECO78_ 00325 (b4484 (cpxP)) | 149-248 | AAGTTTAACCGAACATCAGCGTCAGCAGATGCGAGATCTTATGCAACAGG CCCGGCACGAACAGCCTCCTGTTAATGTTAGCGAACTGGAGACAATGCAT | SEQ ID NO: 387 | R | up | |
| Ec_mero | APECO78_ 00495 | 133-232 | ATCGATCGCCTTAGCAGCCTGAAACCGAAGTTTGTATCGGTGACCTATGG CGCGAACTCCGGCGAGCGCGACCGTACGCACAGCATTATTAAAGGCATTA | SEQ ID NO: 388 | R | up | |
| Ec_mero | APECO78_ 00935 | 111-210 | TGGGACAGTCTGTTCGGCACGCCAGGCGTACAGCTGACGGACGATGATAT TCAAAATATGCCCTACGCCAGCCAGTACATGCAGCTTAATGGCGGGCCGC | SEQ ID NO: 389 | R | up | |
| Ec_mero | APECO78_ 00940 | 572-671 | GGACGCACGCAAAAAGCGCCGGTGGCTTACTGGAACAAGCGTCACGTAGA GCCGATGCCCGGCAGCATTATTTATGTTGGCCTCGCGGACTCCGTCTGGA | SEQ ID NO: 390 | R | up | |
| Ec_mero | APECO78_ 00945 | 1408-1507 | CAACTACGACAAGTTTAACTACACCAATCCGCCGCAGGACTCGCACTTAC CGCGCGTGCGTACCCATGTGCGCGAGTATGTGCAGAACGATGTCTATGTG | SEQ ID NO: 391 | R | up | |
| Ec_mero | APECO78_ 03465 | 695-794 | ATACCTGCGACCCGCGTCAGGTGCCCGATGCGAGGTTGTTGAAGTCGATG TCCTACCAGGAAGCGATGGAGCTTTCCTACTTCGGCGCTAAAGTTCTTCA | SEQ ID NO: 392 | R | up | |
| Ec_mero | APECO78_ 03815 | 578-677 | GCAGGCGGCACCGGGCATGTGGTGGAGTTTTGCGGCGAAGCAATCCGTGA TTTAAGCATGGAAGGTCGTATGACCCTGTGCAATATGGCAATCGAAATGG | SEQ ID NO: 393 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_mero | APECO78_ 03820 | 712-811 | ATCACAGTTTGACGTTCTGCTGTGCTCCAACCTGTTTGGCGACATTCTGT CTGACGAGTGCGCAATGATCACTGGCTCGATGGGGATGTTGCCTTCCGCC | SEQ ID NO: 394 | R | up | |
| Ec_mero | APECO78_ 03825 | 809-908 | CACACCGCCATTAATCACCAGGAGATATGGCGCACCAGCCAGTTAGTTAG CCAGATTTGTAATATGCCGATCCCGGCAAACAAAGCCATTGTTGGCAGCG | SEQ ID NO: 395 | R | up | |
| Ec_mero | APECO78_ 04245 (b0161 (degP)) | 164-263 | TTAACGTAGAAGGTAGCACAACCGTTAATACGCCGCGTATGCCGCGTAAT TTCCAGCAGTTCTTCGGTGATGATTCTCCGTTCTGCCAGGAAGGTTCTCC | SEQ ID NO: 396 | R | up | |
| Ec_mero | APECO78_ 04985 | 4-103 | CCTTTACGACGGTTCTCCCCAGGACTGAAAGCCCAGTTTGCCTTCGGCAT GGTCTTTTTGTTCGTTCAGCCCGATGCCAGCGCTGCTGACATAAGTGCGC | SEQ ID NO: 397 | R | up | |
| Ec_mero | APECO78_ 04995 | 190-289 | ACGCCACTCGGTAGCCTGGCGTTCCAGTATGCCGAAGGCATTAAAGGTTT TAACTCACAGAAAGGTCTATTTGACGTGGCTATCGAGGGTGACTCAACGG | SEQ ID NO: 398 | R | up | |
| Ec_mero | APECO78_ 05000 | 227-326 | CCGTGATAATGAGTGGTTATCCGCGGTAAAGGGGAAACAGGTCGTATTGA TTGCGGCCAGAAAGTCAGAAGCCTTAGCAAATTATTGGTATTACAACAGC | SEQ ID NO: 399 | R | up | |
| Ec_mero | APECO78_ 05395 (b0379 (yaiY)) | 177-276 | GGAAACAGGTCGCCCACGGGTGGAAATTGGTTTAGGTGTCGGCACCATTT TCGGGCTGATCCCGTTTTTAGTAGGCTGCCTCATTTTTGCAGTGGTGGCG | SEQ ID NO: 400 | R | up | |
| Ec_mero | APECO78_ 05500 (b0399 (phoB)) | 47-146 | AAATGGTCTGCTTCGTGCTCGAACAAAATGGCTTTCAGCCGGTCGAAGCG GAAGATTATGACAGTGCTGTGAATCAACTGAATGAACCCTGGCCGGATTT | SEQ ID NO: 401 | R | up | |
| Ec_mero | APECO78_ 05505 | 524-623 | TGGAAATTCGCGTCATGCCTTATACCCACAAACAGTTGCTGATGGTGGCG CGTGATGTCACGCAAATGCATCAACTGGAAGGGGCGCGGCGTAACTTTTT | SEQ ID NO: 402 | R | up | |
| Ec_mero | APECO78_ 05995 | 181-280 | GACGGCAGCAGTGGCGAAGTGAGTCTGGTGGGACAACCGCTACATAATAT GGACGAAGAAGCGCGGGCAAAGTTGCGCGCGAAGCACGTCGGCTTTGTTT | SEQ ID NO: 403 | R | up | |
| Ec_mero | APECO78_ 09510 (b1110 (ycfJ)) | 393-492 | AGCGATACTTACACGACTACGCAACAGCGTTGTAAAACGGTGTATGACAA GTCAGAAAAAATGCTCGGTTATGATGTGACCTATAAGATTGGCGATCAGC | SEQ ID NO: 404 | R | up | |
| Ec_mero | APECO78_ 09535 | 513-612 | TACTGCTGAGTGTGGCGGTTAATTTCGTTCCCACGCCGTGGTGGGGAATG AACAGTGTGATCCGCAATTTGCCTTATTACAGCCTTGGCGCATGGTTTGG | SEQ ID NO: 405 | R | up | |
| Ec_mero | APECO78_ 09705 (b1171 (ymgD)) | 120-219 | CCAACGAAATGGCAAAAACTGACAGCGCACAGGTTGCAGAAATTGTTGCG GTAATGGGTAATGCCAGCGTTGCCAGCCGTGATTTAAAAATTGAGCAATC | SEQ ID NO: 406 | R | up | |
| Ec_mero | APECO78_ 09710 (b1172 (ymgG)) | 105-204 | AGGCGTTGGTTTACTTACTGGCAATGGTGTTAATGGCGTACTGAAAGGTG CAGCTGTTGGCGCTGGTGTTGGTGCAGTAACAGAAAAAGGCCGCGACGGT | SEQ ID NO: 407 | R | up | |
| Ec_mero | APECO78_ 10895 | 58-157 | CTCATGGCAGGGCACAAAGGACATGAATTTGTGTGGGTAAAGAATGTGGA TCATCAGCTGCGTCATGAAGCGGACAGCGATGAATTGCGTGCTGTGGCGG | SEQ ID NO: 408 | R | up | |
| Ec_mero | APECO78_ 11400 | 60-159 | GGTTAATCAGAAGAAAGATCGTCTGCTTAACGAGTATCTGTCTCCGCTGG ATATTACCGCGGCACAGTTTAAGGTGCTCTGCTCTATCCGCTGCGCGGCG | SEQ ID NO: 409 | R | up | |
| Ec_mero | APECO78_ 12545 (b1743 (spy)) | 309-408 | ACCTTCGATAAAGCAAAAGCTGAAGCGCAGATCGCAAAAATGGAAGAACA GCGCAAAGCTAACATGCTGGCGCACATGGAAACCCAGAACAAAATTTACA | SEQ ID NO: 410 | R | up | |
| Ec_mero | APECO78_ 13545 | 395-494 | ATGCCGACGTTATCATTGAGCCGAACCGAATCGAGTATGTTGCGAATGTG GATGGCAGGTCAGGGAACCATTCAAATCTCTGACCAAATGAATATCAAAG | SEQ ID NO: 411 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_mero | APECO78_ 13965 | 19-118 | CGCGAGCGAGCGAAAACCAATGCATCGTTAATCTCTATGGTGCAACGCTT TTCAGATATCACCATCATGTTTGCCGGACTATGGCTGGTTTGCGAAGTGA | SEQ ID NO: 412 | R | up | |
| Ec_mero | APECO78_ 13975 | 522-621 | CCTTTGAAGTGGCGCAGTTTGTCGAAAAACCGAATCTGGAAACCGCCCAG GCCTATGTGGCAAGCGGCGAATATTACTGGAACAGCGGTATGTTCCTGTT | SEQ ID NO: 413 | R | up | |
| Ec_mero | APECO78_ 13985 | 125-224 | AGGGTTACTGGTTTGTGCCGGGAGGGCGCGTGCAGAAAGACGAAACGCTG GAAGCCGCATTTGAGCGGCTGACGATGGCGGAACTGGGGCTGCGTCTGCC | SEQ ID NO: 414 | R | up | |
| Ec_mero | APECO78_ 13995 | 647-746 | CTCGGCAATATGGATTCCCTGCGTGACTGGGGCCATGCCAAAGACTACGT AAAAATGCAGTGGATGATGCTGCAACAGGAACAGCCGGAAGATTTCGTTA | SEQ ID NO: 415 | R | up | |
| Ec_mero | APECO78_ 14000 | 259-358 | TATACCCTCGGTGAAATAACCATTGGCGCACATTCGGTGATATCGCAAAA AAGTTATTTATGCACCGGTAGCCACGACCATGCAAGTCAACATTTCACCA | SEQ ID NO: 416 | R | up | |
| Ec_mero | APECO78_ 14010 | 523-622 | CGAACCGGCATTTTTCGCTCTGGCATTAATCTCAATTTGGCTCAGCATCA AACAGTTTGGTATCAAAACGCCTAAAACCGATGCTATGATTCTCGCAGGG | SEQ ID NO: 417 | R | up | |
| Ec_mero | APECO78_ 14025 | 475-574 | AGGTCTTTACCTGGGCGTGGCGTTTCAAAGAGTGTTTGTTCGATACCGAA CTGAAAGCGGCACAGGATTACGACATCTTCCTGCGGATGGTGGTGGAGTA | SEQ ID NO: 418 | R | up | |
| Ec_mero | APECO78_ 14030 | 2020-2119 | ATGGTGGCGCGTTATGCGGTCAACACATTGAAAGAAGTGGAAACCAGTCT GAGCCGCTTTGAGCAAAACGGTATTCCGGTGAAAGGGGTGATTCTGAACT | SEQ ID NO: 419 | R | up | |
| Ec_mero | APECO78_ 14035 | 231-330 | CTGATTTTGACCATGGAAAAGCGCCATATCGAACGCTTATGCGAGATGGC ACCTGAGATGCGCGGCAAAGTGATGCTGTTTGGTCACTGGGATAACGAAT | SEQ ID NO: 420 | R | up | |
| Ec_mero | APECO78_ 14040 | 1035-1134 | CCCGGTTTCCCGCTGGAACCGTCTGATCAATCAGTTGCTGCCAACTATTA GCGGTGTCCGTTACATGACGGATACAGCCAGCGACATTCATAACTGGTAA | SEQ ID NO: 421 | R | up | |
| Ec_mero | APECO78_ 14100 | 153-252 | AGGCAGTTATAAATCCCGTTGGGTAATCGTAATCGTGGTGGTTATCGCCG CCATCGCCGCATTCTGGTTCTGGCAAGGCCGCAATGACTCCCAGAGTGCA | SEQ ID NO: 422 | R | up | |
| Ec_mero | APECO78_ 15715 | 22-121 | GCGGCCGCCCTGATGGCATTTACCCCGCTTGCAGCAAACGCAGGTGAAAT CACCCTACTGCCATCAATCAAATTACAAATTGGCGATCGCGATCATTACG | SEQ ID NO: 423 | R | up | |
| Ec_mero | APECO78_ 19610 | 111-210 | CGAGTTCCGTAAAGCCGGACACGAAGTGATTACCATTGAAAAACAAGCGG GTAAAACGGTGAAAGGCAAAAAAGGAGAAGCCAGCGTGACCATCGATAAA | SEQ ID NO: 424 | R | up | |
| Ec_mero | APECO78_ 21920 (b3615 (waaH)) | 788-887 | TTCATCAGCAAATAACTTACGAAGCATTGCGTGTTTGCCATGCGGTGCGC AAAGAGCCGGATATTCTTACCCGCCAACGGATGATTGCCGAGATATTTAC | SEQ ID NO: 425 | R | up | |
| Ec_mero | APECO78_ 22490 | 263-362 | TGGTTATGGTGATCAGTAAAACCATTGCCGAGCTGGAGCGTATTGGCGAC GTGGCGGACAAAATCTGCCGTACTGCGCTGGAGAAATTCTCCCAGCAGCA | SEQ ID NO: 426 | R | up | |
| Ec_mero | APECO78_ 22505 | 5-104 | CTGCAACCAAGCCTGCTTTTAACCCACCGGGTAAAAAGGGCGACATAATT TTCAGCGTGCTGGTAAAACTGGCGGCGCTGATTGTGCTATTGATGTTGGG | SEQ ID NO: 427 | R | up | |
| Ec_mero | APECO78_ 22510 (b3728 (pstS)) | 9-108 | TATGCGTACCACCGTCGCAACTGTTGTCGCCCGCGACCTTATCGATGAGCG CTTTCTCTGTGTTTGCAGAAGCAAGCCTGACAGGTGCAGGTGCAACCTTC | SEQ ID NO: 428 | R | up | |
| Ec_mero | APECO78_ 22685 | 525-624 | AAAACGAAGTGACTTTCCCACATGCCGAAGTTGAGCAAGCGCGCCAGATG CTGGCAAAAGCGCAAAAACCGATGCTGTACGTTGGCGGTGGCGTGGGTAT | SEQ ID NO: 429 | R | up | |
| Ec_cip GeneID = NC_ 000913 | b0176 | 432-531 | GTGGTTGGTGAAATAGCAGCCAATTCGATAGCTGCGGAAGCACAAATTGC ACCAGGTACGGAACTAAAAGCCGTAGATGGTATCGAAACGCCTGATTGGG | SEQ ID NO: 430 | C | | x |
| Ec_cip | b0179 | 374-473 | TCCGGCGTTGAACTGGGCGATAACGTGATTATCGGTGCCGGTTGCTTCGT AGGTAAAAACAGCAAAATCGGTGCAGGTTCGCGTCTCTGGGCGAACGTAA | SEQ ID NO: 431 | C | | |
| Ec_cip | b0761 | 223-322 | GGCGCAGTACTGACCCGCTATGGTCAGCGACTGATTCAGCTCTATGACTT ACTGGCGCAAATCCAGCAAAAAGCCTTTGATGTGTTAAGTGACGATGACG | SEQ ID NO: 432 | C | | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_cip | b1280 | 439-538 | TGCTACAAATCTACCAGGCTACCAGTGAGTGGCAGAAAGCAATTGATGTT GCCGAACGCCTGGTGAAGCTGGGTAAAGATAAACAGCGCGTCGAAATTGC | SEQ ID NO: 433 | C | | x |
| Ec_cip | b1827 | 1-100 | ATGGCTAACGCAGATCTGGATAAACAGCCTGATTCTGTATCTTCCGTGCT AAAAGTTTTTGGCATTTTGCAGGCGCTGGGTGAAGAGCGCGAAATAGGGA | SEQ ID NO: 434 | C | | x |
| Ec_cip | b1870 | 142-241 | ATGTTAGCCGAGCGCTTCGTTCAACCTGGTACGCAGGTTTACGATCTGGG TTGTTCTCTGGGCGCGGCGACGCTCTCGGTGCGTCGCAACATTCATCATG | SEQ ID NO: 435 | C | | |
| Ec_cip | b2065 | 100-199 | GATGTACGCCTGGGCAATAAATTTCGTACCTTCCGTGGTCACACGGCAGC GTTTATCGATCTGAGCGGTCCCAAAGATGAAGTGAGCGCCGCGCTTGACC | SEQ ID NO: 436 | C | | x |
| Ec_cip | b2153 | 167-266 | CTGATGACAGTTTGATGGAAACGCCGCATCGCATCGCTAAAATGTATGTC GATGAAATTTTCTCCGGTCTGGATTACGCCAACTTCCCGAAAATCACCCT | SEQ ID NO: 437 | C | | |
| Ec_cip | b2411 | 504-603 | GAAGTGCGTGGTGAAGTGTTCCTGCCGCAGGCGGGGTTCGAAAAGATTAA CGAAGATGCGCGACGCACGGGCGGGAAAGTGTTTGCTAACCCACGTAATG | SEQ ID NO: 438 | C | | |
| Ec_cip | b2515 | 277-376 | ATTGCGCTGAAAGTAGCGGAATACGGCGTCGATTGTCTGCGTATTAACCC TGGCAATATCGGTAATGAAGAGCGTATTCGCATGGTGGTTGACTGTGCGC | SEQ ID NO: 439 | C | | x |
| Ec_cip | b2516 | 91-190 | CAGGCCGTTGCCGAGCGACTTTGCCTGAAGGTTTCCACGGTACGCGACAT TGAAGAAGATAAGGCACCCGCCGATCTTGCTTCAACATTCCTGCGCGGAT | SEQ ID NO: 440 | C | | |
| Ec_cip | b2829 | 781-880 | GGTTGATAAAGGCTCGGTGGCAGAGTGGGCGGTAAAAACGGTCATTGAAA AATTTGCCGAACAGTTTGCCGCGCTAAGCGATAACTATCTCAAAGAGCGG | SEQ ID NO: 441 | C | | |
| Ec_cip | b2830 | 223-322 | TTGCGCTACAAATTACCGAAACGTTTGGTGCGTTGGGACACGAAGCCGGT TTGTATCGGCCAAAAACAAAAATGGTTTCTCTTGCAGCTGGTGAGCGGCG | SEQ ID NO: 442 | C | | x |
| Ec_cip | b2907 | 605-704 | TTTACGCAACATGGCCCGCTGGCGATGTTGCCGATGTCTGACGGACGCTG TTCGCTGGTCTGGTGTCATCCACTGGAACGGCGCGAAGAGGTGCTGTCGT | SEQ ID NO: 443 | C | | |
| Ec_cip | b3252 | 1103-1202 | CCACGCGTAATGCGGGATTGCAGGGCGGCAATAGCTGGGCTATTTACGAT GACTCGTTGCCTGAAAAAGGACGCGGTAATGTTCGCTGGCGTACGCTTAT | SEQ ID NO: 444 | C | | x |
| Ec_cip | b3346 | 176-275 | AGGATCTAAAATGTTCAGCCATTCGCATTGCTAACGGTGAACATACAGGC CGGAAGATTGGTTCGCCAATTACTGACCTGGCGCTACGTATGCTGCACGA | SEQ ID NO: 445 | C | | |
| Ec_cip | b3803 | 50-149 | CCGTGGACACCACGTCACAACCTGTCGCAACAGAAAAAAAGAGTAAGAAC AATACCGCATTGATTCTCAGCGCGGTGGCTATCGCTATTGCTCTGGCGGC | SEQ ID NO: 446 | C | | |
| Ec_cip | b4136 | 548-647 | GAGCAGCCCACCGCGCAATTGCCCTTTTCCGCGCTCTGGGCGTTGTTGAT CGGTATTGGTATCGCCTTTACGCCATGCGTGCTGCCAATGTACCCACTGA | SEQ ID NO: 447 | C | | |
| Ec_cip | b4175 | 175-274 | ATTGAAACGGTGAAAATGCTCGACGCACGTATTCAGACCATGGACAACCA GGCCGACCGCTTTGTGACCAAAGAGAAGAAAGACCTGATCGTCGACTCTT | SEQ ID NO: 448 | C | | |
| Ec_cip | b4178 | 208-307 | CGGCGAGTGCGATACGTATTGGTGATGTGGTGCGCGAGCTGGAGCCCTTA TCGCTGGTGAATTGCAGCAGTGAGTTTTGCCACATTACACCTGCCTGTCG | SEQ ID NO: 449 | C | | |
| Ec_cip | b0754 | 276-375 | GTCTATTTTGAAAAGCCGCGTACCACGGTGGGCTGGAAAGGGCTGATTAA CGATCCGCATATGGATAACAGCTTCCAGATCAACGACGGTCTGCGTATAG | SEQ ID NO: 450 | R | dn | |
| Ec_cip | b0893 | 488-587 | GTAATGAAAGGGCAGATTGCTCGCATGCACCGCGCACTGTCGCAGTTTAT GCTGGATCTGCATACCGAACAGCATGGCTACAGTGAGAACTATGTTCCGT | SEQ ID NO: 451 | R | dn | |
| Ec_cip | b0894 | 1466-1565 | TCTGAAATCAACCGTACCCATGAAATCCTTCAGGATGATAAGAAGTGCGA GCTGATTGTGGTTATCGACTGCCACATGACCTCATCGGCGAAATATGCTG | SEQ ID NO: 452 | R | dn | |
| Ec_cip | b0926 | 311-410 | CGCAAACCGGTGCAACTCATTTCCGGTTATCGTTCCATTGATACCAACAA TGAACTACGCGCCCGCAGCCGTGGAGTAGCGAAGAAAAGCTATCACACTA | SEQ ID NO: 453 | R | dn | |
| Ec_cip | b0929 | 1-100 | ATGATGAAGCGCAATATTCTGGCAGTGATCGTCCCTGCTCTGTTAGTAGC AGGTACTGCAAACGCTGCAGAAATCTATAACAAAGATGGCAACAAAGTAG | SEQ ID NO: 454 | R | dn | |
| Ec_cip | b1120 | 116-215 | AAAAACCAAGAGTACTCGTACTGACAGGGGCAGGGATTTCTGCGGAATCA GGTATTCGTACCTTTCGCGCCGCAGATGGCCTGTGGGAAGAACATCGGGT | SEQ ID NO: 455 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_cip | b1794 | 244-343 | ACCTACCTGACCAAAGTGGATGTCGAAGCGCGCCTGCAGCATATTATGTT TGCCCGTAACAGCCAGAAAATGCACATCCCGGAGAATTTTACCGTCTCGT | SEQ ID NO: 456 | R | dn | |
| Ec_cip | b1895 | 28-127 | GTTGCGGTTACACCGGAAAGTCAGCAACTGCTGGCAAAAGCGGTATCTAT CGCCAGGCCAGTAAAGGGACACATCAGTTTAATTACTCTCGCTTCCGACC | SEQ ID NO: 457 | R | dn | |
| Ec_cip | b2276 | 182-281 | TGGACGTTACGCCGCTGATGCGCGTTGATGGTTTCGCCATGCTTTACACC GGGCTGGTATTGTTGGCGAGCCTCGCCACCTGTACTTTCGCCTACCCGTG | SEQ ID NO: 458 | R | dn | |
| Ec_cip | b2277 | 421-520 | CTTCTGGGAAATGATGCTGGTGCCGATGTACTTCCTGATCGCACTGTGGG GGCATAAAGCCTCTGACGGTAAAACGCGTATCACGGCGGCAACCAAGTTC | SEQ ID NO: 459 | R | dn | |
| Ec_cip | b2281 | 47-146 | GTATCTGGATGATCGGCCTGCACGCGTTCGCCAAACGCGAAACGCGAATG TACCCGGAAGAGCCGGTCTATCTGCCGCCCCGTTATCGTGGTCGTATCGT | SEQ ID NO: 460 | R | dn | |
| Ec_cip | b2903 | 1501-1600 | CTCACCCATCCGGTGTTTAATCGCTACCACAGCGAAACCGAAATGATGCG CTATATGCACTCGCTGGAGCGTAAAGATCTGGCGCTGAATCAGGCGATGA | SEQ ID NO: 461 | R | dn | |
| Ec_cip | b3409 | 824-923 | CCACTGCGGTAGATAAAATCGTGCTCAACCGTTTCCTCGGTCTGCCGATT TTCCTCTTTGTGATGTACCTGATGTTCCTGCTGGCTATCAACATCGGCGG | SEQ ID NO: 462 | R | dn | |
| Ec_cip | b3746 | 495-594 | CGGAAGCAGACAGCAGTCTGGAAGCGTTATATGACCGCATGCTGATTCGT CTGTGGTTAGATAAAGTGCAGGATAAAGCGAATTTCCGCTCCATGCTGAC | SEQ ID NO: 463 | R | dn | |
| Ec_cip | b3771 | 967-1066 | AAGATGTTCACCGTGCTGGTGGTGTTATCGGTATTCTCGGCGAACTGGAT CGCGCGGGGTTACTGAACCGTGATGTGAAAAACGTACTTGGCCTGACGTT | SEQ ID NO: 464 | R | dn | |
| Ec_cip | b3863 | 693-792 | TGGCAGCGAAGCTCGAGCAAAACAAAGAAGTTGCTTATCTCTCATACCAG CTGGCGACGATTAAAACCGACGTTGAACTGGAGCTGACCTGTGAACAACT | SEQ ID NO: 465 | R | dn | |
| Ec_cip | b0060 | 865-964 | CTTCATTCTCGCTGGAAACTGTCGCTCAGGAGCTATTAGGCGAAGGAAAA TCTATCGATAACCCGTGGGATCGAATGGACGAAATTGACCGCCGTTTCGC | SEQ ID NO: 466 | R | up | |
| Ec_cip | b0068 | 577-676 | AAAACGGTCACGGTCACCAAAGGCTGGAGCGAAGCCTACGGCCTGTTTTT AAAAGGTGAAAGCGATCTGGTACTGAGTTACACCACCTCTCCGGCTTATC | SEQ ID NO: 467 | R | up | |
| Ec_cip | b0231 | 102-201 | CCGCGAACGTCGGGGGGTGATCAGCACCGCCAATTATCCCGCGCGTAAAT TTGGCGTACGTAGCGCTATGCCGACAGGGATGGCGCTCAAATTATGCCCG | SEQ ID NO: 468 | R | up | |
| Ec_cip | b0241 | 367-466 | CGTGGAAGCCTGGACCGATATGTTCCCGGAATTTGGTGGCGACTCCTCGG CGCAGACCGACAACTTTATGACCAAACGCGCCAGCGGTCTGGCGACGTAT | SEQ ID NO: 469 | R | up | |
| Ec_cip | b0313 | 137-236 | GCGTTTCTACGGGGATCATCAGCCACTATTTCAGGGACAAAAATGGTCTG CTGGAAGCAACCATGCGCGATATCACCAGTCAGCTGCGTGACGCGGTTTT | SEQ ID NO: 470 | R | up | |
| Ec_cip | b0399 | 46-145 | GAAATGGTCTGCTTCGTGCTCGAACAAAATGGCTTTCAGCCGGTCGAAGC GGAAGATTATGACAGTGCTGTGAATCAACTGAATGAACCCTGGCCGGATT | SEQ ID NO: 471 | R | up | |
| Ec_cip | b0400 | 334-433 | GTGCTGACCACGGAAGAGGGCGGTATTTTCTGGTGTAACGGTCTGGCGCA ACAAATTCTTGGTTTGCGCTGGCCGGAAGATAACGGGCAGAACATCCTTA | SEQ ID NO: 472 | R | up | |
| Ec_cip | b0458 | 275-374 | TCGATGTCTACCCACGCTACCGCTATGAAGATATCGACGTGCTGGATTTC CGCGTTTGCTATAACGGCGAATGGTACAACACGCGCTTTGTACCTGCCGC | SEQ ID NO: 473 | R | up | |
| Ec_cip | b0683 | 116-215 | TATACAAACGTCTGATCGATATGGGTGAAGAAATTGGTCTGGCTACGGTA TATCGCGTACTGAACCAGTTTGACGACGCTGGTATCGTCACCCGCCACAA | SEQ ID NO: 474 | R | up | |
| Ec_cip | b0698 | 1234-1333 | TACGGCATGATGCTGTTTGTCCTGCTGGCGGTGTTTATTGCCGGGCTGAT GATTGGTCGTACACCGGAATATCTGGGTAAAAAAATCGACGTACGCGAGA | SEQ ID NO: 475 | R | up | |
| Ec_cip | b0779 | 881-980 | GAGATGATGAACGAGCTGGGCTACTGTTCGGGGATTGAAAACTACTCGCG CTTCCTCTCCGGTCGTGGACCGGGTGAGCCACCGCCGACGCTGTTTGATT | SEQ ID NO: 476 | R | up | |
| Ec_cip | b0958 | 114-213 | TGTCTATCGCGAAGATCAGCCCATGATGACGCAACTTCTACTGTTGCCAT TGTTACAGCAACTCGGTCAGCAATCGCGCTGGCAACTCTGGTTAACACCG | SEQ ID NO: 477 | R | up | |
| Ec_cip | b1061 | 134-233 | TGCGAATTGAAGTCACCATAGCGAAAACTTCTCCATTGCCAGCTGGGGCT ATTGACGCCCTGGCTGGCGAACTTTCCCGCCGTATTCAGTATGCGTTTCC | SEQ ID NO: 478 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_cip | b1183 | 129-228 | GTTGATCCAGCATCCCAGCGCGACTTACTTCGTCAAAGCAAGTGGTGATT CTATGATTGATGGTGGAATTAGTGACGGTGATTTACTGATTGTCGATAGC | SEQ ID NO: 479 | R | up | |
| Ec_cip | b1184 | 453-552 | CGGCAAAAAAATGGCAGCGGCAGACGGGTGGGGTGGTGGATTTATCAAAT CTGGAACGCCAGCGTAAATTAATGTCTGCTCTCCCCGTGGATGACGTCTG | SEQ ID NO: 480 | R | up | |
| Ec_cip | b1207 | 255-354 | AACGACAACCTGATGGAATTAGTCGTTATGGTTGATGCCCTGCGTCGTGC TTCCGCAGGTCGTATCACCGCTGTTATCCCCTACTTTGGCTATGCGCGCC | SEQ ID NO: 481 | R | up | |
| Ec_cip | b1728 | 40-139 | TCTATTGCTTGTGCGGTATTTGCCAAAAATGCCGAGCTGACGCCCGTGCT GGCACAGGGTGACTGGTGGCATATTGTCCCTTCCGCAATCCTGACGTGTT | SEQ ID NO: 482 | R | up | |
| Ec_cip | b1848 | 117-216 | CACCTGGCTGACAAATTCTCCAGTGCAAATGGAAGACGAGCAACGTGAAG CCCTTTCGCTATGGCTGGCAGAACAAAAAGATGTGCTGAGCACCATTCTG | SEQ ID NO: 483 | R | up | |
| Ec_cip | b2231 | 100-199 | CTGCCAGATGTCCGAGATGGCCTGAAGCCGGTACACCGTCGCGTACTTTA CGCCATGAACGTACTAGGCAATGACTGGAACAAAGCCTATAAAAAATCTG | SEQ ID NO: 484 | R | up | |
| Ec_cip | b2234 | 21-120 | GACAAAGCGCGACGGTAGCACAGAGCGCATCAATCTCGACAAAATCCATC GCGTTCTGGATTGGGCGGCAGAAGGACTGCATAACGTTTCGATTTCCCAG | SEQ ID NO: 485 | R | up | |
| Ec_cip | b2498 | 318-417 | GTTGTCGGTATGTACCGTAATGAAGAAACGCTGGAGCCGGTACCGTACTT CCAGAAACTGGTTTCTAACATCGATGAGCGTATGGCGCTGATCGTTGACC | SEQ ID NO: 486 | R | up | |
| Ec_cip | b2582 | 110-209 | TGATTAATGCGACCGGTGAAACGCTCGACAAATTGCTGAAGGATGATCTA CCTGTGGTGATCGACTTCTGGGCACCGTGGTGCGGCCCCTGCCGTAATTT | SEQ ID NO: 487 | R | up | |
| Ec_cip | b2616 | 597-696 | TAATCCGCAGCCCGGAGAGTTTGAACAAATCGACGAAGAGTACAAACGTC TGGCGAACAGCGGTCAATTGCTGACCACCAGCCAGAATGCATTGGCATTA | SEQ ID NO: 488 | R | up | |
| Ec_cip | b2670 | 153-252 | GAACATCTTAATTGCATGGCCATACGGTATGTACCGCGATCTGTTTATGC GCGCGGCACGCAAAGTTAGCCCGTCGGGCTGGATAAAAAATCTGGCGGAT | SEQ ID NO: 489 | R | up | |
| Ec_cip | b2698 | 310-409 | AAGCGACAGAAAAAGCGATGCGTGAATGTGACATCGACTGGTGCGCACTG GCGCGCGATCAGGCGACGCGAAAATATGGCGAACCTTTGCCAACTGTCTT | SEQ ID NO: 490 | R | up | |
| Ec_cip | b2699 | 40-139 | AAAGCGTTGGCGGCAGCACTGGGCCAGATTGAGAAACAATTTGGTAAAGG CTCCATCATGCGCCTGGGTGAAGACCGTTCCATGGATGTGGAAACCATCT | SEQ ID NO: 491 | R | up | |
| Ec_cip | b2700 | 274-373 | TGAAAGCGGCTCGTGCTGATTATGCCGTGTCTATTAGTGGTATCGCCGGG CCGGATGGCGGCAGTGAAGAGAAGCCTGTCGGCACCGTCTGGTTTGCTTT | SEQ ID NO: 492 | R | up | |
| Ec_cip | b2980 | 427-526 | GATAACCCGCTGTTATGAAAAAATGCTCGCCGCCAGTGAGAACAACAAAG AGATTTCGCTGATCGAACATGCGCAGTTGGATCACGCTTTCCATCTCGCC | SEQ ID NO: 493 | R | up | |
| Ec_cip | b3065 | 56-155 | TCAAGCGTTCCTGCGAAAAAGCAGGTGTTCTGGCGGAAGTTCGTCGTCGT GAGTTCTATGAAAAACCGACTACCGAACGTAAGCGCGCTAAAGCTTCTGC | SEQ ID NO: 494 | R | up | |
| Ec_cip | b3173 | 625-724 | AGAGCATCAAAGATTACTCTCAATTGCAAACACGGTGCCGTATTTTCAAT TATCAGTCAGGGATACAGGTATTGATACCTACGTGTTGATTGTGGGGGAG | SEQ ID NO: 495 | R | up | |
| Ec_cip | b3348 | 41-140 | AGAGCCGACTGGCTTTTCAGGAAATCACCATTGAAGAACTGAACGTCACG GTGACCGCTCATGAAATGGAGATGGCGAAACTGCGCGATCATCTGCGTCT | SEQ ID NO: 496 | R | up | |
| Ec_cip | b3434 | 64-163 | CCTATTTTCATGTCCGTACTGAAACATACTGAACCGAAAAGACGGCGGGC AATCATGGTGCGAGAGTTGCTTATTGCTCTCCTGGTGATGCTGGTGTTCC | SEQ ID NO: 497 | R | up | |
| Ec_cip | b3452 | 487-586 | TTGCCTCAGTATGGAAGCAAATCAGCTACAACTTCCTGTTCTTCTATGCC GCGCTGCAATCCATTCCCCGTTCGTTGATCGAAGCCGCAGCCATCGACGG | SEQ ID NO: 498 | R | up | |
| Ec_cip | b3453 | 100-199 | AAGGGGAACTGGGTAAAGAGGTGGATTCTCTGGCCCAACGTTTTAACGCC GAAAACCCGGATTACAAAATTGTACCGACCTATAAAGGCAACTACGAACA | SEQ ID NO: 499 | R | up | |
| Ec_cip | b3645 | 256-355 | TTCATCTCTCCCGCTATGCCTGTTACCTGGTAGTACAAAACGGCGACCCT GCGAAACCGGTTATTGCGGCAGGGCAAACTTATTTTGCTATCCAGACCCG | SEQ ID NO: 500 | R | up | |
| Ec_cip | b3666 | 700-799 | AAGAGGACAAAGAGACAGAATCTACCGATATGACCAAGTGGCAGATCTTT GTTGAGTATGTGCTGAAAAACAAAGTGATCTGGCTGCTGTGCTTCGCCAA | SEQ ID NO: 501 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_cip | b3700 | 817-916 | GCTTAAGCTGTTGATGTGCGCCTTACGTCTGGCGCAAGGAGAGTTCCTCA CCCGTGAAAGCGGGCGGCGGTGTCTCTACCTGATAGATGATTTTGCCTCT | SEQ ID NO: 502 | R | up | |
| Ec_cip | b3701 | 37-136 | CCGCTACAACAGGTGAGCGGTCCGTTAGGTGGTCGTCCTACGCTACCGAT TCTCGGTAATCTGCTGTTACAGGTTGCTGACGGTACGTTGTCGCTGACCG | SEQ ID NO: 503 | R | up | |
| Ec_cip | b3702 | 370-469 | TCCCGGCCCCGGCAGAACCGACCTATCGTTCTAACGTAAACGTCAAACAC ACGTTTGATAACTTCGTTGAAGGTAAATCTAACCAACTGGCGCGCGCGGC | SEQ ID NO: 504 | R | up | |
| Ec_cip | b3727 | 5-104 | CTGCAACCAAGCCTGCTTTTAACCCACCGGGTAAAAAGGGCGACATAATT TTCAGCGTGCTGGTAAAACTGGCGGCGCTGATTGTGCTATTGATGTTGGG | SEQ ID NO: 505 | R | up | |
| Ec_cip | b3728 | 8-107 | TTATGCGTACCACCGTCGCAACTGTTGTCGCCGCGACCTTATCGATGAGC GCTTTCTCTGTGTTTGCAGAAGCAAGCCTGACAGGTGCAGGTGCAACCTT | SEQ ID NO: 506 | R | up | |
| Ec_cip | b3820 | 241-340 | GTGTGCGTGGGAAGTACCTTAACCCGCCACGAAACCATCAGTGAAGATGA ACTACGCCAGCGGCTATCGCGGATGGGGACCATTGATCTTCGCGTTGATT | SEQ ID NO: 507 | R | up | |
| Ec_cip | b3832 | 833-932 | CGCTACAGGAACATATCGCGTCGGTGCGTAACCATATCCGTTTGCTGGGA CGCAAAGATTATCAACAGCTGCCGGGGCTGCGAACTCTGGATTACGTGCT | SEQ ID NO: 508 | R | up | |
| Ec_cip | b3846 | 168-267 | AGATGGCATTGCCGAACTGGTATTTGATGCCCCAGGTTCAGTTAATAAAC TCGACACTGCGACCGTCGCCAGCCTCGGCGAGGCCATCGGCGTGCTGGAA | SEQ ID NO: 509 | R | up | |
| Ec_cip | b4043 | 11-110 | TAACGGCCAGGCAACAAGAGGTGTTTGATCTCATCCGTGATCACATCAGC CAGACAGGTATGCCGCCGACGCGTGCGGAAATCGCGCAGCGTTTGGGGTT | SEQ ID NO: 510 | R | up | |
| Ec_cip | b4044 | 509-608 | TACTCGGCGTGCAATATGCCCGTGCGCCAGTAATTTTGTTAGTGGTCGGC AATATCCTCAACATTGTGCTGGATGTCTGGCTGGTGATGGGGCTGCATAT | SEQ ID NO: 511 | R | up | |
| Ec_cip | b4058 | 64-163 | CCCCGCGACAAGCTCATTGTCGTGACCGGGCTTTCGGGTTCTGGCAAATC CTCGCTCGCTTTCGACACCTTATATGCCGAAGGGCAGCGCCGTTACGTTG | SEQ ID NO: 512 | R | up | |
| Ec_cip | b4060 | 100-199 | ATGGCTACCCTCACCACTGGCGTGGTTCTTCTTCGCTGGCAACTTCTTAG TGCCGTAATGATGTTTCTGGCCAGCACACTCAACATCCGTTTTCGTCGGT | SEQ ID NO: 513 | R | up | |
| Ec_cip | b4062 | 171-270 | CGCCTGTTACTGGCCGCCGTTGAGTTGCGCACCACCGAGCGTCCGATTTT TGATATCGCAATGGACCTGGGTTATGTCTCGCAGCAGACCTTCTCCCGCG | SEQ ID NO: 514 | R | up | |
| Ec_cip | b4105 | 374-473 | AACAAAGATAGTCCGATCAACAACCTGAACGATCTGCTGGCGAAGCGGAA AGATCTCACCTTCGGCAATGGCGATCCTAACTCCACCTCNNNNNNNNNNN | SEQ ID NO: 515 | R | up | |
| Ec_cip | b4106 | 610-709 | ACCGTGGTCGTCACGCTGCATCAGGTGGATTACGCCCTGCGCTACTGCGA ACGCATCGTCGCCCTGCGCCAGGGGCACGTCTTCTACGACGGCAGCAGCC | SEQ ID NO: 516 | R | up | |
| Ec_cip | b4142 | 24-123 | TTGCATGATCGCGTGATCGTCAAGCGTAAAGAAGTTGAAACTAAATCTGC TGGCGGCATCGTTCTGACCGGCTCTGCAGCGGCTAAATCCACCCGCGGCG | SEQ ID NO: 517 | R | up | |
| Ec_cip | b4143 | 490-589 | AGCGATGGACAAAGTCGGTAAAGAAGGCGTTATCACCGTTGAAGACGGTA CCGGTCTGCAGGACGAACTGGACGTGGTTGAAGGTATGCAGTTCGACCGT | SEQ ID NO: 518 | R | up | |
| Ec_cip | b4166 | 397-496 | AAACTCGGCTATGTTAGCCGTTATGCGCTGGGCCGTGACTATCACAAACT TCTGCGCAACCGACTCAAAAAGCTGGGCGAGATGATTCAGCAACATTGTG | SEQ ID NO: 519 | R | up | |
| Ec_cip | b4242 | 808-907 | CGTGTTAGTGAGCAGGAAAGCGAGCCGAATGCCTTTCAGCAAGGGATCAG CCGCGTCAGTATGCTGCTGATTCGCTTTATGCTGGTGATGGCTCCGGTGG | SEQ ID NO: 520 | R | up | |
| Ec_gent GeneID = NC_ 000913 | b1272 | 523-622 | GCTGCCAGCGGCGGTTACATGATGGCCTGTGTGGCGGACAAAATTGTTTC CGCACCGTTTGCTATTGTGGGTTCCATTGGGGTGGTGGCGCAAATGCCCA | SEQ ID NO: 521 | C | | x |
| Ec_gent | b1719 | 481-580 | ACGAAAACATCGCCCATGATGACAAGCCAGGTCTGTACTTCCATGAAGAA TATGTCGATATGTGCCGCGGTCCGCACGTACCGAACATGCGTTTCTGCCA | SEQ ID NO: 522 | C | | x |
| Ec_gent | b1914 | 392-491 | ACAAATGGCGTTAAGCCAGATCGAACCAGAAAAAACAGAAAGCCCATTTG CCAGTTTGTCTGAACGTGAATTGCAGATTATGCTGATGATCACCAAGGGC | SEQ ID NO: 523 | C | | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_gent | b2821 | 743-842 | CGGACACCTTTGGTCGCGTGCCGAACAAAGAGAGCAAAAAACCGGAAATC ACCGTGCCGGTAGTCACCGACGCGCAAAAGGGCATTATCATTCATTACGT | SEQ ID NO: 524 | C | | x |
| Ec_gent | b2830 | 223-322 | TTGCGCTACAAATTACCGAAACGTTTGGTGCGTTGGGACACGAAGCCGGT TTGTATCGGCCAAAAACAAAAATGGTTTCTCTTGCAGCTGGTGAGCGGCG | SEQ ID NO: 525 | C | | x |
| Ec_gent | b2910 | 23-122 | TCCAAATTTTTGGCCGTTCACTGCGTGTGAACTGCCCGCCTGACCAAAGG GATGCGTTGAATCAGGCAGCGGACGATCTGAACCAACGGTTGCAAGATCT | SEQ ID NO: 526 | C | | x |
| Ec_gent | b3040 | 300-399 | CATGCGCATCCGCAGGATTTAATGCAAAAATCGGTGCAGCCGTTGCCAAA ATCGATCAAGCGCACAGCCATTCTGCTCACTCTCGGCATCAGTCTGCATA | SEQ ID NO: 527 | C | | x |
| Ec_gent | b3389 | 102-201 | CGAGCAGGTCATGTTGGTCACCAACGAAACCCTGGCTCCTCTGTATCTCG ATAAGGTCCGCGGCGTACTTGAACAGGCGGGTGTTAACGTCGATAGCGTT | SEQ ID NO: 528 | C | | |
| Ec_gent | b3929 | 443-542 | GGTTGGTGCCGCTGGCGAAGGCATTGGCGAAAGCGATGTCCGCGTCAATT TTGGCGGTGTCACCTTCTTCTCCGGCGACCATCTTNNNTATGCCGACAAT | SEQ ID NO: 529 | C | | |
| Ec_gent | b4041 | 1507-1606 | ACTGGCGTGAATCTATCGATCCCATCGAAGCGGTGCGTCCGGCCTGGTTA ACGCCGACGGTCAATAATATTGCTGCCGATCTGATGGTACGCATTAACAA | SEQ ID NO: 530 | C | | x |
| Ec_gent | b4059 | 171-270 | CGTTGTGCTGTTCGGCAAACTGGCAGAAGTGGCCAGCGAATATCTGCGTA AAGGTTCTCAGGTTTATATCGAAGGTCAGCTGCGTACCCGTAAATGGACC | SEQ ID NO: 531 | C | | |
| Ec_gent | b4169 | 448-547 | GCCTGCGGTTGTCGCACCGCGCGTCAGCGAACCGGCGCGCAATCCGTTTA AAACGGAAAGTAACCGCACTACGGGTGTTATCAGCAGTAATACGGTAACG | SEQ ID NO: 532 | C | | |
| Ec_gent | b4174 | 729-828 | GAAGAAGTAAAAGCGGCGTTTGACGATGCGATTGCCGCGCGTGAAAACGA ACAGCAATACATTCGTGAAGCAGAAGCGTATACCAACGAAGTTCAGCCGC | SEQ ID NO: 533 | C | | |
| Ec_gent | b4175 | 175-274 | ATTGAAACGGTGAAAATGCTCGACGCACGTATTCAGACCATGGACAACCA GGCCGACCGCTTTGTGACCAAAGAGAAGAAAGACCTGATCGTCGACTCTT | SEQ ID NO: 534 | C | | x |
| Ec_gent | b4220 | 495-594 | CGCAGCTGGGCATTGCGCTCGGCCTGCATAAAGCCTTCTGGGATATTGAT TATAACAGTGGCGAACGTTACCGCTTTGGGCATGTGACCTTTGAAGGATC | SEQ ID NO: 535 | C | | x |
| Ec_gent | b4255 | 100-199 | ACACCATCGAACACCATCTTTCCGCAGACGATCTGGAAACCCTGGAAAAA GCAGCAGTTGAAGCGTTTAAACTCGGTTACGAAGTGACCGATCCAGAAGA | SEQ ID NO: 536 | C | | x |
| Ec_gent | b0085 | 379-478 | TGGCGCAGTGGAGCCAACTGCTTGGCGAAACCAGCGCGGTAATGGGCACC GTTGGTAACGGCCTGCTGGGGAAAGTGATCCCGACAGAAAATACCACCGG | SEQ ID NO: 537 | R | dn | |
| Ec_gent | b0086 | 362-461 | TTTTAAGCCAGTGCGGCAACACGCTTTATACGGCAGGCAATCTCAACAAC GACATCGGTGTACCGATGACGCTGTTGCGCTTAACGCCGGAATACGATTA | SEQ ID NO: 538 | R | dn | |
| Ec_gent | b0087 | 860-959 | CCTGCTGGTGATTATGGGGGGCGTGTTCGTGGTAGAAACGCTTTCTGTCA TCCTGCAGGTCGGCTCCTTTAAACTGCGCGGACAACGTATTTTCCGCATG | SEQ ID NO: 539 | R | dn | |
| Ec_gent | b0428 | 254-353 | GGACGAAGAATCGGGTGCTGGTTAAAGGCCTGATCTCTCCTGCTGTCTCG CTGGTGTACGCCACCTTGCTGGGTATTGCTGGCTTTATGCTGCTGTGGTT | SEQ ID NO: 540 | R | dn | |
| Ec_gent | b0429 | 156-255 | GATCATTCTGACGGTGATTCCGTTCTGGATGGTGATGACAGGGGCTGCCT CTCCGGCCGTAATTCTGGGAACAATCCTGGCAATGGCAGTGGTACAGGTT | SEQ ID NO: 541 | R | dn | |
| Ec_gent | b0430 | 163-262 | GCAGGCGGCCCGACAGGTAAGGACATTTTCGAACTGCCGTTCGTTCTGGT TGAAACTTTCTTGCTGTTGTTCAGCTCCATCACCTACGGCATGGCGGCTA | SEQ ID NO: 542 | R | dn | |
| Ec_gent | b0733 | 1104-1203 | TCTCCCGCTATGCGCCGGATATGAATCATGTCACAGCCGCACAGTACCAG GCGGCGATGCGTGGCGCGATACCTCAGGTTGCGCCGGTATTCTGGAGTTT | SEQ ID NO: 543 | R | dn | |
| Ec_gent | b0734 | 291-390 | TCTTCCGTCCGGTCGGTTTTGACTACCGCTCCAAGATTGAAGAAACCCGC TGGCGTAACATGTGGGACTGGGGCATCTTCATTGGTAGCTTCGTTCCGCC | SEQ ID NO: 544 | R | dn | |
| Ec_gent | b0735 | 95-194 | TGTTTTGGGACCCATCTCGTTTTGCCGCGAAGACCAGTGAACTGGAAATC TGGCATGGTTTATTGCTGATGTGGGCCGTCTGTGCTGGTGTGATTCACGG | SEQ ID NO: 545 | R | dn | |
| Ec_gent | b0794 | 563-662 | TGGCGGGCGAAGGGATGTTAATCCTCTGGAGTACCTCGTATCTCGACGAA GCCGAGCAGTGCCGTGACGTGTTACTGATGAACGAAGGCGAGTTGCTGTA | SEQ ID NO: 546 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Ec_gent | b1049 | 748-847 | CCGGAGCATCGCACGGCGTTGATCATGCCTATCTGTAACGAAGACGTGAA CCGTGTTTTTGCTGGCCTGCGTGCAACGTGGGAATCAGTAAAAGCCACCG | SEQ ID NO: 547 | R | dn | |
| Ec_gent | b1244 | 397-496 | GCTGGCAATGACCGGGGTTGTTATCCCCAGTTTTGTGGTTGCGCCATTAT TAGTCATGATATTTGCGATCATTTTGCATTGGCTGCCGGGCGGTGGCTGG | SEQ ID NO: 548 | R | dn | |
| Ec_gent | b1378 | 1056-1155 | GAAACTCTGCCCCGTGTCATTGGTGGGCGCTATGGTCTTTCATCCAAAGA ATTTGGCCCGGACTGTGTACTGGCGGTATTTGCCGAGCTCAACGCGGCTA | SEQ ID NO: 549 | R | dn | |
| Ec_gent | b2255 | 944-1043 | CCGGGTACTCATCCTCGGGGTGAATGGCTTTATTGGCAACCATCTGACAG AACGCCTGCTGCGCGAAGATCATTATGAAGTTTACGGTCTGGATATTGGC | SEQ ID NO: 550 | R | dn | |
| Ec_gent | b2276 | 182-281 | TGGACGTTACGCCGCTGATGCGCGTTGATGGTTTCGCCATGCTTTACACC GGGCTGGTATTGTTGGCGAGCCTCGCCACCTGTACTTTCGCCTACCCGTG | SEQ ID NO: 551 | R | dn | |
| Ec_gent | b2277 | 421-520 | CTTCTGGGAAATGATGCTGGTGCCGATGTACTTCCTGATCGCACTGTGGG GGCATAAAGCCTCTGACGGTAAAACGCGTATCACGGCGGCAACCAAGTTC | SEQ ID NO: 552 | R | dn | |
| Ec_gent | b2278 | 904-1003 | GACATCAAACGTGTTCTCGCTTACTCTACCATGAGCCAGATTGGCTACAT GTTCCTCGCGCTTGGCGTGCAGGCATGGGATGCGGCGATTTTCCACTTGA | SEQ ID NO: 553 | R | dn | |
| Ec_gent | b2279 | 178-277 | GTGATGTACATTCTCGCCATCAGCCTCGCGGCGGCAGAAGCGAGTATCGG CCTTGCGCTGCTGCTGCAACTTCACCGTCGTCGCCAGAACCTGAACATCG | SEQ ID NO: 554 | R | dn | |
| Ec_gent | b2280 | 311-410 | TGGTGGTGATTGTTTACGCCATCCTCGGTGTTAACGATCAGGGTATCGAC GGTACGCCAATCAGTGCTAAAGCAGTGGGTATTACGCTGTTCGGGCCTTA | SEQ ID NO: 555 | R | dn | |
| Ec_gent | b2281 | 47-146 | GTATCTGGATGATCGGCCTGCACGCGTTCGCCAAACGCGAAACGCGAATG TACCCGGAAGAGCCGGTCTATCTGCCGCCCCGTTATCGTGGTCGTATCGT | SEQ ID NO: 556 | R | dn | |
| Ec_gent | b2282 | 723-822 | ATCGGGATTGTGACCATCTCTGCATTGATGGTGACGCTGTTCTTCGGTGG CTGGCAAGGCCCGTTGTTACCGCCATTCATCTGGTTCGCGCTGAAAACCG | SEQ ID NO: 557 | R | dn | |
| Ec_gent | b2283 | 160-259 | CAATACCAAAACGCGGAAGACACGCGTGGTCGCCTGGTGATGTCCTGTAT GACACCGGCTTCCGATGGCACCTTTATTTCCATTGACGACGAAGAAGCGA | SEQ ID NO: 558 | R | dn | |
| Ec_gent | b2284 | 655-754 | GAAACCCTGTGTAACGTTCCGGCGATCCTCGCTAACGGCGTGGAGTGGTA TCAGAACATCTCGAAAAGTAAAGATGCTGGCACCAAGCTGATGGGCTTCT | SEQ ID NO: 559 | R | dn | |
| Ec_gent | b2285 | 32-131 | CTTTTGAGCTGAGTGCGGCAGAGCGTGAAGCGATTGAGCACGAGATGCAC CACTACGAAGACCCGCGTGCGGCGTCCATTGAAGCGCTGAAAATCGTTCA | SEQ ID NO: 560 | R | dn | |
| Ec_gent | b2286 | 192-291 | AAAGAAACTGCCGAAACCTTACGTCATGCTGTTTGACTTACACGGCATGG ACGAACGTCTGCGCACACACCGCGAAGGGTTACCTGCCGCGGATTTTTCC | SEQ ID NO: 561 | R | dn | |
| Ec_gent | b2726 | 31-130 | TGCCAACGGGCACTGGAATTGATCGAACAGCAGGCCGCAAAACACGGCGC AAAACGCGTAACTGGGGTCTGGCTCAAAATTGGCGCATTTTCTTGTGTCG | SEQ ID NO: 562 | R | dn | |
| Ec_gent | b2727 | 1-100 | ATGTGTACAACATGCGGTTGCGGTGAAGGCAACCTGTATATCGAGGGTGA TGAACATAACCCTCATTCCGCGTTTCGTAGCGCGCCATTTGCCCCGGCGG | SEQ ID NO: 563 | R | dn | |
| Ec_gent | b2729 | 725-824 | AAATAGCGGCCCACAGCAAGGTAGAGAATCAGTATCGTCGGGTGGTACCG GATGCCGGTAACCTGCTGGCGCAACAGGCGATTGCCGATGTGTTCTGTGT | SEQ ID NO: 564 | R | dn | |
| Ec_gent | b2957 | 72-171 | CAATATCACCATTTTAGCAACCGGCGGGACCATTGCCGGTGGTGGTGACT CCGCAACCAAATCTAACTACACAGCGGGTAAAGTTGGCGTAGAAAATCTG | SEQ ID NO: 565 | R | dn | |
| Ec_gent | b2996 | 917-1016 | GGTTCTGGTACTGACGGGTGTGCCTTATGAAAATCTCGACCTGCCGAAAC TGGACGATCTTTCTACCGGTGCGCGTTCCGAANNNNNNNNNNNNNNNNNN | SEQ ID NO: 566 | R | dn | |
| Ec_gent | b3118 | 187-286 | TAACACCTGCCGGTCAATTGTTACTCTCCCGTTCCGAATCCATTACCCGT GAAATGAAAAATATGGTTAATGAGATAAGCGGTATGTCTTCTGAGGCGGT | SEQ ID NO: 567 | R | dn | |
| Ec_gent | b3745 | 435-534 | CAGCTATTAGAAGAAGAACGCGAACAACTGTTGAGTGAAGTTCAGGAACG CATGACGCTGAGCGGACAACTTGAACCGATTCTCGCAGATAACAATACCG | SEQ ID NO: 568 | R | dn | |
| Ec_gent | b3891 | 371-470 | CAGTGATTGAGAATCTGGAGAAGGCATCGACTCAGGAGCTGGAAGATATG GCCAGCGCACTGTTTGCCTCTGATTTCTCGTCCGTCAGCAGCGATAAAGC | SEQ ID NO: 569 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_gent | b3892 | 287-386 | TCGTCAACGAGGAAGTAGGTGACACCGGGCGTTATAACTTCGGTCAGAAA TGCGTTTTCTGGGCGGCGATTATTTTCCTGGTTCTGCTGCTGGTGAGCGG | SEQ ID NO: 570 | R | dn | |
| Ec_gent | b4139 | 503-602 | TGGGTCACCAGAAAGGTGAATATCAGTACCTGAACCCGAACGACCATGTT AACAAATGTCAGTCCACTAACGACGCCTACCCGACCGGTTTCCGTATCGC | SEQ ID NO: 571 | R | dn | |
| Ec_gent | b4152 | 140-239 | TGTTTGCCCTGAAAAATGGCCCGGAAGCCTGGGCGGGATTCGTCGACTTT TTACAAAACCCGGTTATCGTGATCATTAACCTGATCACTCTGGCGGCAGC | SEQ ID NO: 572 | R | dn | |
| Ec_gent | b4153 | 169-268 | TCCTGCCGTATGGCGATTTGTGGTTCCTGCGGCATGATGGTTAACAACGT GCCAAAACTGGCATGTAAAACCTTCCTGCGTGATTACACCGACGGTATGA | SEQ ID NO: 573 | R | dn | |
| Ec_gent | b4154 | 959-1058 | GCGAGAAAAAACTGCATGAACGTCTGCCGTTCATCTGCGAACTGGCGAAA GCGTACGTTGGCGTCGATCCGGTTAAAGAACCGATTCCGGTACGTCCGAC | SEQ ID NO: 574 | R | dn | |
| Ec_gent | b0014 | 208-307 | ACGCCTGATTGGCCGCCGCTTCCAGGACGAAGAAGTACAGCGTGATGTTT CCATCATGCCGTTCAAAATTATTGCTGCTGATAACGGCGACGCATGGGTC | SEQ ID NO: 575 | R | up | |
| Ec_gent | b0015 | 289-388 | TTTCGGCGATATTTTTGGCGGCGGACGTGGTCGTCAACGTGCGGCGCGCG GTGCTGATTTACGCTATAACATGGAGCTCACCCTCGAAGAAGCTGTACGT | SEQ ID NO: 576 | R | up | |
| Ec_gent | b0019 | 464-563 | TTGATGGCTCTGGCTATTATCGACGATCTTGGGGCCATCATTATCATCGC ATTGTTCTACACTAATGACTTATCGATGGCCTCTCTTGGCGTCGCGGCTG | SEQ ID NO: 577 | R | up | |
| Ec_gent | b0161 | 769-868 | CGGCGGCAACATCGGTATCGGTTTTGCTATCCCGAGCAACATGGTGAAAA ACCTGACCTCGCAGATGGTGGAATACGGCCAGGTGAAACGCGGTGAGCTG | SEQ ID NO: 578 | R | up | |
| Ec_gent | b0199 | 787-886 | CTGACTGCGTGCCGATGCTGCGTCTGGAGTTTACCGGTCAATCGGTCGAT GCCCCACTGCTTTCTGAAACCGCGCGTCGTTTCAACGTCAACAACAACAT | SEQ ID NO: 579 | R | up | |
| Ec_gent | b0313 | 137-236 | GCGTTTCTACGGGGATCATCAGCCACTATTTCAGGGACAAAAATGGTCTG CTGGAAGCAACCATGCGCGATATCACCAGTCAGCTGCGTGACGCGGTTTT | SEQ ID NO: 580 | R | up | |
| Ec_gent | b0460 | 298-397 | TGCCAGACAATTGACACGCTGGAGCGTGTTATCGAGAAAAATAAATACGA ATTATCAGATAATGAACTGGCGGTATTTTACTCAGCCGCAGATCACCGCC | SEQ ID NO: 581 | R | up | |
| Ec_gent | b0631 | 67-166 | GCGTTACCTGAGCTGGTTGATCAGGTGGTTGAAGTGGTACAGCGCCATGC GCCAGGTGACTACACCCCAACGGTAAAACCAAGCAGCAAAGGCAACTACC | SEQ ID NO: 582 | R | up | |
| Ec_gent | b0841 | 233-332 | TCCGCACGACCGACCCTTTGTCGAAAATATCGGCTATAACTTCCTGCATC ATGCGGCGGATGACTCATTCCCAAGCGATCACGGTACGGTGATTTTCACC | SEQ ID NO: 583 | R | up | |
| Ec_gent | b1113 | 737-836 | GTCTGGCGGCCTATGGCGGCGTTTATTTGCTTCACGGTACGAACGCCGAT TTCGGCATTGGCATGCGGGTAAGTTCTGGCTGTATTCGTCTGCGGGATGA | SEQ ID NO: 584 | R | up | |
| Ec_gent | b1304 | 368-467 | CGAGCTGGAAAACAAATTGAGCGAAACACGCGCTCGCCAGCAGGCATTGA TGTTACGCCATCAGGCGGCAAACTCGTCGCGCGATGTGCGTCGTCAGCTG | SEQ ID NO: 585 | R | up | |
| Ec_gent | b1305 | 72-171 | GCATTACAGCAATCGTTCTGGTCGCAGTGAATTGTCGCAAAGTGAGCAGC AGCGATTAGCGCAACTGGCTGATGAAGCAAAACGGATGCGCGAACGTATT | SEQ ID NO: 586 | R | up | |
| Ec_gent | b1306 | 91-190 | GATGTACCGGTAAAACTGGTGCGTATCCTGGTGGTGCTGTCGATTTTCTT CGGTCTGGCGCTGTTTACCCTGGTTGCTTACATCATTTTGTCATTTGCGC | SEQ ID NO: 587 | R | up | |
| Ec_gent | b1436 | 58-157 | CTCATGGCAGGGCACAAAGGACATGAATTTGTGTGGGTAAAGAATGTGGA TCATCAGCTGCGTCATGAAGCGGACAGCGATGAATTGCGTGCTGTGGCGG | SEQ ID NO: 588 | R | up | |
| Ec_gent | b1530 | 73-172 | AAAGATCGTCTGCTTAACGAGTATCTGTCTCCGCTGGATATTACCGCGGC ACAGTTTAAGGTGCTCTGCTCTATCCGCTGCGCGGCGTGTATTACTCCGG | SEQ ID NO: 589 | R | up | |
| Ec_gent | b1531 | 112-211 | GGTTACTCCAAATGGCACCTGCAACGGATGTTTAAAAAAGAAACCGGTCA TTCATTAGGCCAATACATCCGCAGCCGTAAGATGACGGAAATCGCGCAAA | SEQ ID NO: 590 | R | up | |
| Ec_gent | b1599 | 127-226 | CGGCGGTGCTGGCTGCCTTTAGTGCGCTTTCTCAGGCCGTTAAAGGGATC GACTTGTCTGTCGCTTATGCATTGTGGGGGGGGTTTGGTATTGCCGCCAC | SEQ ID NO: 591 | R | up | |
| Ec_gent | b1728 | 40-139 | TCTATTGCTTGTGCGGTATTTGCCAAAAATGCCGAGCTGACGCCCGTGCT GGCACAGGGTGACTGGTGGCATATTGTCCCTTCCGCAATCCTGACGTGTT | SEQ ID NO: 592 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ec_gent | b1829 | 27-126 | AACGAACCTGGCCGTAATGGTCGTTTTCGGGCTGGTACTGAGCCTGACAG GGATACAGTCGAGCAGCGTTCAGGGGCTGATGATCATGGCCTTGCTGTTC | SEQ ID NO: 593 | R | up | |
| Ec_gent | b2106 | 505-604 | AGGATGCCCATGCACGAGCCCATGCCAATGACATTAAACGACGCTTTGAT GGTAGAGAGGTCACCAACTGGCAAATTTTGCTATTTGGCTTAACCGGTGG | SEQ ID NO: 594 | R | up | |
| Ec_gent | b2119 | 114-213 | ATACGCCGATGAACTGGCAAAATTAAAACAAAATGATAACGCACCTTGCC CGCCCGGTTGGCAGTTAAGTTTGCCTGCGGCCCGTGCTTTTATCCTTGGC | SEQ ID NO: 595 | R | up | |
| Ec_gent | b2181 | 108-207 | CGGTGACAACAGCCTGGTGGCGCTTAAATTGCTTAGCCCGGATGGTGATA ATGCATGGTCGGTGATGTATAAACTAAGCCAGGCGTTAAGCGACATCGAA | SEQ ID NO: 596 | R | up | |
| Ec_gent | b2392 | 669-768 | ATGGCGGTTCGCGTCAACAACGTTATTCCGCCACCAAATGGGATGTGGCT ATCGCCATGACGATTGCCGGTTTTGTCAATCTGGCGATGATGGCTACAGC | SEQ ID NO: 597 | R | up | |
| Ec_gent | b2531 | 137-236 | TTTCCCGTCTGCGTAAAAATGGTCTGGTTTCCAGCGTACGTGGACCAGGC GGTGGTTATCTGTTAGGCAAAGATGCCAGCAGCATCGCCGTTGGCGAAGT | SEQ ID NO: 598 | R | up | |
| Ec_gent | b2582 | 110-209 | TGATTAATGCGACCGGTGAAACGCTCGACAAATTGCTGAAGGATGATCTA CCTGTGGTGATCGACTTCTGGGCACCGTGGTGCGGCCCCTGCCGTAATTT | SEQ ID NO: 599 | R | up | |
| Ec_gent | b2667 | 113-212 | GCACCAGCGCGGGAGAGCTGACGCGCATTACCGGACTGAGTGCCTCTGCG ACATCACAGCATCTCGCTCGTATGCGGGACGAAGGGCTTATCGACAGCCA | SEQ ID NO: 600 | R | up | |
| Ec_gent | b2980 | 427-526 | GATAACCCGCTGTTATGAAAAAATGCTCGCCGCCAGTGAGAACAACAAAG AGATTTCGCTGATCGAACATGCGCAGTTGGATCACGCTTTCCATCTCGCC | SEQ ID NO: 601 | R | up | |
| Ec_gent | b3184 | 20-119 | TTGGCATTCTTTTGGCGCTCACCACAGCAATTTGCTGGGGGGCGTTGCCA ATCGCAATGAAGCAGGTGCTGGAGGTGATGGAACCTCCGACAATCGTGTT | SEQ ID NO: 602 | R | up | |
| Ec_gent | b3343 | 1-100 | ATGCTGCACACATTACATCGTTCACCCTGGCTGACGGATTTTGCTGCGCT GCTGCGTCTGCTCAGTGAAGGAGACGAACTGCTATTATTGCAAGATGGCG | SEQ ID NO: 603 | R | up | |
| Ec_gent | b3399 | 178-277 | GTTACGCCACAGGAAGCGATGGAATATATGCGCCAGCAATATCACGACGT ACAGCATACGCTAAACTGGTACTGTCTTGATTACTGGAGTGAGCAACTGG | SEQ ID NO: 604 | R | up | |
| Ec_gent | b3400 | 147-246 | GAGCTGAATGCCACGCTCACTCTGCGCCAGGGAAATGACGAACGCACGGT GATTGTAAAGGCGATTACTGAACAGCGTCGCCCCGCCAGCGAGGCAGCCT | SEQ ID NO: 605 | R | up | |
| Ec_gent | b3401 | 390-489 | GTTGGTCTGGAAGGTGATACCCTGGCGGCCTGCCTGGAAGATTACTTTAT GCGTTCTGAACAGCTGCCGACGCGCCTGTTTATTCGCACCGGCGACGTAG | SEQ ID NO: 606 | R | up | |
| Ec_gent | b3461 | 130-229 | CATGGCGATCTGGAAGCAGCTAAAACGCTGATCCTGTCTCACCTGCGGTT TGTTGTTCATATTGCTCGTAATTATGCGGGCTATGGCCTGCCACAGGCGG | SEQ ID NO: 607 | R | up | |
| Ec_gent | b3635 | 113-212 | CAGAAGAGATCTACCGTTTAAGCGACCAACCAGTGCTTAGCGTGCAGCGG CGGGCTAAATATCTGCTGCTGGAGCTGCCTGAGGGCTGGATTATCATTCA | SEQ ID NO: 608 | R | up | |
| Ec_gent | b3686 | 100-199 | TTCCCGCCGTACAACATTGAGAAAAGCGACGATAACCACTACCGCATTAC CCTTGCGCTGGCAGGTTTCCGTCAGGAAGATTTAGAGATTCAACTGGAAG | SEQ ID NO: 609 | R | up | |
| Ec_gent | b3687 | 101-200 | GCGGCTACCCTCCGTATAACGTTGAACTGGTAGACGAAAACCATTACCGC ATTGCTATCGCTGTGGCTGGTTTTGCTGAGAGCGAACTGGAAATTACCGC | SEQ ID NO: 610 | R | up | |
| Ec_gent | b3743 | 149-248 | GGATCATTACCGGGGCGCGTATTGATGTCAGCCCGAAGCAGCTCGGTTAT GACGTAGGCTGCTTTATCGGCATTATATTAAAGAGCGCCAAAGACTACCC | SEQ ID NO: 611 | R | up | |
| Ec_gent | b3820 | 241-340 | GTGTGCGTGGGAAGTACCTTAACCCGCCACGAAACCATCAGTGAAGATGA ACTACGCCAGCGGCTATCGCGGATGGGGACCATTGATCTTCGCGTTGATT | SEQ ID NO: 612 | R | up | |
| Ec_gent | b3828 | 62-161 | CCGCTGCGGCGACGTTGCATCAGACGCAATCCGCCCTGTCTCACCAGTTT AGCGATCTGGAACAACGCCTTGGCTTCCGGCTATTTGTGCGTAAGAGCCA | SEQ ID NO: 613 | R | up | |
| Ec_gent | b3932 | 133-232 | GCGGGCTTTGCGGGCGGTACTGCGGATGCTTTTACGCTGTTCGAACTGTT TGAACGTAAACTGGAAATGCATCAGGGCCATCTGGTCAAAGCCGCCGTTG | SEQ ID NO: 614 | R | up | |
| Ec_gent | b3941 | 125-224 | GGAACTCCATCGATCGCCTTAGCAGCCTGAAACCGAAGTTTGTATCGGTG ACCTATGGCGCGAACTCCGGCGAGCGCGACCGTACGCACAGCATTATTAA | SEQ ID NO: 615 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Ec_gent | b4060 | 100-199 | ATGGCTACCCTCACCACTGGCGTGGTTCTTCTTCGCTGGCAACTTCTTAG TGCCGTAATGATGTTTCTGGCCAGCACACTCAACATCCGTTTTCGTCGGT | SEQ ID NO: 616 | R | up | |
| Ec_gent | b4062 | 171-270 | CGCCTGTTACTGGCCGCCGTTGAGTTGCGCACCACCGAGCGTCCGATTTT TGATATCGCAATGGACCTGGGTTATGTCTCGCAGCAGACCTTCTCCCGCG | SEQ ID NO: 617 | R | up | |
| Ec_gent | b4242 | 808-907 | CGTGTTAGTGAGCAGGAAAGCGAGCCGAATGCCTTTCAGCAAGGGATCAG CCGCGTCAGTATGCTGCTGATTCGCTTTATGCTGGTGATGGCTCCGGTGG | SEQ ID NO: 618 | R | up | |
| Ec_gent | b4321 | 100-199 | GCGGCGCTGTCCGTCGGGATGCTGGCGGGCATGGATTTGATGTCGCTGCT GCACACCATGAAAGCGGGCTTCGGCAACACGCTGGGGGAACTGGCTATCA | SEQ ID NO: 619 | R | up | |
| Ec_gent | b4322 | 867-966 | GGTCCGCGTATTTACTTCACCCATCTGCGCTCCACCATGCGTGAAGATAA CCCGAAAACCTTCCACGAAGCGGCGCACCTGAACGGTGACGTTGATATGT | SEQ ID NO: 620 | R | up | |
| Ec_gent | b4484 | 128-227 | GAGCCATATGTTCGACGGCATAAGTTTAACCGAACATCAGCGTCAGCAGA TGCGAGATCTTATGCAACAGGCCCGGCACGAACAGCCTCCTGTTAATGTT | SEQ ID NO: 621 | R | up | |
| Ec_gent | b4550 | 6-105 | CCGATATCAGCATACTAAAGGGCAGATAAAGGATAATGCGATAGAAGCAT TACTACATGATCCCTTATTCCGACAGCGCGTAGAGAAAAATAAGAAGGGG | SEQ ID NO: 622 | R | up | |
| Ab_mero GeneID = NC_ 021726 (alt GeneID = NC_ 017847, used for FIG. 6 heatmap) | BJAB07104_ 00229 (ABTJ_ 03609) | 1591-1690 | GGACCAATATTTAAGTCATGCTGTCGGGAAAACCAATCAGCGAGTTTACT TCCTTGATGAAACAGGGCGCAGCTATGCCTTGCCAATTAGTAACTTACCT | SEQ ID NO: 623 | C | | x |
| Ab_mero | BJAB07104_ 00412 (ABTJ_ 03419) | 877-976 | GATTTTGCACTATAACCCTTCGCAAGAATATTGGGCCGATAGTGTCGACC CACTCTGGAAACAGCGCTATGACTTAGGGGTAAAAGAGCGTTTTATAGCG | SEQ ID NO: 624 | C | | x |
| Ab_mero | BJAB07104_ 00560 (ABTJ_ 03270) | 163-262 | ACGAATAAGGCAGATCCATTACGTTTACAACTTGATGCTAGCGAAGGTGT TGTTTTTACCCTTGATCCTAAAGGTGAAGTTGCTGCATACCGTGGTAAAC | SEQ ID NO: 625 | C | | x |
| Ab_mero | BJAB07104_ 01090 (ABTJ_ 02819) | 326-425 | TCCTGACACGGTTACTTGATGAAGTGCATCAACAATTACCGAAGATTCAG TTGCATTTACATGAAGCTCAAAGTGAGAAGATTGTAGAGCGCCTAGAACA | SEQ ID NO: 626 | C | | x |
| Ab_mero | BJAB07104_ 01651 | 58-157 | GCTAATGCAGCTGGTTATGGGGTAATTGATCTAGCTAAAGTTGTTGAAAG TAGTACTTATTTGAAACAGCAAAATGCAAGCTTAAACCAGTCAGTGAAAC | SEQ ID NO: 627 | C | | |
| Ab_mero | BJAB07104_ 01716 (ABTJ_ 01686) | 419-518 | TAAGCAAGCTCAAGTCATTGGTAATCCGGGTTGTTACCCAACGACTGTTC AACTGGGCTTGGCTCCACTTTTAAAATCAGCACAAGCATTGATTGAAACA | SEQ ID NO: 628 | C | | x |
| Ab_mero | BJAB07104_ 02033 | 221-320 | CAGCTGCGGTGAATGATGCTGTGCGTCAAGCTGAAGTAGTTTCTGAAGAA AAAATGCAAAAAGCTAACTCTGGTATGGGTTTACCTCCTGGTTTAGCAGG | SEQ ID NO: 629 | C | | |
| Ab_mero | BJAB07104_ 02399 | 139-238 | GTAGATGTTAATGAAGTGGCTGCGGAAAGCCAGCGAAAAGCAGCATTAAG TGAACATGACAACTTAGAACCGGGGTCAAATTTATGGATTGCTCGTCAGG | SEQ ID NO: 630 | C | | |
| Ab_mero | BJAB07104_ 03654 (ABTJ_ 00121) | 896-995 | TACCACGTAATCTTAAACTTTCGGCTGAAGATGTTTGGGATGGCGTGAAC TATATTTTATCGCTTAAGTTCCAAGAACCACAGTTCTCTGGTCAAACCAA | SEQ ID NO: 631 | C | | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_mero | BJAB07104_ 03685 (ABTJ_ 00092) | 148-247 | GACCAGTCAACTCGTTGCAGACAGCTTATCTGAGCTTGAACCTGCCAATA CGGTCTCTTTAGCTCTGATTGCCAATCGCTATGCGACCAATCCAAGTGTG | SEQ ID NO: 632 | C | | x |
| Ab_mero | BJAB07104_ 03755 (ABTJ_ 00027) | 466-565 | TTGTGTCTGGCGGACCAATGGAAGCAGGTAAGGTTAAATTCCGCGGTGAT GAAAAAGCAATTGACCTTGTAGATGCTATGGTTGTTGCAGCTGATGACAG | SEQ ID NO: 633 | C | | x |
| Ab_mero | BJAB07104_ 00185 | 361-460 | CTCATGAACTTAATGGACTTGATCCCAGTTGACTGGATTCCTCAAGTTGC TGCATTTGTGGGTGCTAACGTATTTGGTATGGACCCTCACCACGTTTACT | SEQ ID NO: 634 | R | dn | |
| Ab_mero | BJAB07104_ 00186 (ABTJ_ 03655) | 105-204 | AGAAGCTGTTGCTCGTCAACCAGAATTAGCTCCACAACTTCAAACTCGTA TGTTCTTAATCGCGGGTCTTCTTGATGCTGTGCCTATGATCGGTGTTGGT | SEQ ID NO: 635 | R | dn | x |
| Ab_mero | BJAB07104_ 00187 | 227-326 | TCGAACAAGCGAACCGTCGTGCAGCGCAATTGATCGAAGAAGCTCGTACT CAAGCTGCGGCTGAAGGTGAGCGTATTCGTCAACAGGCTAAAGAAGCTGT | SEQ ID NO: 636 | R | dn | |
| Ab_mero | BJAB07104_ 00188 (ABTJ_ 03653) | 404-503 | CAGCACAGTAACTGTTTCAGTTGAAGTTAAACCTGAGCTTATTGCAGGTG TTGTAATTCGTGCAGGCGATCAAGTGATAGATGATTCTGCGCTTAACAAG | SEQ ID NO: 637 | R | dn | x |
| Ab_mero | BJAB07104_ 00189 | 410-509 | AAGTAGCACCAGGTGTAATTTGGCGTCAATCTGTAGACCAACCTGTTCAA ACTGGTTATAAATCAGTTGATACCATGATTCCTGTGGGTCGTGGTCAGCG | SEQ ID NO: 638 | R | dn | |
| Ab_mero | BJAB07104_ 00190 (ABTJ_ 03651) | 730-829 | CACGTATGGTCGCAATGAAAGCAGCGACAGATAACGCAGGTCAGCTTATC AAAGACTTACAACTCATCTATAACAAGCTGCGTCAAGCCGCGATTACTCA | SEQ ID NO: 639 | R | dn | x |
| Ab_mero | BJAB07104_ 00191 (ABTJ_ 03650) | 868-967 | ACTAAATCTGGTTCGATCACTTCGATCCAAGCAGTATATGTACCTGCCGA TGACTTAACAGACCCATCGCCTGCAACTACATTTGCTCACTTAGACGCAA | SEQ ID NO: 640 | R | dn | x |
| Ab_mero | BJAB07104_ 00192 (ABTJ_ 03649) | 215-314 | AACCTCATGTTGTGACGGTTCTTGCAGATACTGCAATCCGTGCTGACAAT TTGGATGAAGCTGCAATTTTAGAAGCACGTAAAAATGCTGAACAATTGCT | SEQ ID NO: 641 | R | dn | x |
| Ab_mero | BJAB07104_ 00485 | 1153-1252 | AGCATTTATTGCTGGTGTTGACCGTATCATGGATATGGCTCGTACTGCGT TGAACGTTGTAGGTAACGCGCTTGCTGTACTTGTAATCAGTAAATGGGAA | SEQ ID NO: 642 | R | dn | |
| Ab_mero | BJAB07104_ 00893 | 336-435 | TAACCATATTCAACATGATGATGCCGATTATGTGGGGGCAGTAAAAGAAA ATATGATGGGGATTATTAGAGAAAAAGAAAAGAAGAAAGGAAAGAACTGG | SEQ ID NO: 643 | R | dn | |
| Ab_mero | BJAB07104_ 01701 | 93-192 | TTTACTGGTGCATCCTTCCCTCATGTTAGATGCAAACGGACACTACAATC ATAGCCAGCTTATGCTGGTGATGGTGGGTATTTCCGGAGGCTTCATTTAT | SEQ ID NO: 644 | R | dn | |
| Ab_mero | BJAB07104_ 01703 | 381-480 | CAACATCTAGGAGTAACTTGGTTAGTTGCCCTAGGTTCTAACATGTCAGC GCTCTGGATTTTAGTTGCGAATGGCTGGATGCAAAACCCTGTAGGTGCAG | SEQ ID NO: 645 | R | dn | |
| Ab_mero | BJAB07104_ 03045 | 361-460 | AGCCGTTTCTTCAATGGTTTCCGTCGTGATGCTCACCCTATGGCAATCAT GGTTGGTGTAGTAGGCGCATTATCTGCTTTCTATCACAACAACCTTGACA | SEQ ID NO: 646 | R | dn | |
| Ab_mero | BJAB07104_ 03047 | 673-772 | TTTAGAAGAAACTCCTCCTGATGAAAGCCTTTGGGAAGGTGAATGTTTCG TATTTGATGGACGTACTGCTGTAACTCATGGTGTTGAAGAAGGTGCAAAC | SEQ ID NO: 647 | R | dn | |
| Ab_mero | BJAB07104_ 03111 | 62-161 | TCAATAGCTGCTATATGTTGAATGACCAAGGTAAAGAAGTACCAATCACA ACTGCAATGATTCGTTCAGTATGTCATCAGTTACTTAACCAGTGCCGCGC | SEQ ID NO: 648 | R | dn | |
| Ab_mero | BJAB07104_ 00049 | 107-206 | ATCATGATGACGATCGTTATGACCGTAACGATGGACGTCGATATAGTGAG TGGGAACGCAAACGTTGGGAAGAGCGTAAAAGATTATATGAACAACAACG | SEQ ID NO: 649 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Ab_mero | BJAB07104_ 00069 (ABTJ_ 03781) | 132-231 | TATGGCAAGCTTTGCTGATCCTCCTTTTGACCGAGGACATGGCCCGAAAG GTCCTAAAGGCGGACCTCGTGGTGAATGGAATGATCGTGGGCATAAATTT | SEQ ID NO: 650 | R | up | x |
| Ab_mero | BJAB07104_ 00138 | 260-359 | AAGACTTGATCCGTGCCAACATGAAAGAAATCGCACAAGTATTGACGGCT GAACAAGGTAAAACTTTGGCAGATGCCGAAGGTGATATTCAACGTGGTCT | SEQ ID NO: 651 | R | up | |
| Ab_mero | BJAB07104_ 00139 | 518-617 | ATAACCTGATTTTAGGAATTTCAATGGCTGCGGTGGCCGAAGGCATGGCA CTCGGTGTGAAGCTAGGCATCGACCCACAAGCATTGGCAGGTGTAATTAA | SEQ ID NO: 652 | R | up | |
| Ab_mero | BJAB07104_ 00140 | 1011-1110 | GGGCAAACTGAAGTAGGCATGGTGGTGTGTAATCATCATGGTTTAAAACA TGAAATTCATGCTGGTTCAGCAGGTTTTCCAAGTCCGGGCTATCGTGTTG | SEQ ID NO: 653 | R | up | |
| Ab_mero | BJAB07104_ 00444 | 132-231 | TGTGACTCTTGATATTTCAAGTGCATCACACCCGTTCTACACAGGTGAAG TACGTCAAGCAAGTAATGAAGGGCGTGTTGCAAGCTTTAACAAACGCTTC | SEQ ID NO: 654 | R | up | |
| Ab_mero | BJAB07104_ 00589 | 373-472 | GCTGATTTAACCGCGAATAAACAAGGCTTACGGACCAACTCTAGTGTTTC TACAGGACATTCTTTCGACTTAAATTCGGGAGATGACAGCGCGAAAGGTT | SEQ ID NO: 655 | R | up | |
| Ab_mero | BJAB07104_ 00590 | 1663-1762 | GAATATTATGCTGGTTTCGGTGACTGAACGTACGCAAGAAATTGGTGTGC GTATGGCTGTGGGTGCTCGACAAAGTGATATTTTGCAGCAGTTCCTGATT | SEQ ID NO: 656 | R | up | |
| Ab_mero | BJAB07104_ 00591 (ABTJ_ 03239) | 1104-1203 | TGAACAAAAACAACTTATTGAACAAGGCAAAGCAACACTAAGTGTAGTTC GCGTTTTACAAGCAGATGGTACGACTAAACCAACACAAATTTTGGTAGGT | SEQ ID NO: 657 | R | up | x |
| Ab_mero | BJAB07104_ 00622 | 436-535 | TGATTAATGGCACAGATATGCCACGCTTTTTGGTACAGAACATTGCCCAA GCCCAAGAAATGCTAGAAGCAGTCAATCACCCTGCCTTAAAAATGCAATA | SEQ ID NO: 658 | R | up | |
| Ab_mero | BJAB07104_ 01132 | 328-427 | CGTTCTAAGTTGAAAAAAATTATCGATGAAGATAGTTATTTGACTGCCGA ACATGAATTAAGTCCAATGACGATTAATGTAGATAAGGCAACGCAAGAAA | SEQ ID NO: 659 | R | up | |
| Ab_mero | BJAB07104_ 01335 | 1390-1489 | CTGGTAGAAGGCACTAAACAAGCTCAGGTTGAACTTGATAAAGCACGTAT TGCTTTTGAAAAAGCTCAGCGCGAAGGCGATTTGGCAGAAGCAGCACGTT | SEQ ID NO: 660 | R | up | |
| Ab_mero | BJAB07104_ 01499 | 775-874 | ACAGGCCAAAAACTACGTAACCACCCTCACCTCAATAAATATTCGATTCC ATTTAGTATGGAAGCCGACTCGGTAAACAGTGCAATTTTAAGCCCTGAGG | SEQ ID NO: 661 | R | up | |
| Ab_mero | BJAB07104_ 01500 | 798-897 | TAAAGTTCAATGAAGAAACAGGCCACTATGAGTTTGGCGAGATTGACTGG CACGAATTTAATGAAGTGATTGCCGGACGTGGACCATGTAATCACGAGCG | SEQ ID NO: 662 | R | up | |
| Ab_mero | BJAB07104_ 01502 | 227-326 | AGAACGTGAGTTTTTAAACCTCTTGTTGTGCGAACAACCCAATGGTGACT TTGCACAAACGATTGTACGCCAATGGTTGATGGACCATTACCATCTTCAT | SEQ ID NO: 663 | R | up | |
| Ab_mero | BJAB07104_ 01504 | 472-571 | GCCGAGCAAATTATGGATTTGAAAGATCAGTTCAAAGAACGCTTTCAACT TATCAATATTTTTTCTCGTGAGTTCAACGATAGTGAACTAATGAACGGTC | SEQ ID NO: 664 | R | up | |
| Ab_mero | BJAB07104_ 01505 | 525-624 | TGCAGTCAAGTGGTTCCGACCGAATTAACCGTTGAATATGCGGTTCAACT TGCAGCCAAAATTGCCAAACAAGCGCCTTTAGCGATTCGCGTGATTAAAC | SEQ ID NO: 665 | R | up | |
| Ab_mero | BJAB07104_ 01508 | 927-1026 | CAGGTTTAACGCTAGATCAGATGGATGTGATTGAGCTGAATGAAGCATTC GCAGCCCAATCTTTGGCTTGTATGCGTGAACTTGGTCTAAAAGATGACGA | SEQ ID NO: 666 | R | up | |
| Ab_mero | BJAB07104_ 01509 | 228-327 | AGACAACTATCCGTTTGGTATGTTTGCCGTACCGCAAGAGCAAATTGTGC GTTTACATGCATCATCTGGTACAACGGGTAAACCGACTGTGGTGGGTTAT | SEQ ID NO: 667 | R | up | |
| Ab_mero | BJAB07104_ 01629 | 567-666 | GAGTATGTAGCACAGCTCCCTAAAAATATTGTACCGCTTGCCATGCAAGT TGCAGCGATGCAACGTGATTTAATTGAGTTACAGGATCAGTCTTCTACCG | SEQ ID NO: 668 | R | up | |
| Ab_mero | BJAB07104_ 01630 | 1236-1335 | ATTGGTTATGAAAACTCTGCAAAAGTGGCGAAAACTGCTTATAAAGAGAA TAAAACTTTAAAACAAGTTGCTGTAGAGCTAGGACTTGTTACAGCAGAGC | SEQ ID NO: 669 | R | up | |
| Ab_mero | BJAB07104_ 01739 | 705-804 | AATTGCAAGTGTGCTTGGCATGATTGTCGGGAATACGGGCAAGATGGCAC GGGATTGGTCACTCATGATGCAAACTGAAATTGCAGAGTTGTTTGAGCCA | SEQ ID NO: 670 | R | up | |
| Ab_mero | BJAB07104_ 01740 | 425-524 | TTTAGCCGAGCTAGTTAAAACTACCCATACCCGCTGGTTCAGTGAAAAAT TTGACTATCAGCATAATGTGGTTGCACAGACAACGATTCAAAGTCTCGCA | SEQ ID NO: 671 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_mero | BJAB07104_ 01741 | 792-891 | CCAAAGGTACGGTTTTGCTTTGGGTGACTTACTTCATGGGACTCGTGGTT GTTTACTTGCTAACAAGTTGGTTACCAACACTTATGCGTGAAACAGGTGC | SEQ ID NO: 672 | R | up | |
| Ab_mero | BJAB07104_ 01742 | 268-367 | ACTAAAGAAGATTTAAAAGAGCTGATCTTACACAGTTCACTCTATGCGGG TTTACCTGCTGCAAACGCTGCAATGCATATGGCTGAAGAAGTCTTTAAAG | SEQ ID NO: 673 | R | up | |
| Ab_mero | BJAB07104_ 01743 | 291-390 | TCTAGAAGTATGGCAAGCCAATGCTTCTGGTCGTTACCGCCATCCAAACG ATAAGTTTATTGGTGCAATGGACCCTAACTTTGGTGGGTGTGGTCGTACC | SEQ ID NO: 674 | R | up | |
| Ab_mero | BJAB07104_ 01744 | 459-558 | TTTGAAGATGAAGCAGAGGCAAATGCTAACGATCCAATTCTAAATAGCAT TGAATGGGCACCACGTCGCCAAACACTTATTGCGAAACGTTTTGAAGAAA | SEQ ID NO: 675 | R | up | |
| Ab_mero | BJAB07104_ 01747 | 393-492 | TCGCGGGAAAATTTGGCGTTTATCCCAAGCATGGGTGAAGAAGGGCTTTG TTGATAATACTGTACAGGTCAAATTTGGTCGTATGGGAATGTCAGAGGAC | SEQ ID NO: 676 | R | up | |
| Ab_mero | BJAB07104_ 01949 | 63-162 | ATTAGGAACAGGTATTGCGATTGGCATGTGTATGTACAAGAAAAAGCAAA AGAACAGTAAGAGCTTCTCTACTGATAGTGATACCGACTCATTGATTAGT | SEQ ID NO: 677 | R | up | |
| Ab_mero | BJAB07104_ 01991 | 713-812 | TATTAGTGGTTGGATACACTTCTGCTGGTTCATTAACGTTTTATGTAGAG ACCGTTTATTCAAAAACCTATTTAACCAACTTAGGGATGGACGGAAAAAC | SEQ ID NO: 678 | R | up | |
| Ab_mero | BJAB07104_ 02013 | 837-936 | GGACTAGAACGTTTAGGTGTAGAACTCAATCCACAAGGTTTTGTGGCAAT TGATGACTATTGTAAAACCAACGTAGCAGGGCTTTATGCCATTGGTGATG | SEQ ID NO: 679 | R | up | |
| Ab_mero | BJAB07104_ 02014 | 1274-1373 | GGTGGTAGCTTTAGCATTTCAAATTTAGGAATGTTAGGCATTAAACAGTT CGATGCCATTATTAACCCACCGCAAGGTGCAATTATGGCATTAGGTGCTT | SEQ ID NO: 680 | R | up | |
| Ab_mero | BJAB07104_ 02015 | 459-558 | TCCGTTATATGTTTGGCGGAAAAGCAAAAGCACCAATGGTTGTACGTGGC ATGATTGGCGCAGGTTTCTCTGCGGCAGCTCAGCATTCTCAGTCACCATA | SEQ ID NO: 681 | R | up | |
| Ab_mero | BJAB07104_ 02016 | 305-404 | TTGCCGATTTAGATAAAGGTATGCTCGGTGCCAACGGGATTGTGGGTGGT GGGCCTCCTTTAGCAATTGGTGCAGCGTTGACAGCGAAAACCTTAAAGAC | SEQ ID NO: 682 | R | up | |
| Ab_mero | BJAB07104_ 02018 | 727-826 | CTATGCCTTATATGGCGATCGACCAGTGAGTACCACTACACTAAAAGCTG AGCTCTCACAGCTTCGAAACCTGATTCCCGATGTGATCGAGTCACGACCA | SEQ ID NO: 683 | R | up | |
| Ab_mero | BJAB07104_ 02356 | 1747-1846 | GTGACTGATGAAATCAAACTGTTAAATGAAGAAGACGGTATTGCGCCAGG TGTAGAAATTCGCCACCGTAATGAACTTGACGCAGTTCAACGTGAGCTGC | SEQ ID NO: 684 | R | up | |
| Ab_mero | BJAB07104_ 02449 | 155-254 | ATGACGCCTTAGGTAAAGTGAAATTACCAAATAAAAAAGTGCAGGCACTG ATCAATGCCAAAAAACTTGGACAAAATGATGAGACCTTGCCGTGCCCTGT | SEQ ID NO: 685 | R | up | |
| Ab_mero | BJAB07104_ 02515 (ABTJ_ 01386) | 227-326 | ATCTGCAATTGGCGGTGGTTTAGGTGGCGGTGCAGGTTATACTGTTGGTA AAAGCATGGGTGGTACAAACGGTGGTTACATCGGTGCTGCTTTAGGTGCA | SEQ ID NO: 686 | R | up | x |
| Ab_mero | BJAB07104_ 02516 (ABTJ_ 01385) | 229-328 | GCGACCGTCGTAACCGTACAGAAGCGGCTATTGGTGGTGCTTTAGGCGGT GGCGCGGGTTACACCGTTGGTAAAAACATGGGCGGTACAAATGGCGGATA | SEQ ID NO: 687 | R | up | x |
| Ab_mero | BJAB07104_ 02813 | 410-509 | CGGCATTAACTTGGTAAATGTCCGCTTTTTTGGGGAATCGGAGTTCTTAT TTTCCTGCATTAAAATTGTTGCGATTTTAAGTATGATTGGCTTCGGTGCT | SEQ ID NO: 688 | R | up | |
| Ab_mero | BJAB07104_ 02814 | 398-497 | TTGCCCAAACTCGTTTAACTCCTGCAAATGCAGCTTCTGAAATTGACCGC GTATTGCGTCAGTGTTTCCTTGAACGCCGTCCTGTACACATCCAACTACC | SEQ ID NO: 689 | R | up | |
| Ab_mero | BJAB07104_ 02816 | 606-705 | TGTGGTTGGTGCTGGTGAGATTGGTGAAGCATTATCTTCTCATCCAGATG TGCAAAAAGTCGTGTTTACGGGATCAACTCGAACAGGGCAGCACATTATG | SEQ ID NO: 690 | R | up | |
| Ab_mero | BJAB07104_ 02819 | 240-339 | AATACCCACAAGTGAAAGTGGAAACTGGTGCCCAAAGCACTTATCCAATT TATGACAATGACAGTAATAAATTAAAAGAATGGCGTGGCCGCGCGGAAAT | SEQ ID NO: 691 | R | up | |
| Ab_mero | BJAB07104_ 02995 | 847-946 | GGCTATCCTGCCGCAGGTTTGGGTATTTCTTTATCTTCGGGTGCAAATGC AATTCAGACCTCTAAGCTCATCCACCAAACTCTAGATCAGCTTACAACGA | SEQ ID NO: 692 | R | up | |
| Ab_mero | BJAB07104_ 03220 | 980-1079 | TTACATCAGCATGAAGAATCACGACGTCAATGGGTTGCAGATACCTCTCA TGAATTGAAAACTCCATTGGCTGTTTTGCAAGCGCAGATTGAAGCGATGC | SEQ ID NO: 693 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_mero | BJAB07104_ 03221 | 183-282 | TGGGAACAACACCGTGCAGAGCGTAAAGCTCGTTTTGAGCAAATTCAAAA AGCATGTGAAGGTAAAGCTGTTGGACAAACTGTCAATGTTCAAGTTGGAG | SEQ ID NO: 694 | R | up | |
| Ab_mero | BJAB07104_ 03416 | 84-183 | ACTTGCTTCTGCCTCTATTTTTGCACAAAGTGCGGGCGTTAATGCAGGTG CATCTGCTCAAGTCAACGTACAACCAGGTGGTCTTGTTAGTGGCGTAGCC | SEQ ID NO: 695 | R | up | |
| Ab_mero | BJAB07104_ 03517 | 916-1015 | GGTTTAATTGGCGGAATGCCAGTGACCTCAGTGATTGTCCGTAGTTCTGT AAATGCCAATACAGGTGCACGTAGTAAATGCTCAACCATTATTCACGGTG | SEQ ID NO: 696 | R | up | |
| Ab_mero | BJAB07104_ 03543 | 158-257 | AAAGCTTATCTAAAGTAAAAGTGACTACAACCGTCAACGGCCAACCAGGT TCTATTAGCGATTTGGTCAATAGCGGACAAGTACAGCAAGTTTCTGCTGC | SEQ ID NO: 697 | R | up | |
| Ab_mero | BJAB07104_ 03610 (ABTJ_ 00167) | 255-354 | CGGCACAAAAGACACTCAATATGGCGTAGGCGTTGAGTACTTCGTTCCTA ACTCTGACTTTTACCTTAGCGGTGATGTAGGCAGAAACGAACGTGAAATC | SEQ ID NO: 698 | R | up | x |
| Ab_mero | BJAB07104_ 03637 | 67-166 | CTAAACGGAACGGTATGGAAAACGATTGATGACCAAACCAATAAGCCCAA AGCCGTAGTAAAATTTACGGAACAGAAGGATGGAACCTTAACTGCAACCA | SEQ ID NO: 699 | R | up | |
| Ab_cip GeneID = NC_ 017847 | ABTJ_00146 | 382-481 | TCAGTGATTGCTGAATTGGGGTTGCCTGTCATTATCAAGCCTGTACATGA AGGTTCAAGTGTAGGCATGAGTAAAGTTGAGAAAGCTGAAGATTTTGCGG | SEQ ID NO: 700 | C | | |
| Ab_cip | ABTJ_00148 | 617-716 | ATGGTGTCTGTCTTGTCGATATTGGTGCAGGTATTACCAATCTGGCAGTT TATTTAGATGGCCGTTTGGCTTTAGCACGCACCTTACAGCGTGGAGGTGA | SEQ ID NO: 701 | C | | |
| Ab_cip | ABTJ_00291 | 614-713 | ATTGGTTTGACCAATAGTGAAGGTCAAGGTATCGAAGGCTTGGAAATGCA GTTGAATAAGCAACTGTCAGGTGTAGACGGTGAGCAAAAAATTATTCGCG | SEQ ID NO: 702 | C | | |
| Ab_cip | ABTJ_00304 | 588-687 | TTTGGCTTGAAGAAAATATGGATGGCCTAGTTGCAAGAGATGCTGACCTT TTAGCAGAGGCTGTTTATCGTTCATGTGCTCACAAAGCCCGCATTGTTGC | SEQ ID NO: 703 | C | | x |
| Ab_cip | ABTJ_00727 | 257-356 | TATTTGCTGAAGGAAGCTATGTTCGTGAAGGTCAGGCGCTTTATGAGCTC GACTCTAGAACGAACCGTGCAACGTTAGAAAATGCAAAAGCATCACTCCT | SEQ ID NO: 704 | C | | x |
| Ab_cip | ABTJ_00860 | 314-413 | TGACAGGAGTTGCACCTTTTACCCAATTGCAAGGTATGTTAACTGCTCAA GGGCAAGTGGCAGGTATTATGGTGACGGGTATTGACCCTAAATATGAAAA | SEQ ID NO: 705 | C | | x |
| Ab_cip | ABTJ_01079 | 1236-1335 | TCATTGGCTTAGTAAAATCTGGAAAACCGCTTGATATGGTGGATGTCCAA ATTGGGAATAACCATTATAAAGTGAAGCCAGATGAAGTGGGGTATTGGAA | SEQ ID NO: 706 | C | | x |
| Ab_cip | ABTJ_02056 | 1002-1101 | CCAGTTTCCACGAATGCTTGTAAGCGCAGAAACTATTGAAGAAAAAGCTG GTGCACTTAATCTTAAAACTGAACAACCACCCAAGTTGCCAGTCGATCCG | SEQ ID NO: 707 | C | | x |
| Ab_cip | ABTJ_02093 | 213-312 | TGTGAAAGTCGTTATATTAGGGCAAGATCCATATCATGGTCCAAATCAGG CAAATGGCTTAAGTTTCTCGGTTCAAAGAGGGGTTGCATTACCACCATCT | SEQ ID NO: 708 | C | | x |
| Ab_cip | ABTJ_02114 | 722-821 | CTGGGCGCGGTGTTACGCGCGGAACAAAACTATATGTAAAAGATGTTCCA GTTCTAGCAGTTCCCTACTTTAACTTCCCGATCGATGACCGCCGTACTAC | SEQ ID NO: 709 | C | | x |
| Ab_cip | ABTJ_02477 | 288-387 | CGTGAAATTCAAACGATCACTGCTAAAGGTAGACCGTCTAAGTTTCAGCA ACAAATAAGTGCTGATAAAGGTATTGCACGCGGTGAAGGACAAACGATTG | SEQ ID NO: 710 | C | | x |
| Ab_cip | ABTJ_02640 | 997-1096 | GCACATGAACAAACCTTAATGCGTTATGAACACCGCCGTAAAGGACAAAA TGATGCGATGATGCATAGTATGTCGGCAATTGGTTGGCTAGAAAGCAGTG | SEQ ID NO: 711 | C | | x |
| Ab_cip | ABTJ_02817 | 536-635 | AGCGCCTCAACCATTAGGCCGTTTATTACCTTCACACATTGCTTCAGCAT TCCAGCAGAATCTTGAAGAAGCGGGTGTTAAATTTGCCTTAGGCACAACC | SEQ ID NO: 712 | C | | x |
| Ab_cip | ABTJ_02821 | 1195-1294 | TGGTAAAGAAGTGACGGCGGTAATTGAATTACGTGCCCGTTTCGATGAAG AGTCGAATATCGAAGTGGCTAACGTTTTACAAGAAGCAGGGGCAGTCGTT | SEQ ID NO: 713 | C | | |
| Ab_cip | ABTJ_02920 | 831-930 | TGTGCAGTTGGCTAGAGAACAACTTGCTCAGCGTCAGCTTATGCCTGTTT TACAATGGGTGATTATTGTTGTAGCAATTGCAGTTTGGGCTGTGCCGGAA | SEQ ID NO: 714 | C | | |
| Ab_cip | ABTJ_03202 | 1860-1959 | ATTGATGGTTTAGACAATGTTGAGCTACATATTGCGCAGTGTTGCCAACC AGTTCATGGTGAATCAATTGCCGGTTATATCACGTTGAACCGTGGGGTAA | SEQ ID NO: 715 | C | | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_cip | ABTJ_03302 | 360-459 | TATGGTCCAGATTTCCCGTTAGTAACGGTCCGTGACTGGGTCAAAACTCA AGCCATGCTTTCTGACCGCTTAGGAATAAGTGTCTGGTATGCGGTGGTCG | SEQ ID NO: 716 | C | | |
| Ab_cip | ABTJ_03330 | 249-348 | TGAAGAGCATATGGCGGCAAAAGGACAAGTTTCTCCGGAAGTTTCTGTTT TGCAGCAATTGGCAAAAGATGGCTTCGTTGCAGAATTAAAACGTGCTTAC | SEQ ID NO: 717 | C | | x |
| Ab_cip | ABTJ_03425 | 576-675 | CAAGACTACCGCCAAATCATTTTAAATGAGCTGGACTTGAGTATTGAGGC AGATAACACCCGTCGTATGCGCCATTACTTCACTGGTTCAACCATGATGT | SEQ ID NO: 718 | C | | x |
| Ab_cip | ABTJ_03503 | 352-451 | GATTTAAGCGATCAAGGTATGCCAAGTATTGCGGAGCGTGCAGCAGAAAC TGAAGTGAGTCGTGATGGAATGCCTCAGCGAGTTTCTGTGCCAAAACCAG | SEQ ID NO: 719 | C | | x |
| Ab_cip | ABTJ_03544 | 97-196 | AAATACTTTGGTGTGGCGGCACAGGGGCGACTAGATGCCAGTATCTTGTT TAGCATCATTGGATATCGTTTACCTGAATTTCTAACCCTCATTTTACCAC | SEQ ID NO: 720 | C | | |
| Ab_cip | ABTJ_03793 | 1243-1342 | ACACTGCTGGCGTCATAAGACTCCGATTATTTTCCGTGCTACACCACAAT GGTTTATCAGCATGGATCAAAAAGGTTTACGTGACGGTGCGCTTAATGCC | SEQ ID NO: 721 | C | | x |
| Ab_cip | ABTJ_00185 | 132-231 | CATGTTAGTGCTTTATGTGGGCTTTATGCTACTTGTGGGCTACAACAAAG AATTTTTGATGAGTTCCTTTAGTGGTGGTGTAACGACATGGGGGATCCCG | SEQ ID NO: 722 | R | dn | |
| Ab_cip | ABTJ_00186 | 798-897 | TGCTGCAAAAATTATGGGACCAGGTAAACTTGCCGCAAACCCGATTGATG CCTTATCTCTTGGCTTAGCACTCATGTTTGGTACAGCAGGTCTTCCACAC | SEQ ID NO: 723 | R | dn | |
| Ab_cip | ABTJ_00204 | 60-159 | TAAATCACGCCACTTAACCATGATCTCGATTGCAGGGGTTATTGGTGGCT CTCTCTTTGTTGGCTCAGGCAGTATTATCTACAACACCGGCCCTGTAGTT | SEQ ID NO: 724 | R | dn | |
| Ab_cip | ABTJ_00510 | 339-438 | GCGAACCTCTTCTTGACTCACGGTTTTAAAAAGGAAAATATTTACGTTAT TGGACGTGGTTCAACTCAACCGTATGTACCGAATACAACCAATGAAAATC | SEQ ID NO: 725 | R | dn | |
| Ab_cip | ABTJ_00536 | 182-281 | TTTCAGCTGAGCTTAACTATGCTCAGCCAGCAAATCAGGCAGAAGTTATT CAGGCTCTCGACAAAGCTGGTTTTAAAGATGCTGTAGTACAAACTTTAGG | SEQ ID NO: 726 | R | dn | |
| Ab_cip | ABTJ_00689 | 390-489 | TGACCAAAAGCGTGAGTCGGTTAAAGCACTACATGGTTTGAATTTCCGTG TGATTGCAGCAGGTGATTCATATAATGATACAACGATGCTTGGTGAAGCC | SEQ ID NO: 727 | R | dn | |
| Ab_cip | ABTJ_00700 | 68-167 | GTGGAGCAATTGGTACCGGATTATTTTTAGGCTCGGCGCAAGTGATTCAA TCTGCGGGACCATCCATTATTTTAGGATATGCCATTGGTGGCTTAATTGC | SEQ ID NO: 728 | R | dn | |
| Ab_cip | ABTJ_01148 | 1608-1707 | GGCAGGTACAAACTTATGTCCAAGCGGGTTCAAATTTAGATAAAGGCTGG CGTGTGGGAGTAGGGCCGACATTAGGATGTATGAATCAGTGGCTTGAAAA | SEQ ID NO: 729 | R | dn | |
| Ab_cip | ABTJ_01199 | 313-412 | AAGTTTAGCCAAACTGGCATGGCATCGTGGTATGGTCGTCAATTTCATGG CCGTAAAACTGCAAGTGGTGAAACATTCGATATGAATGCACTTACTGCTG | SEQ ID NO: 730 | R | dn | |
| Ab_cip | ABTJ_01403 | 122-221 | TGATGGCAATTGTATGGCTTGGAACAGTGGTTACAGGCATTAGTACAATC TTAGGTTACACCACGCTGATATTTGGTTTAGTGGTTACAGCAATTCTGTT | SEQ ID NO: 731 | R | dn | |
| Ab_cip | ABTJ_01442 | 391-490 | TGTATTCGTGCTCAAGAAGGCGGCATCTCTGAAATTGATGAAGATACCAT TGCCTACCATTTCCATGAACCACTAGGTGTGGTTGGTCAAATCATTCCAT | SEQ ID NO: 732 | R | dn | |
| Ab_cip | ABTJ_01445 | 306-405 | TGTCCACAACGGTGTGAATGCCTATAACGAAAATGGCTGTGACTTTATTG TGTCGTTAGGCGGTGGCTCATCTCATGACTGTGCAAAAGGGATTGGCTTA | SEQ ID NO: 733 | R | dn | |
| Ab_cip | ABTJ_01669 | 93-192 | TTTACTGGTGCATCCTTCCCTCATGTTAGATGCAAACGGACACTACAATC ATAGCCAGCTTATGCTGGTGATGGTGGGTATTTCCGGAGGCTTCATTTAT | SEQ ID NO: 734 | R | dn | |
| Ab_cip | ABTJ_01671 | 518-617 | TTGTCAGCCTTTCTATGTTGTGTGCTCATGGCGGCGCTTGGCTTATGCTA CGCACAGACGGTGCCTTGAAACAACGCTCTGCTAAAGCAACTCAAATTAT | SEQ ID NO: 735 | R | dn | |
| Ab_cip | ABTJ_01672 | 381-480 | CAACATCTAGGAGTAACTTGGTTAGTTGCCCTAGGTTCTAACATGTCAGC GCTCTGGATTTTAGTTGCGAATGGCTGGATGCAAAACCCTGTAGGTGCAG | SEQ ID NO: 736 | R | dn | |
| Ab_cip | ABTJ_01946 | 1188-1287 | ACGGCGAACCCTGAACACTGTAAAGCTTTGGTTGAAAATTCAATTGGTAT TGTGACTGCACTTAACCCATACCTAGGTTATGAAACTACAACTCGTATTG | SEQ ID NO: 737 | R | dn | |
| Ab_cip | ABTJ_02134 | 1959-2058 | AAACGCGCAGCTGACCTCATGGAAAGCCGTATTCAAGAGTTGATGGTATT ACTTTGCCGTGAAAGTGGTAAAACTTATGCCAATGCGATTGCAGAAGTTC | SEQ ID NO: 738 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Ab_cip | ABTJ_02204 | 280-379 | GTCTCACTTGCCATCGGTATGGGTTTAGCAAACTTTTTCCAACCTGGCGC GGCGCTAGACCTAGCATTACCAACAGCTCAACAACTTAGTAGTTCTTCTC | SEQ ID NO: 739 | R | dn | |
| Ab_cip | ABTJ_02806 | 402-501 | GGCAGCCATGCTCCCTCTTTATCAACGCCTCGGTATGAATACACTGATCA TGACAGCACTTATGTTGTTATGTAGTGGTGTAATGAATCTGACCCCATGG | SEQ ID NO: 740 | R | dn | |
| Ab_cip | ABTJ_03051 | 1030-1129 | GCAGTAGCGTTAATGTCTAGCCCATATAACAACGTAGATGAAGCGCAAAG CCTTGCAGACTACCGTGGTTTGTTCTGGCGCCGTCCAGTACTTACAGCAA | SEQ ID NO: 741 | R | dn | |
| Ab_cip | ABTJ_03052 | 710-809 | TTGCAGTGAAGTTACCAGTTTTCCCATTGCATGGCTGGTTACCGGATGCC CATGCTCAAGCACCTACAGCGGGTTCTGTAGACTTGGCGGGTATCTTGAT | SEQ ID NO: 742 | R | dn | |
| Ab_cip | ABTJ_03390 | 176-275 | AGGTGAAGACCTTGTCAAAAAATTTGCTGTGAATGGTGTGTACCGTTGGT TTTGTAGCGAATGTGGTTCACCGCTTATTAGCTCGCGTGATGCTCAGCCT | SEQ ID NO: 743 | R | dn | |
| Ab_cip | ABTJ_03431 | 100-199 | GGCTTAGCAGTGCTGGGCTATGCGGTTAACTTATTTTTGTTTGCGATGGG TCGTTTGCAAGTCAGCTCACCAGCCATCCTAACCGAAACCACCAATATTA | SEQ ID NO: 744 | R | dn | |
| Ab_cip | ABTJ_03432 | 1131-1230 | TTAAAGATTGCACCGAGAATTAAACAAGAAAAAGCAGCCATGCTGACTTA TTTCCTGATTGCCATGATGCTCGCAGGCTTACCACCTTTTAGTGGCTTCT | SEQ ID NO: 745 | R | dn | |
| Ab_cip | ABTJ_03433 | 394-493 | GAGCGTGGTGATATTTTGGTCCACTCTCTTAGCACAGAAAATACTGAAAG TGATGTGCAAGACATCAAACAACGCTATGAGGCTCCACTCATGGAAATTT | SEQ ID NO: 746 | R | dn | |
| Ab_cip | ABTJ_03506 | 544-643 | CAGAACGGACAGCTACAAGTGGACATCCGTGATCAGCGTAATCAAAAAAT GGCCAATCTTTTACTAGATGCCAATATGATGCTGGATGTTCAGCTCACAC | SEQ ID NO: 747 | R | dn | |
| Ab_cip | ABTJ_03507 | 1-100 | ATGAAACCGGATATTAGTGAATTATCTGTTGAAGAGTTAAAACGCTTACA AGAAGAAGCAGAAGCTTTAATTGCAAGCAAAAAAGATCAAGCAATCGAAG | SEQ ID NO: 748 | R | dn | |
| Ab_cip | ABTJ_03734 | 909-1008 | TGTTCTACATCGACCAAAACACAATCGACTACTTACGCCTAACAGGCCGT GAAGATGCTCAAGTGGCATTGGTTGAACAGTACGCAAAAGAAATTGGCCT | SEQ ID NO: 749 | R | dn | |
| Ab_cip | ABTJ_03735 | 126-225 | TGTACCGTAGGACGTAGCGGTAACGACTTGCACTATCGTGGCTATGACAT TCTTGACCTTGCGGCAGGTAGCGAGTTTGAAGAAGTTGCTCACTTGCTCG | SEQ ID NO: 750 | R | dn | |
| Ab_cip | ABTJ_03736 | 885-984 | TTACCACTGAAGAGTTAGCATCTGCCGATGTAAGCCTTGCGCTTTATCCG CTTTCTGCTTTCCGTGCCATGAACAAGGCAGCCGAAACTGTGTATGAAAC | SEQ ID NO: 751 | R | dn | |
| Ab_cip | ABTJ_00004 | 1055-1154 | GTATCAAGTGAGGTAAAACCAGCGGTAGAGCAAGCAATGAACAAAGAGTT CTCTGCTTACTTACTTGAGAATCCACAAGCTGCAAAATCAATTGCAGGCA | SEQ ID NO: 752 | R | up | |
| Ab_cip | ABTJ_00094 | 125-224 | GGCTTGGTTTTATGCTTGCAGGGATGTTTTTTTGGGGGCTATTGGAAGTG GTCCGTTTTGGAGTTCAAGTCACTTTTGAAATGCCAGTCACATATAGTTA | SEQ ID NO: 753 | R | up | x |
| Ab_cip | ABTJ_00120 | 100-199 | TTGCCAGATTTAAATAGATCTCCGGAACAGGTAGTAGCACAGGTTTCAGA GCTGATTGAGTCTTTACAAGAGGTGGCTTTAGTCGGCAGTAGTCTTGGTG | SEQ ID NO: 754 | R | up | |
| Ab_cip | ABTJ_00121 | 880-979 | GAGTTACGTAATTTATTACCACGTAATCTTAAACTTTCGGCTGAAGATGT TTGGGATGGCGTGAACTATATTTTATCGCTTAAGTTCCAAGAACCACAGT | SEQ ID NO: 755 | R | up | x |
| Ab_cip | ABTJ_00192 | 1893-1992 | AACCATCCCACTTGGCATTATGACTTGTGTCACGGGTGTTTCAGGTTCAG GTAAATCAACACTGATTAACCGTACGTTACTCCCACTGGCTGCAACACAG | SEQ ID NO: 756 | R | up | x |
| Ab_cip | ABTJ_00357 | 160-259 | GACGACGGTTCAATCCAGCACTTTGAAGGCTACCGTGTACAACACAACTT GTCTCGTGGTCCTGGTAAAGGTGGTGTTCGTTACCATCCAAATGTTGACT | SEQ ID NO: 757 | R | up | x |
| Ab_cip | ABTJ_00375 | 427-526 | CTAAAAACAATTCCGGGTGCATCGCCTGAACTGATCCATGAAGCAGGTTT ATATGCTGACCGGATGAGTATTAATTTAGAGATGCCGACTGAGATTGGGT | SEQ ID NO: 758 | R | up | x |
| Ab_cip | ABTJ_00376 | 440-539 | AGTCTGGTTCGTCCTGATTTTAATGTCTTACCACTCATTCAGCCGCATTT TAAACGGCGTTATCAAGATCAGCGTTGGCTCATTTATGATGAGCAACGTA | SEQ ID NO: 759 | R | up | |
| Ab_cip | ABTJ_00886 | 398-497 | CTTTGGCACAAGGAACTTCTAGCGCTGCGGCCCTGCCTCAGATTCAATTT GTTTCGAACTCACCTGTTGCAGAAGCAGAAGCAGCCTTACAGTCACTAGG | SEQ ID NO: 760 | R | up | |
| Ab_cip | ABTJ_00887 | 874-973 | ACATGGCAACAAAAAATTTCGGCATTGCGTGGCCGTGTTATGAAGCGTCT GGTTGATGAAGTCACTACAGCTTTTGCCAAACATCATTATGAAATTATTA | SEQ ID NO: 761 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_cip | ABTJ_00930 | 31-130 | GCTTTGGTGAAATTGCCATTTCCAATGCCGAATGAAAGTAACCAAGCAGG CGATGCTGTACACAACCAAGTACGTCCGAAACCTGAACAATATGCAGATA | SEQ ID NO: 762 | R | up | |
| Ab_cip | ABTJ_01450 | 1020-1119 | ATATTTGTACAACCTGTATGGAAAGCATGGCGAAAAATCGAACCTCGTTT AAACTTTTACTCGGTTAAACGTTGTATGTACTGTGGTTCAAATGATCTAA | SEQ ID NO: 763 | R | up | |
| Ab_cip | ABTJ_01576 | 525-624 | CATCACCTTAGATCCATTAATTATGGAAGACCTCATGCAACAGACATCAG TCAAAGAGGTATGGGGAATCGGCTATCAATTAGTCAAACAGCTACAAAGT | SEQ ID NO: 764 | R | up | |
| Ab_cip | ABTJ_01625 | 25-124 | TCTCAGCAGCGCCCTCCTCTTACTGGCCAACGTTTACGCTCATATGCTTT TGCTTTACTCACTCGCCGAGATTACTCTAAAGCAGAGCTTATCGAGAAAT | SEQ ID NO: 765 | R | up | |
| Ab_cip | ABTJ_01626 | 446-545 | CTAAAGCAGAAATCGAAGGTGAGATGGGTGACTCTCATATGGGTCTACAA GCACGTCTTATGAGCCAGGCACTTCGTAAAATTACGGGTAATGCTAAACG | SEQ ID NO: 766 | R | up | x |
| Ab_cip | ABTJ_02066 | 269-368 | AAAACATACTTATAACGCCCGTCATGAAACAATTTTCCAAAAACCGAGTT TTCAAGAAGCTGCTCTTAAATGTAAGTTCGGTGTAATACCCGTGACGGAG | SEQ ID NO: 767 | R | up | x |
| Ab_cip | ABTJ_02280 | 200-299 | ACAACGATAAAATTTACCACATTCCTTTGGCGACAGAACGTGTTGCTGCG GGTTTCCCATCACCAGCGCAAGACGATATTGAGCAAGCACTCGATTTAAA | SEQ ID NO: 768 | R | up | |
| Ab_cip | ABTJ_02632 | 77-176 | GGGTCGCCAGTAATTATCATTCACGCCGTGGAGAGGTCGATCTGATTGTA AAACGCGGTAACGAATTGATTTTTGTTGAGGTAAAAGCGCGAGGGCAGGG | SEQ ID NO: 769 | R | up | |
| Ab_cip | ABTJ_02906 | 812-911 | ACATGAAATCGCGCTTGATATTCAAGAAGGCGCCGACATGGTGATTGTAA AACCGGGCATGCCATATCTGGATGTGGTACGTGAAGTGAAAGATACCTTT | SEQ ID NO: 770 | R | up | |
| Ab_cip | ABTJ_03068 | 1045-1144 | TTATGACATTTATGGTGCAATGCGTGACAACGCGATGCTCTCTAAATGGG CAGGTGGTTTAGGTAATGACTGGACACCTGTACGTGCCTTGAACTCTTAT | SEQ ID NO: 771 | R | up | x |
| Ab_cip | ABTJ_03070 | 377-476 | TTAAATATGAGTGGGCTTGGCAAAAAATATCTAGATGGTTGTGCAAACCAC TGGATGCCTCAAGAAGTGAACATGAACCACGATATCGCACTTTGGAAGTC | SEQ ID NO: 772 | R | up | x |
| Ab_cip | ABTJ_03340 | 1-100 | ATGACTAAACCACCATATCATGATGATCAAGCGTCATTTTCCGCACCCAT TGAAGATTTGCAAGTGCGAATTGCATTTTTAGATGATTTAGTTGAGGAAT | SEQ ID NO: 773 | R | up | |
| Ab_cip | ABTJ_03609 | 1577-1676 | AACTACCGTGCTGGGGACCAATATTTAAGTCATGCTGTCGGGAAAACCAA TCAGCGAGTTTACTTCCTTGATGAAACAGGGCGCAGCTATGCCTTGCCAA | SEQ ID NO: 774 | R | up | x |
| Ab_cip | ABTJ_03784 | 72-171 | GCTAGGTGGTTGTGCCAAAAAAGAGGAGCACACCACAACAACTTTAAATA TCGGCTATCAGAAATATGGCATCCTTCCTATTCTAAAAGCACGTGGTGAC | SEQ ID NO: 775 | R | up | |
| Ab_cip | ABTJ_03785 | 197-296 | AATTTCCAAATGCCAAAATCACTTGGAATGAGTTCCCCGCTGGCCCTCAA ATTTTAGAAGCCTTAGCTGTTGGCTCACTCGATGTTGGCGTTACTGGAGA | SEQ ID NO: 776 | R | up | |
| Ab_cip | ABTJ_03808 | 298-397 | CAGTATTTCCCGAATGTACAGATCATTGCTACGCCGGAAACAGTAAAGCA TATTCAGGATACTCAAGCGCTTAAAGTTAAATATTGGGGGCCACAAATGG | SEQ ID NO: 777 | R | up | |
| Ab_cip | ABTJ_03827 | 339-438 | CCCAACTGAAATCCAGTTTCAAGACAAAACATATGCAAGCGAAATTGCCC AGTTCTTTGTTCAGGAACTCTTAAAACACGGTACAACCACGGCCCTCGTT | SEQ ID NO: 778 | R | up | |
| Ab_cip | ABTJ_03829 | 144-243 | CATGGCAGACTTATGCCGTACGATTACCAAACCACATGAACTCGACTTTA TGACAGTGTCTAGCTATGGCGGCGGTACCACTTCAAGTCGAGACGTTAAA | SEQ ID NO: 779 | R | up | |
| Ab_gent GeneID = NC_ 017847 | ABTJ_00113 | 325-424 | TGTATGCTAGATGACAATGAAGAACGTATTCGTCTAGCTCAATATGGCAC TTCTAATATTGGCCGTTTCAAGACGCTTTATCGCCGTGGTTTAGGTATTC | SEQ ID NO: 780 | C | | x |
| Ab_gent | ABTJ_00134 | 254-353 | GCCTAAAGCAGTTTCTCAATATGATGAGAACTATGGCCAAAGCCAAGTTT ATTACCATCAAGTCAACTTCCAGATTAAAACCAAGCCTTCAGAGCACTAC | SEQ ID NO: 781 | C | | x |
| Ab_gent | ABTJ_00655 | 351-450 | TATATCTATATTCATGGTACACCTGATAAAGAACCGATGGGGGTTCCAAT GTCACATGGGTGTATTCGAATGCGTAATGAAGAAATCATTGAATTGTTTG | SEQ ID NO: 782 | C | | x |
| Ab_gent | ABTJ_00666 | 964-1063 | AGGAATTGGTTTAACTGGACCAAATGCTATGGCTCTAGCCATGTCAAAGC AAGGTGCTCGTGCAGGAACAGCCAGTGCAATTATGGGCAGTATGCAATTT | SEQ ID NO: 783 | C | | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_gent | ABTJ_00735 | 95-194 | GGGCATCTTTAGAGACTCGCCGTAAAGACTTGCAATCAAAAACTGAAAAG TTACAGGCAGAGCGAAATGCCGGTGCTAAACAAGTGGGTCAGATTAAAAA | SEQ ID NO: 784 | C | | x |
| Ab_gent | ABTJ_00860 | 314-413 | TGACAGGAGTTGCACCTTTTACCCAATTGCAAGGTATGTTAACTGCTCAA GGGCAAGTGGCAGGTATTATGGTGACGGGTATTGACCCTAAATATGAAAA | SEQ ID NO: 785 | C | | x |
| Ab_gent | ABTJ_00885 | 565-664 | TCGTGTCACGATCTGCAAACCTCATGGATGTACCCATTACAGTTGAGGGT GCAGAAGAAGTTGCACGCCGTTCACGCGGAACACCGCGTATTGCCAATCG | SEQ ID NO: 786 | C | | |
| Ab_gent | ABTJ_00886 | 398-497 | CTTTGGCACAAGGAACTTCTAGCGCTGCGGCCCTGCCTCAGATTCAATTT GTTTCGAACTCACCTGTTGCAGAAGCAGAAGCAGCCTTACAGTCACTAGG | SEQ ID NO: 787 | C | | |
| Ab_gent | ABTJ_01254 | 645-744 | GTAGAAAATGAGGATTGGGAAGAACAAAGTACATCTGCTTTGCATGACGC AATGAACCAGCTAGATGACCGTTCACGTAATATTTTGCAGCGCCGTTGGT | SEQ ID NO: 788 | C | | |
| Ab_gent | ABTJ_02479 | 378-477 | TTACTGTTCCAAACGGACATGAGGAAGTGCGCCGTCGTGCGGATTTGGTA ACACAGGCGATGGGTGGCCGTGGAGCTGTGCGTGAAGTTTGTGATATGTT | SEQ ID NO: 789 | C | | |
| Ab_gent | ABTJ_02819 | 326-425 | TCCTGACACGGTTACTTGATGAAGTGCATCAACAATTACCGAAGATTCAG TTGCATTTACATGAAGCTCAAAGTGAGAAGATTGTAGAGCGCCTAGAACA | SEQ ID NO: 790 | C | | x |
| Ab_gent | ABTJ_03131 | 621-720 | TGCTTTTTATGCACAAAGTAAATTACTTCATGATGCTTTAGAGCAAGTTC AATATGGTGAGTTAGCTAAAAGTCATTGGTATTTCTTGGGTGTTGCAGGC | SEQ ID NO: 791 | C | | |
| Ab_gent | ABTJ_03399 | 562-661 | AAACTGGTGACATGGGTATTGGTAAAGATGGCGAGCCTACACATAACTTT ACTCCGGGTTATGAACTTCACGCTAAATACACTCTCTTTGCTGAAGGCTG | SEQ ID NO: 792 | C | | x |
| Ab_gent | ABTJ_00211 | 1097-1196 | AAGTGACCTTAACGCGTGCAGTTGTAGACTCGCAAACTATTGCTTTAAAC AAAGAGCTACAACAACGTCACTTAGAACCAAACCGTAAAGTATTCTACTG | SEQ ID NO: 793 | R | dn | |
| Ab_gent | ABTJ_00526 | 25-124 | GAATTAGAGTTATTTGAAGTTAATCACGCTGTACAAAACACCCAAAAAGA GATTGCAACACGTTTTGACTTCCGTGGTCATGATGTTTCTATCGAATTAA | SEQ ID NO: 794 | R | dn | |
| Ab_gent | ABTJ_00537 | 519-618 | GATCACTGTTCAGTTTGCTGACAATGCGGATCGTGATGCAGCAATGGATT TTTTACGCCGTAATGGTAATGAATATACCCAACAGGCATTAGCGAGCACG | SEQ ID NO: 795 | R | dn | |
| Ab_gent | ABTJ_00669 | 139-238 | TTCTTGCAAAGTATTCGTGTTATGAAAAGCAGCCGTACAGAAGGCGAAGA TGAGCATGGCCTTACACCTTTCCAAGCGTTTGTAACTGGTCTTGCGAGCC | SEQ ID NO: 796 | R | dn | |
| Ab_gent | ABTJ_00709 | 85-184 | AATGCGGCAACTTCTGATAAAGAGGAAATTCGAAAGCTTCGTCAAGAAGT TGAAGCATTAAAAGCATTAGTTCAAGAACAACGTCAAGTACAGCAACAAC | SEQ ID NO: 797 | R | dn | |
| Ab_gent | ABTJ_00759 | 769-868 | AAGGTAACATCGGTTGTATGGTTAACGGTGCTGGTCTTGCAATGGCAACT ATGGACATCATTAAACTTTATGGTGGTCAGCCTGCAAACTTCCTTGACGT | SEQ ID NO: 798 | R | dn | x |
| Ab_gent | ABTJ_00816 | 116-215 | CAGATGCTTCTGGAAATACCGAATTAGCGTTAGATGGGGGTAAAATCCAA AAAGGTTTGTCTTCAAATGCCAAAACTACATTAAACATGGATGCTGAAAC | SEQ ID NO: 799 | R | dn | |
| Ab_gent | ABTJ_01072 | 647-746 | AACGGTATCAAACAAGGTAACCGTAATGCTTTACTTTACACTGACCCAAG TGTTGATGGCTTAAAAACAGGCCATACTGATGAAGCTGGTTACTGCTTAA | SEQ ID NO: 800 | R | dn | |
| Ab_gent | ABTJ_01672 | 381-480 | CAACATCTAGGAGTAACTTGGTTAGTTGCCCTAGGTTCTAACATGTCAGC GCTCTGGATTTTAGTTGCGAATGGCTGGATGCAAAACCCTGTAGGTGCAG | SEQ ID NO: 801 | R | dn | |
| Ab_gent | ABTJ_02058 | 423-522 | GGCGTGCGATTATTGGCTTTGTAGATGGAACAGAAAATCCTGAACCTGTA ATTGCTGCACAATGGGCATTAGTGGGTAACGAAGATCCTGACTTTATTGG | SEQ ID NO: 802 | R | dn | |
| Ab_gent | ABTJ_02610 | 667-766 | TGAAAGACGCAATCTTCCGTGAGCCAATCGATCAGTCTACTAAGCTTTAT GTCAACTTATTGGGTGTTGCTGAAGCGAACAAAAATGACCCGATCTATAC | SEQ ID NO: 803 | R | dn | |
| Ab_gent | ABTJ_02809 | 620-719 | AAATGGCGATAACGTTGTAAATCCATCAGCTCATACTCCTTGGTACAAGG GGCAAACCTTAATGAGTATTCTTGAGTCTGTGGAAATCAACCGCGAGTCA | SEQ ID NO: 804 | R | dn | x |
| Ab_gent | ABTJ_02810 | 411-510 | GCGCCGTGACGAAGAAAAATCACGTGCGAAAGAGCGTGTGTATTCATTCC GTGATAGTAAACATCGTTGGGATCCTAAAAACCAACGTCCTGAACTTTGG | SEQ ID NO: 805 | R | dn | |
| Ab_gent | ABTJ_02921 | 338-437 | ACCATATTCAACATGATGATGCCGATTATGTGGGGGCAGTAAAAGAAAAT ATGATGGGGATTATTAGAGAAAAAGAAAAGAAGAAAGGAAAGAACTGGTT | SEQ ID NO: 806 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_gent | ABTJ_03051 | 1024-1123 | TTTGGTGCAGTAGCGTTAATGTCTAGCCCATATAACAACGTAGATGAAGC GCAAAGCCTTGCAGACTACCGTGGTTTGTTCTGGCGCCGTCCAGTACTTA | SEQ ID NO: 807 | R | dn | |
| Ab_gent | ABTJ_03052 | 717-816 | GAAGTTACCAGTTTTCCCATTGCATGGCTGGTTACCGGATGCCCATGCTC AAGCACCTACAGCGGGTTCTGTAGACTTGGCGGGTATCTTGATTAAAACA | SEQ ID NO: 808 | R | dn | |
| Ab_gent | ABTJ_03053 | 683-782 | TAAATCTGCACAAATTCCATTGCAAACATGGTTAGCAGATGCGATGGCAG GTCCTACACCTGTTTCTGCATTAATCCACGCAGCAACAATGGTAACAGCT | SEQ ID NO: 809 | R | dn | |
| Ab_gent | ABTJ_03054 | 128-227 | CTGCAGCGTTAGCATTCGTTCTTGCGGGTAGCGTATGGGCACAACCAGAT GGACAAGTCATGTTCATTCTGATTTTAACCCTTGCTGCGGCAGAGGCGTG | SEQ ID NO: 810 | R | dn | x |
| Ab_gent | ABTJ_03056 | 168-267 | GGAAGAGCGTTGTGTGGCATGTAACCTTTGTGCGGTTGCATGTCCGGTTG GCTGTATTTCACTGCAAAAAGCTGAAAAAGAAGACGGACGTTGGTATCCG | SEQ ID NO: 811 | R | dn | |
| Ab_gent | ABTJ_03057 | 341-440 | TGGGTGTTGCGGACATGAGCATCGGTTTGTTGTTCTTTATGGCAATGGCT GGTATTGCGGTTTATGCAGTGTTATTCGGTGGTTGGTCATCAAATAACAA | SEQ ID NO: 812 | R | dn | x |
| Ab_gent | ABTJ_03058 | 1755-1854 | GTGAAACTGAAACTGTGAAACAGGCTGATATTGTACTTTCAGCAGCAAGC TTTGCCGAAGGTGATGGTACTGTCGTAAGCCAAGAAGGTCGTGCACAACG | SEQ ID NO: 813 | R | dn | |
| Ab_gent | ABTJ_03242 | 220-319 | TTTGCTGAGCAATTCGGTTCTAAGCTTGTGTTTCCATGTGATGTTGCCGT TGATGCTGAAATTGATAATGCATTTGCGGAACTTGCAAAACATTGGGACG | SEQ ID NO: 814 | R | dn | |
| Ab_gent | ABTJ_00249 | 526-625 | TGCTGGAAAGGTAAATTTGCGTCGCGTCACCATTATTCAACTTGGTGTCG CCTCTCTACTTTCTTTTACCATTATGCCTATAGTAGGTGAACATACAATT | SEQ ID NO: 815 | R | up | |
| Ab_gent | ABTJ_00346 | 530-629 | GCAATTGCTTTACTTGCACTGCTGAGTTGGGTTGGCTTAAAGAAACAAAT GCCTAGTCATAAGGTGAGTGTAACCAAACAGCCTTTTAGTTATCTTTTTG | SEQ ID NO: 816 | R | up | x |
| Ab_gent | ABTJ_00618 | 443-542 | TAAAAAGCATCCGGGTCTTGTCCGAATGCTTCGTCAGTTTGAGGCAACAT GGCAAAAACAGTTGGGCACTTTAGGCGGCGGTAATCACTTTATAGAGTTA | SEQ ID NO: 817 | R | up | |
| Ab_gent | ABTJ_00738 | 190-289 | TTAGAGAGAGACGGTTTTATCGAACGAAAAATTCAGGATACTTCCCCTAT TCGTGTCGATTATTCCCTCACGCCACTTGGGCAAAATGTAGCTGCTATGG | SEQ ID NO: 818 | R | up | |
| Ab_gent | ABTJ_00744 | 34-133 | ATGTTAGACCGCACTCCATCTCGCGAACTCCGTGAAGACCTTTGGGTATT TCCAATGGACTATCCAATTAAACTCATTGGCGATGCGGGTGAAGAATTAC | SEQ ID NO: 819 | R | up | x |
| Ab_gent | ABTJ_00745 | 647-746 | AGGTGATGATGATTCTGAAGGTGATTCAGGTCCAGACCCTGAAGTTGCAA AAGTTCGTTTTGCTGAATTAGAAGCTGCATGGGCTCAAACTAAAGCTGTC | SEQ ID NO: 820 | R | up | |
| Ab_gent | ABTJ_01034 | 324-423 | GCTTAATGAATGTATGCAGCAACATCCGAATCTGCCGCTTGAACTTCAAA CTCACCCGACAGGATATTTGTTAAATGCTGTGCAACAAGGAGAAGTCGAT | SEQ ID NO: 821 | R | up | |
| Ab_gent | ABTJ_01384 | 484-583 | GTGGACATCAGGAAACAGAAGATCAGTTCCCGAGAGATGTTGTAGAAATC TTGCAATATTTCAAAGCACCTCAAGTGGGCCAAAAGATTATTGCGACACC | SEQ ID NO: 822 | R | up | |
| Ab_gent | ABTJ_01385 | 224-323 | AGCAAGCGACCGTCGTAACCGTACAGAAGCGGCTATTGGTGGTGCTTTAG GCGGTGGCGCGGGTTACACCGTTGGTAAAAACATGGGCGGTACAAATGGC | SEQ ID NO: 823 | R | up | x |
| Ab_gent | ABTJ_01403 | 122-221 | TGATGGCAATTGTATGGCTTGGAACAGTGGTTACAGGCATTAGTACAATC TTAGGTTACACCACGCTGATATTTGGTTTAGTGGTTACAGCAATTCTGTT | SEQ ID NO: 824 | R | up | |
| Ab_gent | ABTJ_01486 | 329-428 | GGGAAAGAACGATCTCTGTGCGGATTTTACATGCGATTGGTTTTGAGGGT GGTTTGCTGATTGCGACTGTTCCAATGATTGCATATATGATGCAGATGAC | SEQ ID NO: 825 | R | up | |
| Ab_gent | ABTJ_01492 | 127-226 | AGTGCAGCATTGAATTTAACTGCCAATCAGCTTTTATGGATTATTGATAT TTATTCGCTGATTATGGCGGGTTTGATTTTACCGATGGGTGCACTCGGTG | SEQ ID NO: 826 | R | up | |
| Ab_gent | ABTJ_01592 | 443-542 | GCATCGGCGATTTATACATGCTTATTGCAATTATTTTGTGTGGATTTGGC TATGCAGAAGGCGGAGTACTTTCGAAAAAAATAGGTGGATGGCAGGTGAT | SEQ ID NO: 827 | R | up | |
| Ab_gent | ABTJ_01709 | 705-804 | AATTGCAAGTGTGCTTGGCATGATTGTCGGGAATACGGGCAAGATGGCAC GGGATTGGTCACTCATGATGCAAACTGAAATTGCAGAGTTGTTTGAGCCA | SEQ ID NO: 828 | R | up | |
| Ab_gent | ABTJ_01710 | 425-524 | TTTAGCCGAGCTAGTTAAAACTACCCATACCCGCTGGTTCAGTGAAAAAT TTGACTATCAGCATAATGTGGTTGCACAGACAACGATTCAAAGTCTCGCA | SEQ ID NO: 829 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_gent | ABTJ_01711 | 792-891 | CCAAAGGTACGGTTTTGCTTTGGGTGACTTACTTCATGGGACTCGTGGTT GTTTACTTGCTAACAAGTTGGTTACCAACACTTATGCGTGAAACAGGTGC | SEQ ID NO: 830 | R | up | |
| Ab_gent | ABTJ_01787 | 465-564 | AGGTGCGCTTGCCGAAGTTACACTTAATTTTATTGCCCAAGACCCTTCTC AAGCCGAGCGTTACCGCAAATCTGGTTTTGAAGCATTTTGGCATGCAGTT | SEQ ID NO: 831 | R | up | |
| Ab_gent | ABTJ_01807 | 39-138 | AATGGGGCTATCGGTCGAAGCTGGGCTTTTAGGGCCGTTAGGAAAGGAAG TAGGTGAGTTGTGGGCCACTTTTAGTATTTTTGGTGTGGGTGCAGCACTT | SEQ ID NO: 832 | R | up | |
| Ab_gent | ABTJ_01924 | 178-277 | ACTATGCACCATGTTAAAACAGGCGCATTGTCTATTAGCCGCTTGGAATA TGGCGCAGATGTTATTATTGAACCAGATCATCTTGATAACTTTTACTTAA | SEQ ID NO: 833 | R | up | |
| Ab_gent | ABTJ_02047 | 380-479 | AAATCACTCTTGCCAACCTCATTAGCCGAGACAACGTTCAAACTGTTGCA TTACGCCAAAATGTAACTGGCACAGATTCAGCTCTTTTATCGGGTACAGG | SEQ ID NO: 834 | R | up | |
| Ab_gent | ABTJ_02050 | 125-224 | AATTTGTAGATGATATCGATGAACATGATCAAATTTTCGAACAATTCGGC GTTAAGGTTTTTGTAGATCCTAAAAGCTTAGTTTACTTAGACGGCTTAGA | SEQ ID NO: 835 | R | up | x |
| Ab_gent | ABTJ_02051 | 219-318 | AGCTCTTAAAAAGCAAGATCATCATCTTGATCAATCTATTAGTGATTTCG AATTTCTACAATCCGCTTTAGAACTTCGTGAACAACTTGATGAAGCGACA | SEQ ID NO: 836 | R | up | |
| Ab_gent | ABTJ_02052 | 1358-1457 | TACTTCATGGCATTCCACCAATGACTGCAGGCCAAGCTCGTATTGAAGTC ACTTTCCAAGTTGATGCAGATGGCTTACTCACCGTTTCTGCTCGTGAAGC | SEQ ID NO: 837 | R | up | |
| Ab_gent | ABTJ_02215 | 737-836 | AGCTTACCTTTAGATGTATTACGTATTGCGATTCCACTCACGATTTACTT TGTAGTGATGTTCTTTATTAGTTTCTTTATGAGTAAACGGATGAGGAATA | SEQ ID NO: 838 | R | up | |
| Ab_gent | ABTJ_02315 | 151-250 | GACGGGGCCGACTTAGGTTTTTTGGCATTAAGCCTCACTAGTCTTAAAGC AGAGTTTCATTTAACTGGTGTGCAAGCCGGAACATTAGGAAGCTTGACAC | SEQ ID NO: 839 | R | up | |
| Ab_gent | ABTJ_02317 | 229-328 | GCAGGTGCAGATCTAAAAGAAATGGCAACCGCAACTTCCACAGAAATGTT ATTGCGTCATACAGAACGTTATTGGAACGCGATTGCCCAGTGCCCTAAAC | SEQ ID NO: 840 | R | up | |
| Ab_gent | ABTJ_02318 | 367-466 | TTAAAGCAAGCACAGGCAGGCGTGATTATAAATATGTCATCTATTGCCGG ACGCTTAGGCTATCCATATCGATTGGCCTATTCCACTTCAAAATGGGGAC | SEQ ID NO: 841 | R | up | |
| Ab_gent | ABTJ_02324 | 591-690 | GTGGTTGAAGATGTGGCAATTAAACTTGCTCACAAACCAAGCCAAGCCTT ACAGCTCAGTAAAAAGTTACTAAGAGATATGCCAATTGATGATCTACTCA | SEQ ID NO: 842 | R | up | |
| Ab_gent | ABTJ_02325 | 220-319 | CAGATGACAGGTTTGCCAAAACCAACCATTACTCGCCTCACACATACCTT GTCGCGTTTGGGTTATATCAAACAAGTACCTAACTCAAGCAAATTTCAGC | SEQ ID NO: 843 | R | up | |
| Ab_gent | ABTJ_02327 | 148-247 | TTCGGTCTTACAATTCCCGAAGAATATGGTGGCTTAGGCATCACTATGGA AGAGGAAGTCAGAGTTGCATTTGAACTTGGACAAACTTCACCGGCTTTTC | SEQ ID NO: 844 | R | up | |
| Ab_gent | ABTJ_02445 | 190-289 | GGTCAAACCCTTAAAAAAGATTATGCTTCTGTTGCATCAAAATTTAAGTT TTCTGAAAAGCAATTAGGTAATGCTTCTGAAGGTTCAAATTGTAGTCAGT | SEQ ID NO: 845 | R | up | |
| Ab_gent | ABTJ_02507 | 111-210 | CAATGCCAATGGTTCAGTTTTGTATATTGTTAAAGAGGAAAGTAAGATTC CACTGGATGTAGAAAAGTTTAAAACTGACCGACCTAAAATCTATGATGCG | SEQ ID NO: 846 | R | up | |
| Ab_gent | ABTJ_02808 | 2-101 | TGAATACTAAAATCACCTATACTGCTTTCACTGGAAGCACGCTTATTGCG AGTGACTCCCTTGTTGAACTTGCAAAGAAACTAAAAGCTCTTCCTAAAAC | SEQ ID NO: 847 | R | up | |
| Ab_gent | ABTJ_02847 | 1054-1153 | GCAGGTTTAATGTTTGGCCTTATGTTTGGGGTAAGTGGTATTGCCGCAGC GGGGCTAGGGCATTTAGCGGATATTAACGGCATTGAATGGGTATTTGGTT | SEQ ID NO: 848 | R | up | x |
| Ab_gent | ABTJ_02861 | 756-855 | CTGGTACGTCAACTCACCATTGGGTGGTGCATTTGAATATTACACCAACG ATGATTATTTGACCGAAGAATGGCAGCCACGTGTAGAAGAACATCGTCTA | SEQ ID NO: 849 | R | up | |
| Ab_gent | ABTJ_02862 | 623-722 | TTGAAGCAACCGAGTATGTGCCACAGGAACGTCATGATTTATATGTCAAC GGAAGAGCGATTCAACGCCAGCAACTTCCACAAGATTTAAATGGAACAGC | SEQ ID NO: 850 | R | up | |
| Ab_gent | ABTJ_02863 | 315-414 | AATGACTGGAACCAAGTGTTTAAAGAGCTATCCGGTCATTGAACAGCATG GTGCAATCTTCATCTGGTTTGGTATCGATGCAAATGAACAACCCGCACCG | SEQ ID NO: 851 | R | up | |
| Ab_gent | ABTJ_03055 | 151-250 | GCCGGCGCCCTCGAAATCATTGTTTATGCTGGTGCGATTATGGTCTTGTT CGTATTCGTTGTGATGATGCTTAACTTAGGGCAACACACAGTTGAACAAG | SEQ ID NO: 852 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Ab_gent | ABTJ_03456 | 118-217 | CCGTGGACACGTGATGGTCGAGTTCGTGGTGACGTTATTCAGGTCTCTTC AGATGTAGCAGGACTTGTAACGGAAGTATTGGTTCAAGATAACCAGACTG | SEQ ID NO: 853 | R | up | |
| Ab_gent | ABTJ_03457 | 67-166 | CCTGCTTTGCTCGTCCAAGCCATTTTTGCATATATATGTTTTCGCTGGTT AAGTCCCTTAACCAACAAATGGATTGCACAAGGCTGGATTGCATTACCCA | SEQ ID NO: 854 | R | up | |
| Ab_gent | ABTJ_03458 | 851-950 | GAACAAAAAGATCAGATGACTGATGAAAATATTCTGCAGTTACCTGACGA GTTTGAAAATGATTTCTTGAACTTAAATGATTCGGCTTCTGAACATCAGC | SEQ ID NO: 855 | R | up | |
| Ab_gent | ABTJ_03715 | 235-334 | GGCGATGTATTTGATCAGGTGGCTAGAGACTTAGTTGAGATTCCTGAAGT ACTCGAATGTCACCTCATTTCAGGTGAATTTGACTACCTTGTAAAAGCGC | SEQ ID NO: 856 | R | up | |
| Ab_gent | ABTJ_03774 | 235-334 | TACCAACAACGTAGCTATTCGATTATTGAAGTAACCACTCAAGGTGAAAT CGCTTTAGGTATTAAAGTACAAGGCTTGGTGTCTCGTGCAGCTCAACTAT | SEQ ID NO: 857 | R | up | x |
| Pa_cip GeneID = NC_ 008463 | PA14_04390 | 12-111 | CGATGGTTTTCGCCCGAATGTCGGCATCATTCTCGCCAACGAGGCGGGGC AGGTGCTGTGGGCGCGGCGTATCAATCAGGAAGCCTGGCAGTTCCCGCAG | SEQ ID NO: 858 | C | | x |
| Pa_cip | PA14_04630 | 1118-1217 | CCTTCTTCAAGGCCGGTCCGGCGGGCATCCCGACCCAGACCGCGTTCAGC CAGAACACCCGCTGGCCGAGCCTGGACGACGACCGCGCCGAGGGCTGCAT | SEQ ID NO: 859 | C | | x |
| Pa_cip | PA14_05480 | 542-641 | AGCGTATCCGTTCGCGCTACGACGAACCGTCGCGCCTGTCGCTGCTCTAC CTCGCCCAGCAGGGCCGCGCCTACCGTGGCGTCGACGACCGCGACCTGCG | SEQ ID NO: 860 | C | | |
| Pa_cip | PA14_05560 | 714-813 | TGCTGGCGCACCTGGTAACCGTCGGCGCCTGGGAACAGGTGCTGGTCTTC ACCCGTACCAAGCACGGCGCCAACCGTCTCGCCGAGTACCTGACCAAGCA | SEQ ID NO: 861 | C | | x |
| Pa_cip | PA14_05920 | 764-863 | ACGAGCGCGCCAGTTCCTCGCACTACCCGTACAACCGGCTGGCCGAGGCG TTCTTCCACAGCGACGTGCTGTTCCGCTGCCAGCGCCTGCTCAACCAGCA | SEQ ID NO: 862 | C | | x |
| Pa_cip | PA14_07700 | 157-256 | TATGCCATGCGCGAGTCGGTGGTCAGCGTCCTGGGCAACCACGACCTGCA CCTGCTGGCGGTGGCGCACAAGTCCGAGCGCCTGAAGAAGTCCGACACGC | SEQ ID NO: 863 | C | | x |
| Pa_cip | PA14_10040 | 711-810 | TCGCCGACGATCCCGATACCCGCGGCGACCTCTGGCGCATGCAGCCCTGG GTGCCGATCCCCAAGGCCTCCGAGGTACGCCCGGCGAGCTACCCGGCCCT | SEQ ID NO: 864 | C | | x |
| Pa_cip | PA14_14900 | 290-389 | GTTCGTGGCCAAGGTCGCGGTCGACAGCGGCAAGCTGGATGACGCCGTTG CCGAGCTGAAGGCGGTCATGGACAAGCCGGCCGACGCCACCCTCGGCGAA | SEQ ID NO: 865 | C | | x |
| Pa_cip | PA14_25000 | 743-842 | CGCGGCAGGACCCGGAAAAGGCCCTTAGCCTGCTCGACTACTACAGCTCG GCGCTACCCTTCTCCAGCGACGAGAAGGTCGCCATCGCCCCGCGAGATCGG | SEQ ID NO: 866 | C | | |
| Pa_cip | PA14_25880 | 335-434 | CGAGATCGTCGAAGTGGTCAGCCCCGACACCTTCAAGCGTCCGATCTACG CCGGTAACGCCATCGCTACCGTGCAGTCCTCGGCTGCGGTCAAGGTGATC | SEQ ID NO: 867 | C | | x |
| Pa_cip | PA14_30230 | 281-380 | GTGCAGAGTTCCGGCAAGCGCGAAGTGACCGGGGCCAATGTCCTGGTGGC GATCTTCAGCGAACAGGAAAGCCAGGCGGTGTTCCTGCTCAAGCAGCAGA | SEQ ID NO: 868 | C | | x |
| Pa_cip | PA14_02520 | 120-219 | ATGGGCTGCGGCAACGGCGCCAGCCGCACCCAGCATCCCAGCGAACTGTT CGGCGAGGACTGGGCCGGTGAATGGGAAGTCGAAGGAACGGAGGACGCCA | SEQ ID NO: 869 | R | dn | |
| Pa_cip | PA14_16860 | 2184-2283 | GACCGCCGAGGAACTGGAGAACCTCTGCACCGTGATGGCCCAGCGCCTGT CGATCCTGCATGGCCTGAACGCCCCGGAGTTCTTCGACAAGAGCCTGTTC | SEQ ID NO: 870 | R | dn | |
| Pa_cip | PA14_17550 | 383-482 | CATGGCCGCCGCCCACGAAGGCGCCGGGCTGGAGAACAGCCTGGGCTTCA ACATCACCCTGCCCTTCGAGCAGCACGCCAACCATACGGTGGACGGCAGC | SEQ ID NO: 871 | R | dn | |
| Pa_cip | PA14_25130 | 211-310 | GCTCCTCGCGTGGATGCATTGCTGAATGCCGAAGTGCTGGCGGCCGCGCC CAGCCCCGAGCTGGCTGAACTGGTGGAGTTGGCGTCGCAGCCGGAAACCT | SEQ ID NO: 872 | R | dn | |
| Pa_cip | PA14_29590 | 70-169 | CTGAAAAGCGACAGCAGCCTGAAGCAGGAACTGGAATTCAAGGACAAGTT GCAGGCGTTGATGGACAAGTACGGCATGACCCTGCACAACATCATCGCCA | SEQ ID NO: 873 | R | dn | x |
| Pa_cip | PA14_00810 | 616-715 | GCCCTCGGCGCGACTGCGGGCGATCCGCACGCTCAGCGGCAACGGCATCC CGGTGGGCGTGCTCTGCTCGCCGATGATCCCGATGGTCAACGACATGGAG | SEQ ID NO: 874 | R | up | |
| Pa_cip | PA14_04310 | 471-570 | CGGTCTACCGCGAAGGCGTGCTGACCGACAACGGCAATATCATCCTCGAC GTGCACAACCTGCGCATCGACAGCCCGGTGGAACTGGAAGAGAAGATCAA | SEQ ID NO: 875 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Pa_cip | PA14_05620 | 409-508 | TGGACGACGGCGGTGACCTGACCGAGATCCTGCACAAGAAATACCCGCAG ATGCTCGAGCGCATCCACGGCATCACCGAAGAGACCACCACCGGGGTCCA | SEQ ID NO: 876 | R | up | |
| Pa_cip | PA14_07770 | 62-161 | TGGCTCTGCAGCCGGTCGCAGCATTGACTGTACAGGCCGCCGATCAGTTC GACTGCAAGGTATCGGCCACCGGCGGCTGGGATTGCTCCCCGCTGCAGAA | SEQ ID NO: 877 | R | up | |
| Pa_cip | PA14_07960 | 2-101 | TGGACAAGAGCACCCAGATCCCGCCCGACAGCTTCGCCGCTCGCCTCAAG CAGGCCATGGCGATGCGCAACCTGAAGCAGGAAACCCTCGCCGAAGCGGC | SEQ ID NO: 878 | R | up | x |
| Pa_cip | PA14_07970 | 4-103 | GCTGACCTTGCCGATCACGCCAACGAACTGGTCCTGGCTCGCCTCGACGG CCTCCTGGCGGCGCGCCCGGCGCTGGCCATCCGCGAGTCCGCGGAAGACT | SEQ ID NO: 879 | R | up | |
| Pa_cip | PA14_07980 | 130-229 | CGCGGCCACCGTGGCAGCCGGGTGATCCTCGACCGTGTGGCGGAGGTCGA TCGCCTGGTAAATCGCCTACCCGAGGAACTGAAGAACGTGGTGGTGGAGC | SEQ ID NO: 880 | R | up | x |
| Pa_cip | PA14_07990 | 108-207 | CCGCAGACACTGACGGAAATGCCGCTCTGGGTACTGATCCTGCTCGCCGC GCTGGGCGGCGTCAGCGGCGAGATGTGGCGTGCCGACAAGGCCGGTCTCG | SEQ ID NO: 881 | R | up | |
| Pa_cip | PA14_08180 | 13-112 | GCTCTGCTCCTGCCGGCCGTGTTGCTGGTCCTGCTGGCCGGCGCCTTGCT CGGCGGCGGCCTGGTTGCCCGCCACTATCGTCCGCAACTGGAGGAGGCCC | SEQ ID NO: 882 | R | up | |
| Pa_cip | PA14_12010 | 131-230 | CCGCCCGCGCGGAGTTGTCCCACGCCAACGAGCAGGACCTCGCCGCCGGC CGCGCCAATGGCCTGGAGCCGGCGATGCTGGACCGCCTGGCGCTGACCCC | SEQ ID NO: 883 | R | up | |
| Pa_cip | PA14_12550 | 291-390 | GATGGCGGTCGCCGAGCACGACCGCGACTGCGACGCCGAGACCCGCGACG CCTGGCGCGACGTGATGGGTCGCGGCATCGCCGTGATCAAGTCGTACTAC | SEQ ID NO: 884 | R | up | |
| Pa_cip | PA14_13030 | 536-635 | CGTTCCCCTACCGCCTGCTGCACATGTCGGTCGCCGCGTTCCTCGCCACC GCCTTCTTCGTCGGCGCCTCGGCCGCCTGGCACCTGCTGCGCGGGCGCGA | SEQ ID NO: 885 | R | up | |
| Pa_cip | PA14_13520 | 363-462 | CACCGCTGGCCGGACGACTATTTCTACGGCCCCGGCGACCTGGCGCGGAC CACTTCCTGGAACAACTCCACCGAGATCGGCCTGAACTACAAGCTCGATC | SEQ ID NO: 886 | R | up | |
| Pa_cip | PA14_13530 | 1282-1381 | GCCCCACGGCGGCACCTTCGCCCTCACCGCGGTACTGATCTCGGCGCTCT CCTCGACCTCGCCGAATCCCGGCCGGTTGTCGCTGCAACTCACCCTCGGG | SEQ ID NO: 887 | R | up | |
| Pa_cip | PA14_14500 | 313-412 | CGGCGCTGCTGGTGGCGATCCTGGTGGCCTGGCTGAGCCTGTTCCTGGCG CCCCAGGGCATCAACCAGTTCGCCCTGCTGTTGAACAAGCAGGATACCCT | SEQ ID NO: 888 | R | up | |
| Pa_cip | PA14_14600 | 645-744 | GTCGGTGGGCGAGCCGAAGGAAGAGATGATCCGCGTGCTCGATTTCCTGC CGCCGCAGATGCCGGCCGACAAGCCGCGCTACCTGATGGGCGTGGGCAAG | SEQ ID NO: 889 | R | up | |
| Pa_cip | PA14_14610 | 197-296 | TCACTTCCGGCGGTATCGCCGGCAAGGTGACCAAGGTCGCCGACGATTTC GTCGTCGTCGAGGTTTCCGACAACGTCGAGCTGAAGTTCCAGAAGGCCGC | SEQ ID NO: 890 | R | up | |
| Pa_cip | PA14_14680 | 299-398 | ACTTCGCCGTGAGCATCGCCTGCAAGTACAAGGGCCGCCTGGAGCACGCC GTGGTCCTCGACCCGGTACGCCAGGAAGAATTCACCGCCAGCCGCGGTCG | SEQ ID NO: 891 | R | up | x |
| Pa_cip | PA14_15310 | 33-132 | CGACGACGTCCTTCTGATCCCCGGTTATTCCGAAGTCCTGCCCAAGGACG TGAGTTTGAAAACTCGCCTGACCCGCGGCATCGAACTGAACATCCCGCTG | SEQ ID NO: 892 | R | up | |
| Pa_cip | PA14_15740 | 1382-1481 | CGACTTCGCCTCGGTGCAGCGCGACAACCCGGAAATGGAGCGACGTTGCC AGGAAGTGATCGACCGCTGCTGGCAGCTCGGCGAGCGCAACCCGATCAGC | SEQ ID NO: 893 | R | up | |
| Pa_cip | PA14_15960 | 62-161 | AGCTGACCGAGGACAACATCAAGGACACTCTGCGCGAAGTGCGCATGGCC CTGCTCGAGGCCGACGTGGCCCTGCCGGTGGTCAAGGACTTCGTCAACAA | SEQ ID NO: 894 | R | up | |
| Pa_cip | PA14_15970 | 60-159 | CGTGACCAACAGCCGCAATGCGCGCGATGGTCGCTTCGTCGAGCGCATCG GTTTCTTCAACCCGGTTGCGACTGGTGGCGAAGTGCGTCTGTCCGTCGAC | SEQ ID NO: 895 | R | up | |
| Pa_cip | PA14_15980 | 241-340 | GCCCGCACCTTCACCGGTTACGAGATCTGCATCCCGCGTAGCGAGTTGCC CTCTCTCGAGGAAGGTGAGTACTACTGGCACCAGCTGGAAGGCCTGAAGG | SEQ ID NO: 896 | R | up | |
| Pa_cip | PA14_15990 | 417-516 | CGATTATGTCCTGTCCGGCGGTGAGTTGCCGGCCATGGTGCTGGTCGATG CAGTGACGCGGTTGCTGCCCGGTGCATTGGGTCATGCAGATTCCGCCGAG | SEQ ID NO: 897 | R | up | |
| Pa_cip | PA14_16010 | 21-120 | AATCCTGCGTCGCACCGAGCTTTCCGAAACCCGTGTGACCAAGGCGGTAT TCCCGCCCACCACCAATCACCACAACACCCTGTTCGGCGGGACTGCGCTG | SEQ ID NO: 898 | R | up | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Pa_cip | PA14_17530 | 347-446 | CAGCCGGACACCGGCGAGCAGGCCCTGGAAATCACCGACATGCTGGTGCG CTCCAACGCGGTCGACGTGATCATCGTCGACTCCGTGGCCGCGCTGGTAC | SEQ ID NO: 899 | R | up | |
| Pa_cip | PA14_17540 | 141-240 | CGACCGCCTGGCCGAGGAAGGTCTGCTCGACGAATCCCGCTATCTCGAAA GCTTCATCGCCAGTCGCGCCCGTAGCGGCCATGGGCCGTTGCGCATCCGT | SEQ ID NO: 900 | R | up | x |
| Pa_cip | PA14_18690 | 197-296 | AGGCGCGCAACGTCGAGGTGATCGGCGTTTCCATCGACTCCCACTTCACC CACAACGCCTGGCGCAACACCCCGGTGGACAAGGGCGGCATCGGCGCCGT | SEQ ID NO: 901 | R | up | |
| Pa_cip | PA14_18750 | 271-370 | CCAGGCCTGCGACGACATCCGCAACAACGGCGGCCAGGTCACCCGCGAAG CCGGGCCGATGAAGCACGGTACCACCGTGATCGCCTTCGTGACCGACCCG | SEQ ID NO: 902 | R | up | |
| Pa_cip | PA14_19940 | 417-516 | CAGCCGCTACCGCGTGGCCGGCACCGAGGTCTATCGCCTGCGCGGCAGCC AGGCCGGCAAGCCCTACCACGCGCTCTACCTGCTCGACGGTCCCCAGGTG | SEQ ID NO: 903 | R | up | |
| Pa_cip | PA14_19950 | 44-143 | GTTTGTTCATGGACAAGGCTGAAGCCGATCGTTACGACAAGATGCTGGAG CTGGCGGAAACGCTGGCCGAGGTGCTGCAGAAGGCGGTGCCGTCGCTGAA | SEQ ID NO: 904 | R | up | x |
| Pa_cip | PA14_23250 | 51-150 | GGACGGTACGCTGCGGTTGCTGGATCAGCGCCTGCTGCCCCAGGAGGAGG TCTGGCTCGAACACGAGTCGGCGGCCGAGGTGGCCAAGGCCATTCGCGAT | SEQ ID NO: 905 | R | up | |
| Pa_cip | PA14_23900 | 52-151 | ATCGTCGTTTCCAGCCTGATCAGTCTGAGTCGCGGCTTCGTCAAGGAAGC CTTGTCCCTGCTTACCTGGATAGTCGCCGGCGCGGTGGCCTGGATGTTCG | SEQ ID NO: 906 | R | up | |
| Pa_cip | PA14_23920 | 457-556 | TTCGCCGCGGTTTCCTGCGTGCACGACCGTTGCGTCGGCGGCTACGCGGT GGTGGCGATGATCACCGGCCATGGCATCGTCGGTTTCCGCGACCCCAATG | SEQ ID NO: 907 | R | up | |
| Pa_cip | PA14_25160 | 298-397 | TCGAGGAATCCTGCCGTATCAATCCCGCCTTCTTCAATCCTCGCGCCGAC TACCTGTTGCGCGTGCGCGGCATGAGCATGAAGGACATCGGCATCCTCGA | SEQ ID NO: 908 | R | up | x |
| Pa_cip | PA14_25620 | 404-503 | CCATGACCCCGAAGTATGTCAGCACCCGGCTGGATTCGTCGTCGAAGACG AGCCGGAGTCGAGCGAAGTCGAGGACAAGCGTCCTAATCCGTTCAGCGTA | SEQ ID NO: 909 | R | up | |
| Pa_cip | PA14_25630 | 40-139 | GACATGCGTCGTTCCCACGATGCGCTCGAGTCCAATGCTCTGTCCGTGGA AAAGAGCACCGGTGAAGTCCACCTGCGCCACCACGTATCCCCGGACGGCT | SEQ ID NO: 910 | R | up | |
| Pa_cip | PA14_27050 | 695-794 | CTGCGCGTCGACCGCCACCTGGTGCTGGACAATCGCGCCGACATGGCCTG GTACGTGCGCCGCGATGCCAGCACCCTGCGCGCGACCATCGACCGCTTCC | SEQ ID NO: 911 | R | up | |
| Pa_cip | PA14_27370 | 659-758 | GCCGCCAAGACCCAGACCGTGGCGCGCATCGAGCAGGTCCACCTGATGGT CCATGCCGACCAGAAGGCCGGTTCGATCCAGCGTCTGCTGGAAGTCGAGC | SEQ ID NO: 912 | R | up | x |
| Pa_cip | PA14_27980 | 536-635 | CGCCATCCTCGAAGGGCTCTCGCCCAAGGAAAACCGCGAGGTGCCGCCGC TGCGCTACGAGGTCGCGGCGCAATTGAAGAAGGACTTCCCGGACCTGGAG | SEQ ID NO: 913 | R | up | |
| Pa_cip | PA14_28450 | 8-107 | CACTACTGATCGCCGCCGGCGTTGCCGCTCTTTCCAGCACCGCCATGGCC GCCAAACTGGATGAAAAGGTTCCCTACCCGAANNNNNNNNNNNNNNNNNN | SEQ ID NO: 914 | R | up | |
| Pa_cip | PA14_28650 | 1644-1743 | CCGATTTCGCCGCCGAGGTGGTGCGGATCCTCGGGGAAAGCGGATTCCGT GCCAAGTCCGACTTGAGAAACGAGAAGATCGGCTTTAAAATCCGCGAGCA | SEQ ID NO: 915 | R | up | |
| Pa_cip | PA14_28660 | 246-345 | GAAGCAGGCTGCGGTCGCCAAGAAGAACCAGAAGCAGGCGCAGGTCAAAG AAATCAAGTTTCGTCCAGGGACGGAAGAAGGGGATTACCAGGTAAAACTA | SEQ ID NO: 916 | R | up | |
| Pa_cip | PA14_30180 | 761-860 | AGGCGACCATGATGAAGATTTCCCACCCGATCGTCTTCGGACATGCGGTG AGCGTCTACTACAAGGACGTCTTCGACAAGTGGGGCCAACTCTTCGAAGA | SEQ ID NO: 917 | R | up | x |
| Pa_cip | PA14_30190 | 348-447 | AACGTGGCCCTGCGCCAGCAACTCGATCTCTACGTCTGCCAGCGCCCGGT ACGCTGGTTCGAAGGCGTGCCCAGCCCGGTGAAGAAGCCCGGCGACGTGG | SEQ ID NO: 918 | R | up | |
| Pa_cip | PA14_30240 | 55-154 | AACACCATGTTCCGTGTGGAGTTGGAAAATGGGCACGTCGTCACCGCGCA CATCTCCGGCAAAATGCGCAAGAACTACATCCGCATCCTCACCGGCGACA | SEQ ID NO: 919 | R | up | |
| Pa_cip | PA14_52480 | 260-359 | ACTTCACTGCAAGGCGCTTCCGAAACGGTGGACGTGCAAACGGGATTCCA CCTGTATCGCGGTCTGTTCATCACGCGCGTTGTTGCCCGGCGAACCGCAG | SEQ ID NO: 920 | R | up | |
| Pa_cip | PA14_52510 | 85-184 | AACGCCTTGCTGGGAGGCTTCGGCGGCGCCATCTTCTTTGTCGTGTTCGC CCGTGACTACAACGCCCTGACCCGCCTCGGCTACCTGCTGGTGTCCTGGG | SEQ ID NO: 921 | R | up | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha- se 2?[e] |
|---|---|---|---|---|---|---|---|
| Sa_levo GeneID = NC_ 002745 | SA0013 | 1180-1279 | AAAAAGCCAGAGTTAAGAGAGCGATTTATTACATCAGATGATGCTTGGGA TATGATGACATCTAAGACAACCGTAGTGATTGTTGATACGCATAAACCGG | SEQ ID NO: 922 | C | | x |
| Sa_levo | SA0441 | 183-282 | CAAACGTGTGGTAATAGAGAACAGTTGGTTTCACCTATTACACCTATGGG AGGCAGTGCGGATTCGTACATTCCATATCCAGTTGAAGTTGAAGTTGGCG | SEQ ID NO: 923 | C | | x |
| Sa_levo | SA0448 | 1526-1625 | ATGGTTACTGGGCAACCTAAACCTATTTTCCCAAGATTGGATAGCGAAGC GGAAATTGCATATATCAAAGAATCAATGCAACCGCCTGCTACTGAAGAGG | SEQ ID NO: 924 | C | | x |
| Sa_levo | SA0490 | 501-600 | TGGCTTTTGGGTAGCTGGCACTGAAGCTAATAATGCAACAGATTATAGAA ATCTAGAAGCGGACATGTCATTGGCTATTGTAATTGGTAGCGAAGGACAG | SEQ ID NO: 925 | C | | x |
| Sa_levo | SA0491 | 302-401 | TACAGTTGTAACAAGTGATATGAGTGAGCAACATGCTATCTTTGGATCAG GTGCATATAGAATATCATCTCGCGAAATGTGGAGAGATTTAAAAGAAAAT | SEQ ID NO: 926 | C | | |
| Sa_levo | SA0811 | 226-325 | TATGAAGCGAACGTAAAAAGCTATGTTGATCCTATCCCGCAAGCACTTAT TTTAACAGCAATCGTTATCGCCTTTGCGACAACAGCCTTTTTCTTAGTAT | SEQ ID NO: 927 | C | | x |
| Sa_levo | SA0869 | 572-671 | TCCAATCCGTACATTAAGTGCAAAAGGTGTGGGTGGTTTCAATACAATTC TTAAAGAAATCGAAGAGCGTGCACCTTTAAAACGTAACGTTGATCAAGTA | SEQ ID NO: 928 | C | | |
| Sa_levo | SA1055 | 1574-1673 | CATAAAACGACAGACTTATTAAAATGTCACTATTGTGGTTACCAAGAGAC GCCACCGAATCAATGTCCAAATTGTGAGAGTGAACACATTCGACAAGTAG | SEQ ID NO: 929 | C | | |
| Sa_levo | SA1077 | 1584-1683 | TTGATGTGCCATCTAAATTAACTCAGGCAATTGAAACAGCATTAGGTGCT TCATTACAACATGTCATTGTAGATTCAGAAAAAGATGGACGCCAGGCTAT | SEQ ID NO: 930 | C | | x |
| Sa_levo | SA1135 | 147-246 | GCATCAAAAACAAGCAGTAAACTTTCAAAATTACGGGAAACAAAATGCGC TAGAACAGTCGGAACATACCATTCAAAGTATAGAAGCAGAAATAAATACA | SEQ ID NO: 931 | C | | x |
| Sa_levo | SA1288 | 754-853 | GACCGCAACAATTATATTTAGCGGAAACTATATTAGATCAGCTCATGCAT AGTGAAAAAGCAATGATTGAAGCATCACTAGGCAGTGGTAAATCATTAGC | SEQ ID NO: 932 | C | | x |
| Sa_levo | SA1296 | 540-639 | GTAACTATAGTGATGCGATTCGCTTATACGATGAAATTAATGAAGATGAA ATGACTTCAGAAGATTATCTCAAAAAAGCCATTTCTTACGATAAAAATGA | SEQ ID NO: 933 | C | | |
| Sa_levo | SA1394 | 596-695 | AAATTGGTAAATCATTCCGTAATGAAATCACTCCAGGTAACTTCATTTTC AGAACAAGAGAATTTGAACAAATGGAACTTGAATTCTTCTGTAAACCTGG | SEQ ID NO: 934 | C | | |
| Sa_levo | SA1445 | 90-189 | TTATCGAACATTAGATGAACGAGGATATAATGCCGTAAACCAAATTGTAG GTTATTTATTATCAGGTGACCCTGCGTATATTCCACGCCAAAATGAAGCA | SEQ ID NO: 935 | C | | x |
| Sa levo | SA1525 | 1358-1457 | ACACATGCGGCAGGAATTATTATTAATGACCATCCATTATATGAATATGC CCCTTTAACGAAAGGGGATACAGGATTATTAACGCAATGGACAATGACTG | SEQ ID NO: 936 | C | | x |
| Sa_levo | SA1526 | 870-969 | GATATTGCGCAAGATTTTGGTGGCGGTGGTCATCCGAATGCGTCAGGAGT TTCAGTGAACAGCTGGGATGAATTTGAGCAACTTGCTACAGCTTTACGCA | SEQ ID NO: 937 | C | | |
| Sa levo | SA1579 | 1311-1410 | ACAATGACAACTGTTCCTGAAGAAGAGCTACCATTGTTGTTACCTGAAAC AGATGAAATCAAGCCATCAGGGACTGGTGAGTCTCCACTAGCTAATATTG | SEQ ID NO: 938 | C | | x |
| Sa_levo | SA1654 | 427-526 | TTTGGAGTCAGTGCATTAATTTTTCCATATGTTGGTTTACGCTTAAGATG GCAATGGTATCAATCGGGACTTAAAACATGGCAAGTTAATTTAATATCAT | SEQ ID NO: 939 | C | | |
| Sa levo | SA1682 | 685-784 | ACTATAGCGAAGAACGTCCTATTACAAAAAAACATATTCACCAACAGAAT AGAAAGAAAATACTTTTCAGAGAAGTAGTTCAGACGACTAGACAAGCTTA | SEQ ID NO: 940 | C | | |
| Sa levo | SA1687 | 282-381 | TTTAATATTTCCGCAGCGACGCCAGTAGTTATTATGTCTATTTTAAGTTT TATTATGCTAGTCATTTTGACGATGATTAGTGCATTGGTTAAACCAGTAA | SEQ ID NO: 941 | C | | x |
| Sa_levo | SA1886 | 282-381 | CAATTGGCACAAGCTTACTTGAGACATGTAAACCCTAAAGTAATTGCCGT CACAGGGTCTAATGGTAAAACAACGACTAAAGATATGATTGAAAGTGTAT | SEQ ID NO: 942 | C | | x |
| Sa_levo | SA2055 | 211-310 | TTCCAAAAGAGAATTGGTGGGTATTTATCGTCTTATTACTCTTAGTCGGT AATGTCGAAGTGACAGGATTTAAAATGCTTAAAAAAGATCTAAAAGGCGT | SEQ ID NO: 943 | C | | |
| Sa_levo | SA0269 | 688-787 | ATTAAGGTTAATGGTGAAAAGTACAAAGTTAGACCTGTCACGTTAACACT TAGCAGAGCTGACACTAAAAAAATTACATTAGCTGTATTAGAAGAAGCTA | SEQ ID NO: 944 | R | dn | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Sa_levo | SA0682 | 100-199 | TTCTGGGAAAGGTTTAGTTATTATGGCATGCGTGCCCTACTCATTTTCTA CATGTACTTTGCCGTAACAGATAATGGCCTTGGAATTGATAAAACAACAG | SEQ ID NO: 945 | R | dn | |
| Sa_levo | SA0730 | 115-214 | AAATATCCAACGACTCAAATCGAAGCGAGTGGCTTAGATGTTGGACTACC TGAAGGACAAATGGGTAACTCAGAAGTTGGTCATATGAATATCGGTGCAG | SEQ ID NO: 946 | R | dn | |
| Sa_levo | SA1021 | 288-387 | CGCTAATTTAACTAAAGAATGTACAGTAATCGGTGTTTCAAATCGTATTG AGATTTGGGATAGAGAAACTTGGAATGATTTCTATGAAGAATCTGAAGAA | SEQ ID NO: 947 | R | dn | |
| Sa levo | SA1022 | 294-393 | TTACGACTTGGGTGTTTCAAGCCCACAACTCGACATTCCAGAACGAGGAT TCAGTTATCACCATGACGCAACATTAGACATGCGTATGGACCAAACACAA | SEQ ID NO: 948 | R | dn | x |
| Sa_levo | SA1023 | 326-425 | AGAATTCTTCTTATGAACGCATATACGAAAAGGCTAAGAAACAGGGGATG AGCCTTGAGAACGATAATGTAAAGGTAGTGCGTAGTAATGGCGAAGCAAA | SEQ ID NO: 949 | R | dn | x |
| Sa_levo | SA1987 | 541-640 | GTGGACCTTTAGGTGGTGCCATTGATGTATTGGCAGTCATAGCTACAGTA ACAGGCGTTGCTGCAACATTAGGTTTCGGTGCATTGCAAATAAACGAAGG | SEQ ID NO: 950 | R | dn | |
| Sa_levo | SA0128 | 188-287 | TACCGGAAGCGATGAGGATGTCAGTCCGTAATAATGGCGGTGGTCATTTT AACCATTCATTATTCTGGGAAATACTATCACCTAATTCTGAAGAAAAAGG | SEQ ID NO: 951 | R | up | |
| Sa_levo | SA0480 | 150-249 | ACACGATTCACTAATGAACATGGTTATGAAATCGAAAGTAAACGTGGTGG TGGTGGTTACATCCGAATCACTAAAATTGAAAATAAAGATGCAACAGGTT | SEQ ID NO: 952 | R | up | |
| Sa_levo | SA0481 | 279-378 | TTTGAAAGATATTGCACATGTTGGTAAATTTGGGTGTGCTAATTGTTATG CAACATTTAAAGATGACATCATTGATATCGTCCGCAGAGTTCAAGGTGGA | SEQ ID NO: 953 | R | up | |
| Sa_levo | SA0482 | 744-843 | CGACAAAAGTTAGACACTTATAATCAATTAGAAACACAAGACCGTGTTTT TCGCTCGCTAGGTATTTTACAAAACTGTAGAATGATAACTATGGAAGAGG | SEQ ID NO: 954 | R | up | |
| Sa_levo | SA0685 | 274-373 | GCGGGTCGCACGATATCAGAAGAGTATAATGTCCCTTTATTAATGAAGTT TGAGTTACATGGAAAAAACAAAGACGTTATTGAATTTAAGAACAAGGTGG | SEQ ID NO: 955 | R | up | x |
| Sa_levo | SA0686 | 559-658 | AGCTAGTGTCATGTTTCTTATTAGAAGTGGATGACAGCTTAAATTCAATT AACTTTATTGATTCAACTGCAAAACAATTAAGTAAAATTGGGGGCGGCGT | SEQ ID NO: 956 | R | up | x |
| Sa_levo | SA0687 | 18-117 | GAACACACAAGAAGATATGACGAATATGTTTTGGAGACAAAATATATCTC AAATGTGGGTTGAAACAGAATTTAAAGTATCAAAAGACATTGCAAGTTGG | SEQ ID NO: 957 | R | up | x |
| Sa_levo | SA0713 | 492-591 | GGTTTAGGTAATCCTGAAGAATATAAAGATTTAGTAGTAAGTGTTCGAGT TGGTATGGAAATGGATAGAAGTGAATTACTTAGAAAACTTGTAGATGTGC | SEQ ID NO: 958 | R | up | x |
| Sa_levo | SA0714 | 2434-2533 | TGGTCTTGGATACGTCACATTAGGTCAACAAGCTACAACGTTATCAGGTG GTGAGGCTCAACGTGTGAAACTTGCATCTGAACTTCATAAACGTTCAACT | SEQ ID NO: 959 | R | up | |
| Sa_levo | SA0835 | 1313-1412 | AAAGCGCACTTAAAAATGAATCTGACAATGCGAGCAAACAGAGATTACAA GAACTACAAGAAGAGCTTGCCAATGAAAAAGAGAAACAAGCAGCACTTCA | SEQ ID NO: 960 | R | up | |
| Sa_levo | SA1128 | 605-704 | TCGGTAATCCAGAGACTACACCAGGTGGACGTGCATTAAAATTCTATAGT TCAGTAAGACTAGAAGTACGTCGTGCAGAACAGCTTAAACAAGGACAAGA | SEQ ID NO: 961 | R | up | x |
| Sa_levo | SA1174 | 321-420 | TCCATTACCTGAACACTTAACATCGACACATAATAGCGACATATTCATAT TAAACGTCGTAGGCGACAGTATGATTGAGGCTGGTATATTAGACGGAGAC | SEQ ID NO: 962 | R | up | |
| Sa_levo | SA1175 | 178-277 | GCTCACTCGGAACAAGTGTACGAAATGACTGACCATCAAATTAAGAACAA TACGATAAATAAAGCATACGAACATAAAGACCCTACAAACAATAGCGAAC | SEQ ID NO: 963 | R | up | |
| Sa_levo | SA1180 | 499-598 | ATTGATGAAGATGCCGTCAATATTTTAATTAGTCATCTGACTGTTCAAGG TGGAAAGACATCTGATTCTGAAAGACCATTAACTATTGGAACGGTTGAAT | SEQ ID NO: 964 | R | up | x |
| Sa levo | SA1181 | 133-232 | GATGCAATGACTTATGCCTTGTTTGGTAAAGCATCAACTGAACAAAGAGA AGAAAATGATTTGAGAAGTCATTTCGCTGATGGTAAACAGCCGATGTCAG | SEQ ID NO: 965 | R | up | x |
| Sa levo | SA1196 | 864-963 | AGCAGAGTTCGAGCAAGAAAAAAAGTGGCAAGAACGATACATTTTGCCTT TGGCTATAGTGATGAAGGCGGTGTACATAAGCAATATACTTTGAAAGATC | SEQ ID NO: 966 | R | up | |
| Sa levo | SA1198 | 144-243 | AATAACAGTGCCAGGCAAAAATGATGAAGTACAACGCTGTATTACTGCTC ATGTTGATACTTTAGGTGCAATGGTTAAAGAAATTAAAGAAGATGGTCGC | SEQ ID NO: 967 | R | up | x |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Pha-se 2?[e] |
|---|---|---|---|---|---|---|---|
| Sa_levo | SA1221 | 3-102 | GAAAAAATGGCAATTTGTTGGTACTACAGCTTTAGGTGCAACACTATTAT TAGGTGCTTGTGGTGGCGGTAATGGTGGCAGTGGTAATAGTGATTTAAAA | SEQ ID NO: 968 | R | up | |
| Sa_levo | SA1315 | 49-148 | GCATGCGGTGCAGCAGCGCCAGATATATATGATTACGACGACGAAGGTAT TGCTTTCGTAATCCTTGACGATAACCAAGGTACTGCAGAAGTACCTGAGG | SEQ ID NO: 969 | R | up | |
| Sa levo | SA1411 | 8-107 | CAGATAGGCAATTGAGTATATTAAACGCAATTGTTGAGGATTATGTTGAT TTTGGACAACCCGTTGGTTCTAAAACACTAATTGAGCGACATAACTTGAA | SEQ ID NO: 970 | R | up | |
| Sa_levo | SA1738 | 209-308 | GGCTACACGAGGCGCTACAATATGCCCAACCTGTAGAAGTTAAATTTTAT AATAATGGCTTTGTAGATTCAGTACGCTTAACCATTTATCGTATTGATGC | SEQ ID NO: 971 | R | up | |
| Sa_levo | SA1759 | 134-233 | TGTGGGGAAATGCAAAAGATGCAATCAATAACGATTTTAAAAACATGGCA ACAGTATATGAAAACACACCATCGTTTGTTCCACAAATAGGTGATGTGGC | SEQ ID NO: 972 | R | up | |
| Sa_levo | SA1764 | 1165-1264 | AGTGATACACCGCCAGAAAATCCAGTCAATGATATGCTTTGGTATGATAC AAGTAACCCTGATGTTGCTGTCTTGCGTAGATATTGGAATGGTCGATGGA | SEQ ID NO: 973 | R | up | |
| Sa_levo | SA1765 | 686-785 | GTCGGCGGTGACTTTGTGATATCCAATCTTGGCGAAGGATATAAAGCAAC TAATTTTCCTGATGCAAAAGGTTGGGTTGGTGCTGGCACGAAACGAGGGC | SEQ ID NO: 974 | R | up | |
| Sa_levo | SA1811 | 696-795 | AAAGGCACTCCAGAGTTCAAAGATATGCTTAAAAACTTGAATGTAAATGA TGTTCTATATGCAGGTCATAATAGCACATGGGACCCTCAATCAAATTCAA | SEQ ID NO: 975 | R | up | |
| Sa_levo | SA1898 | 25-124 | TCATTAGCAGTAGGTTTAGGAATCGTAGCAGGAAATGCAGGTCACGAAGC CCATGCAAGTGAAGCGGACTTAAATAAAGCATCTTTAGCGCAAATGGCGC | SEQ ID NO: 976 | R | up | |
| Sa_levo | SA2097 | 268-367 | GCTAATAATTGGGCTGCTGCTGCACAAGGTGCTGGATTCACAGTAAATCA TACACCTTCTAAAGGCGCTATCCTACAATCTTCTGAAGGACCATTTGGTC | SEQ ID NO: 977 | R | up | |
| Sa_levo | SA2420 | 962-1061 | GTCGTTGCAACAGCAGATCACTCTACTGGTGGTCTAACAATTGGTAAAGA TAAAGGATACGAATGGAATCCTCAACCGATTAAATCGATGAAACACTCTG | SEQ ID NO: 978 | R | up | |
| Sa_levo | SAS009 | 34-133 | CAAGAATTCCAAGAGATACTTAATAGTGGCATTCATCCTGAATGGCTTTA TTGTGCAAAGGCTAATCTTGTTTTAGAGCCTGCTTATACTGGCGAAGGCA | SEQ ID NO: 979 | R | up | |
| Sa_levo | SAS016 | 6-105 | TATTTATCGACAGTATCACCATGAAGGCGCACCAGTTTATGAAATTATAA CCAAAACGTTTCAGCATGTTTCAATTAAATGTGACGATTCATTTAGTGAT | SEQ ID NO: 980 | R | up | |
| Cpase_ ESBL | KPC | 314-413 | ACCCATCTCGGAAAAATATCTGACAACAGGCATGACGGTGGCGGAGCTGT CCGCGGCCGCCGTGCAATACAGTGATAACGCCGCCGCCAATTTGTTGCTG | SEQ ID NO: 981 | carba pene mase | | |
| Cpase_ ESBL | NDM | 112-211 | CAAATGGAAACTGGCGACCAACGGTTTGGCGATCTGGTTTTCCGCCAGCT CGCACCGAATGTCTGGCAGCACACTTCCTATCTCGACATGCCGGGTTTCG | SEQ ID NO: 982 | carba pene mase | | |
| Cpase_ ESBL | OXA48 | 413-512 | TGCTACATGCTTTCGATTATGGTAATGAGGACATTTCGGGCAATGTAGAC AGTTTCTGGCTCGACGGTGGTATTCGAATTTCGGCCACGGAGCAAATCAG | SEQ ID NO: 983 | carba pene mase | | |
| Cpase_ ESBL | IMP_A | 37-136 | GAAGAAGGTGTTTATGTTCATACATCGTTCGAAGAAGTTAACGGTTGGGG TGTTGTTTCTAAACACGGTTTGGTGGTTCTTGTAAACACTGACGCCTATC | SEQ ID NO: 984 | carba pene mase | | |
| Cpase_ ESBL | IMP_B | 45-144 | GAAAAGTTAGTCAATTGGTTTGTGGAGCGCGGCTATAAAATCAAAGGCAC TATTTCCTCACATTTCCATAGCGACAGCACAGGGGGAATAGAGTGGCTTA | SEQ ID NO: 985 | carba pene mase | | |
| Cpase_ ESBL | IMP_C | 45-144 | GAAAAGTTAGTCACTTGGTTTGTGGAACGTGGCTATAAAATAAAAGGCAG TATTTCCTCTCATTTTCATAGCGACAGCACGGGCGGAATAGAGTGGCTTA | SEQ ID NO: 986 | carba pene mase | | |
| Cpase_ ESBL | IMP_D | 1-100 | TATGCATCTGAATTAACAAATGAACTTCTTAAAAAAGACGGTAAGGTACA AGCTAAAAATTCATTTAGCGGAGTTAGCTATTGGCTAGTTAAGAAAAAGA | SEQ ID NO: 987 | carba pene mase | | |

TABLE 9-continued displays the initially selected responsive and control genes for each pathogen-antibiotic pair disclosed herein, and all probes for carbapenemase and ESBL gene family detection, including probe sequences, and also 12fc thresholds used to generate each responsive and control gene list for each bug-drug pair. Also append reliefF ranking for the top 10 chosen.

| Strain/ Ab | GeneID[a] | Position[b] | Target Sequence[c] | SEQ ID NO: | Ctrl/ Resp | Up/ Dn[d] | Phase 2?[e] |
|---|---|---|---|---|---|---|---|
| Cpase_ ESBL | VIM | 477-576 | CTCTAGTGGAGATGTGGTGCGCTTCGGTCCCGTAGAGGTTTTCTATCCTG GTGCTGCGCATTCGGGCGACAATCTTGTGGTATACGTGCCGGCCGTGCGC | SEQ ID NO: 988 | carba pene mase | | |
| Cpase_ ESBL | CTXM15 | 259-358 | AGTGAAAGCGAACCGAATCTGTTAAATCAGCGAGTTGAGATCAAAAAATC TGACCTTGTTAACTATAATCCGATTGCGGAAAAGCACGTCAATGGGACGA | SEQ ID NO: 989 | ESBL | | |
| Cpase_ ESBL | OXA10 | 246-345 | CATAAAGAATGAGCATCAGGTTTTCAAATGGGACGGAAAGCCAAGAGCCA TGAAGCAATGGGAAAGAGACTTGACCTTAAGAGGGGCAATACAAGTTTCA | SEQ ID NO: 990 | ESBL | | |

Reverse complement sequences of select 100 mer target sequences are presented in SEQ ID NOs: 991-1876 of the accompanying Sequence Listing, with SEQ ID NOs: 1877-2762 presenting select "Probe B" sequences (without terminal tag sequences) and SEQ ID NOs: 2763-3648 presenting select "Probe A" sequences (also without terminal tag sequences).

Table legend:

[a]GeneID refers to reference genome as indicated, with alternate GeneID references in parentheses; when GeneID is NC_009648, reference is using what is currently referred to as "old_locus_tag";

[b]Position is listed relative to the start codon of that locus;

[c]100-mer target selected based on homology masking of full-length gene, used to design hybridization probes. Probe A is complementary to the first half; probe B is complementary to the second half of the target sequence;

[d]for responsive genes, listing whether they are predicted to be up-regulated ("up") or down-regulated ("dn") based on RNA-Seq results. Note that for all genes selected by reliefF, the direction of change expected from RNA-Seq matched that seen in NanoString® data;

[e]selected by reliefF as top 10 responsive feature, or by variation on geNorm algorithm as top ~10 control feature, and thus used in phase 2 experiments.

TABLE 10 every strain, MIC, CLSI class, and GoPhAST-R call, sorted by MIC. For phase 1, separate train and test.

| | | | | | | | | |
|---|---|---|---|---|---|---|---|---|
| KpMero_ Phase 1 | Species: | *K. pneumoniae* | | | | | | |
| | Drug: | meropenem | | | | | | |
| | Concentration treated: | 2 mg/L | | | | | | |
| | CLSI breakpoints (2018 M100) | | | GoPhAST-R class | | | | |
| | S≤ | 1 | mg/L | S | | | | |
| | I= | 2 | mg/L | R | | | | |
| | R≥ | 4 | mg/L | R | | | | |
| | Aggregate performance: Confusion matrix | | | | | | | |
| | | | Reference (MIC by CLSI) | | | | | |
| | | SPD | S | I | R | | | |
| | Prediction | S | 5 | 1 | 0 | | | |
| | | NS (I or R) | 0 | 0 | 6 | | | |
| PHASE 1 | | Broth microdilution | | GoPhAST-R | | CPase/select | | |
| STATUS: | Strain | MIC | class | Res_prob | class | ESBL | agreement | |
| Strains used for phase 1 testing (classifier validation) | RB274 | 0.5 | S | 0.026 | S | | concordant | S_concordant |
| | RB404 | 0.5 | S | 0.104 | S | | concordant | S_concordant |
| | RB419 | 0.5 | S | 0.014 | S | | concordant | S_concordant |
| | RB288 | 0.5 | S | 0.114 | S | | concordant | S_concordant |
| | RB587 | 1 | S | 0.066 | S | CTX-M-15 | concordant | S_concordant |
| | RB411 | 2 | I | 0.366 | S | | discordant | I_discordant |
| | RB400 | 8 | R | 0.992 | R | KPC (unknown type) | concordant | R_concordant |
| | RB271 | 16 | R | 0.722 | R | KPC-3 | concordant | R_concordant |
| | RB401 | 32 | R | 1 | R | KPC (unknown type) | concordant | R_concordant |
| | RB408 | 64 | R | 1 | R | VIM-27; CTX-M-15 | concordant | R_concordant |

TABLE 10-continued every strain, MIC, CLSI class, and GoPhAST-R call, sorted by MIC. For phase 1, separate train and test.

| | | | | | | | | |
|---|---|---|---|---|---|---|---|---|
| | RB579 | 64 | R | 0.994 | R | NDM-1; CTX-M15 | concordant | R_concordant |
| | RB596 | 64 | R | 0.898 | R | | concordant | R_concordant |
| Strains used for phase 1 testing (feature selection and classifier derivation) | RB039 | 0.5 | S | n/a | n/a | | | |
| | RB270 | 0.5 | S | n/a | n/a | | | |
| | RB275 | 0.5 | S | n/a | n/a | | | |
| | RB405 | 0.5 | S | n/a | n/a | | | |
| | RB410 | 0.5 | S | n/a | n/a | CTX-M15; OXA-10 | | |
| | RB417 | 1 | S | n/a | n/a | | | |
| | RB268 | 8 | R | n/a | n/a | s | | |
| | RB414 | 8 | R | n/a | n/a | CTX-M15 | | |
| | RB290 | 32 | R | n/a | n/a | KPC-3 | | |
| | RB285 | 64 | R | n/a | n/a | KPC-2 | | |
| | RB402 | 64 | R | n/a | n/a | KPC (unknown type) | | |
| | RB552 | 64 | R | n/a | n/a | OXA-10 | | |

| | | | | | |
|---|---|---|---|---|---|
| KpMero_ Phase2 | Species: | *K. pneumoniae* | | | |
| | Drug: | meropenem | | | |
| | Concentration treated: | 2 mg/L | | | |
| | CLSI breakpoints (2018 M100) | | | GoPhAST-R class | |
| | S≤ | 1 | mg/L | S | |
| | I= | 2 | mg/L | R | |
| | R≥ | 4 | mg/L | R | |
| | Aggregate performance: Confusion matrix | | | | |
| | | | Reference (MIC by CLSI) | | |
| | | SPD | S | I | R |
| | Prediction | S | 5 | 1 | 0 |
| | | NS (I or R) | 0 | 0 | 6 |

| PHASE 2 | | Broth microdilution | | GoPhAST-R | | CPase/select | | |
|---|---|---|---|---|---|---|---|---|
| STATUS: | Strain | MIC | class | probR | class | ESBL | agreement | |
| Strains used for phase 2 testing (classifier validation) | RB565 | 0.125 | S | 0.042 | S | | concordant | S_concordant |
| | RB483 | 0.25 | S | 0.002 | S | | concordant | S_concordant |
| | RB540 | 0.25 | S | 0 | S | | concordant | S_concordant |
| | RB541 | 0.25 | S | 0 | S | | concordant | S_concordant |
| | RB564 | 0.25 | S | 0 | S | | concordant | S_concordant |
| | RB039 | 0.5 | S | 0 | S | | concordant | S_concordant |
| | RB274 | 0.5 | S | 0 | S | | concordant | S_concordant |
| | RB041 | 0.5 | S | 0 | S | | concordant | S_concordant |
| | RB042 | 0.5 | S | 0.012 | S | | concordant | S_concordant |
| | RB273 | 0.5 | S | 0 | S | | concordant | S_concordant |
| | RB276 | 0.5 | S | 0.074 | S | | concordant | S_concordant |
| | RB280 | 0.5 | S | 0 | S | | concordant | S_concordant |
| | RB284 | 0.5 | S | 0 | S | | concordant | S_concordant |
| | RB554 | 0.5 | S | 0.746 | R | OXA-48 | discordant | S_discordant |
| | AR0034 | 2 | I | 0.682 | R | IMP-4 | concordant | I_concordant |
| | RB543 | 2 | I | 0.93 | R | CTX-M-15 | concordant | I_concordant |
| | RB780 | 2 | I | 0.656 | R | KPC-3 | concordant | I_concordant |
| | AR0044 | 4 | R | 0.72 | R | CTX-M-15 | concordant | R_concordant |
| | RB584 | 4 | R | 0.774 | R | CTX-M-15 | concordant | R_concordant |
| | AR0047 | 4 | R | 0.992 | R | | concordant | R_concordant |
| | AR0135 | 8 | R | 0.79 | R | VIM-1 | concordant | R_concordant |
| | RB291 | 8 | R | 0.968 | R | | concordant | R_concordant |
| | RB289 | 16 | R | 0.76 | R | KPC-3 | concordant | R_concordant |
| | RB551 | 16 | R | 0.762 | R | CTX-M-15; OXA-48 | concordant | R_concordant |
| | RB826 | 16 | R | 0.996 | R | NDM-1; CTX-M-15; OXA-10 | concordant | R_concordant |
| | RB401 | 32 | R | 0.998 | R | KPC (unknown type) | concordant | R_concordant |
| | AR0139 | 32 | R | 0.728 | R | NDM-1; CTX-M-15; OXA-10 | concordant | R_concordant |

TABLE 10-continued

| | | | | | | | | |
|---|---|---|---|---|---|---|---|---|
| every strain, MIC, CLSI class, and GoPhAST-R call, sorted by MIC. For phase 1, separate train and test. | | | | | | | | |
| | RB462 | 32 | R | 0.858 | R | KPC-2; OXA-10 | concordant | R_concordant |
| | RB480 | 32 | R | 0.772 | R | KPC-2 | concordant | R_concordant |
| | RB285 | 64 | R | 0.978 | R | KPC-2 | concordant | R_concordant |
| Strains used for phase 2 testing (feature selection and classifier derivation) | RB274 | 0.5 | S | n/a | n/a | | | |
| | RB404 | 0.5 | S | n/a | n/a | | | |
| | RB419 | 0.5 | S | n/a | n/a | | | |
| | RB288 | 0.5 | S | n/a | n/a | | | |
| | RB039 | 0.5 | S | n/a | n/a | | | |
| | RB270 | 0.5 | S | n/a | n/a | | | |
| | RB275 | 0.5 | S | n/a | n/a | | | |
| | RB405 | 0.5 | S | n/a | n/a | | | |
| | RB410 | 0.5 | S | n/a | n/a | CTX-M15; OXA-10 | | |
| | RB587 | 1 | S | n/a | n/a | CTX-M-15 | | |
| | RB417 | 1 | S | n/a | n/a | | | |
| | RB411 | 2 | I | n/a | n/a | | | |
| | RB400 | 8 | R | n/a | n/a | KPC (unknown type) | | |
| | RB268 | 8 | R | n/a | n/a | KPC-4 | | |
| | RB414 | 8 | R | n/a | n/a | CTX-M15 | | |
| | RB271 | 16 | R | n/a | n/a | KPC-3 | | |
| | RB401 | 32 | R | n/a | n/a | KPC (unknown type) | | |
| | RB290 | 32 | R | n/a | n/a | KPC-3 | | |
| | RB408 | 64 | R | n/a | n/a | VIM-27; CTX-M-15 | | |
| | RB579 | 64 | R | n/a | n/a | NDM-1; CTX-M15 | | |
| | RB596 | 64 | R | n/a | n/a | | | |
| | RB285 | 64 | R | n/a | n/a | KPC-2 | | |
| | RB402 | 64 | R | n/a | n/a | KPC (unknown type) | | |
| | RB552 | 64 | R | n/a | n/a | OXA-10 | | |
| KpCip_phase1 | Species: | *K. pneumoniae* | | | | | | |
| | Drug: | ciprofloxacin | | | | | | |
| | Concentration treated: | 1 mg/L | | | | | | |
| | CLSI breakpoints (2018 M100) | | | GoPhAST-R class | | | | |
| | S≤ | 1 | mg/L | S | | | | |
| | I= | 2 | mg/L | R | | | | |
| | R≥ | 4 | mg/L | R | | | | |
| | Aggregate performance: | | | | | | | |
| | Confusion matrix | | | | | | | |
| | | | Reference (MIC by CLSI) | | | | | |
| | | SPD | S | I | R | | | |
| | Prediction | S | 5 | 1 | 0 | | | |
| | | NS (I or R) | 0 | 0 | 0 | | | |
| PHASE 1 | | Broth microdilution | | GoPhAST-R | | | | |
| STATUS: | Strain | MIC | class | probR | class | | agreement | |
| Strains used for phase 1 testing (classifier validation) | RB041 | 0.03 | S | 0.004 | S | | concordant | S_concordant |
| | RB416 | 0.03 | S | 0.138 | S | | concordant | S_concordant |
| | RB268 | 0.125 | S | 0.042 | S | | concordant | S_concordant |
| | RB405 | 0.5 | S | 0.012 | S | | concordant | S_concordant |
| | RB418 | 1 | S | 0.074 | S | | concordant | S_concordant |
| | RB122 | 2 | I | 0.48 | S | | discordant | I_discordant |
| | RB400 | 32 | R | 0.868 | R | | concordant | R_concordant |
| | RB595 | 64 | R | 0.786 | R | | concordant | R_concordant |
| | RB039 | 128 | R | 0.906 | R | | concordant | R_concordant |

TABLE 10-continued every strain, MIC, CLSI class, and GoPhAST-R call, sorted by MIC. For phase 1, separate train and test.

| | | | | | | | |
|---|---|---|---|---|---|---|---|
| Strains used for phase 1 training (feature selection and classifier derivation) | RB040 | 0.03 | S | n/a | n/a | | |
| | RB123 | 0.03 | S | n/a | n/a | | |
| | RB403 | 0.06 | S | n/a | n/a | | |
| | RB592 | 0.25 | S | n/a | n/a | | |
| | RB415 | 0.5 | S | n/a | n/a | | |
| | RB401 | 16 | R | n/a | n/a | | |
| | RB578 | 64 | R | n/a | n/a | | |
| | RB013 | 128 | R | n/a | n/a | | |
| | RB402 | 128 | R | n/a | n/a | | |
| KpCip_ phase2 | Species: | *K. pneumoniae* | | | | | |
| | Drug: | ciprofloxacin | | | | | |
| | Concentration treated: | 1 mg/L | | | | | |
| | CLSI breakpoints (2018 M100) | | | GoPhAST-R class | | | |
| | S≤ | 1 | mg/L | S | | | |
| | I= | 2 | mg/L | R | | | |
| | R≥ | 4 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 5 | 1 | 0 | | |
| | | NS (I or R) | 0 | 0 | 6 | | |
| PHASE 2 | | Broth microdilution | | GoPhAST-R | | | |
| STATUS: | Strain | MIC | class | probR | class | agreement | |
| Strains used for phase 2 testing (classifier validation) | RB040 | 0.03 | S | 0.084 | S | concordant | S_concordant |
| | RB041 | 0.03 | S | 0.048 | S | concordant | S_concordant |
| | RB572 | 0.03 | S | 0.112 | S | concordant | S_concordant |
| | RB564 | 0.03 | S | 0.292 | S | concordant | S_concordant |
| | RB568 | 0.06 | S | 0.236 | S | concordant | S_concordant |
| | RB780 | 0.06 | S | 0.452 | S | concordant | S_concordant |
| | AR0160 | 0.06 | S | 0.366 | S | concordant | S_concordant |
| | RB274 | 0.125 | S | 0.164 | S | concordant | S_concordant |
| | RB277 | 0.125 | S | 0.216 | S | concordant | S_concordant |
| | RB565 | 0.125 | S | 0.11 | S | concordant | S_concordant |
| | RB571 | 0.125 | S | 0.428 | S | concordant | S_concordant |
| | AR0126 | 0.125 | S | 0.73 | R | discordant | S_discordant |
| | AR0034 | 1 | S | 0.58 | R | discordant | S_discordant |
| | RB419 | 16 | R | 0.866 | R | concordant | R_concordant |
| | RB583 | 16 | R | 0.784 | R | concordant | R_concordant |
| | RB287 | 64 | R | 0.994 | R | concordant | R_concordant |
| | RB290 | 64 | R | 0.998 | R | concordant | R_concordant |
| | RB543 | 64 | R | 0.848 | R | concordant | R_concordant |
| | RB563 | 64 | R | 0.994 | R | concordant | R_concordant |
| | RB569 | 64 | R | 0.872 | R | concordant | R_concordant |
| | RB579 | 64 | R | 0.88 | R | concordant | R_concordant |
| | RB582 | 64 | R | 0.98 | R | concordant | R_concordant |
| | RB013 | 128 | R | 0.994 | R | concordant | R_concordant |
| | RB039 | 128 | R | 0.996 | R | concordant | R_concordant |
| | RB408 | 128 | R | 0.998 | R | concordant | R_concordant |
| Strains used for phase 2 training (feature selection and classifier derivation) | RB041 | 0.03 | S | n/a | n/a | | |
| | RB416 | 0.03 | S | n/a | n/a | | |
| | RB040 | 0.03 | S | n/a | n/a | | |
| | RB123 | 0.03 | S | n/a | n/a | | |
| | RB403 | 0.06 | S | n/a | n/a | | |
| | RB268 | 0.125 | S | n/a | n/a | | |
| | RB592 | 0.25 | S | n/a | n/a | | |
| | RB405 | 0.5 | S | n/a | n/a | | |
| | RB415 | 0.5 | S | n/a | n/a | | |
| | RB418 | 1 | S | n/a | n/a | | |
| | RB122 | 2 | I | n/a | n/a | | |
| | RB401 | 16 | R | n/a | n/a | | |
| | RB400 | 32 | R | n/a | n/a | | |
| | RB595 | 64 | R | n/a | n/a | | |
| | RB578 | 64 | R | n/a | n/a | | |
| | RB039 | 128 | R | n/a | n/a | | |
| | RB013 | 128 | R | n/a | n/a | | |
| | RB402 | 128 | R | n/a | n/a | | |

TABLE 10-continued every strain, MIC, CLSI class, and GoPhAST-R call, sorted by MIC. For phase 1, separate train and test.

| | | | | | | | |
|---|---|---|---|---|---|---|---|
| KpGent_ phase1 | Species: | *K. pneumoniae* | | | | | |
| | Drug: | gentamicin | | | | | |
| | Concentration treated: | 4 mg/L | | | | | |
| | CLSI breakpoints (2018 M100) | | | GoPhAST-R class | | | |
| | S≤ | 4 | mg/L | S | | | |
| | I= | 8 | mg/L | R | | | |
| | R≥ | 16 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 5 | 1 | 0 | | |
| | | NS (I or R) | 0 | 0 | 4 | | |
| PHASE 1 | | Broth microdilution | | GoPhAST-R | | | |
| STATUS: | Strain | MIC | class | probR | class | agreement | |
| Strains used for phase 1 testing (classifier validation) | IDR1600039511-01-00 | 0.5 | S | 0.004 | S | concordant | |
| | UCI_7 | 0.5 | S | 0.016 | S | concordant | |
| | AR0080 | 1 | S | 0.084 | S | concordant | |
| | MGH_30 | 1 | S | 0.064 | S | concordant | |
| | RB042 | 2 | S | 0.362 | S | concordant | |
| | BIT-10 | 4 | S | 0.952 | R | discordant | 1-dilution error (S called R, i.e. not-S) |
| | UCI_63 | 4 | S | 0.948 | R | discordant | 1-dilution error (S called R, i.e. not-S) |
| | UCI_37 | 16 | R | 0.916 | R | concordant | R_concordant |
| | AR0042 | 32 | R | 0.728 | R | concordant | R_concordant |
| | BIDMC_34 | 32 | R | 0.94 | R | concordant | R_concordant |
| | MGH_63 | 32 | R | 0.95 | R | concordant | R_concordant |
| | ATCC 700721 | 64 | R | 0.816 | R | concordant | R_concordant |
| | RB122 | 128 | R | 0.932 | R | concordant | R_concordant |
| Strains used for phase 1 training (feature selection and classifier derivation) | RB040 | 0.5 | S | n/a | n/a | | |
| | UCI_13 | 0.5 | S | n/a | n/a | | |
| | BAC0800007138 | 0.5 | S | n/a | n/a | | |
| | RB121 | 1 | S | n/a | n/a | | |
| | AR0043 | 1 | S | n/a | n/a | | |
| | BWH_15 | 4 | S | n/a | n/a | | |
| | BIDMC_2A | 4 | S | n/a | n/a | | |
| | UCI_67 | 8 | I | n/a | n/a | | "I" called "R" for training |
| | RB012 | 32 | R | n/a | n/a | | |
| | AR0076 | 32 | R | n/a | n/a | | |
| | MGH_35 | 32 | R | n/a | n/a | | |
| | RB826 | 64 | R | n/a | n/a | | |
| | IDR1600031102-01-00 | 64 | R | n/a | n/a | | |
| EcMero_phase1 | Species: | *E. coli* | | | | | |
| | Drug: | meropenem | | | | | |
| | Concentration treated: | 2 mg/L | | | | | |
| | CLSI breakpoints (2018 M100) | | | GoPhAST-R class | | | |
| | S≤ | 1 | mg/L | S | | | |
| | I= | 2 | mg/L | R | | | |
| | R≥ | 4 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 5 | 1 | 0 | | |
| | | NS (I or R) | 0 | 0 | 3 | | |

TABLE 10-continued every strain, MIC, CLSI class, and GoPhAST-R call, sorted by MIC. For phase 1, separate train and test.

| PHASE 1 | | Broth mircodilution | | GoPhAST-R | | CPase/select | | |
|---|---|---|---|---|---|---|---|---|
| STATUS: | Strain | MIC | class | probR | class | ESBL | agreement | |
| Strains used for phase 1 testing (classifier validation) | AR0058 | 0.25 | S | 0.078 | S | | concordant | S_concordant |
| | BAA2523* | 0.5 | S | 0.702 | R | OXA-48 | discordant | *large inoculum effect (MIC 0.5 → 32); S called R; +CPase |
| | AR0089 | 0.5 | S | 0.204 | S | | concordant | S_concordant |
| | AR0104* | 1 | S | 0.904 | R | KPC-4 | discordant | *large inoculum effect (MIC 1 → >32); S called R; +CPase |
| | IDR1300027657 | 1 | S | 0.116 | S | | concordant | S_concordant |
| | IDR1600043633 | 2 | I | 0.874 | R | CTX-M-15 | concordant | I_concordant |
| | UVI_51 | 4 | R | 0.168 | S | CTX-M-15 | discordant | R called A, 1-dilution from int'd breakpoint, 2 from susc |
| | IDR1600029769 | 8 | R | 1 | R | OXA-48 | concordant | R_concordant |
| | BAA2469 | 16 | R | 1 | R | NDM-1 | concordant | R_concordant |
| | AR0048 | 32 | R | 0.822 | R | NDM-1; CTX-M-15 | concordant | R_concordant |
| | RB767 | 64 | R | 0.91 | R | NDM | concordant | R_concordant |
| | RB765 | 64 | R | 1 | R | NDM; KPC | concordant | R_concordant |
| | * = large inoculum effect | | | | | | | |
| Strains used for phase 1 training (feature selection and classifier derivation) | RB001 | 0.25 | S | n/a | n/a | | | |
| | RB002 | 0.25 | S | n/a | n/a | | | |
| | AR0077 | 0.5 | S | n/a | n/a | | | |
| | BIDMC_77 | 0.5 | S | n/a | n/a | CTX-M-15 | | |
| | RB076 | 0.5 | S | n/a | n/a | | | |
| | IDR1600035372 | 0.5 | S | n/a | n/a | CTX-M-15 | | |
| | RB076 | 1 | S | n/a | n/a | | | |
| | MGH_57 | 4 | R | n/a | n/a | CTX-M-15 | | |
| | AR0055 | 8 | R | n/a | n/a | NDM-1 | | |
| | AR0061 | 8 | R | n/a | n/a | KPC-3 | | |
| | AR0069 | 16 | R | n/a | n/a | NDM-1 | | |
| | IDR120024571 | 64 | R | n/a | n/a | | | |
| | IDR120039757 | 64 | R | n/a | n/a | | | |

| | | | | |
|---|---|---|---|---|
| EcCip_phase1 | Species: | *E. coli* | | |
| | Drug: | ciprofloxacin | | |
| | Concentration treated: | 1 mg/L | | |
| | CLSI breakpoints (2018 M100) | | | GoPhAST-R class |
| | S≤ | 1 | mg/L | S |
| | I= | 2 | mg/L | R |
| | R≥ | 4 | mg/L | R |
| | Aggregate performance: | | | |
| | Confusion matrix | | | |

| | | Reference (MIC by CLSI) | | |
|---|---|---|---|---|
| | SPD | S | I | R |
| Prediction | S | 5 | 1 | 0 |
| | NS (I or R) | 0 | 0 | 0 |

| PHASE 1 | | Broth microdilution | | GoPhAST-R | | | |
|---|---|---|---|---|---|---|---|
| STATUS: | Strain | MIC | class | probR | class | agreement | |
| Strains used for phase 1 testing (classifier validation) | RB001 | 0.03 | S | 0.002 | S | concordant | S_concordant |
| | RB025 | 0.25 | S | 0.156 | S | concordant | S_concordant |
| | AR0089 | 0.25 | S | 0.088 | S | concordant | S_concordant |
| | IDR1200024571 | 0.5 | S | 0.034 | S | concordant | S_concordant |
| | RB110 | 8 | R | 1 | R | concordant | R_concordant |
| | AR0085 | 16 | R | 0.972 | R | concordant | R_concordant |
| | RB086 | 64 | R | 1 | R | concordant | R_concordant |
| | BAA2469 | 64 | R | 0.9 | R | concordant | R_concordant |
| | BAC0800005647 | 64 | R | 1 | R | concordant | R_concordant |

TABLE 10-continued

| every strain, MIC, CLSI class, and GoPhAST-R call, sorted by MIC. For phase 1, separate train and test. | | | | | | | |
|---|---|---|---|---|---|---|---|
| Strains used for phase 1 training (feature selection and classifier derivation) | RB075 | 0.03 | S | n/a | n/a | | |
| | IDR1300034680 | 0.03 | S | n/a | n/a | | |
| | AR0061 | 0.25 | S | n/a | n/a | | |
| | BAA2523 | 0.5 | S | n/a | n/a | | |
| | RB077 | 1 | S | n/a | n/a | | |
| | AR0081 | 16 | R | n/a | n/a | | |
| | AR0104 | 32 | R | n/a | n/a | | |
| | RB051 | 64 | R | n/a | n/a | | |
| | RB057 | 64 | R | n/a | n/a | | |
| EcGent_phase1 | Species: | *E. coli* | | | | | |
| | Drug: | gentamicin | | | | | |
| | Concentration treated: | 4 mg/L | | | | | |
| | CLSI breakpoints (2018 M100) | | | GoPhAST-R class | | | |
| | S≤ | 4 | mg/L | S | | | |
| | I= | 8 | mg/L | R | | | |
| | R≥ | 16 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 5 | 1 | 0 | | |
| | | NS (I or R) | 0 | 0 | 0 | | |
| PHASE 1 | | Broth microdilution | | GoPhAST-R | | | |
| STATUS: | Strain | MIC | class | probR | class | agreement | |
| Strains used for phase 1 testing (classifier validation) | RB075 | 0.5 | S | 0.106 | S | concordant | S_concordant |
| | MGH_57 | 0.5 | S | 0.474 | S | concordant | S_concordant |
| | IDR1300034680 | 1 | S | 0.002 | S | concordant | S_concordant |
| | BAC0800005647 | 1 | S | 0 | S | concordant | S_concordant |
| | AR0061 | 32 | R | 1 | R | concordant | R_concordant |
| | AR0055 | 64 | R | 1 | R | concordant | R_concordant |
| | IDR1600047120 | 64 | R | 0.928 | R | concordant | R_concordant |
| | RB051 | 256 | R | 0.916 | R | concordant | R_concordant |
| Strains used for phase 1 training (feature selection and classifier derivation) | AR0081 | 0.5 | S | n/a | n/a | | |
| | AR0084 | 0.5 | S | n/a | n/a | | |
| | RB001 | 1 | S | n/a | n/a | | |
| | RB076 | 1 | S | n/a | n/a | | |
| | AR0085 | 2 | S | n/a | n/a | | |
| | BAA2469 | 64 | R | n/a | n/a | | |
| | IDR1300027657 | 64 | R | n/a | n/a | | |
| | RB765 | 64 | R | n/a | n/a | | |
| | RB057 | 256 | R | n/a | n/a | | |
| AbMero_phase1 | Species: | *A. baumanii* | | | | | |
| | Drug: | meropenem | | | | | |
| | Concentration treated: | 2 mg/L | | | | | |
| | CLSI breakpoints (2018 M100) | | | | | | |
| | S≤ | 2 | mg/L | | | | |
| | I= | 4-8 | mg/L | | | | |
| | R≥ | 16 | mg/L | | | | |
| | Aggregate performance: | | | | | | |
| | Confusion matrix | | | | | | |
| | | | Reference (MIC by CLSI) | | | | |
| | | SPD | S | I | R | | |
| | Prediction | S | 5 | 1 | 0 | | |
| | | NS (I or R) | 0 | 0 | 0 | | |

TABLE 10-continued every strain, MIC, CLSI class, and GoPhAST-R call, sorted by MIC. For phase 1, separate train and test.

| PHASE 1 | | Broth microdilution | | GoPhAST-R | | CPase/select | | |
|---|---|---|---|---|---|---|---|---|
| STATUS: | Strain | MIC | class | probR | class | ESBL | agreement | |
| Strains used for phase 1 testing (classifier validation) | RB197 | 0.5 | S | 0.042 | S | | concordant | S_concordant |
| | RB197s | 0.5 | S | 0.19 | S | | concordant | S_concordant |
| | RB206 | 1 | S | 0.6 | R | | discordant | S misclassified as R, 1 dilution from breakpoint, 2-dilution error |
| | AR0063 | 4 | I | 0.702 | R | | concordant | R_concordant |
| | RB204 | 16 | R | 0.754 | R | | concordant | R_concordant |
| | AR0036 | 16 | R | 0.668 | R | | concordant | R_concordant |
| | AR0045 | 32 | R | 0.948 | R | | concordant | R_concordant |
| | AR0101 | 64 | R | 0.882 | R | | concordant | R_concordant |
| | RB203 | 64 | R | 0.998 | R | | concordant | R_concordant |
| | AR0078 | 64 | R | 0.88 | R | | concordant | R_concordant |
| | AR0035 | 64 | R | 0.834 | R | | concordant | R_concordant |
| Strains used for phase 1 training (feature selection and classifier derivation) | RB201 | 0.25 | S | n/a | n/a | | | |
| | ATCC 17978 | 0.5 | S | n/a | n/a | | | |
| | RB205 | 1 | S | n/a | n/a | | | |
| | AR0052 | 2 | S | n/a | n/a | | | |
| | AR0102 | 4 | I | n/a | n/a | | | "I" called "R" for training |
| | RB198 | 8 | I | n/a | n/a | | | "I" called "R" for training |
| | AR0070 | 16 | R | n/a | n/a | | | |
| | RB202 | 32 | R | n/a | n/a | | | |
| | RB200 | 64 | R | n/a | n/a | | | |
| | AR0033 | 64 | R | n/a | n/a | NDM-1 | | |
| | AR0037 | 64 | R | n/a | n/a | NDM-1 | | |
| | AR0056 | 64 | R | n/a | n/a | | | |
| | NOTE: "s" modifier to strain name denotes small colony morphotype of RB197 | | | | | | | |

| | | | |
|---|---|---|---|
| AbCip_phase1 | Species: | *A. baumanii* | |
| | Drug: | ciprofloxacin | |
| | Concentration treated: | 1 mg/L | |
| | CLSI breakpoints (2018 M100) | | |
| | S≤ | 1 | mg/L |
| | I= | 2 | mg/L |
| | R≥ | 4 | mg/L |
| | Aggregate performance: | | |
| | Confusion matrix | | |

| | | Reference (MIC by CLSI) | | |
|---|---|---|---|---|
| | SPD | S | I | R |
| Prediction | S | 5 | 1 | 0 |
| | NS (I or R) | 0 | 0 | 3 |

| PHASE 1 | | Broth microdilution | | GoPhAST-R | | | |
|---|---|---|---|---|---|---|---|
| STATUS: | Strain | MIC | class | probR | class | agreement | |
| Strains used for phase 1 testing (classifier validation) | RB201 | 0.25 | S | 0.308 | S | concordant | S_concordant |
| | RB201a | 0.25 | S | 0.136 | S | concordant | S_concordant |
| | RB197s | 0.25 | S | 0.114 | S | concordant | S_concordant |
| | RB205 | 1 | S | 0.012 | S | concordant | S_concordant |
| | AR0063 | 8 | R | 1 | R | concordant | R_concordant |
| | RB198 | 64 | R | 0.942 | R | concordant | R_concordant |
| | RB203 | 64 | R | 1 | R | concordant | R_concordant |
| | RB206 | 64 | R | 1 | R | concordant | R_concordant |
| | AR0035 | 64 | R | 1 | R | concordant | R_concordant |
| | AR0045 | 64 | R | 1 | R | concordant | R_concordant |
| | AR0078 | 64 | R | 1 | R | concordant | R_concordant |
| | AR0102 | 64 | R | 1 | R | concordant | R_concordant |

TABLE 10-continued

| every strain, MIC, CLSI class, and GoPhAST-R call, sorted by MIC. For phase 1, separate train and test. | | | | | | |
|---|---|---|---|---|---|---|
| Strains used for phase 1 training (feature selection and classifier derivation) | RB197 | 0.25 | S | n/a | n/a | |
| | RB197b | 0.25 | S | n/a | n/a | |
| | RB197a | 0.25 | S | n/a | n/a | |
| | ATCC 17978 | 0.5 | S | n/a | n/a | |
| | AR0052 | 4 | R | n/a | n/a | |
| | AR0070 | 8 | R | n/a | n/a | |
| | RB202 | 64 | R | n/a | n/a | |
| | RB204 | 64 | R | n/a | n/a | |
| | AR0033 | 64 | R | n/a | n/a | |
| | AR0037 | 64 | R | n/a | n/a | |
| | AR0056 | 64 | R | n/a | n/a | |
| | AR0101 | 64 | R | n/a | n/a | |
| | AR0036 | 64 | R | n/a | n/a | |
| | NOTE: "a", "b", and "c" modifier to strain names denote biological replicates: separate colonies of each isolate, grown and treated separately (done because of paucity of cip-S *A. baumanii* strains in the collection) | | | | | |
| AbGent_phase1 | Species: | *A. baumanii* | | | | |
| | Drug: | gentamicin | | | | |
| | Concentration treated: | 4 mg/L | | | | |
| | CLSI breakpoints (2018 M100) | | | | | |
| | S≤ | 4 | mg/L | | | |
| | I= | 8 | mg/L | | | |
| | R≥ | 16 | mg/L | | | |
| | Aggregate performance: | | | | | |
| | Confusion matrix | | | | | |
| | | | Reference (MIC by CLSI) | | | |
| | | SPD | S | I | R | |
| | Prediction | S | 5 | 1 | 0 | |
| | | NS (I or R) | 0 | 0 | 1 | |
| PHASE 1 | | Broth microdilution | | GoPhAST-R | | |
| STATUS: | Strain | MIC | class | probR | class | agreement |
| Strains used for phase 1 testing (classifier validation) | ATCC 17978 | 0.5 | S | 0.162 | S | concordant |
| | RB205 | 2 | S | 0.248 | S | concordant |
| | AR0063 | 4 | S | 0.088 | S | concordant |
| | AR0035 | 16 | R | 0.958 | R | concordant |
| | AR0052 | 32 | R | 1 | R | concordant |
| | RB200 | 64 | R | 1 | R | concordant |
| | RB204 | 64 | R | 0.958 | R | concordant |
| | AR0037 | 64 | R | 1 | R | concordant |
| | AR0056 | 64 | R | 1 | R | concordant |
| | AR0078 | 64 | R | 1 | R | concordant |
| Strains used for phase 1 training (feature selection and classifier derivation) | RB197 | 0.5 | S | n/a | n/a | |
| | RB201 | 1 | S | n/a | n/a | |
| | RB203 | 4 | S | n/a | n/a | |
| | AR0101 | 8 | I | n/a | n/a | "I" called "R" for training |
| | AR0033 | 32 | R | n/a | n/a | |
| | RB198 | 64 | R | n/a | n/a | |
| | RB202 | 64 | R | n/a | n/a | |
| | RB206 | 64 | R | n/a | n/a | |
| | AR0045 | 64 | R | n/a | n/a | |
| | AR0070 | 64 | R | n/a | n/a | |
| | AR0102 | 64 | R | n/a | n/a | |
| PaCip_phase1 | Species: | *P. aeruginosa* | | | | |
| | Drug: | ciprofloxacin | | | | |
| | Concentration treated: | 1 mg/L | | | | |
| | CLSI breakpoints (2018 M100) | | | GoPhAST-R class | | |
| | S≤ | 0.5 | mg/L | S | | |
| | I= | 1 | mg/L | R | | |

TABLE 10-continued every strain, MIC, CLSI class, and GoPhAST-R call, sorted by MIC. For phase 1, separate train and test.

| | | | | | | | |
|---|---|---|---|---|---|---|---|
| | R≥ | 2 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 6 | 0 | 0 | | |
| | | NS (I or R) | 0 | 1 | 5 | | |
| PHASE 1 | | Broth microdilution | | GoPhAST-R | | | |
| STATUS: | Strain | MIC | class | probR | class | agreement | |
| Strains used for phase 1 testing (classifier validation) | BL08 | 0.06 | S | 0.242 | S | concordant | |
| | BWHPSA043 | 0.06 | S | 0.024 | S | concordant | |
| | CF18 | 0.06 | S | 0.198 | S | concordant | |
| | BL11 | 0.125 | S | 0.394 | S | concordant | |
| | UDL | 0.125 | S | 0.332 | S | concordant | |
| | BL22 | 0.5 | S | 0.498 | S | concordant | |
| | CF27 | 1 | I | 0.86 | R | concordant | |
| | BWHPSA048 | 8 | R | 0.678 | R | concordant | |
| | X13273 | 8 | R | 0.896 | R | concordant | |
| | BL17 | 16 | R | 0.994 | R | concordant | |
| | BWHPSA006 | 16 | R | 1 | R | concordant | |
| | BWH053 | 16 | R | 1 | R | concordant | |
| Strains used for phase 1 training (feature selection and classifier derivation) | BWH029 | 0.03 | S | n/a | n/a | | |
| | BWH033 | 0.06 | S | n/a | n/a | | |
| | BWHPSA046 | 0.06 | S | n/a | n/a | | |
| | BL01 | 0.125 | S | n/a | n/a | | "I" called "R" for training |
| | BWH055 | 0.125 | S | n/a | n/a | | |
| | BWH050 | 0.25 | S | n/a | n/a | | |
| | BWHPSA041 | 2 | R | n/a | n/a | | |
| | CF5 | 8 | R | n/a | n/a | | |
| | BL03 | 16 | R | n/a | n/a | | |
| | BWHPSA003 | 16 | R | n/a | n/a | | |
| | BWH049 | 16 | R | n/a | n/a | | |
| | X24509 | 64 | R | n/a | n/a | | |

| | | | | | | | |
|---|---|---|---|---|---|---|---|
| Sa_Levo_phase1 | Species: | *S. aureus* | | | | | |
| | Drug: | levofloxacin | | | | | |
| | Concentration treated: | 1 mg/L | | | | | |
| | CLSI breakpoints (2018 M100) | | | GoPhAST-R class | | | |
| | S≤ | 1 | mg/L | S | | | |
| | I= | 2 | mg/L | R | | | |
| | Aggregate performance: | | | | | | |
| | Confusion matrix | | | | | | |
| | | | Reference (MIC by CLSI) | | | | |
| | | SPD | S | I | R | | |
| | Prediction | S | 6 | 0 | 0 | | |
| | | NS (I or R) | 0 | 0 | 6 | | |
| PHASE 1 | | Broth microdilution | | GoPhAST-R | | | |
| STATUS: | Strain | MIC | class | probR | class | agreement | Comments |
| Strains used for phase 1 testing (classifier validation) | RB065 | 0.06 | S | 0.002 | S | concordant | |
| | RB067 | 0.13 | S | 0.012 | S | concordant | |
| | RB069 | 0.13 | S | 0 | S | concordant | |
| | RB098 | 0.13 | S | 0 | S | concordant | |
| | RB223 | 0.13 | S | 0.002 | S | concordant | |
| | RB247 | 0.5 | S | 0.006 | S | concordant | |
| | RB064 | 8 | R | 1 | R | concordant | |
| | RB211 | 16 | R | 1 | R | concordant | |
| | RB045 | 32 | R | 1 | R | concordant | |
| | RB090 | 32 | R | 1 | R | concordant | |
| | RB219 | 32 | R | 1 | R | concordant | |
| | RB047 | 64 | R | 1 | R | concordant | |

TABLE 10-continued

| every strain, MIC, CLSI class, and GoPhAST-R call, sorted by MIC. For phase 1, separate train and test. | | | | | |
|---|---|---|---|---|---|
| Strains used for phase 1 training (feature selection and classifier derivation) | RB006 | 0.06 | S | n/a | n/a |
| | RB066 | 0.06 | S | n/a | n/a |
| | RB003 | 0.125 | S | n/a | n/a |
| | RB096 | 0.13 | S | n/a | n/a |
| | RB221 | 0.13 | S | n/a | n/a |
| | RB245 | 0.25 | S | n/a | n/a |
| | RB072 | 4 | R | n/a | n/a |
| | RB007 | 16 | R | n/a | n/a |
| | RB004 | 32 | R | n/a | n/a |
| | RB074 | 32 | R | n/a | n/a |
| | RB095 | 32 | R | n/a | n/a |
| | RB010 | 64 | R | n/a | n/a |

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms “a” and “an” and “the” and similar referents in the context of describing the disclosure (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., “such as”) provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed disclosure. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms “comprising”, “consisting essentially of”, and “consisting of” may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the disclosure disclosed herein without departing from the scope and spirit of the disclosure. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

REFERENCES

Abeel, T., T. Van Parys, Y. Saeys, J. Galagan, and Y. Van de Peer. 2012. ‘GenomeView: a next-generation genome browser’, Nucleic Acids Res, 40: e12.

Adams-Sapper, S., S. Nolen, G. F. Donzelli, M. Lal, K. Chen, L. H. Justo da Silva, B. M. Moreira, and L. W. Riley. 2015. ‘Rapid induction of high-level carbapenem resistance in heteroresistant KPC-producing *Klebsiella pneumoniae*’, Antimicrob Agents Chemother, 59:3281-9.

Adler, A., M. Ben-Dalak, I. Chmelnitsky, and Y. Carmeli. 2015. ‘Effect of Resistance Mechanisms on the Inoculum Effect of Carbapenem in *Klebsiella pneumoniae* Isolates with Borderline Carbapenem Resistance’, Antimicrob Agents Chemother, 59:5014-7.

Allcock, R. J. N., A. V. Jennison, and D. Warrilow. 2017. ‘Towards a Universal Molecular Microbiological Test’, J Clin Microbiol, 55:3175-82.

Anderson, K. F., D. R. Lonsway, J. K. Rasheed, J. Biddle, B. Jensen, L. K. McDougal, R. B. Carey, A. Thompson, S. Stocker, B. Limbago, and J. B. Patel. 2007. 'Evaluation of methods to identify the *Klebsiella pneumoniae* carbapenemase in Enterobacteriaceae', J Clin Microbiol, 45:2723-5.

Arnold, R. S., K. A. Thom, S. Sharma, M. Phillips, J. Kristie Johnson, and D. J. Morgan. 2011. 'Emergence of *Klebsiella pneumoniae* carbapenemase-producing bacteria', South Med J, 104:40-5.

Arzanlou, M., Chai, W. C. & Venter, H. Intrinsic, adaptive and acquired antimicrobial resistance in Gram-negative bacteria. Essays Biochem 61, 49-59, doi: 10.1042/EBC20160063 (2017).

Barczak, A. K., J. E. Gomez, B. B. Kaufmann, E. R. Hinson, L. Cosimi, M. L. Borowsky, A. B. Onderdonk, S. A. Stanley, D. Kaur, K. F. Bryant, D. M. Knipe, A. Sloutsky, and D. T. Hung. 2012. 'RNA signatures allow rapid identification of pathogens and antibiotic susceptibilities', Proc Natl Acad Sci USA, 109: 6217-22.

Bhattacharyya, R. P., M. Walker, R. Boykin, S. S. Son, J. Liu, A. C. Hachey, P. Ma, L. Wu, K. Choi, K. C. Cummins, M. Benson, J. Skerry, H. Ryu, S. Y. Wong, M. B. Goldberg, J. Han, V. M. Pierce, L. A. Cosimi, N. Shoresh, J. Livny, J. Beechem, and D. T. Hung. 2019. 'Rapid identification and phylogenetic classification of diverse bacterial pathogens in a multiplexed hybridization assay targeting ribosomal RNA', Sci Rep.

Bhattacharyya, R. P., Grad, Y. H. & Hung, D. T. in Harrison's Principles of Internal Medicine (eds J. L. Jameson et al.) Ch. 474, 3491-3504 (McGraw-Hill Education, 2018).

Boehme, C. C. et al. Rapid molecular detection of tuberculosis and rifampin resistance. N Engl J Med 363, 1005-1015, doi: 10.1056/NEJMoa0907847 (2010). Bradley, P., H. C. den Bakker, E. P. C. Rocha, G. Mc Vean, and Z. Iqbal. 2019. 'Ultrafast search of all deposited bacterial and viral genomic data', Nat Biotechnol, 37:152-59.

Bradley, P., N. C. Gordon, T. M. Walker, L. Dunn, S. Heys, B. Huang, S. Earle, L. J. Pankhurst, L. Anson, M. de Cesare, P. Piazza, A. A. Votintseva, T. Golubchik, D. J. Wilson, D. H. Wyllie, R. Diel, S. Niemann, S. Feuerriegel, T. A. Kohl, N. Ismail, S. V. Omar, E. G. Smith, D. Buck, G. McVean, A. S. Walker, T. E. Peto, D. W. Crook, and Z. Iqbal. 2015. 'Rapid antibiotic-resistance predictions from genome sequence data for *Staphylococcus aureus* and *Mycobacterium tuberculosis*', Nat Commun, 6:10063.

Bradley, P., den Bakker, H. C., Rocha, E. P. C., McVean, G. & Iqbal, Z. Ultrafast search of all deposited bacterial and viral genomic data. Nat Biotechnol 37, 152-159, doi: 10.1038/s41587-018-0010-1 (2019).

Brown, L. D., Cai, T. T. & DasGupta, A. Interval Estimation for a Binomial Proportion. Statist Sci 16, 101-133, doi: 10.1214/ss/1009213286 (2001).

Burnham, C. D., Leeds, J., Nordmann, P., O'Grady, J. & Patel, J. Diagnosing antimicrobial resistance. Nat Rev Microbiol 15, 697-703, doi: 10.1038/nrmicro.2017.103 (2017).

Caniaux, I., A. van Belkum, G. Zambardi, L. Poirel, and M. F. Gros. 2017. 'MCR: modern colistin resistance', Eur J Clin Microbiol Infect Dis, 36:415-20.

Canton, R., Gonzalez-Alba, J. M. & Galan, J. C. CTX-M Enzymes: Origin and Diffusion. Front Microbiol 3, 110, doi: 10.3389/fmicb.2012.00110 (2012).

Centers for Disease, Control, and Prevention. 2009. 'Guidance for control of infections with carbapenem-resistant or carbapenemase-producing Enterobacteriaceae in acute care facilities', MMWR Morb Mortal Wkly Rep, 58:256-60.

Cermak, N., S. Olcum, F. F. Delgado, S. C. Wasserman, K. R. Payer, A. Murakami M, S. M. Knudsen, R. J. Kimmerling, M. M. Stevens, Y. Kikuchi, A. Sandikci, M. Ogawa, V. Agache, F. Baleras, D. M. Weinstock, and S. R. Manalis. 2016. 'High-throughput measurement of single-cell growth rates using serial microfluidic mass sensor arrays', Nat Biotechnol, 34:1052-59.

Cerqueira, G. C., A. M. Earl, C. M. Ernst, Y. H. Grad, J. P. Dekker, M. Feldgarden, S. B. Chapman, J. L. Reis-Cunha, T. P. Shea, S. Young, Q. Zeng, M. L. Delaney, D. Kim, E. M. Peterson, T. F. O'Brien, M. J. Ferraro, D. C. Hooper, S. S. Huang, J. E. Kirby, A. B. Onderdonk, B. W. Birren, D. T. Hung, L. A. Cosimi, J. R. Wortman, C. I. Murphy, and W. P. Hanage. 2017. 'Multi-institute analysis of carbapenem resistance reveals remarkable diversity, unexplained mechanisms, and limited clonal outbreaks', Proc Natl Acad Sci USA, 114:1135-40.

Charnot-Katsikas, A., V. Tesic, N. Love, B. Hill, C. Bethel, S. Boonlayangoor, and K. G. Beavis. 2018. 'Use of the Accelerate Pheno System for Identification and Antimicrobial Susceptibility Testing of Pathogens in Positive Blood Cultures and Impact on Time to Results and Workflow', J Clin Microbiol, 56.

Chea, N., S. N. Bulens, T. Kongphet-Tran, R. Lynfield, K. M. Shaw, P. S. Vagnone, M. A. Kainer, D. B. Muleta, L. Wilson, E. Vaeth, G. Dumyati, C. Concannon, E. C. Phipps, K. Culbreath, S. J. Janelle, W. M. Bamberg, A. Y. Guh, B. Limbago, and A. J. Kallen. 2015. 'Improved Phenotype-Based Definition for Identifying Carbapenemase Producers among Carbapenem-Resistant Enterobacteriaceae', Emerg Infect Dis, 21:1611-6.

Choi, J., H. Y. Jeong, G. Y. Lee, S. Han, S. Han, B. Jin, T. Lim, S. Kim, D. Y. Kim, H. C. Kim, E. C. Kim, S. H. Song, T. S. Kim, and S. Kwon. 2017. 'Direct, rapid antimicrobial susceptibility test from positive blood cultures based on microscopic imaging analysis', Sci Rep, 7:1148.

Clark, R. B., Lewinski, M. A., Loeffelholz, M. J. & Tibbetts, R. J. Cumitech 31A, Verification and validation of procedures in the clinical microbiology laboratory. (ASM Press, 2009).

CLSI. Methods for Dilution Antimicrobial Susceptibility Tests for Bacteria That Grow Aerobically. 11th edn. CLSI Supplement M07. Wayne, PA: Clinical and Laboratory Standards Institute (2018). CLSI. 2018. Performance Standards for Antimicrobial Susceptibility Testing.

Consortium, C. RyPTIC, Genomes Project the, C. Allix-Beguec, I. Arandjelovic, L. Bi, P. Beckert, M. Bonnet, P. Bradley, A. M. Cabibbe, I. Cancino-Munoz, M. J. Caulfield, A. Chaiprasert, D. M. Cirillo, D. A. Clifton, I. Comas, D. W. Crook, M. R. De Filippo, H. de Neeling, R. Diel, F. A. Drobniewski, K. Faksri, M. R. Farhat, J. Fleming, P. Fowler, T. A. Fowler, Q. Gao, J. Gardy, D. Gascoyne-Binzi, A. L. Gibertoni-Cruz, A. Gil-Brusola, T. Golubchik, X. Gonzalo, L. Grandjean, G. He, J. L. Guthrie, S. Hoosdally, M. Hunt, Z. Iqbal, N. Ismail, J. Johnston, F. M. Khanzada, C. C. Khor, T. A. Kohl, C. Kong, S. Lipworth, Q. Liu, G. Maphalala, E. Martinez, V. Mathys, M. Merker, P. Miotto, N. Mistry, D. A. J. Moore, M. Murray, S. Niemann, S. V. Omar, R. T. Ong, T. E. A. Peto, J. E. Posey, T. Prammananan, A. Pym, C. Rodrigues, M. Rodrigues, T. Rodwell, G. M. Rossolini, E. Sanchez Padilla, M. Schito, X. Shen, J. Shendure, V. Sintchenko, A. Sloutsky, E. G. Smith, M. Snyder, K. Soetaert, A. M.

Starks, P. Supply, P. Suriyapol, S. Tahseen, P. Tang, Y. Y. Teo, T. N. T. Thuong, G. Thwaites, E. Tortoli, D. van Soolingen, A. S. Walker, T. M. Walker, M. Wilcox, D. J. Wilson, D. Wyllie, Y. Yang, H. Zhang, Y. Zhao, and B. Zhu. 2018. 'Prediction of Susceptibility to First-Line Tuberculosis Drugs by DNA Sequencing', N Engl J Med, 379:1403-15.

Cubero, M. et al. Carbapenem-resistant and carbapenem-susceptible isogenic isolates of *Klebsiella pneumoniae* ST101 causing infection in a tertiary hospital. BMC Microbiol 15, 177, doi: 10.1186/s12866-015-0510-9 (2015).

Didelot, X., R. Bowden, D. J. Wilson, T. E. A. Peto, and D. W. Crook. 2012. 'Transforming clinical microbiology with bacterial genome sequencing', Nat Rev Genet, 13:601-12.

Efron, B. & Gong, G. A Leisurely Look at the Bootstrap, the Jackknife, and Cross-Validation. American Statistician 37, 36-48, doi: Doi 10.2307/2685844 (1983).

Ellington, M. J., O. Ekelund, F. M. Aarestrup, R. Canton, M. Doumith, C. Giske, H. Grundman, H. Hasman, M. T. G. Holden, K. L. Hopkins, J. Iredell, G. Kahlmeter, C. U. Koser, A. MacGowan, D. Mevius, M. Mulvey, T. Naas, T. Peto, J. M. Rolain, O. Samuelsen, and N. Woodford. 2017. 'The role of whole genome sequencing in antimicrobial susceptibility testing of bacteria: report from the EUCAST Subcommittee', Clin Microbiol Infect, 23:2-22.

Evans, S. R., A. M. Hujer, H. Jiang, K. M. Hujer, T. Hall, C. Marzan, M. R. Jacobs, R. Sampath, D. J. Ecker, C. Manca, K. Chavda, P. Zhang, H. Fernandez, L. Chen, J. R. Mediavilla, C. B. Hill, F. Perez, A. M. Caliendo, V. G. Fowler, Jr., H. F. Chambers, B. N. Kreiswirth, R. A. Bonomo, and Group Antibacterial Resistance Leadership. 2016. 'Rapid Molecular Diagnostics, Antibiotic Treatment Decisions, and Developing Approaches to Inform Empiric Therapy: PRIMERS I and II', Clin Infect Dis, 62:181-9.

Fauci, A. S. & Morens, D. M. The perpetual challenge of infectious diseases. N Engl J Med 366, 454-461, doi: 10.1056/NEJMra1108296 (2012).

Florio, W., Tavanti, A., Barnini, S., Ghelardi, E. & Lupetti, A. Recent Advances and Ongoing Challenges in the Diagnosis of Microbial Infections by MALDI-TOF Mass Spectrometry. Front Microbiol 9, 1097, doi: 10.3389/fmich.2018.01097 (2018).

Ford, B. A. 2018. 'mecC-Harboring Methicillin-Resistant *Staphylococcus aureus*: Hiding in Plain Sight', J Clin Microbiol, 56.

Garcia-Alvarez, L., M. T. Holden, H. Lindsay, C. R. Webb, D. F. Brown, M. D. Curran, E. Walpole, K. Brooks, D. J. Pickard, C. Teale, J. Parkhill, S. D. Bentley, G. F. Edwards, E. K. Girvan, A. M. Kearns, B. Pichon, R. L. Hill, A. R. Larsen, R. L. Skov, S. J. Peacock, D. J. Maskell, and M. A. Holmes. 2011. 'Meticillin-resistant *Staphylococcus aureus* with a novel mecA homologue in human and bovine populations in the UK and Denmark: a descriptive study', Lancet Infect Dis, 11:595-603.

Geiss, G. K., R. E. Bumgarner, B. Birditt, T. Dahl, N. Dowidar, D. L. Dunaway, H. P. Fell, S. Ferree, R. D. George, T. Grogan, J. J. James, M. Maysuria, J. D. Mitton, P. *Oliveri*, J. L. Osborn, T. Peng, A. L. Ratcliffe, P. J. Webster, E. H. Davidson, L. Hood, and K. Dimitrov. 2008. 'Direct multiplexed measurement of gene expression with color-coded probe pairs', Nat Biotechnol, 26:317-25.

Gotz, S. et al. High-throughput functional annotation and data mining with the Blast2GO suite. Nucleic Acids Res 36, 3420-3435, doi: 10.1093/nar/gkn176 (2008).

Gupta, N., Limbago, B. M., Patel, J. B. & Kallen, A. J. Carbapenem-resistant Enterobacteriaceae: epidemiology and prevention. Clin Infect Dis 53, 60-67, doi: 10.1093/cid/cir202 (2011).

Gupta, S. K. et al. ARG-ANNOT, a new bioinformatic tool to discover antibiotic resistance genes in bacterial genomes. Antimicrob Agents Chemother 58, 212-220, doi: 10.1128/AAC.01310-13 (2014).

Gupta, V., R. Garg, K. Kumaraswamy, P. Datta, G. K. Mohi, and J. Chander. 2018. 'Phenotypic and genotypic characterization of carbapenem resistance mechanisms in *Klebsiella pneumoniae* from blood culture specimens: A study from North India', J Lab Physicians, 10:125-29

Holdren, J. P. et al. President's Council of Advisors on Science and Technology: Report to the President on Combating Antibiotic Resistance. (2014).

Hooper, D. C. New uses for new and old quinolones and the challenge of resistance. Clin Infect Dis 30, 243-254, doi: 10.1086/313677 (2000).

Hou, H. W., R. P. Bhattacharyya, D. T. Hung, and J. Han. 2015. 'Direct detection and drug-resistance profiling of bacteremias using inertial microfluidics', Lab Chip, 15:2297-307.

Humphries, R., and T. Di Martino. 2019. 'Effective implementation of the Accelerate Pheno system for positive blood cultures', J Antimicrob Chemother, 74:140-i43.

Humphries, R. M. CIM City: The game continues for a better carbapenemase test. J Clin Microbiol, doi: 10.1128/JCM.00353-19 (2019).

Ioannidis, P. et al. Cepheid GeneXpert MTB/RIF assay for *Mycobacterium tuberculosis* detection and rifampin resistance identification in patients with substantial clinical indications of tuberculosis and smear-negative microscopy results. J Clin Microbiol 49, 3068-3070, doi: 10.1128/JCM.00718-11 (2011).

Iovleva, A. & Doi, Y. Carbapenem-Resistant Enterobacteriaceae. Clin Lab Med 37, 303-315, doi: 10.1016/j.cll.2017.01.005 (2017).

Jia, B. et al. CARD 2017: expansion and model-centric curation of the comprehensive antibiotic resistance database. Nucleic Acids Res 45, D566-D573, doi: 10.1093/nar/gkw1004 (2017).

Kaase, M., F. Szabados, L. Wassill, and S. G. Gatermann. 2012. 'Detection of carbapenemases in Enterobacteriaceae by a commercial multiplex PCR', J Clin Microbiol, 50:3115-8.

Kadri, S. S. et al. Difficult-to-Treat Resistance in Gram-negative Bacteremia at 173 US Hospitals: Retrospective Cohort Analysis of Prevalence, Predictors, and Outcome of Resistance to All First-line Agents. Clin Infect Dis 67, 1803-1814, doi: 10.1093/cid/ciy378 (2018).

Klungthong, C., P. Chinnawirotpisan, K. Hussem, T. Phonpakobsin, W. Manasatienkij, C. Ajariyakhajorn, K. Rungrojcharoenkit, R. V. Gibbons, and R. G. Jarman. 2010. 'The impact of primer and probe-template mismatches on the sensitivity of pandemic influenza A/H1N1/2009 virus detection by real-time RT-PCR', J Clin Virol, 48:91-5.

Kumar, A., D. Roberts, K. E. Wood, B. Light, J. E. Parrillo, S. Sharma, R. Suppes, D. Feinstein, S. Zanotti, L. Taiberg, D. Gurka, A. Kumar, and M. Cheang. 2006. 'Duration of hypotension before initiation of effective antimicrobial therapy is the critical determinant of survival in human septic shock', Crit Care Med, 34:1589-96.

Letunic, I. & Bork, P. Interactive Tree Of Life (iTOL) v4: recent updates and new developments. Nucleic Acids Res 47, W256-W259, doi: 10.1093/nar/gkz239 (2019).

Li, H., and R. Durbin. 2009. 'Fast and accurate short read alignment with Burrows-Wheeler transform', Bioinformatics, 25:1754-60.

Li, Y. et al. Penicillin-Binding Protein Transpeptidase Signatures for Tracking and Predicting beta-Lactam Resistance Levels in *Streptococcus pneumoniae*. MBio 7, doi: 10.1128/mBio.00756-16 (2016).

Liakopoulos, A., D. J. Mevius, B. Olsen, and J. Bonnedahl. 2016. 'The colistin resistance mcr-1 gene is going wild', J Antimicrob Chemother, 71:2335-6.

Liaw, A. & Wiener, M. Classification and Regression by RandomForest. Vol. 23 (2001).

Liu, B., and M. Pop. 2009. 'ARDB—Antibiotic Resistance Genes Database', Nucleic Acids Res, 37: D443-7.

Liu, Y. Y., Y. Wang, T. R. Walsh, L. X. Yi, R. Zhang, J. Spencer, Y. Doi, G. Tian, B. Dong, X. Huang, L. F. Yu, D. Gu, H. Ren, X. Chen, L. Lv, D. He, H. Zhou, Z. Liang, J. H. Liu, and J. Shen. 2016. 'Emergence of plasmid-mediated colistin resistance mechanism MCR-1 in animals and human beings in China: a microbiological and molecular biological study', Lancet Infect Dis, 16:161-8.

Lomovskaya, O., D. Sun, D. Rubio-Aparicio, K. Nelson, R. Tsivkovski, D. C. Griffith, and M. N. Dudley. 2017. 'Vaborbactam: Spectrum of Beta-Lactamase Inhibition and Impact of Resistance Mechanisms on Activity in Enterobacteriaceae', Antimicrob Agents Chemother, 61.

Longo, G., L. Alonso-Sarduy, L. M. Rio, A. Bizzini, A. Trampuz, J. Notz, G. Dietler, and S. Kasas. 2013. 'Rapid detection of bacterial resistance to antibiotics using AFM cantilevers as nanomechanical sensors', Nat Nanotechnol, 8:522-6.

Love, M. I., W. Huber, and S. Anders. 2014. 'Moderated estimation of fold change and dispersion for RNA-seq data with DESeq2', Genome Biol, 15:550.

Lutgring, J. D., and B. M. Limbago. 2016. 'The Problem of Carbapenemase-Producing-Carbapenem-Resistant-Enterobacteriaceae Detection', J Clin Microbiol, 54:529-34.

Ma, P., H. H. Laibinis, C. M. Ernst, and D. T. Hung. 2018. 'Carbapenem Resistance Caused by High-Level Expression of OXA-663 beta-Lactamase in an OmpK36-Deficient *Klebsiella pneumoniae* Clinical Isolate', Antimicrob Agents Chemother, 62.

Marlowe, E. M. et al. Evaluation of the Cepheid Xpert MTB/RIF assay for direct detection of *Mycobacterium tuberculosis* complex in respiratory specimens. J Clin Microbiol 49, 1621-1623, doi: 10.1128/JCM.02214-10 (2011).

Marner, E. S. et al. Diagnostic accuracy of the Cepheid GeneXpert vanA/vanB assay ver. 1.0 to detect the vanA and vanB vancomycin resistance genes in *Enterococcus* from perianal specimens. Diagn Microbiol Infect Dis 69, 382-389, doi: 10.1016/j.diagmicrobio.2010.11.005 (2011).

Marschal, M., J. Bachmaier, I. Autenrieth, P. Oberhettinger, M. Willmann, and S. Peter. 2017. 'Evaluation of the Accelerate Pheno System for Fast Identification and Antimicrobial Susceptibility Testing from Positive Blood Cultures in Bloodstream Infections Caused by Gram-Negative Pathogens', J Clin Microbiol, 55:2116-26.

Marshall, S., A. M. Hujer, L. J. Rojas, K. M. Papp-Wallace, R. M. Humphries, B. Spellberg, K. M. Hujer, E. K. Marshall, S. D. Rudin, F. Perez, B. M. Wilson, R. B. Wasserman, L. Chikowski, D. L. Paterson, A. J. Vila, D. van Duin, B. N. Kreiswirth, H. F. Chambers, V. G. Fowler, Jr., M. R. Jacobs, M. E. Pulse, W. J. Weiss, and R. A. Bonomo. 2017. 'Can Ceftazidime-Avibactam and Aztreonam Overcome beta-Lactam Resistance Conferred by Metallo-beta-Lactamases in Enterobacteriaceae?', Antimicrob Agents Chemother, 61.

Martinez-Martinez, L., and J. J. Gonzalez-Lopez. 2014. 'Carbapenemases in Enterobacteriaceae: types and molecular epidemiology', Enferm Infecc Microbiol Clin, 32 Suppl 4:4-9.

Maurer, F. P., Christner, M., Hentschke, M. & Rohde, H. Advances in Rapid Identification and Susceptibility Testing of Bacteria in the Clinical Microbiology Laboratory: Implications for Patient Care and Antimicrobial Stewardship Programs. Infect Dis Rep 9, 6839, doi: 10.4081/idr.2017.6839 (2017).

McArthur, A. G. et al. The comprehensive antibiotic resistance database. Antimicrob Agents Chemother 57, 3348-3357, doi: 10.1128/AAC.00419-13 (2013).

McMullen, A. R., Yarbrough, M. L., Wallace, M. A., Shupe, A. & Burnham, C. D. Evaluation of Genotypic and Phenotypic Methods to Detect Carbapenemase Production in Gram-Negative Bacilli. Clin Chem 63, 723-730, doi: 10.1373/clinchem.2016.264804 (2017).

Milheirico, C., de Lencastre, H. & Tomasz, A. Full-Genome Sequencing Identifies in the Genetic Background Several Determinants That Modulate the Resistance Phenotype in Methicillin-Resistant *Staphylococcus aureus* Strains Carrying the Novel mecC Gene. Antimicrob Agents Chemother 61, doi: 10.1128/AAC.02500-16 (2017).

Miller, S., and R. M. Humphries. 2016. 'Clinical laboratory detection of carbapenem-resistant and carbapenemase-producing Enterobacteriaceae', Expert Rev Anti Infect Ther, 14:705-17.

Nathan, C. & Cars, O. Antibiotic Resistance-Problems, Progress, and Prospects. N Engl J Med, doi: 10.1056/NEJMp1408040 (2014).

Nguyen, M. et al. Developing an in silico minimum inhibitory concentration panel test for *Klebsiella pneumoniae*. Sci Rep 8, 421, doi: 10.1038/s41598-017-18972-w (2018).

Nordmann, P., G. Cuzon, and T. Naas. 2009. 'The real threat of *Klebsiella pneumoniae* carbapenemase-producing bacteria', Lancet Infect Dis, 9:228-36.

Nordmann, P., L. Dortet, and L. Poirel. 2012. "Carbapenem resistance in Enterobacteriaceae: here is the storm!" Trends Mol Med, 18:263-72.

Paterson, D. L., W. C. Ko, A. Von Gottberg, J. M. Casellas, L. Mulazimoglu, K. P. Klugman, R. A. Bonomo, L. B. Rice, J. G. McCormack, and V. L. Yu. 2001. 'Outcome of cephalosporin treatment for serious infections due to apparently susceptible organisms producing extended-spectrum beta-lactamases: implications for the clinical microbiology laboratory', J Clin Microbiol, 39:2206-12.

Paterson, G. K., E. M. Harrison, and M. A. Holmes. 2014. 'The emergence of mecC methicillin-resistant *Staphylococcus aureus*', Trends Microbiol, 22:42-7.

Perez, K. K. et al. Integrating rapid pathogen identification and antimicrobial stewardship significantly decreases hospital costs. Arch Pathol Lab Med 137, 1247-1254, doi: 10.5858/arpa.2012-0651-OA (2013).

Quach, D. T., G. Sakoulas, V. Nizet, J. Pogliano, and K. Pogliano. 2016. 'Bacterial Cytological Profiling (BCP) as a Rapid and Accurate Antimicrobial Susceptibility Testing Method for *Staphylococcus aureus*', EBioMedicine, 4:95-103.

Rasko, D. A., D. R. Webster, J. W. Sahl, A. Bashir, N. Boisen, F. Scheutz, E. E. Paxinos, R. Sebra, C. S. Chin, D.

Iliopoulos, A. Klammer, P. Peluso, L. Lee, A. O. Kislyuk, J. Bullard, A. Kasarskis, S. Wang, J. Eid, D. Rank, J. C. Redman, S. R. Steyert, J. Frimodt-Moller, C. Struve, A. M. Petersen, K. A. Krogfelt, J. P. Nataro, E. E. Schadt, and M. K. Waldor. 2011. 'Origins of the *E. coli* strain causing an outbreak of hemolytic-uremic syndrome in Germany', N Engl J Med, 365:709-17.

Robnik-Šikonja, Marko, and Igor Kononenko. 2003. 'Theoretical and Empirical Analysis of ReliefF and RReliefF', Machine Learning, 53:23-69.

Rossen, J. W. A., A. W. Friedrich, J. Moran-Gilad, Escmid Study Group for Genomic, and Diagnostics Molecular. 2018. 'Practical issues in implementing whole-genome-sequencing in routine diagnostic microbiology', Clin Microbiol Infect, 24:355-60.

Salimnia, H. et al. Evaluation of the FilmArray Blood Culture Identification Panel: Results of a Multicenter Controlled Trial. J Clin Microbiol 54, 687-698, doi: 10.1128/JCM.01679-15 (2016).

Shishkin, A. A., G. Giannoukos, A. Kucukural, D. Ciulla, M. Busby, C. Surka, J. Chen, R. P. Bhattacharyya, R. F. Rudy, M. M. Patel, N. Novod, D. T. Hung, A. Gnirke, M. Garber, M. Guttman, and J. Livny. 2015. 'Simultaneous generation of many RNA-seq libraries in a single reaction', Nat Methods, 12:323-5.

Smith, K. P., and J. E. Kirby. 2018. 'The Inoculum Effect in the Era of Multidrug Resistance: Minor Differences in Inoculum Have Dramatic Effect on MIC Determination', Antimicrob Agents Chemother, 62.

Smith, M., B. Diederen, J. Scharringa, M. Leversteijn-van Hall, A. C. Fluit, and J. Cohen Stuart. 2016. 'Rapid and accurate detection of carbapenemase genes in Enterobacteriaceae with the Cepheid Xpert Carba-R assay', J Med Microbiol, 65:951-3.

Sullivan, K. V., B. Deburger, S. S. Roundtree, C. A. Ventrola, D. L. Blecker-Shelly, and J. E. Mortensen. 2014. 'Pediatric multicenter evaluation of the Verigene gram-negative blood culture test for rapid detection of inpatient bacteremia involving gram-negative organisms, extended-spectrum beta-lactamases, and carbapenemases', J Clin Microbiol, 52:2416-21.

Sun, J., H. Zhang, Y. H. Liu, and Y. Feng. 2018. 'Towards Understanding MCR-like Colistin Resistance', Trends Microbiol, 26:794-808.

Tacconelli, E. et al. Discovery, research, and development of new antibiotics: the WHO priority list of antibiotic-resistant bacteria and tuberculosis. Lancet Infect Dis 18, 318-327, doi: 10.1016/S1473-3099 (17) 30753-3 (2018).

Tagini, F., and G. Greub. 2017. 'Bacterial genome sequencing in clinical microbiology: a pathogen-oriented review', Eur J Clin Microbiol Infect Dis, 36:2007-20.

Tanner, H., Evans, J. T., Gossain, S. & Hussain, A. Evaluation of three sample preparation methods for the direct identification of bacteria in positive blood cultures by MALDI-TOF. BMC Res Notes 10, 48, doi: 10.1186/s13104-016-2366-y (2017).

Traczewski, M. M., Carretto, E., Canton, R., Moore, N. M. & Carba, R. S. T. Multicenter Evaluation of the Xpert Carba-R Assay for Detection of Carbapenemase Genes in Gram-Negative Isolates. J Clin Microbiol 56, doi: 10.1128/JCM.00272-18 (2018).

van Belkum, A., M. Welker, D. Pincus, J. P. Charrier, and V. Girard. 2017. 'Matrix-Assisted Laser Desorption Ionization Time-of-Flight Mass Spectrometry in Clinical Microbiology: What Are the Current Issues?', Ann Lab Med, 37:475-83.

van Duin, D., and R. A. Bonomo. 2016. 'Ceftazidime/Avibactam and Ceftolozane/Tazobactam: Second-generation beta-Lactam/beta-Lactamase Inhibitor Combinations', Clin Infect Dis, 63:234-41.

Vandesompele, J. et al. Accurate normalization of real-time quantitative RT-PCR data by geometric averaging of multiple internal control genes. Genome Biol 3, RESEARCH0034 (2002).

Wadsworth, C. B., Sater, M. R. A., Bhattacharyya, R. P. & Grad, Y. H. Impact of species diversity on the design of RNA-based diagnostics for antibiotic resistance in *Neisseria gonorrhoeae*. Antimicrob Agents Chemother, doi: 10.1128/AAC.00549-19 (2019).

Walker, G. T. et al. Analytical Performance of Multiplexed Screening Test for 10 Antibiotic Resistance Genes from Perianal Swab Samples. Clin Chem 62, 353-359, doi: 10.1373/clinchem.2015.246371 (2016).

Walker, T. et al. Clinical Impact of Laboratory Implementation of Verigene BC-GN Microarray-Based Assay for Detection of Gram-Negative Bacteria in Positive Blood Cultures. J Clin Microbiol 54, 1789-1796, doi: 10.1128/JCM.00376-16 (2016).

Weisenberg, S. A., D. J. Morgan, R. Espinal-Witter, and D. H. Larone. 2009. 'Clinical outcomes of patients with *Klebsiella pneumoniae* carbapenemase-producing *K. pneumoniae* after treatment with imipenem or meropenem', Diagn Microbiol Infect Dis, 64:233-5.

Wiegand, I., K. Hilpert, and R. E. Hancock. 2008. 'Agar and broth dilution methods to determine the minimal inhibitory concentration (MIC) of antimicrobial substances', Nat Protoc, 3:163-75.

Wolk, D. M. et al. Multicenter evaluation of the Cepheid Xpert methicillin-resistant *Staphylococcus aureus* (MRSA) test as a rapid screening method for detection of MRSA in nares. J Clin Microbiol 47, 758-764, doi: 10.1128/JCM.01714-08 (2009).

Woodworth, K. R., M. S. Walters, L. M. Weiner, J. Edwards, A. C. Brown, J. Y. Huang, S. Malik, R. B. Slayton, P. Paul, C. Capers, M. A. Kainer, N. Wilde, A. Shugart, G. Mahon, A. J. Kallen, J. Patel, L. C. McDonald, A. Srinivasan, M. Craig, and D. M. Cardo. 2018. 'Vital Signs: Containment of Novel Multidrug-Resistant Organisms and Resistance Mechanisms-United States, 2006-2017', MMWR Morb Mortal Wkly Rep, 67:396-401.

World Health_Organization. Antimicrobial resistance: global report on surveillance 2014. (2014).

Ye, Y., L. Xu, Y. Han, Z. Chen, C. Liu, and L. Ming. 2018. 'Mechanism for carbapenem resistance of clinical Enterobacteriaceae isolates', Exp Ther Med, 15:1143-49.

Zankari, E., H. Hasman, S. Cosentino, M. Vestergaard, S. Rasmussen, O. Lund, F. M. Aarestrup, and M. V. Larsen. 2012. 'Identification of acquired antimicrobial resistance genes', J Antimicrob Chemother, 67:2640-4.

Zhu, Y. Y., E. M. Machleder, A. Chenchik, R. Li, and P. D. Siebert. 2001. 'Reverse transcriptase template switching: a SMART approach for full-length cDNA library construction', Biotechniques, 30:892-7.

SEQUENCE LISTING

The patent contains a lengthy sequence listing. A copy of the sequence listing is available in electronic form from the USPTO web site (https://seqdata.uspto.gov/?pageRequest=docDetail&DocID=US12442035B2). An electronic copy of the sequence listing will also be available from the USPTO upon request and payment of the fee set forth in 37 CFR 1.19(b)(3).

What is claimed is:

1. A method, comprising:

obtaining a sample including one or more bacterial cells, wherein the sample is obtained from a patient;

processing the sample to enrich the one or more bacterial cells;

contacting the sample with one or more antibiotic compounds;

lysing the sample to release messenger ribonucleic acid (mRNA) from the one or more bacterial cells;

hybridizing the released mRNA to at least one set of two nucleic acid probes, wherein each nucleic acid probe includes a unique barcode or tag and wherein the at least one set of nucleic acid probes includes one or more probes from SEQ ID NOs: 74-86 and one or more probes from SEQ ID NOs: 91-103;

detecting the hybridized nucleic acid probes;

identifying one or more genetic resistance determinants;

determining antibiotic susceptibility of the one or more bacterial cells using a machine learning algorithm trained on a susceptibility classification dataset, wherein the machine learning algorithm generates a ranked list of two or more susceptibility features, thereby determining antibiotic susceptibility of the one or more bacterial cells; and selecting an appropriate antibiotic based on the determined antibiotic susceptibility of the one or more bacterial cells; and administering the appropriate antibiotic to the patient.

2. The method of claim 1, wherein the hybridizing occurs at a temperature between about 64° C. and about 69° C.

3. The method of claim 1, wherein the hybridizing occurs at a temperature between about 65° C. and about 67° C.

4. The method of claim 1, wherein the hybridizing occurs at about 65° C. or about 66° C. or about 67° C.

5. The method of claim 1, wherein the at least one set of two nucleic acid probes is selected from the group consisting of: SEQ ID NO: 74 and SEQ ID NO: 91; SEQ ID NO: 75 and SEQ ID NO: 92; SEQ ID NO: 76 and SEQ ID NO: 93; SEQ ID NO: 77 and SEQ ID NO: 94; SEQ ID NO: 78 and SEQ ID NO: 95; SEQ ID NO: 79 and SEQ ID NO: 96; SEQ ID NO: 80 and SEQ ID NO: 97; SEQ ID NO: 81 and SEQ ID NO: 98; SEQ ID NO: 82 and SEQ ID NO: 99; SEQ ID NO: 83 and SEQ ID NO: 100; SEQ ID NO: 84 and SEQ ID NO: 101; SEQ ID NO: 85 and SEQ ID NO: 102; and SEQ ID NO: 86 and SEQ ID NO: 103.

6. The method of claim 5, wherein the at least one set of two nucleic acid probes is selected from the group consisting of: SEQ ID NO: 74 and SEQ ID NO: 91; SEQ ID NO: 75 and SEQ ID NO: 92; SEQ ID NO: 76 and SEQ ID NO: 93; SEQ ID NO: 77 and SEQ ID NO: 94; SEQ ID NO: 78 and SEQ ID NO: 95; SEQ ID NO: 80 and SEQ ID NO: 97; SEQ ID NO: 82 and SEQ ID NO: 99; SEQ ID NO: 83 and SEQ ID NO: 100; and SEQ ID NO: 85 and SEQ ID NO: 102.

7. The method of claim 1, wherein at least two sets of nucleic acid probes are selected.

8. The method of claim 1, wherein at least three sets of nucleic acid probes are selected.

9. The method of claim 1, wherein at least four sets of nucleic acid probes are selected.

10. A method, comprising:

obtaining a sample including one or more bacterial cells, wherein the sample is obtained from a patient;

processing the sample to enrich the one or more bacterial cells;

contacting the sample with one or more antibiotic compounds;

lysing the sample to release messenger ribonucleic acid (mRNA) from the one or more bacterial cells;

hybridizing the released mRNA to at least five nucleic acid probe sets, wherein each nucleic acid probe includes a unique barcode or tag and wherein the at least one set of nucleic acid probes includes one or more probes from SEQ ID NOs: 74-86 and one or more probes from SEQ ID NOs: 91-103;

detecting the hybridized nucleic acid probes;

identifying one or more genetic resistance determinants;

determining antibiotic susceptibility of the one or more bacterial cells using a machine learning algorithm trained on a susceptibility classification dataset, wherein the machine learning algorithm generates a ranked list of two or more susceptibility features, thereby determining antibiotic susceptibility of the one or more bacterial cells; and selecting an appropriate antibiotic based on the determined antibiotic susceptibility of the one or more bacterial cells and administering the appropriate antibiotic to the patient.

11. The method of claim 10, wherein the at least five nucleic acid probe sets comprise: SEQ ID NO: 74 and SEQ ID NO: 91; SEQ ID NO: 75 and SEQ ID NO: 92; SEQ ID NO: 76 and SEQ ID NO: 93; SEQ ID NO: 78 and SEQ ID NO: 95; and SEQ ID NO: 84 and SEQ ID NO: 101.

* * * * *